(12) United States Patent
Henriksson et al.

(10) Patent No.: US 7,253,196 B2
(45) Date of Patent: Aug. 7, 2007

(54) INHIBITORS OF 11-β-HYDROXY STEROID DEHYDROGENASE TYPE 1

(75) Inventors: Martin Henriksson, Uppsala (SE); Evert Homan, Sollentuna (SE); Lars Johansson, Stockholm (SE); Jerk Vallgarda, Uppsala (SE); Meredith Williams, Uppsala (SE); Eric A. Bercot, Moorpark, CA (US); Christopher H. Fotsch, Thousand Oaks, CA (US); Aiwen Li, Westlake Village, CA (US); Guolin Cai, Thousand Oaks, CA (US); Randall W. Hungate, Camarillo, CA (US); Chester Chenguang Yuan, Newbury Park, CA (US); Christopher Tegley, Thousand Oaks, CA (US); David J. St. Jean, Jr., Camarillo, CA (US); Nianhe Han, Thousand Oaks, CA (US); Qi Huang, Moorpark, CA (US); Qingyian Liu, Camarillo, CA (US); Michael D. Bartberger, Sherman Oaks, CA (US); George A. Moniz, Cambridge, MA (US); Matthew J. Frizzle, Arlington, MA (US)

(73) Assignees: Amgen, Inc., Thousand Oaks, CA (US); Biovitrum AB, Stockholm (SE)

( * ) Notice: Subject to any disclaimer, the term of this patent is extended or adjusted under 35 U.S.C. 154(b) by 0 days.

(21) Appl. No.: 11/135,662

(22) Filed: May 24, 2005

(65) Prior Publication Data
US 2006/0142357 A1    Jun. 29, 2006

Related U.S. Application Data

(60) Provisional application No. 60/650,777, filed on Jan. 31, 2005.

(30) Foreign Application Priority Data

| May 24, 2004 | (SE) | .................................... 0401324 |
| Oct. 15, 2004 | (SE) | .................................... 0402509 |

(51) Int. Cl.
  A61K 31/426    (2006.01)
  C07D 279/06    (2006.01)
(52) U.S. Cl. ...................... 514/369; 548/182
(58) Field of Classification Search ................ 514/360, 514/369, 370; 548/184
  See application file for complete search history.

(56) References Cited

U.S. PATENT DOCUMENTS

2005/0009821 A1   1/2005 Pyring et al.

FOREIGN PATENT DOCUMENTS

DE         936 688      12/1955

WO      WO 01/90091 A1    11/2001

(Continued)

OTHER PUBLICATIONS

STN search report : Doran et al. Journal of Organic Chemistry (1938), 3, 193-7.*

(Continued)

Primary Examiner—Kamal A. Saeed
Assistant Examiner—Yong Chu
(74) Attorney, Agent, or Firm—Foley and Lardner LLP

(57) ABSTRACT

The present invention relates to compounds with the formula (I), (II), (III) or (IV):

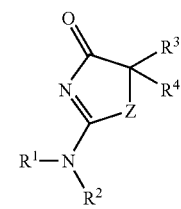

(I)

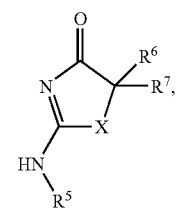

(II)

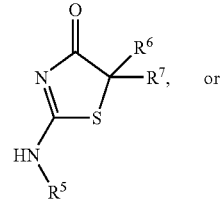

(III)

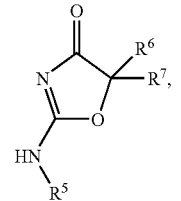

(IV)

wherein $R^1$, $R^2$, $R^3$, $R^4$, $R^5$, $R^6$, $R^7$, X and Z are as defined herein, and also to pharmaceutical compositions comprising the compounds, as well as methods of use of the compounds for treatment of disorders associated with human 11-β-hydroxysteroid dehydrogenase type 1 enzyme and for the preparation of a medicament which acts on the human 11-β-hydroxysteroid dehydrogenase type 1 enzyme.

15 Claims, No Drawings

FOREIGN PATENT DOCUMENTS

| | | |
|---|---|---|
| WO | WO 01/90092 A1 | 11/2001 |
| WO | WO 01/90093 A1 | 11/2001 |
| WO | WO 01/90094 A1 | 11/2001 |
| WO | WO 03/043999 A1 | 5/2003 |
| WO | WO 03/044000 A1 | 5/2003 |
| WO | WO 03/044009 A1 | 5/2003 |
| WO | WO 2004/103980 A1 | 12/2004 |
| WO | WO 2004/112779 A1 | 12/2004 |
| WO | WO 2004/112781 A1 | 12/2004 |
| WO | WO 2004/112782 A1 | 12/2004 |
| WO | WO 2004/112783 A1 | 12/2004 |
| WO | WO 2004/112784 A1 | 12/2004 |
| WO | WO 2004/112785 A1 | 12/2004 |
| WO | WO 2004/113310 A1 | 12/2004 |
| WO | WO 2005/075471 A2 | 8/2005 |

OTHER PUBLICATIONS

Okawara, et al.; "Preparations of Perhydroimidazo[1,5-a]pyridine-3-thiones and Thiazole-5-spirocyclopropan-4(5H)-ones from Thioureas and α,γ-Dibromobutyryl Chloride under Phase-transfer Conditions"; *J. Chem. Soc.*; Perkin Trans. I; 1986; pp. 1733-1735.

Doran et al.; "Dialkyl Thiazolidiones"; *Journal of Organic Chemistry*; vol. 3; 1938; pp. 193-197.

Kvíčala et al.; "Reactions of 3-chloropentafluoropropene-1,2-oxide with bifunctional nucleophiles: a new route to chlorodifluoromethyl-substituted heterocycles"; *Journal of Fluorine Chemistry*; vol. 108; 2001; pp. 1-5.

King et al.; "The Reaction of Diazoketones with Thioamide Derivatives"; *Journal of American Chemical Society*; vol. 71; 1949; pp. 367-368.

Schreiner et al.; "A Convenient Protocol for Selective Cleavage of 2-Hydroxy Acid Amides. Application to Semisynthesis of the Cyclic Heptapeptide Aza HUN-7293"; *Journal of Organic Chemistry*; vol. 67; 2002; pp. 8299-8304.

Moore et al.; "Sulfonamidothiazolones" *Journal of American Chemical Society*; vol. 63; 1941; pp. 2781-2784.

Dixon et al.; "Action between Thiourea and some Haloid Derivatives of Fatty Acids"; *Journal of the Chemical Society*; vol. 63; pp. 815-821.

Mittra et al.; "Reaction of Aromatic Aldehydes with 5-methyl-4-thiazolidones"; *Journal of the Indian Chemical Society*; vol. 36; No. 10; 1959; pp. 723-725.

Vasa et al.; "Thiazolidones Part I"; *Journal of Indian Chemical Society*; vol. 36; No. 9; 1959; pp. 648-650.

Andreasch, R.; "Zur Kenntniss der Thiohydantoine"; *Monatshefte Fur Chemie*; vol. 8; 1887; pp. 407-424.

Heald et al. "Syntheses of Certain Thiazolopyrimidines"; *Journal of Chemical Society*; 1950, pp. 1127-1129.

Hurst, D.T., et al., "The synthesis of some pyrimidinyl and thiazolyl ureas and thioureas and some related compounds", *Australian Journal of Chemistry*, vol. 41, 1988, pp. 1221-1229 (XP009055887).

Aspelund, H., "Einwirkung von natriumhydroxyd auf einige 2-imino-4-oxazolidinone bzw. 2-amino-4-oxazolinone", *Acta Academiae Aboensis*, ser. B, vol. 25, No. 5, 1965, pp. 1-21 (XP001246496).

Leistner, S., et al., "Darstellung von 3-oxo (bzw.imino)-5-(alpha-hydroxy-alkyl)-1,2,4-triaz olinderivaten aus 2-oxo(bzw.lmino)-4-oxo-5-alkyl-oxazolidine n und Hydazinhydrat", *Zeitschrift fuer Chemie*, vol. 14, No. 7, 1974, pp. 267-268 (XP009062313).

Aspelund, H., "Einwirkung von natriumhydroxyd aud einige 2-imino-4-oxazolidinone bzw. 2-amino-4-oxazolinone", *Acta Academiae Aboensis*, ser. B, vol. 26, No. 8, 1967, pp. 1-13 (XP001246495).

Rapi, G., et al., "Tautomerism of 2-amino-2-oxazolin-4-ones", *Journal of Heterocyclic Chemistry*, vol. 9, No. 2; 1972; pp. 285-292 (XP002369328).

Erlenmeyer, H., et al, "Zer kenntnis der Eigenschaften isosterer und strukturahnlicher verbidungen VI. Uber einige derivate des thiazols und des oxazols", *Helvetica Chimica Acta*, vol. 21, 1938, pp. 111-113 (XP009062356).

\* cited by examiner

INHIBITORS OF 11-β-HYDROXY STEROID DEHYDROGENASE TYPE 1

CROSS-REFERENCE TO RELATED PATENT APPLICATIONS

This application claims priority to Swedish Patent Application No. 0401324-9, filed May 24, 2004, Swedish Patent Application No. 0402509-4, filed Oct. 15, 2004, and U.S. Provisional Patent Application No. 60/650,777, filed Jan. 31, 2005.

FIELD OF THE INVENTION

The present invention relates to novel compounds, to pharmaceutical compositions comprising the compounds, as well as to the use of the compounds in medicine and for the preparation of a medicament which acts on the human 11-β-hydroxysteroid dehydrogenase type 1 enzyme (11βHSD1).

BACKGROUND OF THE INVENTION

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identifed in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal develoment leads to male pseudohermaphroditism. Geissler et al., Nat. Genet. 1994, 7:34-39. Both 17β-HSD3 and various 3α-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α,17β-diol and the interconversion of the androgens DHEA and androstenedione and therefore play an important role in androgen metabolism. Ge et al., Biology of Reproduction 1999, 60:855-860.

1. Glucorticoids, Diabetes and Hepatic Glucose Production

It has been known for more than half a century that glucocorticoids have a central role in diabetes. For example, the removal of the pituitary gland or the adrenal gland from a diabetic animal alleviates the most severe symptoms of diabetes and lowers the concentration of glucose in the blood (Long, C. D. and Leukins, F. D. W. (1936) J. Exp. Med. 63: 465-490; Houssay, B. A. (1942) Endocrinology 30: 884-892). It is also well established that glucocorticoids enable the effect of glucagon on the liver.

The role of 11βHSD1 as an important regulator of local glucocorticoid effect and thus of hepatic glucose production is well substantiated (see, e.g., Jamieson et al. (2000) J. Endocrinol. 165: 685-692). Hepatic insulin sensitivity was improved in healthy human volunteers treated with the non-specific 11βHSD1 inhibitor carbenoxolone (Walker, B. R. et al. (1995) J. Clin. Endocrinol. Metab. 80: 3155-3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6Pase) the enzyme catalyzing the last common step of gluconeogenesis and glycogenolysis. Finally, blood glucose levels and hepatic glucose production are reduced in mice in which the 11βHSD1 gene is knocked-out. Data from this model also confirm that inhibition of 11βHSD1 will not cause hypoglycemia, as predicted since the basal levels of PEPCK and G6Pase are regulated independently of glucocorticoids (Kotelevtsev, Y. et al., (1997) Proc. Natl. Acad. Sci. USA 94: 14924-14929).

FR 2,384,498 discloses compounds having a high hypoglycemic effect. Therefore, treatment of hyperglycemia with these compounds may lead to hypoglycemia.

2. Possible Reduction of Obesity and Obesity Related Cardiovascular Risk Factors Obesity is an important factor in syndrome X as well as in the majority (>80%) of type 2 diabetes, and omental fat appears to be of central importance. Abdominal obesity is closely associated with glucose intolerance, hyperinsulinemia, hypertriglyceridemia, and other factors of the so-called syndrome X (e.g. increased blood pressure, decreased levels of HDL and increased levels of VLDL) (Montague & O'Rahilly, Diabetes 49: 883-888, 2000). Inhibition of the 11βHSD1 enzyme in pre-adipocytes (stromal cells) has been shown to decrease the rate of differentiation into adipocytes. This is predicted to result in diminished expansion (possibly reduction) of the omental fat depot, i.e., reduced central obesity (Bujalska, I. J., S. Kumar, and P. M. Stewart (1997) Lancet 349: 1210-1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097-4105). Furthermore, there is a clear correlation between glucocorticoid "activity" and cardiovascular risk factor suggesting that a reduction of the glucocorticoid effects would be beneficial (Walker, B. R. et al. (1998) Hypertension 31: 891-895; Fraser, R. et al. (1999) Hypertension 33: 1364-1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378-1383).

3. Possible Beneficial Effect on the Pancreas

Inhibition of 11βHSD1 in isolated murine pancreatic β-cells improves glucose-stimulated insulin secretion (Davani, B. et al. (2000) J. Biol. Chem. 2000 Nov. 10; 275(45): 34841-4). Glucocorticoids were previously known to reduce pancreatic insulin release in vivo (Billaudel, B. and B. C. J. Sutter (1979) Horm. Metab. Res. 11: 555-560). Thus, inhibition of 11βHSD1 is predicted to yield other beneficial effects for diabetes treatment, besides the effects on liver and fat.

4. Possible Beneficial Effects on Cognition and Dementia

Stress and glucocorticoids influence cognitive function (de Quervain, D. J.-F., B. Roozendaal, and J. L. McGaugh (1998) Nature 394: 787-790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65-70; Seckl, J. R., Front. (2000) Neuroendocrinol. 18: 49-99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99-103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite.

5. Possible Use of Immuno-modulation Using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillièr's Clin. Endocrinol. Metab. 13: 576-581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normaly biased towards a humoral response when in fact the appropriate response would be cell based. Temporal inhibition of 11βHSD1, local or systemic, might be used to push the immune system into the appropriate response (Mason, D. (1991) Immunology Today 12: 57-60; Rook et al., supra).

An analogous use of 11βHSD1 inhibition, in this case temporal, would be to booster the immune response in association with immunization to ensure that a cell based response would be obtained, when desired.

6. Reduction of Intraocular Pressure

Recent data suggest that the levels of the glucocorticoid target receptors and the 11βHSD enzymes determines the susceptibility to glaucoma (Stokes, J. et al. (2000) Invest. Ophthalmol. 41: 1629-1638). Further, inhibition of 11βHSD1 was recently presented as a novel approach to lower the intraocular pressure (Walker E. A. et al, poster P3-698 at the Endocrine society meeting Jun. 12-15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithelialium of the cornea (the site of aqueous production), to ciliary muscle and to the sphincter and dilator muscles of the iris. In contrast, the distant isoenzyme 11βHSD2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., Cheng, S. L. and Kim, G. S. (1999) J. Endocrinol. 162: 371-379). The negative effect on bone nodule formation could be blocked by the non-specific inhibitor carbenoxolone suggesting an important role of 11βHSD1 in the glucocorticoid effect (Bellows, C. G., Ciaccia, A. and Heersche, J. N. M. (1998) Bone 23: 119-125). Other data suggest a role of 11βHSD1 in providing sufficiently high levels of active glucocorticoid in osteoclasts, and thus in augmenting bone resorption (Cooper, M. S. et al. (2000) Bone 27: 375-381). Taken together, these different data suggest that inhibition of 11βHSD1 may have beneficial effects against osteoporosis by more than one mechanism working in parallel.

8. Reduction of Hypertension

Bile acids inhibit 11β-hydroxysteroid dehydrogenase type 2. This results in a shift in the overall body balance in favour of cortisol over cortisone, as shown by studying the ratio of the urinary metabolites (Quattropani, C., Vogt, B., Odermatt, A., Dick, B., Frey, B. M., Frey, F. J. (2001) J Clin Invest. November; 108(9):1299-305. "Reduced activity of 11beta-hydroxysteroid dehydrogenase in patients with cholestasis".). Reducing the activity of 11bHSD1 in the liver by a selective inhibitor is predicted to reverse this imbalance, and acutely counter the symptoms such as hypertension, while awaiting surgical treatment removing the biliary obstruction.

WO 99/65884 discloses carbon substituted aminothiazole inhibitors of cyclin dependent kinases. These compounds may, e.g., be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c]pyridines are disclosed in: Analgesic tetrahydrothiazolo[5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968: 49593 CAPLUS. However, none of the above disclosures discloses the compounds according to the present invention, or their use for the treatment of diabetes, obesity, glaucoma, osteoporosis, cognitive disorders, immune disorders, depression, and hypertension.

WO 98/16520 discloses compounds inhibiting matrix metalloproteinases (MMPs) and TNF-α converting enzyme (TACE). EP 0 749 964 A1 and U.S. Pat. No. 5,962,490 disclose compounds having an endothelin receptor antagonist activity. WO 00/02851 discloses compounds associated with a disturbed cGMP balance. None of these compounds fall within formula (I) according to the present invention. Furthermore, nothing is said about the activity on 11βHSD1.

U.S. Pat. No. 5,783,697 discloses thiophene derivatives as inhibitors of PGE2 and LTB4. Nothing is said about the activity on 11βHSD1.

EP 0 558 258, EP 0 569 193, and EP 1 069 114 disclose isoxazole derivatives as endothelin agonists and antagonists. Nothing is said about the activity on 11βHSD1.

9. Wound Healing

Cortisol performs a broad range of metabolic functions and other functions. The multitude of glucocorticoid action is exemplified in patients with prolonged increase in plasma glucocorticoids, so called "Cushing's syndrome". Patients with Cushing's syndrome have prolonged increase in plasma glucocorticoids and exhibit impaired glucose tolerance, type 2 diabetes, central obesity, and osteoporosis. These patients also have impaired wound healing and brittle skin (Ganong, W. F. Review of Medical Physiology. Eighteenth edition ed. Stamford, Conn.: Appleton & Lange; 1997).

Glucocorticoids have been shown to increase risk of infection and delay healing of open wounds (Anstead, G. M. Steroids, retinoids, and wound healing. Adv Wound Care 1998;11(6):277-85). Patients treated with glucocorticoids have 2-5-fold increased risk of complications when undergoing surgery (Diethelm, A. G. Surgical management of complications of steroid therapy. Ann Surg 1977;185(3):251-63).

The European patent application No. EP 0902288 discloses a method for diagnosing the status of wound healing in a patient, comprising detecting cortisol levels in said wound. The authors suggest that elevated levels of cortisol in wound fluid, relative to normal plasma levels in healthy individuals, correlates with large, non-healing wounds (Hutchinson, T. C., Swaniker, H. P., Wound diagnosis by quantitating cortisol in wound fluids. European patent application No. EP 0 902 288, published 17.03.1999).

In humans, the 11β-HSD catalyzes the conversion of cortisol to cortisone, and vice versa. The parallel function of 11β-HSD in rodents is the interconversion of corticosterone and 11-dehydrocorticosterone (Frey, F. J., Escher, G., Frey, B. M. Pharmacology of 11 beta-hydroxysteroid dehydrogenase. Steroids 1994;59(2):74-9). Two isoenzymes of 11β-HSD, 11β-HSD1 and 11β-HSD2, have been characterized, and differ from each other in function and tissue distribution (Albiston, A. L., Obeyesekere, V. R., Smith, R. E., Krozowski, Z. S. Cloning and tissue distribution of the human 11 beta-hydroxysteroid dehydrogenase type 2 enzyme. Mol Cell Endocrinol 1994;105(2):R11-7). Like GR, 11β-HSD1 is expressed in numerous tissues like liver, adipose tissue, adrenal cortex, gonads, lung, pituitary, brain, eye etc (Monder C, White P C. 11 beta-hydroxysteroid dehydrogenase. Vitam Horm 1993;47:187-271; Stewart, P. M., Krozowski, Z. S. 11 beta-Hydroxysteroid dehydrogenase. Vitam Horm 1999;57:249-324; Stokes, J., Noble, J., Brett, L., Phillips, C., Seckl, J. R., O'Brien, C., et al. Distribution of glucocorticoid and mineralocorticoid receptors and 11beta-hydroxysteroid dehydrogenases in human and rat ocular tissues. Invest Ophthalmol Vis Sci 2000;41(7):1629-38). The function of 11β-HSD1 is to fine-tune local glucocorticoid action. 11β-HSD activity has been shown in the skin of humans and rodents, in human fibroblasts and in rat skin pouch tissue (Hammami, M. M., Siiteri, P. K. Regulation of 11 beta-hydroxysteroid dehydrogenase activity in human skin fibroblasts: enzymatic modulation of glucocorticoid action. J Clin Endocrinol Metab 1991;73(2):326-34); Cooper, M. S., Moore, J., Filer, A., Buckley, C. D., Hewison, M., Stewart, P. M. 11beta-hydroxysteroid dehydrogenase in human fibroblasts: expression and regulation depends on tissue of origin. ENDO 2003 Abstracts 2003; Teelucksingh, S., Mackie, A. D., Burt, D., McIntyre, M. A., Brett, L., Edwards, C. R. Potentiation of hydrocortisone activity in skin by glycyrrhetinic acid. Lancet 1990;335(8697):1060-3; Slight, S. H., Chilakamarri, V. K., Nasr, S., Dhalla, A. K., Ramires, F. J., Sun, Y., et al. Inhibition of tissue repair by spironolactone: role of mineralocorticoids in fibrous tissue formation. Mol Cell Biochem 1998;189(1-2):47-54).

Wound healing consists of serial events including inflammation, fibroblast proliferation, secretion of ground substances, collagen production, angiogenesis, wound contraction and epithelialization. It can be divided in three phases; inflammatory, proliferative and remodeling phase (reviewed in Anstead et al., supra).

In surgical patients, treatment with glucocorticoids increases risk of wound infection and delay healing of open wounds. It has been shown in animal models that restraint stress slows down cutaneous wound healing and increases susceptibility to bacterial infection during wound healing. These effects were reversed by treatment with the glucocorticoid receptor antagonist RU486 (Mercado, A. M., Quan, N., Padgett, D. A., Sheridan, J. F., Marucha, P. T. Restraint stress alters the expression of interleukin-1 and keratinocyte growth factor at the wound site: an in situ hybridization study. J Neuroimmunol 2002;129(1-2):74-83; Rojas, I. G., Padgett, D. A., Sheridan, J. F., Marucha, P. T. Stress-induced susceptibility to bacterial infection during cutaneous wound healing. Brain Behav Immun 2002;16(1):74-84). Glucocorticoids produce these effects by suppressing inflammation, decrease wound strength, inhibit wound contracture and delay epithelialization (Anstead et al., supra). Glucocorticoids influence wound healing by interfering with production or action of cytokines and growth factors like IGF, TGF-β, EGF, KGF and PDGF (Beer, H. D., Fassler, R., Werner, S. Glucocorticoid-regulated gene expression during cutaneous wound repair. Vitam Horm 2000;59:217-39; Hamon, G. A., Hunt, T. K., Spencer, E. M. In vivo effects of systemic insulin-like growth factor-I alone and complexed with insulin-like growth factor binding protein-3 on corticosteroid suppressed wounds. Growth Regul 1993;3(1):53-6; Laato, M., Heino, J., Kahari, V. M., Niinikoski, J., Gerdin, B. Epidermal growth factor (EGF) prevents methylprednisolone-induced inhibition of wound healing. J Surg Res 1989; 47(4):354-9; Pierce, G. F., Mustoe, T. A., Lingelbach, J., Masakowski, V. R., Gramates, P., Deuel, T. F. Transforming growth factor beta reverses the glucocorticoid-induced wound-healing deficit in rats: possible regulation in macrophages by platelet-derived growth factor. Proc Natl Acad Sci USA 1989;86(7):2229-33). It has also been shown that glucocorticoids decrease collagen synthesis in rat and mouse skin in vivo and in rat and human fibroblasts (Oishi, Y., Fu, Z. W., Ohnuki, Y., Kato, H., Noguchi, T. Molecular basis of the alteration in skin collagen metabolism in response to in vivo dexamethasone treatment: effects on the synthesis of collagen type I and III, collagenase, and tissue inhibitors of metalloproteinases. Br J Dermatol 2002;147(5):859-68).

WO 01/90090 discloses thiazole compounds, which compounds inhibit the human 11β-HSD1, and may be useful for treating disorders such as diabetes, obesity, glaucoma, osteoporosis, cognitive disorders and immune disorders. Other 11β-HSD1 inhibitors are disclosed in e.g. WO 01/90091; WO 01/90092; WO 01/90093; WO 01/90094; WO 03/043999; WO 03/044000; WO 03/044009; U.S. Patent Publication No. 2005/009821; WO 04/103980; WO 04/112784; WO 04/112781; WO 04/112785; WO 04/112783; WO 04/112782; WO 04/113310; WO 04/112779; and Swedish patent application No. SE 0400227-5, filed on Feb. 4, 2004. However, the use of the 11β-HSD1 inhibitors according to the present invention for diabetes, obesity, glaucoma, osteoporosis, cognitive disorders, immune disorders, and wound healing has not previously been disclosed.

Although not disclosed as 11-β-HSD1 inhibitors, Okawara et al. disclose the preparation of thiazole-5-spiropropan-4(5H)-ones, see J. Chem. Soc. Perkin Trans. I, 1733-1735 (1986).

SUMMARY OF THE INVENTION

The compounds according to the present invention solves the above problems and embraces a novel class of compounds which has been developed and which inhibit the human 11-β-hydroxysteroid dehydrogenase type 1 enzyme (11-β-HSD1), and may therefore be of use in treating disorders related to 11-β-HSD1 activity, such as, but not limited to diabetes, obesity, glaucoma, osteoporosis, cognitive disorders, immune disorders, hypertension, and wound healing.

One object of the present invention is a compound of the general formula (I)

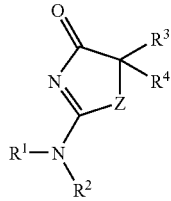

wherein
either
(a) Z is sulfur, $R^1$ is hydrogen, $R^2$ is selected from hydrogen; $C_{3-10}$-cycloalkyl optionally independently substituted by one or more of $C_{1-8}$-alkyl and aryl; $C_{3-10}$-cycloalkyl-$C_{1-8}$-alkyl; aryl; aryl-$C_{1-8}$-alkyl; heterocyclyl; heterocyclyl-$C_{1-8}$-alkyl; wherein any aryl or heterocyclyl residue is optionally independently substituted by one or more $C_{1-8}$-alkyl and halogen; or $R^1$ and $R^2$ form together with the nitrogen atom bonded thereto a monocyclic heterocyclyl optionally independently substituted by one or more of aryl-$C_{1-8}$-alkyl, $C_{1-8}$-alkyl and halogen; $R^3$ and $R^4$ are each independently selected from hydrogen; $C_{1-8}$-alkyl; $C_{3-10}$-cycloalkyl-$C_{1-8}$-alkyl; cyano-$C_{1-8}$-alkyl; aryl; aryl-$C_{1-8}$-alkyl; heterocyclyl-$C_{1-8}$-alkyl; heteroaryl-$C_{1-8}$-alkyl; or $R^3$ and $R^4$ form together with the carbon atom bonded thereto $C_{3-10}$-cycloalkyl, wherein any aryl residue is optionally independently substituted by one or more of hydroxy; or (b) Z is oxygen, $R^1$ is hydrogen, $R^2$ is selected from hydrogen; $C_{5-10}$-cycloalkyl optionally independently substituted by one or more of $C_{1-8}$-alkyl and aryl; $C_{3-10}$-cycloalkyl-$C_{1-8}$-alkyl; aryl, but not an unsubstituted phenyl group; aryl-$C_{1-8}$-alkyl; heterocyclyl; heterocyclyl-$C_{3-8}$-alkyl; wherein any aryl or heterocyclyl residue is optionally independently substituted by one or more of $C_{1-8}$-alkyl and halogen; $R^3$ and $R^4$ are each independently selected from hydrogen; $C_{1-8}$-alkyl; $C_{3-10}$-cycloalkyl-$C_{1-8}$-alkyl; cyano-$C_{1-8}$-alkyl; aryl, but not an unsubstituted phenyl group; aryl-$C_{1-8}$-alkyl; heterocyclyl-$C_{1-8}$-alkyl; heteroaryl-$C_{1-8}$-alkyl; or $R^3$ and $R^4$ form together with the carbon atom bonded thereto $C_{3-10}$-cycloalkyl, wherein any aryl residue is optionally independently substituted by one or more of hydroxy; and pharmaceutically acceptable salts, solvates, hydrates, geometrical isomers, tautomers, optical isomers, N-oxides and prodrug forms thereof; with the proviso that:
when $R^1$ is hydrogen and
Z is sulfur and $R^3=R^4=$methyl, then $R^2$ is not phenyl;
Z is sulfur and $R^3=R^4=$methyl, then $R^2$ is not 4-iodophenyl;
Z is sulfur and $R^3=R^4=$phenyl, then $R^2$ is not phenyl;
Z is sulfur, $R^3=$ethyl and $R^4=$H, then $R^2$ is not 3-methylphenyl;
Z is oxygen and $R^3=$H, then $R^4$ is not methyl.

It is preferred that:
$R^1$ and $R^2$ are each independently selected from hydrogen, cyclohexyl, cycloheptyl, cyclooctyl, 2,2,3,3-tetramethylcyclopropyl, 1-(4-chlorophenyl)cyclobutyl, bicyclo[2.2.1]hept-2-yl, tricyclo[3.3.1.0~3,7~]non-3-yl, cyclohexylmethyl, phenyl, 2-methylphenyl, 3-methylphenyl, 2-isopropylphenyl, 2-fluorophenyl, 2-chlorophenyl, 2-phenylpropyl, 2-chlorobenzyl, 4-chlorobenzyl, 4-(2,2,6,6-tetramethyl)piperidyl, 2-morpholinyl-4-ylethyl, or $R^1$ and $R^2$ form together with the nitrogen atom bonded thereto morpholinyl, azocane, or 4-benzylpiperidyl;

$R^3$ and $R^4$ are each independently selected from hydrogen, methyl, ethyl, isopropyl, isobutyl, tert-butyl, cyclohexylmethyl, cyanomethyl, phenyl, 2-hydroxyphenyl, benzyl, 2-hydroxybenzyl, 4-hydroxybenzyl, 3,4-dihydroxybenzyl, 1H-imidazol-4-ylmethyl, indol-3-ylmethyl, 3-pyridylmethyl, or $R^3$ and $R^4$ form together with the carbon atom bonded thereto cyclopropyl, cyclobutyl, cyclopentyl, cyclohexyl;

provided that when Z is oxygen, then neither of $R^2$, $R^3$, and $R^4$ is phenyl.

In a preferred embodiment of the present invention, when Z is sulfur and both $R^3$ and $R^4$ are methyl or both $R^3$ and $R^4$ are phenyl, then $R^2$ as an aryl group is selected from 2-methylphenyl, 3-methylphenyl, 2-isopropylphenyl, 2-fluorophenyl, and 2-chlorophenyl. When Z is sulfur, $R^3$ is ethyl and $R^4$ is hydrogen, then $R^2$ as an aryl group is selected from 2-methylphenyl, 2-isopropylphenyl, 2-fluorophenyl, and 2-chlorophenyl.

In a preferred embodiment of the present invention, when Z is oxygen, each of $R^2$, $R^3$, and $R^4$ as an aryl group is selected from 2-methylphenyl, 3-methylphenyl, 2-isopropylphenyl, 2-fluorophenyl, and 2-chlorophenyl. When Z is oxygen and $R^3$ is hydrogen, then $R^4$ as a $C_{1-8}$-alkyl group is selected from $C_{2-8}$-alkyl.

Preferred compounds are Examples 1-38, 40-66, 68, and 73-79.

Another object of the present invention is a process for the preparation of a compound above comprising at least one of the following steps:

a) reaction of an isothiocyanate with ammonia to give a thiourea, b) reaction of an amine with ethoxycarbonylisothiocyanate to give a thiourea, c) reaction of a thiourea with an α-bromocarboxylic acid to give a thiazolone, d) reaction of a thiourea with an α-bromocarboxylic ester to give a thiazolone, e) reaction of an amino acid to give an α-bromocarboxylic acid, f) reaction of a thiourea with 3-bromo-2-coumarone, g) reaction of a guanidine with an α-hydroxy ester to give a primary amino-oxazolone, h) reaction of a primary amino-oxazolone and an amine to give a secondary or a tertiary amino-oxazolone, i) reaction of a thiourea and an α-bromocarboxylic acid chloride to give a thiazolone, and j) reaction of a carboxylic acid with thionyl chloride and N-bromosuccinimide to give an α-bromocarboxylic ester.

An additional embodiment is directed to a compound of the general formula (II):

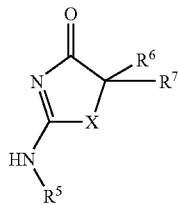

(II)

wherein:

X is S or O;

$R^5$ is selected from hydrogen, $C_1$-$C_8$ alkyl, $C_{3-10}$-cycloalkyl, $C_{3-10}$-cycloalkyl-$C_{1-8}$-alkyl, aryl, aryl-$C_{1-8}$-alkyl, heterocyclyl, heterocyclyl-$C_{1-8}$-alkyl and haloalkyl;

wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^8R^9N$—$C_1$-$C_8$-alkyl, $C_1$-$C_8$-alkyl-$OR^{10}$, —$OR^{10}$, ($C_3$-$C_{10}$)-cycloalkyl or $C_1$-$C_8$-alkyl-sulfonyl;

$R^6$ is selected from $C_{1-8}$-alkyl, $C_{1-8}$-alkoxy, $C_{3-10}$-cycloalkyl, heterocyclyl, $C_{3-10}$-cycloalkyl-$C_{1-8}$-alkyl, CN—$C_{1-8}$-alkyl, aryl, aryl-$C_{1-8}$-alkyl, heterocyclyl-$C_{1-8}$-alkyl and haloalkyl;

$R^7$ is selected from —$NR^8R^9$, halo, $C_{1-8}$-alkyl, —$(CR^8R^9)_n$—$OR^8$, —S—$C_1$-$C_8$alkyl, $C_{3-10}$-cycloalkyl, heterocyclyl, $C_{3-10}$-cycloalkyl-$C_{1-8}$-alkyl, cyano-$C_{1-8}$-alkyl, aryl, aryl-$C_{1-8}$-alkyl, heterocyclyl-$C_{1-8}$-alkyl, heterocyclyl-C(O)—$C_{1-8}$-alkyl, heterocyclyl-$SO_2$—$C_{1-8}$-alkyl, $C_{1-8}$-haloalkyl, $R^8R^9N$—$C_{1-8}$-alkyl, HO—$C_{1-8}$-alkyl, —C(O)—$C_3$-$C_{10}$-cycloalkyl, —C(O)—$C_1$-$C_8$-haloalkyl, —$(CR^8R^9)_n$—Y—$(CR^8R^9)_n$-heterocyclyl and —$(CR^8R^9)_n$—Y—$(CR^8R^9)_n$—C(O)—$R^8$ (wherein n is 0-5, Y is $NR^{10}$, O or S);

wherein any aryl, alkyl, heterocyclyl or cycloalkyl residue is optionally substituted by one or more of —$C_1$-$C_8$-alkyl,
-halo,
—OH,
—$OR^{10}$,
$C_1$-$C_8$-alkyl-$SO_2$—,
—$SO_2$-aryl,
—C(O)—$(CR^8R^9)_n$-carbamate,
—C(O)—O—$C_1$-$C_8$-alkyl,
—C(O)—$C_1$-$C_8$-alkyl,
—C(O)—$(CR^8R^9)_n$—C(O)—$NR^8R^9$,
—C(O)—$(CR^8R^9)_n$—$NR^8$—C(O)—$C_1$-$C_8$-alkyl
—C(O)—$(CR^8R^9)_n$—$NR^8R^9$,
—C(O)—$C_3$-$C_{10}$-cycloalkyl,
—C(O)-aryl,
—C(O)—$(CR^8R^9)_n$-heterocyclyl,
—$C_1$-$C_8$ alkyl-$OR^8$,
—C(O)-halo-$C_1$-$C_8$-alkyl or
—C(O)—$(CR^8R^9)_n$-aryl, wherein any aryl, alkyl, cycloalkyl, or heterocyclyl residue is optionally independently substituted by one or more $C_{1-8}$-alkyl, aryl, halogen, —$NR^{10}R^{10}$, $C_1$-$C_8$-haloalkyl, HO—$C_1$-$C_8$-alkyl, $R^8R^9N$—$C_1$-$C_8$-alkyl, $C_1$-$C_8$-alkyl-$OR^{10}$, —$OR^{10}$, ($C_3$-$C_{10}$)-cycloalkyl or $C_1$-$C_8$-alkyl-sulfonyl, —O—$(CR^8R^9)_n$-heterocyclyl, —O—$(CR^8R^9)_n$—C(O)—$NR^8R^9$, —O—$(CR^8R^9)_n$—$NR^8R^9$, —Y—$(CR^8R^9)_n$—$NR^8$—C(O)—$C_1$-$C_8$-alkyl, —Y—$(CR^8R^9)_n$-heterocyclyl, —O—$(CR^8R^9)_n$—$NR^8R^9$, $C_1$-$C_8$-alkyl-$SO_2$, or —O—$(CR^8R^9)_n$—N—C(O)-heterocyclyl;

wherein $R^8$ and $R^9$ are each independently selected from hydrogen, $C_1$-$C_8$ alkyl, $C_1$-$C_8$ alkoxy, —$NR^{10}R^{10}$, —S—($C_1$-$C_8$)alkyl, aryl and heterocyclyl;

any alkyl, alkoxy, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl;

wherein $R^{10}$ is independently selected from hydrogen, $C_1$-$C_8$ alkyl, aryl-$C_1$-$C_8$ alkyl, $C_1$-$C_8$ alkoxy, —S—($C_1$-$C_8$) alkyl, heterocyclyl and aryl;

any alkyl, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl;

or $R^6$ and $R^7$ form, together with the carbon atom bonded thereto, a saturated, partially unsaturated or unsaturated $C_{3-10}$-cycloalkyl or a saturated, partially unsaturated or unsaturated $C_4$-$C_{14}$ heterocyclyl;

wherein the cycloalkyl or the heterocyclyl may be optionally substituted by one or more of $C_1$-$C_8$-alkyl, aryl, $C_1$-$C_8$-haloalkyl, aryl-$C_1$-$C_8$-alkyl, $C_3$-$C_{10}$-cycloalkyl, —$OR^8$, =O, =$NR^8$, =N—$OR^8$, —$NR^8R^9$, —$SR^8$, -halo, —OC(O)$R^8$, —C(O)$R^8$, —$CO_2R^8$, —$CONR^8R^9$, —OC(O)$NR^8R^9$, —$NR^9C(O)R^8$, —$NR^8C(O)NR^8R^9$, —$NR^8SO_2NR^8R^9$, —$NR^8CO_2R^9$, —NHC($NH_2$)=NH, —$NR^8C(NH_2)$=NH, —NHC($NH_2$)=$NR^8$, —S(O)$R^8$, —$SO_2R^8$, —$SO_2NR^8R^9$, —$NR^8SO_2R^9$, —CN and —$NO_2$;

and pharmaceutically acceptable salts, solvates, hydrates, geometrical isomers, tautomers, optical isomers, N-oxides and prodrug forms thereof, with the proviso that:

when

X is S, $R^6$=$R^7$=methyl, then $R^5$ is not phenyl or 4-iodophenyl,

X is S, $R^6$=$R^7$=phenyl, then $R^5$ is not phenyl, and
X is S, R⁶ and R⁷ combine to form a cyclopropyl ring, then R⁵ is not n-butyl, cyclohexyl, benzyl, phenyl or naphthyl.

In another embodiment is a compound of the general formula (III):

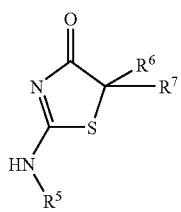

(III)

wherein:

R⁵ is selected from hydrogen, $C_1$-$C_8$ alkyl, $C_{3-10}$-cycloalkyl, $C_{3-10}$-cycloalkyl-$C_{1-8}$-alkyl, aryl, aryl-$C_{1-8}$-alkyl, heterocyclyl, heterocyclyl-$C_{1-8}$-alkyl and haloalkyl;

wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^8R^9N$—$C_1$-$C_8$-alkyl, $C_1$-$C_8$-alkyl-$OR^{10}$, —$OR^{10}$, $(C_3$-$C_{10})$-cycloalkyl or $C_1$-$C_8$-alkyl-sulfonyl;

R⁶ is selected from $C_{1-8}$-alkyl, $C_{1-8}$-alkoxy, $C_{3-10}$-cycloalkyl, heterocyclyl, $C_{3-10}$-cycloalkyl-$C_{1-8}$-alkyl, CN—$C_{1-8}$-alkyl, aryl, aryl-$C_{1-8}$-alkyl, heterocyclyl-$C_{1-8}$-alkyl and haloalkyl;

R⁷ is selected from —$NR^8R^9$, halo, $C_{1-8}$-alkyl, —$(CR^8R^9)_n$—$OR^8$, —S—$C_1$-$C_8$-alkyl, $C_{3-10}$-cycloalkyl, heterocyclyl, $C_3$—O-cycloalkyl-$C_{1-8}$-alkyl, cyano-$C_{1-8}$-alkyl, aryl, aryl-$C_{1-8}$-alkyl, heterocyclyl-$C_{1-8}$-alkyl, heterocyclyl-C(O)—$C_{1-8}$-alkyl, heterocyclyl-$SO_2$—$C_{1-8}$-alkyl, $C_{1-8}$-haloalkyl, $R^8R^9N$—$C_{1-8}$-alkyl, HO—$C_{1-8}$-alkyl, —C(O)—$C_3$-$C_{10}$-cycloalkyl, —C(O)—$C_1$-$C_8$-haloalkyl, —$(CR^8R^9)_n$—Y—$(CR^8R^9)_n$-heterocyclyl and —$(CR^8R^9)_n$—Y—$(CR^8R^9)_n$—C(O)—$R^8$ (wherein n is 0-5, Y is $NR^{10}$, O or S);

wherein any aryl, alkyl, heterocyclyl or cycloalkyl residue is optionally substituted by one or more of
—$C_1$-$C_8$-alkyl,
-halo,
—OH,
—$OR^{10}$,
$C_1$-$C_8$-alkyl-$SO_2$—,
—$SO_2$-aryl,
—C(O)—$(CR^8R^9)_n$-carbamate,
—C(O)—O—$C_1$-$C_8$-alkyl,
—C(O)—$C_1$-$C_8$-alkyl,
—C(O)—$(CR^8R^9)_n$—C(O)_n—$NR^8R^9$,
—C(O)—$(CR^8R^9)_n$—$NR^8$—C(O)—$C_1$-$C_8$-alkyl
—C(O)—$(CR^8R^9)_n$—$NR^8R^9$,
—C(O)—$C_3$-$C_{10}$-cycloalkyl,
—C(O)-aryl,
—C(O)—$(CR^8R^9)_n$-heterocyclyl,
—$C_1$-$C_8$ alkyl-$OR^8$,
—C(O)-halo-$C_1$-$C_8$-alkyl or
—C(O)—$(CR^8R^9)_n$-aryl, wherein any aryl, alkyl, cycloalkyl, or heterocyclyl residue is optionally independently substituted by one or more $C_{1-8}$-alkyl, aryl, halogen, —$NR^{10}R^{10}$, $C_1$-$C_8$-haloalkyl, HO—$C_1$-$C_8$-alkyl, $R^8R^9N$—$C_1$-$C_8$-alkyl, $C_1$-$C_8$-alkyl-$OR^{10}$, —$OR^{10}$, $(C_3$-$C_{10})$-cycloalkyl or $C_1$-$C_8$-alkyl-sulfonyl, —O—$(CR^8R^9)_n$-heterocyclyl, —O—$(CR^8R^9)_n$—C(O)—$NR^8R^9$, —O—$(CR^8R^9)_n$—$NR^8R^9$, —Y—$(CR^8R^9)_n$—$NR^8$—C(O)_n—$C_1$-$C_8$-alkyl, —Y—$(CR^8R^9)_n$-heterocyclyl, —O—$(CR^8R^9)_n$—$NR^8R^9$, $C_1$-$C_8$-alkyl-$SO_2$, or —O—$(CR^8R^9)_n$—N—C(O)-heterocyclyl;

wherein R⁸ and R⁹ are each independently selected from hydrogen, $C_1$-$C_8$ alkyl, $C_1$-$C_8$ alkoxy, —$NR^{10}R^{10}$, —S—$(C_1$-$C_8)$alkyl, aryl and heterocyclyl;

any alkyl, alkoxy, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl;

wherein $R^{10}$ is independently selected from hydrogen, $C_1$-$C_8$ alkyl, aryl-$C_1$-$C_8$ alkyl, $C_1$-$C_8$ alkoxy, —S—$(C_1$-$C_8)$ alkyl, heterocyclyl and aryl;

any alkyl, heterocyclyl or aryl may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl;

or R⁶ and R⁷ form, together with the carbon atom bonded thereto, a saturated, partially unsaturated or unsaturated $C_{3-10}$-cycloalkyl or a saturated, partially unsaturated or unsaturated $C_4$-$C_{14}$ heterocyclyl;

wherein the cycloalkyl or the heterocyclyl may be optionally substituted by one or more of $C_1$-$C_8$-alkyl, aryl, $C_1$-$C_8$-haloalkyl, aryl-$C_1$-$C_8$-alkyl, $C_3$-$C_{10}$-cycloalkyl, —$OR^8$, =O, =$NR^8$, =N—$OR^8$, —$NR^8R^9$, —$SR^8$, -halo, —OC(O)$R^8$, —C(O)$R^8$, —$CO_2R^8$, $CONR^8R^9$, —OC(O)$NR^8R^9$, —$NR^9C(O)R^5$, —$NR^8C(O)NR^8R^9$, —$NR^8SO_2NR^8R^9$, —$NR^8CO_2R^9$, —$NHC(NH_2)$=NH, —$NR^8C(NH_2)$=NH, —$NHC(NH_2)$=$NR^8$, —S(O)$R^8$, —$SO_2R^8$, —$SO_2NR^8R^9$, —$NR^8SO_2R^9$, —CN and —$NO_2$;

and pharmaceutically acceptable salts, solvates, hydrates, geometrical isomers, tautomers, optical isomers, N-oxides and prodrug forms thereof, with the proviso that:

when

R⁶=R⁷=methyl, then R⁵ is not phenyl or 4-iodophenyl,

R⁶=R⁷=phenyl, then R⁵ is not phenyl, and

R⁶ and R⁷ combine to form a cyclopropyl ring, then R⁵ is not n-butyl, cyclohexyl, benzyl, phenyl or naphthyl.

In another embodiment is a compound of the general formula (IV):

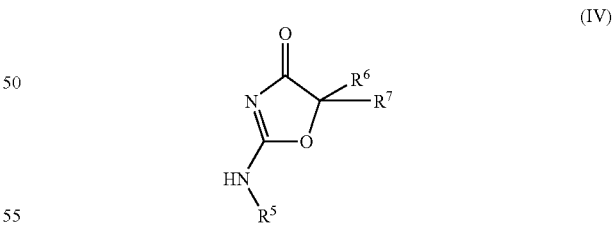

(IV)

wherein:

R⁵ is selected from hydrogen, $C_1$-$C_8$ alkyl, $C_{3-10}$-cycloalkyl, $C_{3-10}$-cycloalkyl-$C_{1-8}$-alkyl, aryl, aryl-$C_{1-8}$-alkyl, heterocyclyl, heterocyclyl-$C_{1-8}$-alkyl and haloalkyl;

wherein any aryl, cycloalkyl, or heterocyclyl residue is optionally independently substituted by one or more $C_{1-8}$-alkyl, aryl, halogen, halo-$C_1$-$C_8$-alkyl, HO—$C_1$-$C_8$-alkyl, $R^8R^9N$—$C_1$-$C_8$-alkyl, $C_1$-$C_8$-alkyl-$OR^{10}$, —$OR^{10}$, $(C_3$-$C_{10})$-cycloalkyl or $C_1$-$C_8$-alkyl-sulfonyl;

R$^6$ is selected from C$_{1-8}$-alkyl, C$_{1-8}$-alkoxy, C$_{3-10}$-cycloalkyl, heterocyclyl, C$_{3-10}$-cycloalkyl-C$_{1-8}$-alkyl, CN—C$_{1-8}$-alkyl, aryl, aryl-C$_{1-8}$-alkyl, heterocyclyl-C$_{1-8}$-alkyl and haloalkyl;

R$^7$ is selected from —NR$^3$R$^9$, halo, C$_{1-8}$-alkyl, —(CR$^8$R$^9$)$_n$—OR$^8$, —S—C$_1$C$_8$-alkyl, C$_{3-10}$-cycloalkyl, heterocyclyl, C$_{3-10}$-cycloalkyl-C$_{1-8}$-alkyl, cyano-C$_{1-8}$-alkyl, aryl, aryl-C$_{1-8}$-alkyl, heterocyclyl-C$_{1-8}$-alkyl, heterocyclyl-C(O)—C$_{1-8}$-alkyl, heterocyclyl-SO$_2$—C$_{1-8}$-alkyl, C$_{1-8}$-haloalkyl, R$^8$R$^9$N—C$_{1-8}$-alkyl, HO—C$_{1-8}$-alkyl, —C(O)—C$_3$-C$_{10}$-cycloalkyl, —C(O)—C$_1$-C$_8$-haloalkyl, —(CR$^8$R$^9$)$_n$—Y—(CR$^8$R$^9$)$_n$-heterocyclyl and —(CR$^8$R$^9$)$_n$—Y—(CR$^8$R$^9$)$_n$—C(O)—R$^8$ (wherein n is 0-5, Y is NR$^{10}$, O or S);

wherein any aryl, alkyl, heterocyclyl or cycloalkyl residue is optionally substituted by one or more of —C$_1$-C$_8$-alkyl,
-halo,
—OH,
—OR$^{10}$,
C$_1$-C$_8$-alkyl-SO$_2$—,
—SO$_2$-aryl,
—C(O)—(CR$^8$R$^9$)$_n$-carbamate,
—C(O)—O—C$_1$-C$_8$-alkyl,
—C(O)—C$_1$-C$_8$-alkyl,
—C(O)—(CR$^8$R$^9$)$_n$—C(O)—NR$^8$R$^9$,
—C(O)—(CR$^8$R$^9$)$_n$—NR$^8$—C(O)—C$_1$-C$_8$-alkyl
—C(O)—(CR$^8$R$^9$)$_n$—NR$^8$R$^9$,
—C(O)—C$_3$-C$_{10}$-cycloalkyl,
—C(O)-aryl,
—C(O)—(CR$^8$R$^9$)$_n$-heterocyclyl,
—C$_1$-C$_8$ alkyl-OR$^8$,
—C(O)-halo-C$_1$-C$_8$-alkyl or
—C(O)—(CR$^8$R$^9$)$_n$-aryl, wherein any aryl, alkyl, cycloalkyl, or heterocyclyl residue is optionally independently substituted by one or more C$_{1-8}$-alkyl, aryl, halogen, —NR$^{10}$R$^{10}$, C$_1$-C$_8$-haloalkyl, HO—C$_1$-C$_8$-alkyl, R$^8$R$^9$N—C$_1$-C$_8$-alkyl, C$_1$-C$_8$-alkyl-OR$^{10}$, —OR$^{10}$, (C$_3$-C$_{10}$)-cycloalkyl or C$_1$-C$_8$-alkyl-sulfonyl, —O—(CR$^8$R$^9$)$_n$-heterocyclyl, —O—(CR$^8$R$^9$)$_n$—C(O)—NR$^8$R$^9$, —O—(CR$^8$R$^9$)$_n$—NR$^8$R$^9$, —Y—(CR$^8$R$^9$)$_n$—NR$^8$—C(O)—C$_1$--C$_8$-alkyl, —Y—(CR$^8$R$^9$)$_n$-heterocyclyl, —O—(CR$^8$R$^9$)$_n$—NR$^8$R$^9$, C$_1$-C$_8$-alkyl-SO$_2$, or —O—(CR$^8$R$^9$)$_n$—N—C(O)-heterocyclyl;

wherein R$^8$ and R$^9$ are each independently selected from hydrogen, C$_1$-C$_8$ alkyl, C$_1$-C$_8$ alkoxy, —NR$^{10}$R$^{10}$, —S—(C$_1$-C$_8$)alkyl, aryl and heterocyclyl;

any alkyl, alkoxy, heterocyclyl or aryl may be substituted with one to three substituents selected from -halo, unsubstituted C$_1$-C$_8$ alkyl, unsubstituted C$_1$-C$_8$ alkoxy, unsubstituted C$_1$-C$_8$ thioalkoxy and unsubstituted aryl(C$_1$-C$_4$)alkyl;

wherein R$^{10}$ is independently selected from hydrogen, C$_1$-C$_8$ alkyl, aryl-C$_1$-C$_8$ alkyl, C$_1$-C$_8$ alkoxy, —S—(C$_1$-C$_8$) alkyl, heterocyclyl and aryl;

any alkyl, heterocyclyl or aryl may be substituted with one to three substituents selected from -halo, unsubstituted C$_1$-C$_8$ alkyl, unsubstituted C$_1$-C$_8$ alkoxy, unsubstituted C$_1$-C$_8$ thioalkoxy and unsubstituted aryl(C$_1$-C$_4$)alkyl;

or R$^6$ and R$^7$ form, together with the carbon atom bonded thereto, a saturated, partially unsaturated or unsaturated C$_{3-10}$-cycloalkyl or a saturated, partially unsaturated or unsaturated C$_{4-14}$ heterocyclyl;

wherein the cycloalkyl or the heterocyclyl may be optionally substituted by one or more of C$_1$-C$_8$-alkyl, aryl, C$_1$-C$_8$-haloalkyl, aryl-C$_1$-C$_8$-alkyl, C$_3$-C$_{10}$-cycloalkyl, —OR$^8$, =O, =NR$^8$, =N—OR$^8$, —NR$^8$R$^9$, —SR$^8$, -halo, —OC(O)R$^8$, —C(O)R$^8$, —CO$_2$R$^8$, CONR$^8$R$^9$, —OC(O)NR$^8$R$^9$, —NR$^9$C(O)R$^8$, —NR$^8$C(O)NR$^8$R$^9$, —NR$^8$SO$_2$NR$^8$R$^9$, —NR$^8$CO$_2$R$^9$, —NHC(NH$_2$)=NH, —NR$^8$C(NH$_2$)=NH, —NHC(NH$_2$)=NR$^8$, —S(O)R$^8$, —SO$_2$R$^8$, —SO$_2$NR$^8$R$^9$, —NR$^8$SO$_2$R$^9$, —CN and —NO$_2$;

and pharmaceutically acceptable salts, solvates, hydrates, geometrical isomers, tautomers, optical isomers, N-oxides and prodrug forms thereof.

One embodiment relates to compounds of Formula (I), (II), (III) or (IV) wherein:

R$^5$ is selected from cyclohexyl, cycloheptyl, cyclooctyl, 2,2,3,3-tetramethylcyclopropyl, 1-(4-chlorophenyl)cyclobutyl, bicyclo[2.2.1]hept-2-yl, tricyclo[3.3.1.0~3,7~]non-3-yl, cyclohexylmethyl, phenyl, 2-methylphenyl, 3-methylphenyl, 2-isopropylphenyl, 2-fluorophenyl, 2-chlorophenyl, 2-phenylpropyl, 2-chlorobenzyl, 4-chlorobenzyl, 4-(2,2,6,6-tetramethyl)piperidyl, 2-morpholinyl-4-ylethyl and tetrahydropyran-4-yl-methyl; and R$^6$ and R$^7$ are each independently selected from methyl, ethyl, isopropyl, isobutyl, tert-butyl, cyclohexylmethyl, cyanomethyl, phenyl, 2-hydroxyphenyl, benzyl, 2-hydroxybenzyl, 4-hydroxybenzyl, 3,4-dihydroxybenzyl, 1H-imidazol-4-ylmethyl, indol-3-ylmethyl, 3-pyridylmethyl;

or R$^6$ and R$^7$ form together with the carbon atom bonded thereto cyclopropyl, cyclobutyl, cyclopentyl, cyclohexyl.

Another embodiment relates to compounds of Formula (I), (II), (III) or (IV) wherein: R$^6$ is methyl and R$^7$ is isopropyl.

Another embodiment relates to compounds of Formula (I), (II), (III) or (IV) wherein: R$^5$ is selected from optionally substituted C$_1$-C$_8$ alkyl, optionally substituted C$_3$-C$_{10}$ cycloalkyl and optionally substituted aryl.

Another embodiment relates to compounds of Formula (I), (II), (III) or (IV) wherein: R$^5$ is C$_3$-C$_8$ alkyl.

Another embodiment relates to compounds of Formula (I), (II), (III) or (IV) wherein: R$^5$ is optionally substituted phenyl-(CR$^{10a}$R$^{10a}$)$_{1-3}$—; and wherein R$^{10a}$ is independently selected from H, methyl, fluoro or R$^{10a}$ and R$^{10a}$ may combine together to form a C$_3$-C$_6$-cycloalkyl ring.

Another embodiment relates to compounds of Formula (I), (II), (III) or (IV) wherein: R$^5$ is (optionally substituted phenyl)-(C(CH$_3$)$_2$)— (optionally substituted phenyl)-(CHCH$_3$) or benzyl.

Another embodiment relates to compounds of Formula (I), (II), (III) or (IV) wherein: R$^5$ is C$_3$-C$_{10}$ cycloalkyl.

Another embodiment relates to compounds of Formula (I), (II), (III) or (IV) wherein: R$^5$ is selected from cyclohexyl, norbornyl and adamantyl.

Another embodiment relates to compounds of Formula (I), (II), (III) or (IV) wherein: R$^5$ is norbornyl.

Another embodiment relates to compounds of Formula (I), (II), (III) or (IV) wherein: R$^5$ is aryl.

Another embodiment relates to compounds of Formula (I), (II), (III) or (IV) wherein: R$^5$ is selected from optionally substituted phenyl.

Another embodiment relates to compounds of Formula (I), (II), (III) or (IV) wherein: R$^6$ is selected from C$_1$-C$_8$ alkyl, C$_3$-C$_{10}$ cycloalkyl, saturated or partially unsaturated heterocyclyl, heteroaryl and aryl.

Another embodiment relates to compounds of Formula (I), (II), (III) or (IV), wherein: R$^6$ is C$_1$-C$_8$ alkyl. Preferably, the alkyl is selected from methyl, ethyl, n-propyl and iso-propyl.

Another embodiment relates to compounds of Formula (I), (II), (III) or (IV) wherein: R$^6$ is C$_3$-C$_{10}$ cycloalkyl.

Another embodiment relates to compounds of Formula (I), (II), (III) or (IV) wherein: R$^6$ is selected from cyclohexyl, norbornyl and adamantyl.

Another embodiment relates to compounds of Formula (I), (II), (III) or (IV) wherein: $R^6$ is saturated or partially unsaturated 5 or 6-membered heterocyclyl.

Another embodiment relates to compounds of Formula (I), (II), (III) or (IV) wherein: $R^6$ is selected from tetrahydrofuryl, piperidinyl and tetrahydropyranyl.

Another embodiment relates to compounds of Formula (I), (II), (III) or (IV) wherein: $R^6$ is a 5 or 6 membered heteroaryl ring.

Another embodiment relates to compounds of Formula (I), (II), (III) or (IV) wherein: $R^6$ is selected from pyridyl, furyl and pyrrolyl.

Another embodiment relates to compounds of Formula (I), (II), (III) or (IV) wherein: $R^6$ is $C_6$-$C_{10}$ aryl.

Another embodiment relates to compounds of Formula (I), (II), (III) or (IV) wherein: $R^6$ is selected from optionally substituted phenyl and optionally substituted benzyl.

Another embodiment relates to compounds of Formula (I), (II), (III) or (IV) wherein: $R^7$ is selected from —$NR^8R^9$, $C_1$-$C_8$ alkoxy, heterocyclyl and heterocyclyl-$C_1$-$C_8$-alkyl.

Another embodiment relates to compounds of Formula (I), (II), (III) or (IV) wherein: $R^7$ is —$NR^8R^9$.

Another embodiment relates to compounds of Formula (I), (II), (III) or (IV) wherein: $R^8$ is methyl, ethyl, isopropyl or butyl.

Another embodiment relates to compounds of Formula (I), (II), (III) or (IV) wherein: $R^8$ is isopropyl.

Another embodiment relates to compounds of Formula (I), (II), (III) or (IV) wherein: $R^9$ is methyl or H.

Another embodiment relates to compounds of Formula (I), (II), (III) or (IV) wherein: $R^7$ is $C_1$-$C_8$ alkoxy.

Another embodiment relates to compounds of Formula (I), (II), (III) or (IV) wherein: $R^7$ is methoxy, ethoxy, propoxy or butoxy.

Another embodiment relates to compounds of Formula (I), (II), (III) or (IV) wherein: $R^7$ is n-butoxy.

Another embodiment relates to compounds of Formula (I), (II), (III) or (IV) wherein: $R^7$ is saturadted or partially unsaturated 5 or 6-membered heterocyclyl.

Another embodiment relates to compounds of Formula (I), (II), (III) or (IV) wherein: $R^7$ is pyrroldinyl, morpholinyl or piperidinyl.

Another embodiment relates to compounds of Formula (I), (II), (III) or (IV) wherein: $R^7$ is piperidinyl.

Another embodiment relates to compounds of Formula (I), (II), (III) or (IV) wherein: $R^7$ is heterocycyl-$C_1$-$C_8$-alkyl.

Another embodiment relates to compounds of Formula (I), (II), (III) or (IV) wherein: $R^7$ is heterocycyl-$C_1$-$C_3$-alkyl.

Another embodiment relates to compounds of Formula (I), (II), (III) or (IV) wherein: $R^7$ is optionally substituted piperidin-4-yl-$CH_2$—.

Another embodiment relates to compounds of Formula (I), (II), (III) or (IV) wherein: $R^7$ is $R^8$-piperidin-4-yl-$CH_2$—.

Another embodiment relates to compounds of Formula (I), (II), (III) or (IV) wherein: $R^6$ and $R^7$ form, together with the carbon atom bonded thereto, an optionally unsaturated $C_{3-10}$-cycloalkyl or an optionally unsaturated $C_4$-$C_{14}$ heterocyclyl.

Another embodiment relates to compounds of Formula (I), (II), (III) or (IV) wherein: $R^6$ and $R^7$ form an optionally unsaturated $C_3$-$C_{10}$ cycloalkyl.

Another embodiment relates to compounds of Formula (I), (II), (III) or (IV) wherein: $R^6$ and $R^7$ form a six-membered spiro ring.

Another embodiment relates to compounds of Formula (I), (II), (III) or (IV) wherein: $R^6$ and $R^7$ form a five-membered spiro ring.

Another embodiment relates to compounds of Formula (I), (II), (III) or (IV) wherein: $R^6$ and $R^7$ form an optionally unsaturated $C_4$-$C_{14}$ heterocyclyl.

Another embodiment relates to compounds of Formula (I), (II), (III) or (IV) wherein: the optionally unsaturated $C_4$-$C_{14}$ heterocyclyl is a six-membered heterocyclic spiro ring.

Another embodiment relates to compounds of Formula (I), (II), (III) or (IV) wherein: the $C_4$-$C_{14}$ heterocyclyl is a cyclic amide spiro ring.

One embodiment relates to a compound which is selected from:

2-(bicyclo[2.2.1]hept-2-ylamino)-5-isopropyl-1,3-thiazol-4(5H)-one, 2-(bicyclo[2.2.1]hept-2-ylamino)-5-ethyl-1,3-thiazol-4(5H)-one, 2-(bicyclo[2.2.1]hept-2-ylamino)-5-phenyl-1,3-thiazol-4(5H)-one, 2-(cyclohexylamino)-5-ethyl-1,3-thiazol-4(5H)-one, 2-(bicyclo[2.2.1]hept-2-ylamino)-5,5-dimethyl-1,3-thiazol-4(5H)-one, 5-Isopropyl-2-(tricyclo[3.3.1.0~3,7~]non-3-ylamino)-1,3-thiazol-4(5H)-one, 6-(tricyclo[3.3.1.0~3,7~]non-3-ylamino)-5-thia-7-azaspiro[3.4]oct-6-en-8-one, 2-(Tricyclo[3.3.1.0~3,7~]non-3-ylamino)-1,3-thiazol-4(5H)-one, 6-(Cyclooctylamino)-5-thia-7-azaspiro[3.4]oct-6-en-8-one, 6-(Cycloheptylamino)-5-thia-7-azaspiro[3.4]oct-6-en-8-one, 6-(Bicyclo[2.2.1]hept-2-ylamino)-5-thia-7-azaspiro[3.4]oct-6-en-8-one, 6-[(2,2,3,3-Tetramethylcyclopropyl)amino]-5-thia-7-azaspiro[3.4]oct-6-en-8-one, 6-[(2-Methylphenyl)amino]-5-thia-7-azaspiro[3.4]oct-6-en-8-one, 2-[(cyclohexylmethyl)amino]-5,5-dimethyl-1,3-thiazol-4(5H)-one, 2-[(2-fluorophenyl)amino]-5-isopropyl-1,3-thiazol-4(5H)-one, 2-[(cyclohexylmethyl)amino]-5-(2-hydroxyphenyl)-1,3-thiazol-4(5H)-one, (5S)-2-(cycloheptylamino)-5-methyl-1,3-thiazol-4(5H)-one, (5R)-2-(cycloheptylamino)-5-methyl-1,3-thiazol-4(5H)-one, 2-(cycloheptylamino)-5-ethyl-1,3-thiazol-4(5H)-one, 2-(cycloheptylamino)-5-isopropyl-1,3-thiazol-4(5H)-one, 5-tert-butyl-2-(cycloheptylamino)-1,3-thiazol-4(5H)-one, 2-(cyclooctylamino)-5-ethyl-1,3-thiazol-4(5H)-one, 5-isopropyl-2-[(2-isopropylphenyl)amino]-1,3-thiazol-4(5H)-one, 5-ethyl-2-[(2-isopropylphenyl)amino]-1,3-thiazol-4(5H)-one, 2-[(2-chlorophenyl)amino]-5-ethyl-1,3-thiazol-4(5H)-one, 5-ethyl-2-[(2-methylphenyl)amino]-1,3-thiazol-4(5H)-one, 5-isopropyl-2-[(2,2,3,3-tetramethylcyclopropyl)amino]-1,3-thiazol-4(5H)-one, 2-(bicyclo[2.2.1]hept-2-ylamino)-5-(4-hydroxybenzyl)-1,3-thiazol-4(5H)-one, 5-[(cyclohexylmethyl)amino]-4-thia-6-azaspiro[2.4]hept-5-en-7-one, 2-(cycloheptylamino)-5-(3,4-dihydroxybenzyl)-1,3-thiazol-4(5H)-one, 2-(cycloheptylamino)-5-(1H-imidazol-4-ylmethyl)-1,3-thiazol-4(5H)-one,
2-(cycloheptylamino)-5-isobutyl-1,3-thiazol-4(5H)-one,
2-(cycloheptylamino)-5-(1H-indol-3-ylmethyl)-1,3-thiazol-4(5H)-one,
2-(cycloheptylamino)-5-(4-hydroxybenzyl)-1,3-thiazol-4(5H)-one,
(5R)-2-(cycloheptylamino)-5-(cyclohexylmethyl)-1,3-thiazol-4(5H)-one,
2-(cyclooctylamino)-5-(4-hydroxybenzyl)-1,3-thiazol-4(5H)-one,
(5S)-2-(cycloheptylamino)-5-(cyclohexylmethyl)-1,3-thiazol-4(5H)-one,
[2-(cycloheptylamino)-4-oxo-4,5-dihydro-1,3-thiazol-5-yl]acetonitrile,
2-(cycloheptylamino)-5-(pyridin-3-ylmethyl)-1,3-thiazol-4(5H)-one,
5-Isopropyl-2-[(2-methylphenyl)amino]-1,3-thiazol-4(5H)-one,
2-(Cyclooctylamino)-5,5-dimethyl-1,3-thiazol-4(5H)-one,
2-(Cyclooctylamino)-5-isopropyl-1,3-thiazol-4(5H)-one,
2-(Bicyclo[2.2.1]hept-2-ylamino)-1-thia-3-azaspiro[4.5]dec-2-en-4-one,
2-(Tricyclo[3.3.1.0~3,7~]non-3-ylamino)-1-thia-3-azaspiro[4.5]dec-2-en-4-one,
2-(Cycloheptylamino)-1-thia-3-azaspiro[4.5]dec-2-en-4-one,
2-(Cyclooctylamino)-1-thia-3-azaspiro[4.5]dec-2-en-4-one,
2-{[1-(4-Chlorophenyl)cyclobutyl]amino}-5-isopropyl-1,3-thiazol-4(5H)-one,
6-{[1-(4-Chlorophenyl)cyclobutyl]amino}-5-thia-7-azaspiro[3.4]oct-6-en-8-one,
2-(cycloheptylamino)-5,5-diethyl-1,3-thiazol-4(5H)-one,
(5S)-5-isopropyl-2-{[(2S)-2-phenylpropyl]amino}-1,3-thiazol-4(5H)-one,
(5R)-5-ethyl-2-{[(2S)-2-phenylpropyl]amino}-1,3-thiazol-4(5H)-one,
(5S)-5-ethyl-2-{[(2S)-2-phenylpropyl]amino}-1,3-thiazol-4(5H)-one,
(5R)-5-isopropyl-2-{[(2R)-2-phenylpropyl]amino}-1,3-thiazol-4(5H)-one,
(5S)-5-isopropyl-2-{[(2R)-2-phenylpropyl]amino}-1,3-thiazol-4(5H)-one,
(5R)-5-ethyl-2-{[(2R)-2-phenylpropyl]amino}-1,3-thiazol-4(5H)-one,
(5S)-5-ethyl-2-{[(2R)-2-phenylpropyl]amino}-1,3-thiazol-4(5H)-one,
2-Anilino-5-isopropyl-1,3-thiazol-4(5H)-one,
5-Isopropyl-2-[(2-morpholin-4-ylethyl)amino]-1,3-thiazol-4(5H)-one,
2-(Bicyclo[2.2.1]hept-2-ylamino)-1-thia-3-azaspiro[4.4]non-2-en-4-one,
2-(Cycloheptylamino)-1-thia-3-azaspiro[4.4]non-2-en-4-one,
2-(Cyclooctylamino)-1-thia-3-azaspiro[4.4]non-2-en-4-one,
2-[(2,2,3,3-Tetramethylcyclopropyl)amino]-1-thia-3-azaspiro[4.4]non-2-en-4-one,
2-[(2-chlorobenzyl)amino]-5-isopropyl-1,3-oxazol-4(5H)-one,
2-[(4-chlorobenzyl)amino]-5-isopropyl-1,3-oxazol-4(5H)-one,
5-isopropyl-2-[(2,2,6,6-tetramethylpiperidin-4-yl)amino]-1,3-oxazol-4(5H)-one,
5-isopropyl-2-[(2-morpholin-4-ylethyl)amino]-1,3-oxazol-4(5H)-one,
5-benzyl-2-[(cyclohexylmethyl)amino]-1,3-oxazol-4(5H)-one,
2-(cycloheptylamino)-5-isopropyl-1,3-oxazol-4(5H)-one,
2-(bicyclo[2.2.1]hept-2-ylamino)-5-isopropyl-1,3-oxazol-4(5H)-one,
2-(bicyclo[2.2.1]hept-2-ylamino)-5-isobutyl-1,3-oxazol-4(5H)-one,
2-(cycloheptylamino)-5-isobutyl-1,3-oxazol-4(5H)-one,
5-isobutyl-2-[(2-methylphenyl)amino]-1,3-oxazol-4(5H)-one,
2-(bicyclo[2.2.1]hept-2-ylamino)-5-isopropyl-5-methyl-1,3-thiazol-4(5H)-one,
5-ethyl-2-[(3-methylphenyl)amino]-1,3-thiazol-4(5H)-one,
5-isopropyl-2-morpholin-4-yl-1,3-oxazol-4(5H)-one,
2-(4-benzylpiperidin-1-yl)-5-isopropyl-1,3-oxazol-4(5H)-one,
2-azocan-1-yl-5-isopropyl-1,3-oxazol-4(5H)-one,
2-[(cyclohexylmethyl)amino]-5-phenyl-1,3-oxazol-4(5H)-one, and
2-(cycloheptylamino)-5-phenyl-1,3-oxazol-4(5H)-one, and pharmaceutically acceptable salts, solvates, hydrates, geometrical isomers, tautomers, optical isomers, N-oxides and prodrug forms thereof.

One embodiment relates to a pharmaceutical formulation comprising a compound according to Formula (I), (II), (III), or (IV) as active ingredient, in combination with a pharmaceutically acceptable diluent or carrier.

In one embodiment, the pharmaceutical formulation is formulated for oral delivery.

In one embodiment, the oral delivery form is a tablet.

One embodiment relates to a method for the prophylaxis or treatment of a 11-β-hydroxysteroid dehydrogenase type 1 enzyme-mediated disorder or achieving immuno-modulation comprising administering the compound of Formula (I), (II), (III), or (IV) to an individual.

In one embodiment, the disorder is selected from diabetes, syndrome X, obesity, glaucoma, hyperlipidemia, hyperglycemia, hyperinsulinemia, hypertension, osteoporosis, dementia, depression, virus diseases, and inflammatory diseases.

Another embodiment relates to the treatment or prophylaxis of a medical condition involving delayed or impaired wound healing.

Another embodiment relates to methods of treatment wherein the medical condition involving delayed or impaired wound healing is diabetes.

Another embodiment relates to methods of treatment wherein the medical condition involving delayed or impaired wound healing is caused by treatment with glucocorticoids.

Another embodiment relates to methods of treatment for the promotion of wound healing in chronic wounds, such as diabetic ulcers, venous ulcers or pressure ulcers.

Another embodiment relates to methods of treatment wherein immuno-modulation is selected from tuberculosis, lepra, and psoriasis.

Another embodiment relates to a method for inhibiting a 11-β-hydroxysteroid dehydrogenase type 1 enzyme, which comprises administering to a subject in need of such treatment an effective amount of a compound according to Formula (I), (II), (III) or (IV).

One embodiment relates to a compound selected from
2-[1-(4-Fluoro-phenyl)-ethylamino]-5-methyl-5-(tetrahydro-pyran-4-ylmethyl)-thiazol-4-one;
(5S)-5-((1-acetyl-4-piperidinyl)methyl)-2-((1S,4R)-bicyclo[2.2.1]hept-2-ylamino)-5-methyl-1,3-thiazol-4(5H)-one;
(5R)-2-((1S,4R)-bicyclo[2.2.1]hept-2-ylamino)-5-methyl-5-(tetrahydro-2H-pyran-4-ylmethyl)-1,3-thiazol-4(5H)-one;

(5S)-2-((1S,4R)-bicyclo[2.2.1]hept-2-ylamino)-5-methyl-5-tetrahydro-2H-pyran-4-yl-1,3-thiazol-4(5H)-one;
2-((1R,2R,4S)-bicyclo[2.2.1]hept-2-ylamino)-8-oxa-1-thia-3-azaspiro[4.5]dec-2-en-4-one;
(5S)-2-((1S,4R)-bicyclo[2.2.1]hept-2-ylamino)-5-((1-(3-furanylcarbonyl)-4-piperidinyl)methyl)-5-methyl-1,3-thiazol-4(5H)-one;
2-(1-Cyclohexyl-ethylamino)-5-isopropyl-5-methyl-thiazol-4-one;
2-(5,5-Difluoro-bicyclo[2.2.1]hept-2-ylamino)-5-isopropyl-5-methyl-thiazol-4-one;
2-[1-(2-Trifluoromethyl-phenyl)-ethylamino]-8-oxa-1-thia-3-aza-spiro[4.5]dec-2-en-4-one;
(5R)-2-((1S,2S,4R)-bicyclo[2.2.1]hept-2-ylamino)-5-methyl-5-(trifluoromethyl)-1,3-thiazol-4(5H)-one;
2-(Bicyclo[2.2.1]hept-2-ylamino)-5-(1-fluoro-1-methyl-ethyl)-5-methyl-thiazol-4-one;
2-[1-(4-Fluoro-phenyl)-ethylamino]-5-methyl-5-pyridin-4-yl-thiazol-4-one;
5-Methyl-5-pyridin-4-yl-2-[1-(2-trifluoromethyl-phenyl)-ethylamino]-thiazol-4-one;
2-[1-(2-Fluoro-phenyl)-ethylamino]-5-methyl-5-pyridin-4-yl-thiazol-4-one;
5-(1-Fluoro-1-methyl-ethyl)-2-[1-(2-fluoro-phenyl)-ethylamino]-5-methyl-thiazol-4-one;
2-[1-(2-Fluoro-phenyl)-ethylamino]-5-methyl-5-trifluoromethyl-thiazol-4-one;
5-(1,1-Difluoro-ethyl)-2-[1-(4-fluoro-phenyl)-ethylamino]-5-methyl-thiazol-4-one;
2-[1-(2-Chloro-phenyl)-ethylamino]-5-methyl-5-trifluoromethyl-thiazol-4-one;
2-[1-(4-Fluoro-phenyl)-ethylamino]-5-methyl-5-trifluoromethyl-thiazol-4-one;
2-[1-(2-Chloro-phenyl)-ethylamino]-5-methyl-5-trifluoromethyl-thiazol-4-one;
2-[1-(4-Fluoro-phenyl)-ethylamino]-5-(2-methoxy-pyridin-4-yl)-5-methyl-thiazol-4-one;
5-(1,1-Difluoro-ethyl)-2-[1-(4-fluoro-phenyl)-ethylamino]-5-methyl-thiazol-4-one; and
5-(1-Fluoro-1-methyl-ethyl)-2-[1-(4-fluoro-phenyl)-ethylamino]-5-methyl-thiazol-4-one, and pharmaceutically acceptable salts, solvates, hydrates, geometrical isomers, tautomers, optical isomers, N-oxides and prodrug forms thereof.

Another object of the present invention is a compound according to general formula (I) for use in therapy:

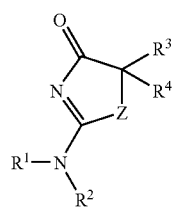

wherein $R^1$ and $R^2$ are each independently selected from hydrogen; $C_{3-10}$-cycloalkyl optionally independently substituted by one or more of $C_{1-8}$-alkyl and aryl; $C_{3-10}$-cycloalkyl-$C_{1-8}$-alkyl; aryl; aryl-$C_{1-8}$-alkyl; heterocyclyl; heterocyclyl-$C_{1-8}$-alkyl; or $R^1$ and $R^2$ form together with the nitrogen atom bonded thereto heterocyclyl optionally independently substituted by one or more of aryl-$C_{1-8}$-alkyl, wherein any aryl or heterocyclyl residue is optionally independently substituted by one or more of $C_{1-8}$-alkyl and halogen;

$R^3$ and $R^4$ are each independently selected from hydrogen; $C_{1-8}$-alkyl; $C_{3-10}$-cycloalkyl-$C_{1-8}$-alkyl; cyano-$C_{1-8}$-alkyl; aryl; aryl-$C_{1-8}$-alkyl; heterocyclyl-$C_{1-8}$-alkyl; heteroaryl-$C_{1-8}$-alkyl; or $R^3$ and $R^4$ form together with the carbon atom bonded thereto $C_{3-10}$-cycloalkyl, wherein any aryl residue is optionally independently substituted by one or more of hydroxy;

Z is sulfur or oxygen; and pharmaceutically acceptable salts, solvates, hydrates, geometrical isomers, tautomers, optical isomers, N-oxides and prodrug forms thereof.

Within the above embodiment, it is preferred that:

$R^1$ and $R^2$ are each independently selected from hydrogen, cyclohexyl, cycloheptyl, cyclooctyl, 2,2,3,3-tetramethylcyclopropyl, 1-(4-chlorophenyl)cyclobutyl, bicyclo[2.2.1]hept-2-yl, tricyclo[3.3.1.0~3,7~]non-3-yl, cyclohexylmethyl, phenyl, 2-methylphenyl, 3-methylphenyl, 2-isopropylphenyl, 2-fluorophenyl, 2-chlorophenyl, 2-phenylpropyl, 2-chlorobenzyl, 4-chlorobenzyl, 4-(2,2,6,6-tetramethyl)piperidyl, 2-morpholinyl-4-ylethyl, or $R^1$ and $R^2$ form together with the nitrogen atom bonded thereto morpholinyl, azocane, or 4-benzylpiperidyl;

$R^3$ and $R^4$ are each independently selected from hydrogen, methyl, ethyl, isopropyl, isobutyl, tert-butyl, cyclohexylmethyl, cyanomethyl, phenyl, 2-hydroxyphenyl, benzyl, 2-hydroxybenzyl, 4-hydroxybenzyl, 3,4-dihydroxybenzyl, 1H-imidazol-4-ylmethyl, indol-3-ylmethyl, 3-pyridylmethyl, or $R^3$ and $R^4$ form together with the carbon atom bonded thereto cyclopropyl, cyclobutyl, cyclopentyl, cyclohexyl.

When using the compounds of Formula (I) in therapy (e.g., Examples 39, 67, and 69-72), they may advantageously be used in the prophylaxis or treatment of an 11-β-hydroxysteroid dehydrogenase type 1 enzyme-mediated disorder or achieving immuno-modulation. In this embodiment, the disorder may be selected from diabetes, syndrome X, obesity, glaucoma, hyperlipidemia, hyperglycemia, hyperinsulinemia, hypertension, osteoporosis, dementia, depression, virus diseases, and inflammatory diseases. It is also possible that the treatment or prophylaxis is of the medical condition involves delayed or impaired wound healing. The medical condition involving delayed or impaired wound healing may be associated with diabetes and may have been caused by treatment with glucocorticoids. The compounds of Formula (I) for use in therapy may be for promotion of wound healing in chronic wounds, such as diabetic ulcers, venous ulcers or pressure ulcers. Iimmuno-modulation may encompass tuberculosis, lepra, and psoriasis.

In addition to the examples, the following compounds, according to Formula (I), may be effectively used in therapy:
5-ethyl-2-[(3-methylphenyl)amino]-1,3-thiazol-4(5H)-one,
5-isopropyl-2-morpholin-4-yl-1,3-oxazol-4(5H)-one,
2-(4-benzylpiperidin-1-yl)-5-isopropyl-1,3-oxazol-4(5H)-one,
2-azocan-1-yl-5-isopropyl-1,3-oxazol-4(5H)-one,
2-[(cyclohexylmethyl)amino]-5-phenyl-1,3-oxazol-4(5H)-one,
2-(cycloheptylamino)-5-phenyl-1,3-oxazol-4(5H)-one.

Another object of the present invention is a pharmaceutical formulation comprising a compound according to Formula (I) for use in therapy as active ingredient, in combination with a pharmaceutically acceptable diluent or carrier, especially for use in the prophylaxis or treatment of a 11-β-hydroxysteroid dehydrogenase type 1 enzyme-mediated disorder or achieving immuno-modulation. The pharmaceutical formulation can include a second active ingredient. The second active ingredient can be an inhibitor of 11-β-hydroxysteroid dehydrogenase type 1 or it can have some other activity.

Another object of the present invention is a method for the prophylaxis or treatment of a 11-β-hydroxysteroid dehydrogenase type 1 enzyme-mediated disorder or achieving immuno-modulation, which comprises administering to a subject in need of such treatment an effective amount of a compound according to Formula (I), (II), (III) and (IV).

Another object of the present invention is a method for inhibiting a 11-β-hydroxysteroid dehydrogenase type 1 enzyme, which comprises administering to a subject in need of such treatment an effective amount of a compound according to Formula (I), (II), (III) and (IV).

Another object of the present invention is the use of a compound according to Formula (I), (II), (III) and (IV) for the manufacture of a medicament for use in the prophylaxis or treatment of a 11-β-hydroxysteroid dehydrogenase type 1 enzyme-mediated disorder or achieving immuno-modulation.

Examples of 11-β-hydroxysteroid dehydrogenase type 1 enzyme-mediated disorders include: diabetes, syndrome X, obesity, glaucoma, osteoporosis, hyperlipidemia, hyperglycemia, hyperinsulinemia, hypertension, osteoporosis, cognitive disorders, dementia, depression, immune disorders, virus diseases, wond healing and inflammatory diseases.

It is preferred that the medical condition involving delayed or impaired wound healing is diabetes.

It is also preferred that the medical condition involving delayed or impaired wound healing is caused by treatment with glucocorticoids.

The compound according to Formula (I), (II), (III) and (IV) may be used for the promotion of wound healing in chronic wounds, such as diabetic ulcers, venous ulcers or pressure ulcers.

It is preferred that the immuno-modulation is selected from tuberculosis, lepra, and psoriasis.

Also, within the scope of this invention is a method for making a compound of formula (I). The method includes taking any intermediate compound delineated herein, reacting it with one or more reagents to form a compound of Formula (I), (II), (III) and (IV) including any processes specifically delineated herein.

Use of a compound of Formula (I), (II), (III) or (IV) for the manufacture of a medicament for use in the prophylaxis or treatment of a 11-β-hydroxysteroid dehydrogenase type 1 enzyme-mediated disorder or achieving immuno-modulation. In one embodiment, the disorder is selected from diabetes, syndrome X, obesity, glaucoma, hyperlipidemia, hyperglycemia, hyperinsulinemia, hypertension, osteoporosis, dementia, depression, virus diseases, and inflammatory diseases. In another embodiment, the medical condition involving delayed or impaired wound healing. In another embodiment, the medical condition involving delayed or impaired wound healing is diabetes. In another embodiment, the medical condition involving delayed or impaired wound healing is caused by treatment with glucocorticoids. In another embodiment, the use is for the promotion of wound healing in chronic wounds, such as diabetic ulcers, venous ulcers or pressure ulcers. In another embodiment, the immuno-modulation is selected from tuberculosis, lepra, and psoriasis.

Other features and advantages of the invention will be apparent from the detailed description and claims.

DETAILED DESCRIPTION OF THE INVENTION

The compounds according to the present invention may be used in several indications which involve 11-β-hydroxysteroid dehydrogenase type 1 enzyme. Thus, the compounds according to the present invention may be used against dementia (see WO97/07789), osteoporosis (see Canalis, E. 1996, Mechanisms of glucocorticoid action in bone: implications to glucocorticoid-induced osteoporosis, Journal of Clinical Endocrinology and Metabolism, 81, 3441-3447) and may also be used for disorders in the immune system (see Franchimont et al, "Inhibition of Th1 immune response by glucocorticoids: dexamethasone selectively inhibits IL-12-induced Stat 4 phosphorylation in T lymphocytes", The journal of Immunology 2000, Feb. 15, vol 164 (4), pages 1768-74) and also in the above listed indications.

The various terms used, separately and in combinations, in the above definition of the compounds having the Formula (I), (II), (III) and (IV) will be explained.

The term "aryl" in the present description is intended to include aromatic rings (monocyclic or bicyclic) having from 6 to 10 ring carbon atoms, such as phenyl (Ph), naphthyl, and indanyl (i.e., 2,3-dihydroindenyl), which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium as part of the ring system. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, benzothiophene, benzofuran, isobenzofuran, benzoxazole, 2,1,3-benzoxadiazole, benzopyrazole; benzothiazole, 2,1,3-benzothiazole, 2,1,3-benzoselenadiazole, benzimidazole, indazole, benzodioxane, indane, 1,5-naphthyridine, 1,8-naphthyridine, acridine, fenazine and xanthene.

The term "heterocyclic" and "heterocyclyl" in the present description is intended to include unsaturated as well as partially and fully saturated mono-, bi- and tricyclic rings having from 4 to 14, preferably 4 to 10 ring atoms having one or more heteroatoms (e.g., oxygen, sulfur, or nitrogen) as part of the ring system and the reminder being carbon, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine, 1,4-oxazepane, azepane, phthalimide, indoline, isoindoline, 1,2,3,4-tetrahydroquinoline, 1,2,3,4-tetrahydroisoquinoline, 3,4-dihydro-2H-1,4-benzoxazine, hexahydroazepine, 3,4-dihydro-2 (1H)isoquinoline, 2,3-dihydro-1H-indole, 1,3-dihydro-2H-isoindole, azocane, 1-oxa-4-azaspiro[4.5]dec-4-ene, decahydroisoquinoline, and 1,4-diazepane. In addition, the heterocyclyl or heterocyclic moiety may optionally be substituted with one or more oxo groups.

$C_{1-8}$-alkyl in the compound of formula (I) according to the present application may be a straight or branched alkyl group containing 1-8 carbon atoms. Exemplary alkyl groups include methyl, ethyl, n-propyl, isopropyl, n-butyl, sec-butyl, tert-butyl, pentyl, isopentyl, hexyl, isohexyl, n-heptyl, and n-octyl. For parts of the range "$C_{1-8}$-alkyl" all subgroups thereof are contemplated such as $C_{1-7}$-alkyl, $C_{1-6}$-alkyl, $C_{1-5}$-alkyl, $C_{1-4}$-alkyl, $C_{2-8}$-alkyl, $C_{2-7}$-alkyl, $C_{2-6}$-alkyl, $C_{2-5}$-alkyl, $C_{3-7}$-alkyl, $C_{4-6}$-alkyl, etc.

$C_{1-8}$-alkoxy in the compound of formula (I) according to the present application may be a straight or branched alkoxy group containing 1-8 carbon atoms. Exemplary alkoxy groups include methoxy, ethoxy, propoxy, isopropoxy, butoxy, sec-butoxy, tert-butoxy, pentyloxy, isopentyloxy, hexyloxy, isohexyloxy, n-heptyloxy, and n-octyloxy. For parts of the range "$C_{1-6}$-alkoxy" all subgroups thereof are contemplated such as $C_{1-7}$-alkoxy, $C_{1-6}$-alkoxy, $C_{1-5}$-alkoxy, $C_{1-4}$-alkoxy, $C_{2-8}$-alkoxy, $C_{2-7}$-alkoxy, $C_{2-6}$-alkoxy, $C_{2-5}$-alkoxy, $C_{3-7}$-alkoxy, $C_{4-6}$-alkoxy, etc.

$C_{1-8}$-acyl in the compound of formula (I) according to the present application may be a straight or branched acyl group containing 1-8 carbon atoms. Exemplary acyl groups include formyl, acetyl, propionyl, butyryl, isobutyryl, valeryl, isovaleryl, n-hexanoyl, n-heptanoyl, and n-octanoyl. For parts of the range "$C_{1-8}$-acyl" all subgroups thereof are contemplated such as $C_{1-7}$-acyl, $C_{1-6}$-acyl, $C_{1-5}$-acyl, $C_{1-4}$-acyl, $C_{2-8}$-acyl, $C_{2-7}$-acyl, $C_{2-6}$-acyl, $C_{2-5}$-acyl, $C_{3-7}$-acyl, $C_{4-6}$-acyl, etc.

$C_{2-8}$-alkenyl in the compound of formula (I) according to the present application may be a straight or branched acyl group containing 2-8 carbon atoms. Exemplary alkenyl groups include vinyl, 1-propenyl, 2-propenyl, isopropenyl, 1-butenyl, 2-butenyl, 1-pentenyl, 2-pentenyl, 1-hexenyl, 2-hexenyl, 1-heptenyl, and 1-octenyl. For parts of the range "$C_{2-8}$-alkenyl" all subgroups thereof are contemplated such as $C_{2-7}$-alkenyl, $C_{2-6}$-alkenyl, $C_{2-5}$-alkenyl, $C_{2-4}$-alkenyl, $C_{3-8}$-alkenyl, $C_{3-7}$-alkenyl, $C_{3-6}$-alkenyl, $C_{3-5}$-alkenyl, $C_{4-7}$-alkenyl, $C_{5-6}$-alkenyl, etc.

$C_{3-10}$-cycloalkyl in the compound of formula (I) according to the present application may be an optionally substituted monocyclic, bicyclic or tricyclic alkyl group containing between 3-10 carbon atoms. Exemplary cycloalkyl groups include cyclopropyl, cyclobutyl, cyclopentyl, cyclohexyl, cycloheptyl, cyclooctyl, cyclononyl, cyclodecyl, bicyclo[2.2.1]hept-2-yl, tricyclo[3.3.1.0~3,7~]non-3-yl, (1R,2R,3R,5S)-2,6,6-trimethylbicyclo[3.1.1]hept-3-yl, (1S,2S,3S,5R)-2,6,6-trimethylbicyclo[3.1.1]hept-3-yl, 1-adamantyl, noradamantyl, and 2,2,3,3-tetramethylcyclopropyl. For parts of the range "$C_{3-10}$-cycloalkyl" all subgroups thereof are contemplated such as $C_{3-9}$-cycloalkyl, $C_{3-8}$-cycloalkyl, $C_{3-7}$-cycloalkyl, $C_{3-6}$-cycloalkyl, $C_{3-5}$-cycloalkyl, $C_{4-10}$-cycloalkyl, $C_{5-10}$-cycloalkyl, $C_{6-10}$-cycloalkyl, $C_{7-10}$-cycloalkyl, $C_{8-9}$-cycloalkyl, etc. In addition, the cycloalkyl moiety may optionally be substituted with one or more oxo groups.

$C_{3-10}$-cycloalkenyl in the compound of formula (I) according to the present application may be an optionally alkyl substituted cyclic, bicyclic or tricyclic alkenyl group containing totally 3-10 carbon atoms. Exemplary cycloalkenyl groups include cyclopropenyl, cyclobutenyl, cyclopentenyl, cyclohexenyl, cycloheptenyl, cyclooctenyl, cyclononenyl, cyclodecenyl, and bicyclo[2.2.1]hept-5-en-2-yl. For parts of the range "$C_{3-10}$-cycloalkenyl" all subgroups thereof are contemplated such as $C_{3-9}$-cycloalkenyl, $C_{3-8}$-cycloalkenyl, $C_{3-7}$-cycloalkenyl, $C_{3-6}$-cycloalkenyl, $C_{3-5}$-cycloalkenyl, $C_{4-10}$-cycloalkenyl, $C_{5-10}$-cycloalkenyl, $C_{6-10}$-cycloalkenyl, $C_{7-10}$-cycloalkenyl, $C_{8-9}$-cycloalkenyl, etc. In addition, the cycloalkenyl moiety may optionally be substituted with one or more oxo groups.

The term "halogen" or "halo" in the present description is intended to include fluorine, chlorine, bromine and iodine.

The term "sulfanyl" in the present description means a thio group.

The term "-hetero($C_1$-$C_8$)alkyl" refers to a moiety wherein a hetero atom, selected from optionally substituted nitrogen, sulfur and oxygen, is the point of attachment to the core molecule and is attached to a $C_1$-$C_8$ alkyl chain.

The term "cyclic amide spiro ring" refers to compounds where the substituents at the 5-position of the thiazolinone or the oxazolone ring combine together to form a cyclic ring having a —$NR^{10}C(O)$— therein. An example of such a moiety is shown in the example below:

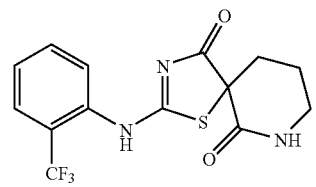

With the expression "mono- or di-substituted" is meant in the present description that the functionalities in question may be substituted with independently $C_{1-8}$-acyl, $C_{2-8}$-alkenyl, $C_{1-8}$-(cyclo)alkyl, aryl, pyridylmethyl, or heterocyclic rings e.g. azetidine, pyrrolidine, piperidine, piperazine, morpholine and thiomorpholine, which heterocyclic rings optionally may be substituted with $C_{1-8}$-alkyl. With the expression "optionally mono- or disubstituted" is meant in the present description that the functionalities in question may also be substituted with independently hydrogen.

When two of the above-mentioned terms are used together, it is intended that the latter group is substituted by the former. For example, $C_{3-10}$-cycloalkyl-$C_{1-8}$-alkyl means a $C_{1-8}$-alkyl group that is substituted by a $C_{3-10}$-cycloalkyl group. Likewise, a $C_{1-8}$-haloalkyl means a $C_{1-8}$-alkyl group that is substituted by a halogen atom.

Metabolites of the compounds of Formula (I), (II), (III) and (IV) can take on many forms and the present invention encompasses the metabolites of the compounds as well as the parent compound.

As used herein, the term "prodrug" means a derivative of a compound that can hydrolyze, oxidize, or otherwise react under biological conditions (in vitro or in vivo) to provide an active compound, particularly a benzamide derivative. Examples of prodrugs include, but are not limited to, derivatives and metabolites of a benzamide derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

"Tautomer" is one of two or more structural isomers that exist in equilibrium and are readily converted from one isomeric form to another, in the present case, tautomers of the structures below are encompassed by the present invention.

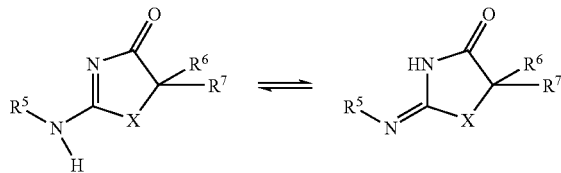

As used herein, "hydrate" is a form of a compound of Formula (I), (II), (III), or (IV) where water molecules are combined in a definite ratio as an integral part of the crystal structure of the compound.

As used herein, "solvate" is a form of of a compound of Formula (I), (II), (III), or (IV) where solvent molecules are combined in a definite ratio as an integral part of the crystal structure of the compound.

Depending on its structure, the phrase "pharmaceutically acceptable salt," as used herein, refers to a pharmaceutically acceptable organic or inorganic acid or base salt of a benzamide derivative. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "geometrical isomers" refers compounds that have the same molecular formula but the atoms are in different non-equivalent positions to one another.

As used herein, the term "optical isomers" refers to compounds with chiral atoms which have the ability to rotate plane polarized light, R/S configuration. The term optical isomer include enantiomers and diastereomers as well as compounds which can be distinguished one from the other by the designations of (D) and (L).

As used herein:
DCM means dichloromethane,
DEAD means diethyl azocarboxylate,
DMF means dimethylformamide,
EDCI means 1-(3-dimethylaminopropyl)-3-ethylcarbodiimide hydrochloride,
Ether means diethyl ether,
EtOAc means ethylacetate,
HOBt means 1-hydroxybenzotriazole,
HPLC means high-performance liquid chromatography,
LC means liquid chromatography,
MeCN means acetonitrile,
DPPA means diphenylphosphoryl azide,
RT means room temperature,
SM means starting material,
TEA means triethylamine, and
THF means tetrahydrofuran.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject for the treatment of disease, 11-β-HSD1 inhibition, 11-β-HSD1-mediated disease).

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, 8$^{th}$ ed., McGraw-Hill, Int. Ed. 1992, "Biotransformation of Drugs, p. 13-15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included in the invention are pharmaceutically acceptable salts or compounds of any of the formulae herein.

Pharmaceutical compositions according to the present invention contain a pharmaceutically acceptable carrier together with at least one of the compounds comprising the formula (I) as described herein above, dissolved or dispersed therein as an active, antimicrobial, ingredient. In a preferred embodiment, the therapeutic composition is not immunogenic when administered to a human patient for therapeutic purposes, unless that purpose is to induce an immune response.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of auxiliary substances such as wetting or emulsifying agents, pH buffering agents and the like which enhance the effectiveness of the active ingredient. Adjuvants may also be present in the composition.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (I), may include pharmaceutically acceptable salts of that component therein as set out above. Pharmaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylaminoethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes are known to those of ordinary skill in the art.

The orally administrable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, calcium hydrogen phosphate, sodium starch glycolate, sorbitol or glycine; tabletting lubricant e.g. magnesium stearate, talc, polyethylene glycol or silicon dioxide (optionally colloidal); disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose (optionally microcrystalline), glucose syrup, gelatin hydrogenated edible fats; emulsifying agents e.g. lecithin, sorbitan monooleate or acacia, non-aqueous vehicles (which may include edible oils), e.g. almond oil, fractionated coconut oil, oily esters such as glycerine, propylene glycol, or ethyl alcohol; preservatives e.g. methyl or propyl p-hydroxybenzoate or sorbic acid, and if desired conventional flavouring or colouring agents.

"An effective amount" refers to an amount of a compound which confers a therapeutic effect on the treated subject. The therapeutic effect may be objective (i.e., measurable by some test or marker) or subjective (i.e., subject gives an indication of or feels an effect). A pharmaceutical composition according to the present invention, may comprise typically an amount of at least 0.1 weight percent of compound comprising the formula (I) per weight of total therapeutic composition. A weight percent is a ratio by weight of total composition. Thus, for example, 0.1 weight percent is 0.1 grams of compound comprising the formula (I) per 100 grams of total composition. A suitable daily oral dose for a mammal, preferably a human being, may vary widely depending on the condition of the patient. However a dose of compound comprising the formula (I) of about 0.1 to 300 mg/kg body weight may be appropriate.

The compositions according to the present invention may also be used veterinarily and thus they may comprise a veterinarily acceptable excipient or carrier. The compounds and compositions may be thus administered to animals, e.g., cats, dogs, or horses, in treatment methods.

The compounds of the present invention in labelled form, e.g. isotopically labelled, may be used as a diagnostic agent.

This invention relates to methods of making compounds of any of the formulae herein comprising reacting any one or more of the compounds of the formulae delineated herein, including any processes delineated herein. The compounds of formula (I) above may be prepared by, or in analogy with, conventional methods, and especially according to or in analogy with the following methods. Further, the pharmacology in-vitro was studied using the following reagents and methods.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

All publications mentioned herein are hereby incorporated by reference. By the expression "comprising" means "including but not limited to." Thus, other non-mentioned substances, additives or carriers may be present.

The invention will now be described in reference to the following Examples. These Examples are not to be regarded as limiting the scope of the present invention, but shall only serve in an illustrative manner.

EXAMPLES

Biological Examples

Scintillation Proximity Assay

[1, 2(n)- $^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-$HSD_1$) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-$HSD_1$ enzyme assay was carried out in 96 well microtiter plates (Packard, Optiplate) in a total well volume of 220 μL and contained 30 mM Tris-HCl, pH 7.2 with 1 mM EDTA, a substrate mixture tritiated Cortisone/NADPH (175 nM/181 μM), G-6-P (1 mM) and inhibitors in serial dilutions (9 to 0.15 μM). Reactions were initiated by the addition of human 11-β-$HSD_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 μL 1 mM GA stop solution. Monoclonal mouse antibody was then added (10 μL of 4 μM) followed by 100 μL of SPA beads (suspended according to the manufacturers instructions). Appropriate controls were set up by omitting the 11-β-$HSD_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter. The calculation of the $K_i$ values for the inhibitors was performed by use of Activity Base. The $K_i$ value is calculated from $IC_{50}$ and the $K_m$ value is calculated using the Cheng Prushoff equation (with reversible inhibition that follows the Michaelis-Menten equation): $K_i=IC_{50}(1+[S]/K_m)$ [Cheng, Y. C.; Prushoff, W. H. Biochem. Pharmacol. 1973, 22, 3099-3108]. The $IC_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 μM. Below follow some Ki examples according to the present invention.

| Example | Ki value (nM) |
| --- | --- |
| 10 | 250 |
| 14 | 107 |
| 48 | 174 |

Cloning, Expression and Purification of 11β-HSD1

The expression and purification of the murine enzyme is described by J. Zhang, et al. Biochemistry, 44, 2005, pp 6948-57. The expression and purification of the human enzyme is similar to that of the murine sequence.

Enzyme Assay:

The IC50 and Ki of the compounds are determined by the following method:

1. Prepare an Assay Buffer, (pH 7.2, 50 mM Tris-HCL, 1 mM EDTA) fresh each week.
2. Prepare the following solutions:
   NADPH (Sigma, 200 μM)
   $^3$H-Cortisone (Amersham Biosciences, 45 Ci/mmol, 200 nM)
   Enzyme Prep (20 nM for human, 10 nM for mouse)
   Cortisol Antibody (East Coast Biologicals, (1:50 dilution)
   Anti-mouse SPA beads (Amersham Biosciences, 15 mg/ml)
   18β-Glycyrrhetinic acid ("GA")(Aldrich, 1 μM)
   Compound Stock Solution (10 mM in DMSO), serially diluted in assay buffer. Each compound is tested at six different concentrations usually (10 μM to 0.1 nM). All of the solutions and dilutions are made in the Assay Buffer.
3. Assay is run using white/white, 96-well assay plates (Corning) in a total volume of 100 μL.
4. Into each well of a 96-well plate is added Assay Buffer (30 μL), compound (10 μL) NADPH (10 μL), and $^3$H-cortisone (10 μL).
5. Initiate reaction by adding 40 μL of HSD-1 enzyme prep to the wells.
6. The plate is covered with tape and incubated on an orbital shaker for 1 h at RT.
7. After 1 h, the tape is removed and anti-cortisol antibody (10 μL), GA solution (10 μL), and SPA bead preparation (100 μL) is added.
8. The plate is incubated (30 min) on an orbital shaker at RT.
9. The counts are read on a TopCount NXT reader.
10. A dose-reponse curve is first plotted using the Graphpad Prism software, to generate the IC50 values.

With this IC50 value and the known Km value for the substrate and HSD1 enzyme, an estimated Ki can be calculated with the Chen and Prusoff equation {Ki=IC50/[1+(substrate/Km)])}.

In addition to the above examples, the compounds of the present invention all show 11β-HSD1 enzyme activity ($IC_{50}$) in the assays ranging from 10 nM and 10 μM.

The following compounds exhibited activity in the Enzyme assay with $IC_{50}$ values less than 20 nM:

2-((3-chloro-2-methylphenyl)amino)-5-(1-methylethyl)-1,3-thiazol-4(5H)-one;

5-methyl-5-(pyridin-4-yl)-2-(2-(trifluoromethyl)phenylamino)thiazol-4(5H)-one;

2-((2-chlorophenyl)amino)-5-methyl-5-phenyl-1,3-thiazol-4(5H)-one;

(5S)-2-((2-chlorophenyl)amino)-5-methyl-5-phenyl-1,3-thiazol-4(5H)-one;

(5R)-2-((2-chlorophenyl)amino)-5-methyl-5-(1-methylethyl)-1,3-thiazol-4(5H)-one;

2-((2-chlorophenyl)amino)-5-methyl-5-(1-methylethyl)-1,3-thiazol-4(5H)-one;

2-((S)-1-cyclohexylethylamino)-5-isopropyl-5-methylthiazol-4(5H)-one;

(5S,7R)-2-(cyclooctylamino)-7-(methyloxy)-1-thia-3-azaspiro[4.5]dec-2-en-4-one;

2-((1S,2S,4R)-bicyclo[2.2.1]heptan-2-ylamino)-5-methyl-5-((tetrahydro-2H-pyran-4-yl)methyl)thiazol-4(5H)-one;

2-((5-fluoro-2-methylphenyl)amino)-5-(1-methylethyl)-1,3-thiazol-4(5H)-one;

2-(2-chlorophenylamino)-5-methyl-5-(tetrahydro-2H-pyran-4-yl)thiazol-4(5H)-one;
2-((R)-1-(4-fluorophenyl)ethylamino)-5-isopropyl-5-methylthiazol-4(5H)-one;
2-((2,5-difluorophenyl)amino)-5-(1-methylethyl)-1,3-thiazol-4(5H)-one;
2-(cyclohexylmethylamino)-5-methyl-5-((S)-tetrahydrofuran-3-yl)thiazol-4(5H)-one;
5-methyl-5-(1-methylethyl)-2-((2-(trifluoromethyl)phenyl)amino)-1,3-thiazol-4(5H)-one;
2-((1R,2R,4S)-bicyclo[2.2.1]heptan-2-ylamino)-5-methyl-5-propylthiazol-4(5H)-one;
2-(o-toluidino)-5-cyclopentylthiazol-4(5H)-one;
2-((2-fluorophenyl)amino)-1-thia-3-azaspiro[4.4]non-2-en-4-one;
2-((3-fluorotricyclo[3.3.1.1~3,7~]dec-1-yl)amino)-5-methyl-5-(1-methylethyl)-1,3-thiazol-4(5H)-one;
(R)-5-isopropyl-5-methyl-2-((S)-1-phenylethylamino)thiazol-4(5H)-one;
2-((2,6-dichlorophenyl)amino)-5-(1-methylethyl)-1,3-thiazol-4(5H)-one;
2-(cyclohexylmethylamino)-5-((S)-tetrahydrofuran-3-yl)thiazol-4(5H)-one;
2-(bicyclo[2.2.1]hept-2-ylamino)-5-isopropyl-5-methyl-1,3-thiazol-4(5H)-one;
2-(2-chlorophenylamino)-5-cyclopentylthiazol-4(5H)-one;
2-(2-chlorophenylamino)-5-cyclohexylthiazol-4(5H)-one;
2-((2-chlorophenyl)amino)-5-(1-methylethyl)-1,3-thiazol-4(5H)-one;
2-((S)-1-(4-fluorophenyl)ethylamino)-5-methyl-5-(pyridin-4-yl)thiazol-4(5H)-one;
2-((S)-1-(2-fluorophenyl)ethylamino)-5-methyl-5-(pyridin-4-yl)thiazol-4(5H)-one;
2-(2-fluorophenylamino)-5-((S)-tetrahydrofuran-3-yl)thiazol-4(5H)-one;
2-((1R,2R,4S)-bicyclo[2.2.1]heptan-2-ylamino)-5-methyl-5-(2,2,2-trifluoroethyl)thiazol-4(5H)-one;
5-ethyl-5-methyl-2-(tricyclo[3.3.1.1~3,7~]dec-1-ylamino)-1,3-thiazol-4(5H)-one;
2-(2-chlorophenylamino)-5-methyl-5-(pyridin-4-yl)thiazol-4(5H)-one;
5-cyclopentyl-2-(2-fluorophenylamino)thiazol-4(5H)-one;
5-cyclohexyl-2-(2-fluorophenylamino)thiazol-4(5H)-one;
2-((R)-1-(2-fluorophenyl)ethylamino)-5-isopropyl-5-methylthiazol-4(5H)-one;
(R)-2-((S)-1-(2-fluorophenyl)ethylamino)-5-isopropyl-5-methylthiazol-4(5H)-one; and 2-((2,4-dichlorophenyl)amino)-5-(1-methylethyl)-1,3-thiazol-4(5H)-one.

SYNTHESIS EXAMPLES

General Reaction schemes

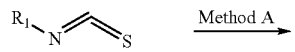
Method A

Method B

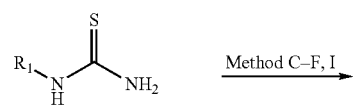
Method C–F, I

-continued

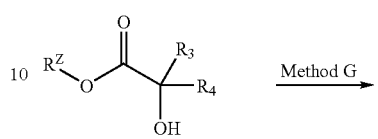
Method G

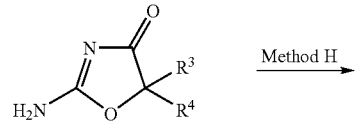
Method H

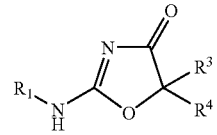

All commercial starting materials are used without any purification.

If the appropriate α-bromocarboxylic acid or ester not is commercially availiable, the substances has been prepared in accordance to this method:

The 2-amino-carboxylic acid (1.0 eq.) was suspended in 2.0 M $H_2SO_4$ (4 eq.), KBr (8 eq.) was added and the mixture was cooled in an ice-bath. $NaNO_2$ (1.3 eq.) dissolved in water was added slowly. The reaction mixture was stirred for 4 h at ice-bath, before allowed to reach room temperature. The reaction mixture was extracted with EtOAc. The organic phase was dried over $MgSO_4$ before concentrated in vacuum. This gave the crude product which was used in the next step without further purification (J. Org. Chem. 2002, 67 (11), 3595-3600; Xinhua Qian; Bin Zheng; Brian Burke; Manohar T. Saindane and David R. Kronenthal).

Methods and Materials $^1H$ nuclear magnetic resonance (NMR) and $^{13}C$ NMR were recorded on a Bruker PMR 500 spectrometer at 500.1 MHz and 125.1 MHz, respectively or on a JEOL eclipse 270 spectrometer at 270.0 MHz and 67.5 MHz, respectively. All spectra were recorded using residual solvent or tetramethylsilane (TMS) as internal standard. IR spectra were recorded on a Perkin-Elmer Spectrum 1000 FT-IR spectrometer. Electrospray mass spectrometry (MS) was obtained using an Agilent MSD mass spectrometer. Accurate mass measurements were performed on a Micromass LCT dual probe. Elemental analyses were performed on a Vario El instrument or sent to Mikro Kemi in Uppsala.

Analytical HPLC were performed on Agilent 1100 system equipped with System A: ACE 3 (C8, 50×3.0 mm) or System B: YMC ODS-AQ, (33×3.0 mm) using the eluent system: water/0.1% TFA and $CH_3CN$, 1 mL/min, with a gradient time of 3 min.

Preparative HPLC was performed on a Gilson system equipped with System A: ACE 5 C8 column (50×20 mm) gradient time 5 min, system B: YMC ODS-AQ (150×30 mm) gradient time 8.5 min or system C: YMC ODS-AQ (50×20 mm) gradient time 5 min using the eluent system: water/0.1% TFA and $CH_3CN$. Preparative flash chromatography was performed on Merck silica gel 60 (230-400 mesh).

Synthetic Methodolology

Method A or B was used depending if the isothiocyanate or of the corresponding amine was used. The amine or the isothiocyanate was purchased from either Maybridge Plc. or from Sigma-Aldrich Co.

Method A 1.0 eq. of the appropriate isothiocyanate was stirred in 2 M ammonia in ethanol (5 eq.) for 18 h at RT. Evaporation in vacuo afforded the crude product, which crystallized upon addition of DCM. The crystals were collected on a filter and air-dried to afford the thiourea.

Method B 1.0 eq. of the amine and ethoxycarbonylisothiocyanate (1.0 eq) were mixed in a test tube. A violently exothermic reaction resulted in a white paste. This was taken up in 5M KOH solution and stirred at 70° C. for 2 hours at which point LC analysis indicated full hydrolysis of the intermediate. The mixture was cooled, diluted with water and extracted 3 times with chloroform. Subsequent preparative LC yielded the desired thiourea.

Method C

The thiourea (1.0 eq.) and the α-bromoester/(α-bromoacid (1.0 eq.) was dissolved in acetone and heated to 60° C. in a sealed tube for 15-72 hours. The solvent was removed. And the product purified by crystallization from MeOH/preparative reverse-phase HPLC.

Method C1

The thiourea (1.0 eq.) and the α-bromoester/α-bromoacid (1.0 eq.) was mixed in water and heated in the microwave at 140° C. for 1 hour. The aqueous phase was extracted twice with DCM. The combined orgaic phases were evaporated and the obtained crude product was purified by preparative reverse-phase HPLC.

Method D

The thiourea (1.0 eq.) and the α-bromoester (1.0 eq.) was dissolved in 1,4-dioxane and heated to 100° C. in a sealed tube for 1-11 days. The solvent was removed, and the residue was purified by preparative reverse-phase HPLC.

Method D1

The thiourea (1.0 eq.) and the α-bromoester (1.0 eq.) was dissolved in THF and heated to 70° C. in a sealed tube for 1 day. The solvent was removed, and the residue was purified by preparative reverse-phase HPLC.

Method D2

The thiourea (1.0 eq.) and the α-bromoester (1.0 eq.) was dissolved in 2-propanol and heated to 95° C. in a sealed tube for 3 days. The solvent was removed, and the residue was purified by preparative reverse-phase HPLC.

Method D3

The thiourea (1.0 eq.) and the α-bromoester/α-bromoacid (1.0 eq.) was dissolved in MeCN and heated to 60° C. in a sealed tube for 2 days. The solvent was removed, and the residue was purified by preparative reverse-phase HPLC.

Method E

The amino acid (1 eq.) was suspended in 2.0 M $H_2SO_4$, KBr (8 eq.) was added and the mixture was cooled in an ice-bath. $NaNO_2$ (1.3 eq.) dissolved in water was slowly added. The reaction mixture was stirred for 4 h while cooling was continued. The reaction mixture was then extracted with EtOAc, washed with brine and brine containing $Na_2S_2O_3$. The organic phase was concentrated in vacuum. The product was used in the next step without further purification.

Method F

The thiourea (1 eq.) and 3-bromo-2-coumarone (1 eq.) was dissolved in acetone and heated to 60° C. for 3 hours. Water was added. The obtained solid was collected. Recrystallised from water/MeCN. The solid was collected. The mother liquor was concentrated and the obtained solid was dried in vaccum to give the product.

Method G

The carbonate salt of guanidine (1 eq.) and the alpha hydroxy ester (1 eq.) was dissolved in EtOH and heated to reflux for 2-10 hours. The mixture was then poured in to $H_2O$ and left at 8° C. for 16 hours. The product was collected by filtration.

Method H

The amino-oxazolone (1 eq.) and the amine (3 eq.) was added to 4 ml EtOH and put in the microwave oven at 130° C. for 30 min. The solvent was removed under vacuum and the products purified by preparative reverse-phase HPLC.

Method I

To an ice-cooled solution with 1 eq. of the thiourea in DCM was 3 eq. 5% NaOH (aq) and 2 eq. dibromobutyryl chloride added followed by a small amount of benzyltriethylammonium chloride. The reaction was allowed to reach rt and additional 5 eq. 5% NaOH (aq) was added. The DCM-layer was separated and washed twice with water, dried over $MgSO_4$, filtered and concentrated. The product was isolated by preparative reverse-phase HPLC.

Method J

The acid (1 eq.) was dissolved in $SOCl_2$ and heated to 60° C. for 2 hours. NBS (2 eq.), $SOCl_2$ and 1 drop of HBr (aq) was added at r.t. The reaction was heated to reflux for 75 min. The solvent was removed under vacuum, $CCl_4$ was added and this was filtered. $CCl_4$ was removed under vacuum. The remaining oil was dissolved in EtOH and left for 16 hours at r.t. The solvent was then removed under vacuum. This gave the product as an α-bromoester.

EXAMPLES

Methods A-J were employed for preparing the compounds of Examples 1-79 as described below.

Example 1

2-(bicyclo[2.2.1]hept-2-ylamino)-5-isopropyl-1,3-thiazol-4(5H)-one

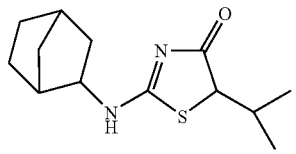

Synthesis was performed from N-bicyclo[2.2.1]hept-2-ylthiourea and ethyl 2-bromoisovalerate according to Method C.

$^1$H NMR (400 MHz, DMSO-$d_6$) δ ppm 0.79 (m, 3 H) 0.97 (m, 3 H) 1.10 (m, 3 H) 1.45 (m, 4 H) 1.69 (m, 1 H) 2.22 (m, 2 H) 2.36 (m, 1 H) 3.74 (m, 1 H) 4.37 (m, 1 H) 9.56 (s, 1 H). MS (ESI+) for $C_{13} H_{20}N_2OS$ m/z 253 (M+H)$^+$.

Example 2

2-(bicyclo[2.2.1]hept-2-ylamino)-5-ethyl-1,3-thiazol-4(5H)-one

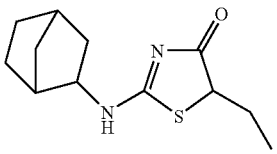

Synthesis was performed from N-bicyclo[2.2.1]hept-2-ylthiourea and ethyl 2-bromobutyrate according to Method C.

$^1$H NMR (400 MHz, DMSO-d$_6$) δ ppm 0.90 (m, 3 H) 1.03-1.23 (m, 3 H) 1.35-1.56 (m, 4 H) 1.65-1.84 (m, 2 H) 1.98 (m, 1 H) 2.24 (m, 2 H) 3.75 (m, 1 H) 4.22-4.40 (m, 1H) 9.84 (s, 1 H). MS (ESI+) for $C_{12}H_{18}N_2OS$ m/z 239 (M+H)$^+$.

Example 3

2-(bicyclo[2.2.1]hept-2-ylamino)-5-phenyl-1,3-thiazol-4(5H)-one

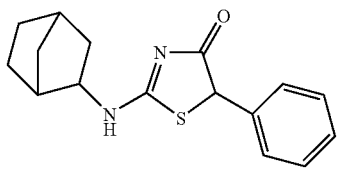

Synthesis was performed from N-bicyclo[2.2.1]hept-2-ylthiourea and methyl alpha-bromophenylacetate according to Method C.

$^1$H NMR (400 MHz, DMSO-d$_6$) δ ppm 1.05-1.24 (m, 3 H) 1.36-1.56 (m, 4 H) 1.66-1.80 (m, 1 H) 2.22-2.33 (m, 2 H) 3.78-3.90 (m, 1 H) 5.41 (s, 0.5 H) 5.43 (s, 0.5 H) 7.21-7.41 (m, 5 H) 9.39 (d, J=6.35 Hz, 1 H). MS (ESI+) for $C_{16}H_{18}N_2OS$ m/z 287 (M+H)$^+$.

Example 4

2-(cyclohexylamino)-5-ethyl-1,3-thiazol-4(5H)-one

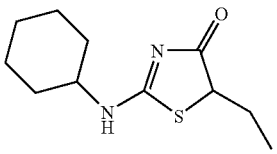

Synthesis was performed from n-cyclohexylthiourea and ethyl 2-bromobutyrate according to Method C. Gave 201 mg (75%).

$^1$H NMR (400 MHz, DMSO-d$_6$) δ ppm 0.91 (m, 3 H) 1.05-2.06 (m, 12 H) 3.76 (m, 1 H) 4.36 (m, 1 H) 10.11 (s, 1 H). MS (ESI+) for $C_{11}H_{18}N_2OS$ m/z 227 (M+H)$^+$

Example 5

2-(bicyclo[2.2.1]hept-2-ylamino)-5,5-dimethyl-1,3-thiazol-4(5H)-one

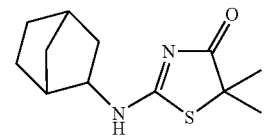

Synthesis was performed from N-bicyclo[2.2.1]hept-2-ylthiourea and Ethyl 2-bromoisobutyrate according to Method C.

$^1$H NMR (400 MHz, DMSO-d$_6$) δ ppm 1.05-1.21 (m, 3 H) 1.34-1.54 (m, 4 H) 1.48 (s, 2 H) 1.49 (s, 2 H) 1.50 (s, 1 H) 1.51 (s, 1 H) 1.67-1.74 (m, 1 H) 2.18-2.28 (m, 2 H) 3.20 (dd, J=7.69, 2.93 Hz, 0.25 H) 3.73-3.82 (m, 0.75 H) 9.12 (d, J=6.59 Hz, 1 H). MS (ESI+) for $C_{12}H_{18}N_2OS$ m/z 239 (M+H)$^+$

Example 6

5-Isopropyl-2-(tricyclo[3.3.1.0~3,7~]non-3-ylamino)-1,3-thiazol-4(5H)-one

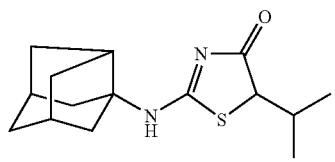

Synthesis was performed from N-tricyclo[3.3.1.0~3,7~]non-3-ylthiourea and ethyl 2-bromo-3-methylbutanoate according to Method C.

$^1$H NMR (400 MHz, DMSO-d$_6$) δ 0.75 (d, J=6.6 Hz, 3 H), 0.95 (d, J=6.8 Hz, 3 H), 1.46-1.57 (m, 4 H), 1.88-2.10 (m, 6H), 2.22-2.37 (m, 3 H), 2.43 (t, J=6.7 Hz, 1 H), 4.23 (d, J=3.5 Hz, 1 H), 9.29 (s, 1 H). MS (ESI+) for $C_{15}H_{22}N_2OS$ m/z 279 (M+H)$^+$.

Example 7

6-(tricyclo[3.3.1.0~3,7~]non-3-ylamino)-5-thia-7-azaspiro[3.4]oct-6-en-8-one

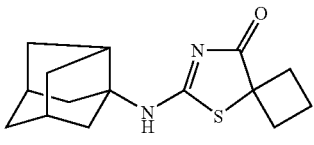

Synthesis was performed from N-tricyclo[3.3.1.0~3,7~]non-3-ylthiourea and ethyl 1-bromocyclobutanecarboxylate according to Method D.

$^1$H NMR (400 MHz, DMSO-d$_6$) δ 1.45-1.57 (m, 4 H), 1.90-2.16 (m, 8 H), 2.22-2.27 (m, 2 H), 2.44-2.55 (m, 5 H, obscured by solvent signal), 9.24 (s, 1 H). MS (ESI+) for $C_{15}H_{20}N_2OS$ m/z 277 (M+H)$^+$.

Example 8

2-(Tricyclo[3.3.1.0~3,7~]non-3-ylamino)-1,3-thiazol-4(5H)-one

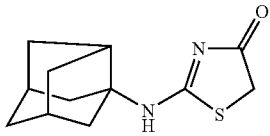

Synthesis was performed from N-tricyclo[3.3.1.0~3,7~]non-3-ylthiourea and ethyl bromoacetate according to Method D1.

$^1$H NMR (400 MHz, DMSO-d$_6$) δ 1.45-1.61 (m, 4 H), 1.92-2.07 (m, 6 H), 2.23 (m, 1.7 H, major rotamer), 2.82 (m, 0.3 H, minor rotamer), 2.45 (t, J=6.7 Hz, 0.85 H, major rotamer), 2.66 (t, J=6.8 Hz, 0.15 H, minor rotamer), 3.83 (s, 1.7 H, major rotamer), 4.09 (s, 0.3 H, minor rotamer), 9.38 (s, 1 H). MS (ESI+) for C$_{12}$H$_{16}$N$_2$OS m/z 237 (M+H)$^+$.

Example 9

6-(Cyclooctylamino)-5-thia-7-azaspiro[3.4]oct-6-en-8-one

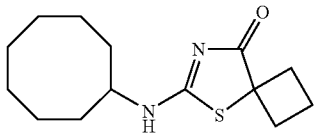

Synthesis was performed from N-cyclooctylthiourea and ethyl 1-bromocyclobutanecarboxylate according to Method D2.

$^1$H NMR (400 MHz, DMSO-d$_6$) δ 1.45-1.79 (m, 14 H), 1.86-2.00 (m, 1 H), 2.05-2.17 (m, 1 H), 2.41-2.53 (m, 4 H, obscured by solvent signal), 4.01 (m, 1 H), 9.09 (d, J=7.5 Hz, 1 H).

$^{13}$C NMR (100 MHz, DMSO-d$_6$) δ 16.31, 23.07, 24.97, 26.69, 30.88, 33.52, 54.69, 60.30, 175.09, 191.25. MS (ESI+) for C$_{14}$H$_{22}$N$_2$OS m/z 267 (M+H)$^+$.

Example 10

6-(Cycloheptylamino)-5-thia-7-azaspiro[3.4]oct-6-en-8-one

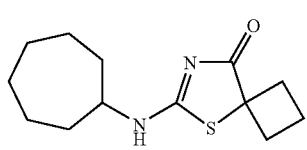

Synthesis was performed from N-cycloheptylthiourea and ethyl 1-bromocyclobutanecarboxylate according to Method D.

$^1$H NMR (400 MHz, DMSO-d$_6$) δ 1.35-1.65 (m, 10 H), 1.83-1.97 (m, 3 H), 2.05-2.17 (m, 1 H), 2.41-2.53 (m, 4 H, obscured by solvent signal), 3.96 (m, 1 H), 9.09 (d, J=7.5 Hz, 1 H). MS (ESI+ for C$_{13}$H$_{20}$N$_2$OS m/z 253 (M+H)$^+$.

Example 11

6-(Bicyclo[2.2.1]hept-2-ylamino)-5-thia-7-azaspiro[3.4]oct-6-en-8-one

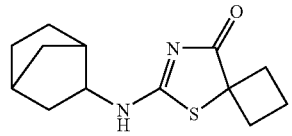

Synthesis was performed from N-bicyclo[2.2.1]hept-2-ylthiourea and ethyl 1-bromocyclobutanecarboxylate according to Method D.

$^1$H NMR (400 MHz, DMSO-d$_6$) δ 1.05-1.22 (m, 3 H), 1.33-1.49 (m, 4 H), 1.63-1.70 (m, 1 H), 1.86-2.00 (m, 1 H), 2.05-2.22 (m, 3 H), 2.42-2.53 (m, 4 H, obscured by solvent signal), 3.74 (m, 1 H) 8.98 (d, J=7.5 Hz, 1 H). MS (ESI+) for C$_{13}$H$_{18}$N$_2$OS m/z 251 (M+H)$^+$.

Example 12

6-[(2,2,3,3-Tetramethylcyclopropyl)amino]-5-thia-7-azaspiro[3.4]oct-6-en-8-one

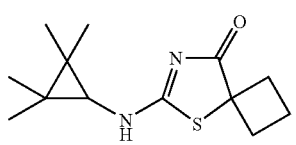

Synthesis was performed from N-(2,2,3,3-tetramethylcyclopropyl)thiourea and ethyl 1-bromocyclobutanecarboxylate according to Method D.

$^1$H NMR (400 MHz, DMSO-d$_6$) δ 0.92 (s, 3 H), 0.94 (s, 3 H), 1.06 (s, 3 H), 1.08 (s, 3 H), 1.88-2.00 (m, 1 H), 2.01 (s, 1 H), 2.06-2.17 (m, 1 H), 2.40-2.54 (m, 4 H, obscured by solvent signal), 8.78 (s br., 1 H). MS (ESI+) for C$_{13}$H$_{20}$N$_2$OS m/z 253 (M+H)$^+$.

Example 13

6-[(2-Methylphenyl)amino]-5-thia-7-azaspiro[3,4]oct-6-en-8-one

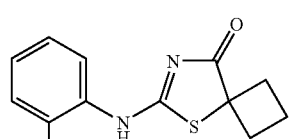

Synthesis was performed from N-(2-methylphenyl)thiourea and ethyl 1-bromocyclobutanecarboxylate according to Method D.

$^1$H NMR (400 MHz, DMSO-d$_6$) δ 1.89 (m, 1 H), 2.04-2.13 (m, 1 H), 2.08 (s, 3 H), 2.39-2.48 (m, 2 H), 2.56-2.66 (m, 2 H), 6.81 (d, J=7.6 Hz, 1 H), 7.03 (m, 1 H), 7.14 (m, 1 H), 7.20 (d, J=7.4 Hz, 1 H), 11.67 (s br., 1 H). MS (ESI+) for C$_{13}$H$_{14}$N$_2$OS m/z 247 (M+H)$^+$.

Example 14

2-[(cyclohexylmethyl)amino]-5,5-dimethyl-1,3-thiazol-4(5H)-one

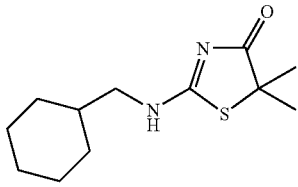

Synthesis was performed from N-(cyclohexylmethyl)thiourea and ethyl 2-bromoisobutyrate according to Method C.

$^1$H NMR (270 MHz, DMSO-d$_6$) δ ppm 0.81-1.04 (m, 2 H) 1.03-1.32 (m, 3 H) 1.43-1.54 (m, 6 H) 1.55-1.78 (m, 6 H) 3.18-3.32 (m, 2 H) 9.28 (s, 1 H). MS (ESI+) for C$_{12}$H$_{20}$N$_2$OS m/z 242 (M+H)$^+$.

Example 15

2-[(2-fluorophenyl)amino]-5-isopropyl-1,3-thiazol-4(5H)-one

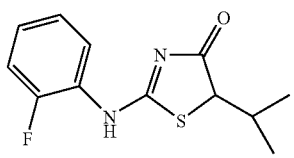

Synthesis was performed from N-(2-fluorophenyl)thiourea and Ethyl 2-bromo-2-methylbutyrate according to Method C.

$^1$H NMR (270 MHz, DMSO-d$_6$) δ ppm 0.79-0.98 (m, 6 H) 2.29-2.44 (m, 1 H) 4.48 (d, J=3.59 Hz, 1 H) 6.91-7.40 (m, 4 H). MS (ESI+) for C$_{12}$H$_{13}$FN$_2$OS m/z 253 (M+H)$^+$.

Example 16

2-[(cyclohexylmethyl)amino]-5-(2-hydroxyphenyl)-1,3-thiazol-4(5H)-one

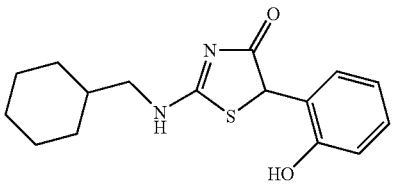

Synthesis was performed from N-(cyclohexylmethyl)thiourea and 3-bromo-2-coumarone according to Method F.

$^1$H NMR (400 MHz, CHLOROFORM-D) δ ppm 0.80-1.00 (m, 2H) 1.05-1.27 (m, 3H) 1.55-1.81 (m, 6H) 3.24-3.34 (m, 2H), 5.42 (s, 1H) 6.73-6.81 (m, 2H) 7.02-7.14 (m, 2H) 9.19 (br.s, 1H, N—H) 9.81 (br.s, 1H, N—H). MS (ESI+) for C$_{16}$H$_{20}$N$_2$O$_2$S m/z 305 (M+H)$^+$.

Example 17

(5S)-2-(cycloheptylamino)-5-methyl-1,3-thiazol-4(5H)-one

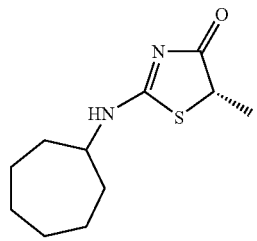

Synthesis was performed from N-cycloheptylthiourea and (2S)-2-bromopropanoic acid according to Method C.

$^1$H NMR (400 MHz, CHLOROFORM-D) δ ppm 1.35-1.70 (m, 12H) 1.45 (d, J=7.3 Hz, 3H) 1.72-2.00 (m, 1H) 3.90-4.03 (m, 1H). MS (ESI+) for C$_{11}$H$_{18}$N$_2$OS m/z 227 (M+H)$^+$.

Example 18

(5R)-2-(cycloheptylamino)-5-methyl-1,3-thiazol-4(5H)-one

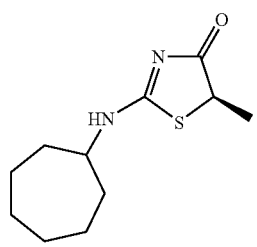

Synthesis was performed from N-cycloheptylthiourea and (2R)-2-bromopropanoic acid according to Method C.

$^1$H NMR (400 MHz, CHLOROFORM-D) δ ppm 1.36-1.70 (m, 12H) 1.45 (d, J=7.5 Hz, 3H) 1.82-1.96 (m, 1H) 3.93-4.02 (m, 1H). MS (ESI+) for C$_{11}$H$_{18}$N$_2$OS m/z 227 (M+H)$^+$.

Example 19

2-(cycloheptylamino)-5-ethyl-1,3-thiazol-4(5H)-one

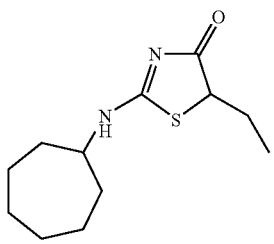

Synthesis was performed from N-cycloheptylthiourea and 2-bromobutyric acid according to Method C.

$^1$H NMR (270 MHz, METHANOL-d$_4$) δ ppm 0.90-1.06 (m, 3 H) 1.40-2.17 (m, 14 H) 4.26 (dd, J=7.86, 4.02 Hz, 1 H) 4.52-4.68 (m, 1 H). MS (ESI+) for C$_{12}$H$_{20}$N$_2$OS m/z 241 (M+H)$^+$.

Example 20

2-(cycloheptylamino)-5-isopropyl-1,3-thiazol-4(5H)-one

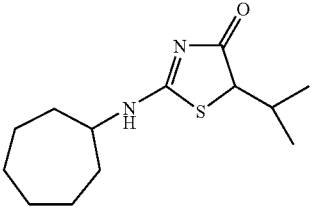

Synthesis was performed from N-cycloheptylthiourea and Ethyl 2-bromo-2-methylbutyrate according to Method C.

$^1$H NMR (270 MHz, METHANOL-$d_4$) mixture of three different rotamers ~40%/30%/30% only the major; δ ppm 0.92-1.08 (m, 6 H) 1.43-2.16 (m, 12 H) 2.39-2.56 (m, 1 H) 3.98-4.20 (m, 1 H) 4.24-4.34 (m, 1 H). MS (ESI+) for $C_{13}H_{22}N_2OS$ m/z 255 (M+H)$^+$.

Example 21

5-tert-butyl-2-(cycloheptylamino)-1,3-thiazol-4(5H)-one

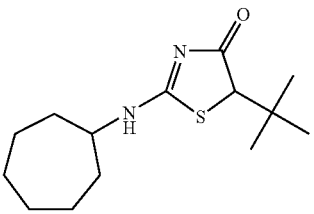

Synthesis was performed from 2-amino-3,3-dimethylbutanoic acid and N-cycloheptylthiourea according to Method E and C.

$^1$H NMR (270 MHz, METHANOL-$d_4$) δ ppm 0.83-0.94 (m, 4.5 H) 0.98-1.12 (m, 4.5 H) 1.47-1.97 (m, 11 H) 2.36-2.58 (m, 1 H) 4.03-4.18 (m, 1 H) 4.34-4.42 (m, 1H). MS (ESI+) for $C_{14}H_{24}N_2OS$ m/z 269 (M+H)$^+$.

Example 22

2-(cyclooctylamino)-5-ethyl-1,3-thiazol-4(5H)-one

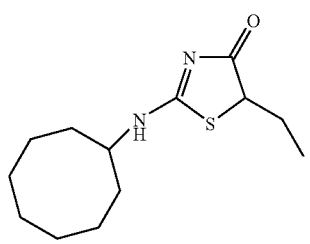

Synthesis was performed from N-cyclooctyl-thiourea and 2-bromo-butyric acid according to Method C1.

$^1$H NMR (270 MHz, METHANOL-$d_4$) δ ppm 0.89-1.03 (m, 3 H) 1.43-1.99 (m, 15 H) 1.98-2.16 (m, 1 H) 4.21-4.32 (m, 1 H) 4.55-4.66 (m, 1 H). MS (ESI+) for $C_{13}H_{22}N_2OS$ m/z 255 (M+H)$^+$.

Example 23

5-isopropyl-2-[(2-isopropylphenyl)amino]-1,3-thiazol-4(5H)-one

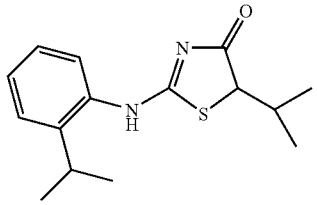

Synthesis was performed from N-(2-isopropylphenyl)thiourea and 2-bromo-3-methylbutyric acid according to Method C1.

$^1$H NMR (270 MHz, DMSO-$d_6$) δ ppm 0.87 (dd, J=8.78, 6.80 Hz, 6 H) 1.12-1.17 (m, 6 H) 2.28-2.44 (m, 1 H) 2.93-3.09 (m, 1 H) 4.40 (d, J=3.46 Hz, 1 H) 6.83 (dd, J=7.24, 1.79 Hz, 1 H) 7.07-7.21 (m, 2 H) 7.26-7.36 (m, 1 H).
MS (ESI+) for $C_{15}H_{20}N_2OS$ m/z 277 (M+H)$^+$.

Example 24

5-ethyl-2-[(2-isopropylphenyl)amino]-1,3-thiazol-4(5H)-one

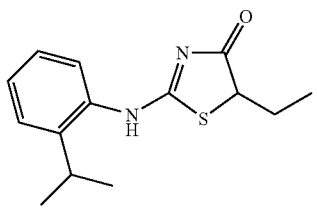

Synthesis was performed from N-(2-isopropylphenyl)thiourea and 2-bromo-butyric acid according to Method C1.

$^1$H NMR (270 MHz, DMSO-$d_6$) δ ppm 0.88 (t, J=7.30 Hz, 3 H) 1.14 (d, J=6.93 Hz, 6 H) 1.63-2.06 (m, 2 H) 2.93-3.11 (m, 1 H) 4.32 (dd, J=7.36, 4.27 Hz, 1 H) 6.75-6.92 (m, 1 H) 7.06-7.21 (m, 2 H) 7.24-7.42 (m, 1 H). MS (ESI+) for $C_{14}H_{18}N_2OS$ m/z 263 (M+H)$^+$.

Example 25

2-[(2-chlorophenyl)amino]-5-ethyl-1,3-thiazol-4(5H)-one

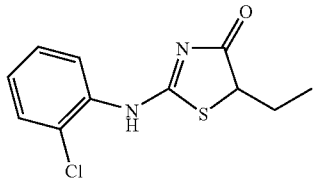

Synthesis was performed from N-(2-chlorophenyl)thiourea and 2-bromo-butyric acid according to Method C1.

$^1$H NMR (270 MHz, METHANOL-$d_4$) δ ppm 1.01-1.23 (m, 3 H) 1.98-2.34 (m, 2 H) 4.58-4.72 (m, 1 H) 7.28-7.54 (m, 3 H) 7.54-7.68 (m, 1 H). MS (ESI+) for $C_{11}H_{11}ClN_2OS$ m/z 255 (M+H)$^+$.

Example 26

5-ethyl-2-[(2-methylphenyl)amino]-1,3-thiazol-4(5H)-one

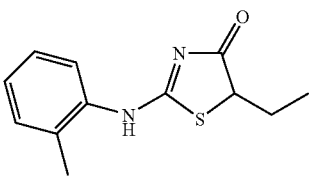

Synthesis was performed from N-(2-methylphenyl)thiourea and 2-bromo-butyric acid according to Method C1.

$^1$H NMR (270 MHz, METHANOL-d$_4$) δ ppm 1.07-1.18 (m, J=7.36, 7.36 Hz, 3H) 1.98-2.36 (m, 2 H) 2.11-2.13 (m, 3H) 4.52-4.75 (m, 1 H) 7.12 (dd, J=20.54, 7.67 Hz, 1 H) 7.22-7.46 (m, 3 H). MS (ESI+) for C$_{12}$H$_{14}$N$_2$OS m/z 235 (M+H)$^+$.

Example 27

5-isopropyl-2-[(2,2,3,3-tetramethylcyclopropyl)amino]-1,3-thiazol-4(5H)-one

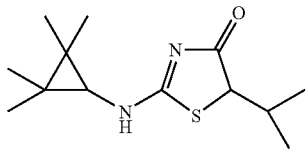

Synthesis was performed from N-(2,2,3,3-tetramethylcyclopropyl)thiourea and ethyl-2-bromoisovalerate according to Method C.

$^1$H NMR (400 MHz, CDCl$_3$) δ ppm 0.99 (d, J=6.6 Hz, 3 H), 1.08-1.16 (m, 9 H), 1.20 (d, J=3.4 Hz, 6 H), 2.17 (s, 1 H), 2.59-2.72 (m, 1 H), 4.25 (d, J=3.9 Hz, 1 H). MS (ES+) m/z 255 (M+H$^+$).

Example 28

2-(bicyclo[2.2.1]hept-2-ylamino)-5-(4-hydroxybenzyl)-1,3-thiazol-4(5H)-one

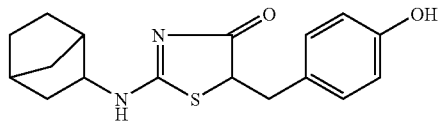

Synthesis was performed from (2S)-2-amino-3-(4-hydroxyphenyl)propanoic acid and N-bicyclo[2.2.1]hept-2-ylthiourea according to Method E and C.

$^1$H NMR (270 MHz, DMSO-d$_6$) δ 1.11 (d, J=9.65 Hz, 3 H) 1.24-1.54 (m, 4 H) 1.56-1.76 (m, 1 H) 2.04-2.27 (m, 2 H) 2.61-2.84 (m, 1 H) 3.26 (dd, J=14.10, 3.96 Hz, 1 H) 3.70 (s, 1 H) 4.42-4.52 (obscured by HDO peak) (m, 1 H) 6.57-6.72 (m, 2 H) 6.92-7.08 (m, 2 H) 9.07 (d, J=6.19 Hz, 1 H) $^1$H NMR (270 MHz, METHANOL-d$_4$) δ 1.07-1.62 (m, 7H) 1.67-1.88 (m, 1 H) 2.07-2.36 (m, 2 H) 2.92-3.11 (m, 1 H) 3.32-3.44 (partly obscured by MeOD peak) (m, 1 H) 3.64-3.76 (m, 1 H) 4.51-4.68 (m, 1 H) 6.62-6.76 (m, 2 H) 6.99-7.12 (m, 2 H). MS (ESI+) for C$_{17}$H$_{20}$N$_2$O$_2$S m/z 317 (M+H)$^+$

Example 29

5-[(cyclohexylmethyl)amino]-4-thia-6-azaspiro[2.4]hept-5-en-7-one

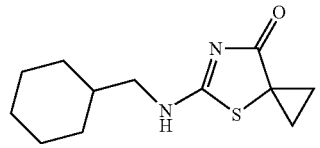

Synthesis was performed from N-(cyclohexylmethyl)thiourea according to Method I.

$^1$H NMR (400 MHz, CHLOROFORM-D) δ ppm 0.94-1.07 (m, 2 H) 1.10-1.36 (m, 3 H) 1.49-1.54 (m, 2 H) 1.66-1.86 (m, 8 H) 3.19 (d, J=6.59 Hz, 2 H). MS m/z 239 (M+H)$^+$

Example 30

2-(cycloheptylamino)-5-(3,4-dihydroxybenzyl)-1,3-thiazol-4(5H)-one

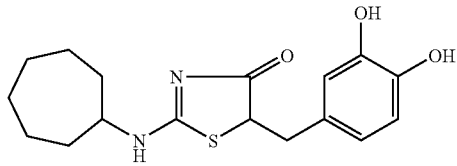

Synthesis was performed from (2S)-2-amino-3-(3,4-dihydroxyphenyl)propanoic acid and N-cycloheptylthiourea according to Method E and C.

$^1$H NMR (500 MHz, Solvent) δ 1.43-1.57 (m, 6 H) 1.56-1.73 (m, 5 H) 1.84-2.01 (m, 2 H) 2.87 (dd, J=14.13, 9.42 Hz, 1 H) (1 H hidden in MeOD peak) 3.97-4.06 (m, 1 H) 4.44-4.51 (m, 1 H) 6.52-6.57 (m, 1 H) 6.64-6.68 (m, 2 H). MS (ESI+) for C$_{17}$H$_{22}$N$_2$O$_3$S m/z 335 (M+H)$^+$

Example 31

2-(cycloheptylamino)-5-(1H-imidazol-4-ylmethyl)-1,3-thiazol-4(5H)-one

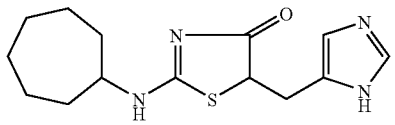

Synthesis was performed from (2S)-2-amino-3-(1H-imidazol-4-yl)propanoic acid and N-cycloheptylthiourea according to Method E and C.

$^1$H NMR (270 MHz, METHANOL-d$_4$) δ 1.43-2.06 (m, 12 H) 3.33-3.56 (m, 2 H) 3.93-4.08 (m, 1 H) 4.57-4.69 (m, 1 H) 7.27-7.42 (m, 1 H) 8.76-8.87 (m, 1 H). MS (ESI+) for C$_{14}$H$_{20}$N$_4$OS m/z 293 (M+H)$^+$

Example 32

2-(cycloheptylamino)-5-isobutyl-1,3-thiazol-4(5H)-one

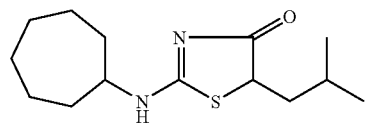

Synthesis was performed from (2S)-2-amino-4-methylpentanoic acid and N-cycloheptylthiourea according to Method E and C.

$^1$H NMR (270 MHz, METHANOL-$d_4$) δ 0.91-1.04 (m, 6 H) 1.43-1.86 (m, 12 H) 1.92-2.12 (m, 3 H) 3.95-4.11 (m, 1 H) 4.29-4.48 (m, 1 H). MS (ESI+) for $C_{14}H_{24}N_2OS$ m/z 269 (M+H)$^+$

Example 33

2-(cycloheptylamino)-5-(1H-indol-3-ylmethyl)-1,3-thiazol-4(5H)-one

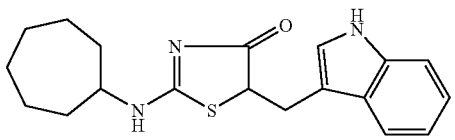

Synthesis was performed from (2S)-2-amino-3-(1H-indol-3-yl)propanoic acid and N-cycloheptylthiourea according to Method E and C.

$^1$H NMR (270 MHz, CHLOROFORM-D) δ 1.27-1.80 (m, 11 H) 1.84-1.99 (m, 1 H) 3.23-3.40 (m, 2 H) 3.76 (dd, J=15.09, 3.46 Hz, 1 H) 4.65 (d, J=9.15, 3.96 Hz, 1 H) 7.10-7.28 (m, 3 H) 7.40 (d, J=7.92 Hz, 1 H) 7.59 (d, J=7.92 Hz, 1 H) 8.26 (s, 1 H). MS (ESI+) for $C_{19}H_{23}N_3OS$ m/z 342 (M+H)$^+$

Example 34

2-(cycloheptylamino)-5-(4-hydroxybenzyl)-1,3-thiazol-4(5H)-one

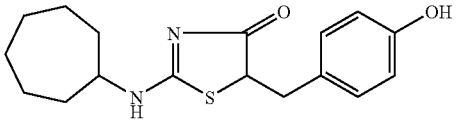

Synthesis was performed from (2S)-2-amino-3-(4-hydroxyphenyl)propanoic acid and N-cycloheptylthiourea according to Method E and C.

$^1$H NMR (270 MHz, METHANOL-$d_4$) δ ppm 1.37-2.07 (m, 12 H) 2.91-3.11 (m, 1 H) 3.32-3.43 (m, 1 H) 3.86-4.02 (m, 1 H) 4.48-4.66 (m, 1 H) 6.60-6.76 (m, 2 H) 6.99-7.11 (m, 2 H). MS (ESI+) for $C_{17}H_{22}N_2O_2S$ m/z 319 (M+H)$^+$

Example 35

(5R)-2-(cycloheptylamino)-5-(cyclohexylmethyl)-1,3-thiazol-4(5H)-one

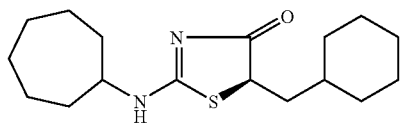

Synthesis was performed from (2S)-2-amino-3-cyclohexylpropanoic acid and N-cycloheptylthiourea according to Method E and C.

$^1$H NMR (270 MHz, CHLOROFORM-D) δ ppm 0.85-1.90 (m, 22 H) 1.93-2.10 (m, 2 H) 2.14-2.30 (m, 1 H) 3.35-3.57 (m, 1 H) 4.23 (dd, J=11.32, 3.77 Hz, 1 H). MS (ESI+) for $C_{17}H_{28}N_2OS$ m/z 309 (M+H)$^+$

Example 36

2-(cyclooctylamino)-5-(4-hydroxybenzyl)-1,3-thiazol-4(5H)-one

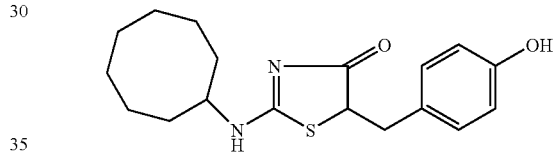

Synthesis was performed from (2S)-2-amino-3-(4-hydroxyphenyl)propanoic acid and N-cyclooctylthiourea according to Method E and C.

$^1$H NMR (270 MHz, CHLOROFORM-D) δ ppm 1.41-1.95 (m, 14 H) 3.07 (dd, J=14.47, 9.65 Hz, 1 H) 3.43-3.59 (m, 2 H) 4.46 (dd, J=9.65, 3.96 Hz, 1 H) 6.81 (d, J=8.41 Hz, 2 H) 7.08 (d, J=8.41 Hz, 2 H). MS (ESI+) for $C_{18}H_{24}N_2O_2S$ m/z 333 (M+H)$^+$

Example 37

(5S)-2-(cycloheptylamino)-5-(cyclohexylmethyl)-1,3-thiazol-4(5H)-one

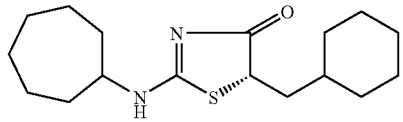

Synthesis was performed from (2R)-2-amino-3-cyclohexylpropanoic acid and N-cycloheptylthiourea according to Method E and C.

$^1$H NMR (270 MHz, CHLOROFORM-D) δ ppm 0.87-1.86 (m, 22 H) 1.89-2.11 (m, 2 H) 2.11-2.30 (m, 1 H) 3.34-3.60 (m, 1 H) 4.23 (dd, J=11.32, 3.77 Hz, 1 H) 8.81 (br.s, 1 H). MS (ESI+) for $C_{17}H_{28}N_2OS$ m/z 309 (M+H)$^+$

Example 38

[2-(cycloheptylamino)-4-oxo-4,5-dihydro-1,3-thiazol-5-yl]acetonitrile

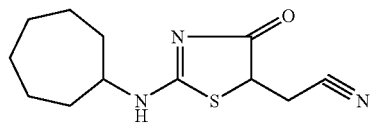

Synthesis was performed from (2S)-2-amino-3-cyanopropanoic acid and N-cycloheptylthiourea according to Method E and C.

$^1$H NMR (270 MHz, CHLOROFORM-D) δ ppm 1.36-2.14 (m, 12 H) 2.85-3.11 (m, 1 H) 3.12-3.32 (m, 1 H) 3.43-3.58 (m, 1 H) 4.31-4.46 (m, 1 H). MS (ESI+) for $C_{12}H_{17}N_3OS$ m/z 252 (M+H)$^+$

Example 39

5-ethyl-2-[(3-methylphenyl)amino]-1,3-thiazol-4(5H)-one

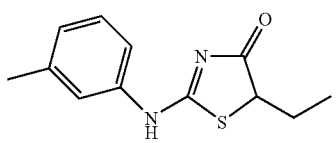

Commercial compound, SPECS.

MS (ESI+) for $C_{12}H_{14}N_2OS$ m/z 235 (M+H)$^+$

HPLC 99%, $R_T$=2.10 min (System A, 10-97% MeCN over 3 min).

HPLC 99%, $R_T$=1.58 min (System B, 10-97% MeCN over 3 min).

Example 40

2-(cycloheptylamino)-5-(pyridin-3-ylmethyl)-1,3-thiazol-4(5H)-one

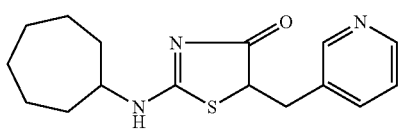

Synthesis was performed from (2S)-2-amino-3-pyridin-3-ylpropanoic acid and N-cycloheptylthiourea according to Method E and C.

$^1$H NMR (270 MHz, CHLOROFORM-D) δ ppm 1.39-1.84 (m, 9 H) 1.88-2.06 (m, 2 H) 3.39-3.54 (m, 1 H) 3.64 (s, 2 H) 3.97 (s, 1 H) 4.75 (s, 1 H) 7.84-7.95 (m, 1 H) 8.34 (d, J=7.67 Hz, 1 H) 8.75 (d, J=5.07 Hz, 1 H) 9.10 (s, 1 H). MS (ESI+) for $C_{16}H_{21}N_3OS$ m/z 304 (M+H)$^+$

Example 41

5-Isopropyl-2-[(2-methylphenyl)amino]-1,3-thiazol-4(5H)-one

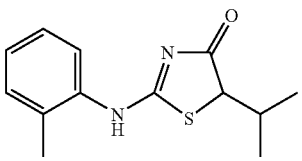

Synthesis was performed from N-(2-methylphenyl)thiourea and ethyl 2-bromo-3-methylbutanoate according to Method C.

$^1$H NMR (400 MHz, DMSO-d$_6$) δ 0.84 (d, J=6.6 Hz, 3 H), 0.88 (d, J=7.0 Hz, 3 H), 2.10 (s, 3 H), 2.34 (m, 1 H), 4.32 (d, J=3.4 Hz, 1 H), 6.83 (d, J=7.8 Hz, 1 H), 7.03 (m, 1 H), 7.16 (m, 1 H), 7.21 (d, J=7.6 Hz, 1 H). MS (ESI+) for $C_{13}H_{16}N_2OS$ m/z 249 (M+H)$^+$.

Example 42

2-(Cyclooctylamino)-5,5-dimethyl-1,3-thiazol-4(5H)-one

Synthesis was performed from ethyl-2-bromo-2-methylpropanoate and N-cyclooctylthiourea according to Method C1.

$^1$H NMR (270 MHz, DMSO-d$_6$) δ ppm 1.46 (s, 3H), 1.47 (s, 3H), 1.81-1.43 (m, 15H). MS (EI+) for $C_{13}H_{22}N_2OS$ m/z 255 (M+H)$^+$.

Example 43

2-(Cyclooctylamino)-5-isopropyl-1,3-thiazol-4(5H)-one

Synthesis was performed from 2-bromo-3-methylbutyric acid and N-cyclooctylthiourea according to Method C1.

$^1$H NMR (270 MHz, METHANOL-d4) Major isomer: δ ppm 0.85 (d, J=6.68 Hz, 3 H) 1.01 (d, J=6.93 Hz, 3 H) 1.44-1.91 (m, 14 H) 2.36-2.52 (m, 1 H) 3.98-4.12 (m, 1 H) 4.36 (d, J=3.71 Hz, 1 H). MS (EI+) for $C_{14}H_{24}N_2OS$ m/z 269 (M+H)$^+$.

Example 44

2-(Bicyclo[2.2.1]hept-2-ylamino)-1-thia-3-azaspiro[4.5]dec-2-en-4-one

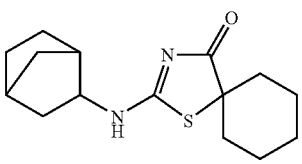

Synthesis was performed from N-bicyclo[2.2.1]hept-2-ylthiourea and methyl 1-bromocyclohexanecarboxylate according to Method D.

$^1$H NMR (400 MHz, CDCl$_3$) δ 1.12-2.44 (m, 21 H), 3.34 (m, 1 H).

MS (ESI+) for $C_{15}H_{22}N_2OS$ m/z 279 (M+H)$^+$.

Example 45

2-(Tricyclo[3.3.1.0~3,7~]non-3-ylamino)-1-thia-3-azaspiro[4.5]dec-2-en-4-one

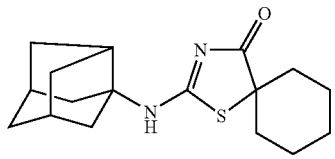

Synthesis was performed from N-tricyclo[3.3.1.0~3,7~]non-3-ylthiourea and methyl 1-bromocyclohexanecarboxylate according to Method D.

$^1$H NMR (400 MHz, CDCl$_3$) δ 1.24-2.19 (m, 20 H), 2.30 (m, 0.5 H, minor rotamer), 2.41 (m, 1.5 H, major rotamer), 2.53 (m, 0.25 H, minor rotamer), 2.75 (m, 0.75 H, major rotamer).

MS (ESI+) for C$_{17}$H$_{24}$N$_2$OS m/z 305 (M+H)$^+$.

Example 46

2-(Cycloheptylamino)-1-thia-3-azaspiro[4.5]dec-2-en-4-one

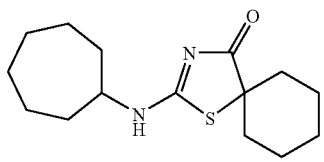

Synthesis was performed from N-cycloheptylthiourea and methyl 1-bromocyclohexanecarboxylate according to Method D.

$^1$H NMR (400 MHz, CDCl$_3$) δ 1.24-2.14 (m, 23 H), 3.48 (m, 1 H).

MS (ESI+) for C$_{15}$H$_{24}$N$_2$OS m/z 281 (M+H)$^+$.

Example 47

2-(Cyclooctylamino)-1-thia-3-azaspiro[4.5]dec-2-en-4-one

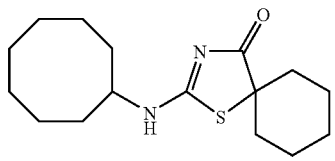

Synthesis was performed from N-cyclooctylthiourea and methyl 1-bromocyclohexanecarboxylate according to Method D.

$^1$H NMR (400 MHz, CDCl$_3$) δ 1.24-2.13 (m, 25 H), 3.55 (m, 1 H).

MS (ESI+) for C$_{16}$H$_{26}$N$_2$OS m/z 295 (M+H)$^+$.

Example 48

2-{[1-(4-Chlorophenyl)cyclobutyl]amino}-5-isopropyl-1,3-thiazol-4(5I)-one

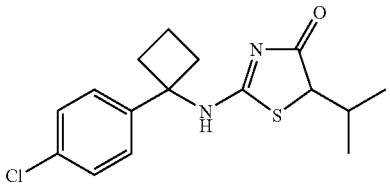

Synthesis was performed from N-[1-(4-chlorophenyl)cyclobutyl]thiourea and ethyl 2-bromo-3-methylbutanoate according to Method D.

$^1$H NMR (400 MHz, DMSO-d$_6$) δ 0.60 (d, J=6.5 Hz, 0.75 H, minor rotamer), 0.68 (d, J=6.6 Hz, 2.25 H, major rotamer), 0.82 (d, J=6.8 Hz, 0.75 H, minor rotamer), 0.92 (d, J=6.8 Hz, 2.25 H, major rotamer), 1.77-1.87 (m, 1 H), 1.93-2.03 (m, 1 H), 2.21-2.33 (m, 1 H), 2.42-2.65 (m, 4 H, obscured by solvent signal), 4.14 (d, J=3.5 Hz, 0.25 H, minor rotamer), 0.68 (d, J=3.7 Hz, 0.75H, major rotamer), 7.38 (m, 3 H, major rotamer), 7.45 (m, 1 H, minor rotamer), 9.87 (s, 1 H).

MS (ESI+) for C$_{16}$H$_{19}$ClN$_2$OS m/z 323 (M+H)$^+$.

Example 49

6-{[1-(4-Chlorophenyl)cyclobutyl]amino}-5-thia-7-azaspiro[3.4]oct-6-en-8-one

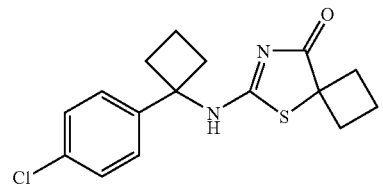

Synthesis was performed from N-[1-(4-chlorophenyl)cyclobutyl]thiourea and ethyl 1-bromocyclobutanecarboxylate according to Method D.

$^1$H NMR (400 MHz, DMSO-d$_6$) δ 1.73-2.12 (m, 4 H), 2.32-2.60 (m, 8 H, obscured by solvent signal), 7.39 (m, 3.3 H, major rotamer), 7.44 (m, 0.7 H, minor rotamer), 9.83 (s, 1 H).

MS (ESI+) for C$_{16}$H$_{17}$ClN$_2$OS m/z 321 (M+H)$^+$.

Example 50

2-(cycloheptylamino)-5,5-diethyl-1,3-thiazol-4(5H)-one

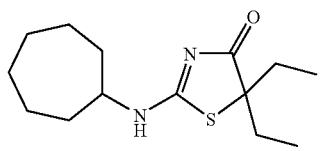

Synthesis was performed from N-cycloheptylthiourea and 2-ethylbutyric acid according to Method J and D.

$^1$H NMR (400 MHz, CHLOROFORM-D) δ ppm 0.89-1.01 (m, 6 H) 1.40-2.09 (m, 16 H) 3.44-3.55 (m, 1 H)

MS (ESI+) for C$_{14}$H$_{24}$N$_2$OS m/z 269 (M+H)$^+$

Example 51

(5S)-5-isopropyl-2-{[(2S)-2-phenylpropyl]amino}-1,3-thiazol-4(5H)-one

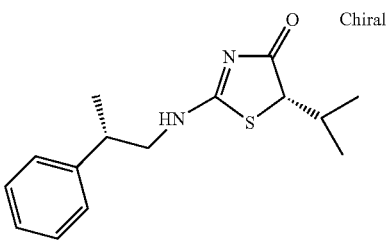

Synthesis was performed from N-[(2S)-2-phenylpropyl] thiourea and 2-bromo-3-methylbutyric acid according to Method D3.

$^1$H NMR (270 MHz, DMSO-$d_6$) the major rotamer δ ppm 0.54-0.85 (m, 3 H) 0.84-1.08 (m, 3 H) 1.08-1.37 (m, 3 H) 2.18-2.43 (m, 1 H) 2.91-3.22 (m, 1 H) 3.27-3.47 (m, J=7.30 Hz, 1 H) 3.44-3.62 (m, 1 H) 4.18-4.37 (m, 1 H) 6.95-7.43 (m, 5 H) 9.26 (s, 1 H, N—H).

MS (ESI+) for $C_{15}H_{20}N_2OS$ m/z 277 (M+H)$^+$.

Example 52

(5R)-5-ethyl-2-{[(2S)-2-phenylpropyl]amino}-1,3-thiazol-4(5H)-one

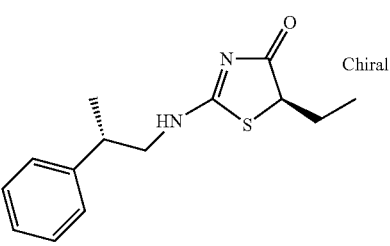

Synthesis was performed from N-[(2S)-2-phenylpropyl] thiourea and 2-bromo-butyric acid according to Method D3.

$^1$H NMR (270 MHz, DMSO-$d_6$) the major rotamer δ ppm 0.51-0.70 (m, 3 H) 1.10-1.36 (m, 3 H) 1.45-1.80 (m, 1 H) 3.11-3.34 (m, 1 H) 3.65-3.84 (m, 2 H) 3.80-4.07 (m, 1 H) 4.30-4.48 (m, 1 H) 7.10-7.41 (m, 5 H).

MS (ESI+) for $C_{14}H_{18}N_2OS$ m/z 263 (M+H)$^+$.

Example 53

(5S)-5-ethyl-2-{[(2S)-2-phenylpropyl]amino}-1,3-thiazol-4(5H)-one

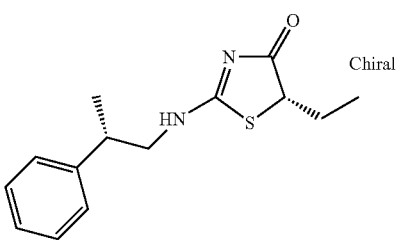

Synthesis was performed from N-[(2S)-2-phenylpropyl] thiourea and 2-bromo-butyric acid according to Method D3.

$^1$H NMR (270 MHz, DMSO-$d_6$) the major rotamer δ ppm 0.73-0.97 (m, 3 H) 1.10-1.35 (m, 3 H) 1.53-1.82 (m, 1 H) 1.83-2.11 (m, 1 H) 2.92-3.13 (m, 1 H) 3.48-3.67 (m, 2 H) 4.10-4.32 (m, 1 H) 7.09-7.45 (m, 5 H) 9.27 (s, 1 H, N—H).

MS (ESI+) for $C_{14}H_{18}N_2OS$ m/z 263 (M+H)$^+$.

Example 54

(5R)-5-isopropyl-2-{[(2R)-2-phenylpropyl]amino}-1,3-thiazol-4(5H)-one

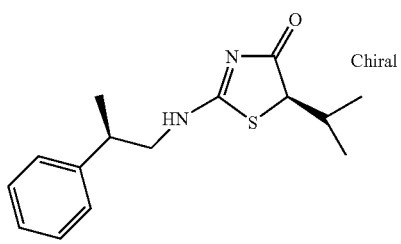

Synthesis was performed from N-[(2R)-2-phenylpropyl] thiourea and 2-bromo-3-methylbutyric acid according to Method D3.

$^1$H NMR (270 MHz, DMSO-$d_6$) the major rotamer δ ppm 0.50-0.80 (m, 3 H) 0.84-1.06 (m, 3 H) 1.09-1.32 (m, 3 H) 2.22-2.43 (m, 1 H) 2.91-3.19 (m, 1 H) 3.27-3.45 (m, 2 H) 4.14-4.38 (m, 1 H) 7.07-7.44 (m, 5 H) 9.25 (s, 1 H, N—H).

MS (ESI+) for $C_{15}H_{20}N_2OS$ m/z 277 (M+H)$^+$.

Example 55

(5S)-5-isopropyl-2-{[(2R)-2-phenylpropyl]amino}-1,3-thiazol-4(5H)-one

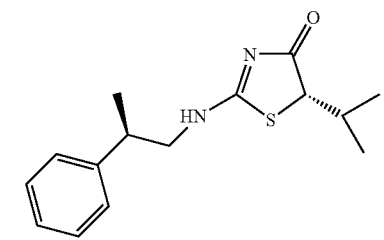

Synthesis was performed from N-[(2R)-2-phenylpropyl] thiourea and 2-bromo-3-methylbutyric acid according to Method D3.

$^1$H NMR (270 MHz, DMSO-$d_6$) the major rotamer δ ppm 0.40-0.58 (m, J=6.68 Hz, 3 H) 0.71-0.87 (m, 3 H) 1.03-1.29 (m, 3 H) 2.11-2.24 (m, 1 H) 3.62-3.81 (m, 2 H) 3.83-4.03 (m, 1 H) 4.36-4.51 (m, 1 H) 7.10-7.41 (m, 5 H).

MS (ESI+) for $C_{15}H_{20}N_2OS$ m/z 277 (M+H)$^+$.

Example 56

(5R)-5-ethyl-2-{[(2R)-2-phenylpropyl]amino}-1,3-thiazol-4(5H)-one

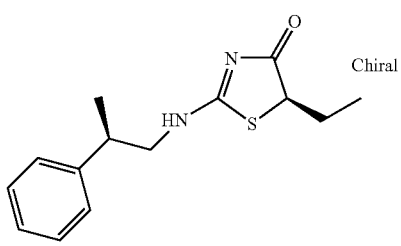

Synthesis was performed from N-[(2R)-2-phenylpropyl] thiourea and 2-bromo-butyric acid according to Method D3.

$^1$H NMR (270 MHz, DMSO-$d_6$) the major rotamer δ ppm 0.75-0.97 (m, 3 H) 1.05-1.35 (m, 3 H) 1.58-1.82 (m, 1 H)

1.82-2.05 (m, 1 H) 2.92-3.17 (m, 1 H) 3.44-3.65 (m, 2 H) 4.12-4.36 (m, 1 H) 7.09-7.49 (m, 5 H) 9.26 (s, 1 H).
MS (ESI+) for $C_{14}H_{18}N_2OS$ m/z 263 (M+H)$^+$.

Example 57

(5S)-5-ethyl-2-{[(2R)-2-phenylpropyl]amino}-1,3-thiazol-4(5H)-one

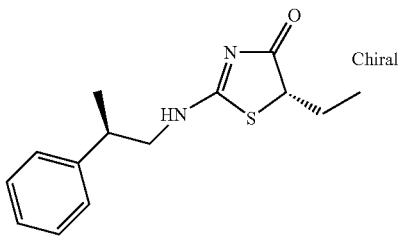

Synthesis was performed from N-[(2R)-2-phenylpropyl]thiourea and 2-bromo-butyric acid according to Method D3.

$^1$H NMR (270 MHz, DMSO-d$_6$) the major rotamer δ ppm 0.53-0.74 (m, J=7.30, 7.30 Hz, 3 H) 1.08-1.33 (m, 3 H) 1.43-1.63 (m, 1 H) 1.62-1.89 (m, 1 H) 3.13-3.36 (m, 1 H) 3.66-3.86 (m, J=13.61, 7.17 Hz, 1 H) 3.83-4.04 (m, 1 H) 4.26-4.51 (m, J=4.95 Hz, 1 H) 7.09-7.44 (m, 5 H).
MS (ESI+) for $C_{14}H_{18}N_2OS$ m/z 263 (M+H)$^+$.

Example 58

2-Anilino-5-isopropyl-1,3-thiazol-4(5H)-one

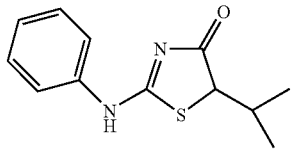

Synthesis was performed from N-phenylthiourea and ethyl 2-bromo-3-methylbutanoate according to Method C.

$^1$H NMR (400 MHz, CHLOROFORM-D) δ ppm 1.00 (s, 6 H), 2.40-2.73 (m, 1 H), 4.04-4.34 (m, 1 H), 7.01-7.56 (m, 6 H); MS [M+H]$^+$ m/z=235.

Example 59

5-Isopropyl-2-[(2-morpholin-4-ylethyl)amino]-1,3-thiazol-4(5H)-one

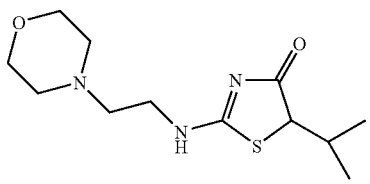

Synthesis was performed from N-(2-morpholin-4-ylethyl)thiourea and ethyl 2-bromo-3-methylbutanoate according to Method C.

$^1$H NMR (400 MHz, CHLOROFORM-D) δ ppm 0.70-1.25 (m, 8 H), 2.58 (s, 1 H), 2.78-4.09 (m, 10 H), 4.18-4.54 (m, 1 H); MS [M+H]$^+$ m/z=272.

Example 60

2-(Bicyclo[2.2.1]hept-2-ylamino)-1-thia-3-azaspiro[4.4]non-2-en-4-one

Example 61

2-(Cycloheptylamino)-1-thia-3-azaspiro[4.4]non-2-en-4-one

Example 62

2-(Cyclooctylamino)-1-thia-3-azaspiro[4.4]non-2-en-4-one

Example 63

2-[(2,2,3,3-Tetramethylcyclopropyl)amino]-1-thia-3-azaspiro[4.4]non-2-en-4-one

Examples 60-63 were prepared using one of the methodologies described above.

Example 64

2-[(2-chlorobenzyl)amino]-5-isopropyl-1,3-oxazol-4(5H)-one

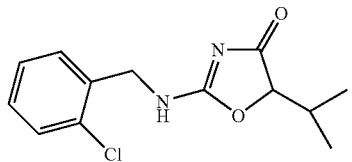

Synthesis was performed from 2-amino-5-isopropyl-1,3-oxazol-4(5H)-one and 2-Chlorobenzylamine according to Method G+H.

$^1$H NMR (400 MHz, DMSO-d$_6$) δ ppm 0.62 (d, J=6.84 Hz, 0.75 H) 0.82 (d, J=6.84 Hz, 2.25 H) 0.90 (d, J=6.96 Hz, 0.75 H) 0.99 (d, J=6.84 Hz, 2.25 H) 1.97-2.13 (m, 1 H) 4.41-4.50 (m, 0.5 H) 4.51-4.56 (m, 1.5 H) 4.59 (d, J=3.66 Hz, 0.25 H) 4.63 (d, J=3.66 Hz, 0.75 H) 7.30-7.41 (m, 3 H) 7.45-7.49 (m, 1 H) 9.30 (s, 1 H). MS (ESI+) for $C_{13}H_{15}ClN_2O_2$ m/z 267 (M+H)$^+$

Example 65

2-[(4-chlorobenzyl)amino]-5-isopropyl-1,3-oxazol-4(5H)-one

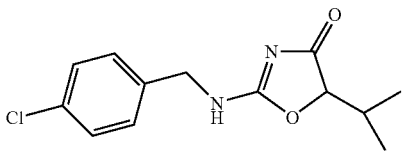

Synthesis was performed from 2-amino-5-isopropyl-1,3-oxazol-4(5H)-one and 4-Chlorobenzylamine according to Method G+H.

$^1$H NMR (400 MHz, DMSO-d$_6$) δ ppm 0.63 (d, J=6.84 Hz, 0.75 H) 0.80 (d, J=6.84 Hz, 2.25 H) 0.90 (d, J=6.96 Hz, 0.75 H) 0.98 (d, J=6.84 Hz, 2.25 H) 1.96-2.13 (m, 1 H) 4.37-4.41 (m, 0.5 H) 4.44 (d, J=6.10 Hz, 1.5 H) 4.58 (d, J=3.54 Hz, 0.25 H) 4.61 (d, J=3.78 Hz, 0.75 H) 7.27-7.34 (m, 2 H) 7.37-7.45 (m, 2 H) 9.28 (t, J=5.98 Hz, 0.75 H) 9.49 (s, 0.25 H).
MS (ESI+) for $C_{13}H_{15}ClN_2O_2$ m/z 267 (M+H)$^+$

Example 66

5-isopropyl-2-[(2,2,6,6-tetramethylpiperidin-4-yl)amino]-1,3-oxazol-4(5H)-one

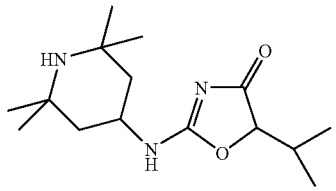

Synthesis was performed from 2-amino-5-isopropyl-1,3-oxazol-4(5H)-one and 4-amino-2,2,6,6-tetramethylpiperidine according to Method G+H.
$^1$H NMR (400 MHz, DMSO-d$_6$) δ ppm 0.78-0.84 (m, 3 H) 0.95-1.04 (m, 3 H) 1.33-1.43 (m, 12 H) 1.44-1.58 (m, 2 H) 1.91-2.16 (m, 3 H) 3.96-4.09 (m, 1 H) 4.60 (d, J=3.78 Hz, 0.9 H) 4.84 (d, J=4.03 Hz, 0.1 H) 7.83 (d, J=11.60 Hz, 0.75 H) 8.16 (s, 0.25 H) 8.76 (d, J=11.48 Hz, 1 H) 9.00 (d, J=7.45 Hz, 1 H). MS (ESI+) for $C_{15}H_{27}N_3O_2$ m/z 282 (M+H)$^+$

Example 67

5-isopropyl-2-morpholin-4-yl-1,3-oxazol-4(5H)-one

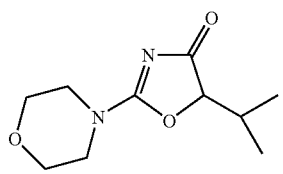

Synthesis was performed from 2-amino-5-isopropyl-1,3-oxazol-4(5H)-one and morpholine according to Method G+H.
$^1$H NMR (400 MHz, DMSO-d$_6$) δ ppm 0.81 (d, J=6.84 Hz, 2 H) 0.87 (d, J=6.84 Hz, 1 H) 0.97-1.01 (m, 3 H) 2.02-2.17 (m, 1 H) 3.06-3.13 (m, 2 H) 3.53-3.77 (m, 6 H) 4.66 (d, J=3.91 Hz, 0.67 H) 4.84 (d, J=4.15 Hz, 0.33H). MS (ESI+) for $C_{10}H_{16}N_2O_3$ m/z 213 (M+H)$^+$

Example 68

5-isopropyl-2-[(2-morpholin-4-ylethyl)amino]-1,3-oxazol-4(5H)-one

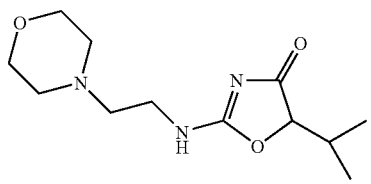

Synthesis was performed from 2-amino-5-isopropyl-1,3-oxazol-4(5H)-one and N-(2-aminoethyl)morpholine according to Method G+H.
$^1$H NMR (400 MHz, DMSO-d$_6$) δ ppm 0.87 (d, J=6.84 Hz, 1 H) 0.92 (d, J=6.84 Hz, 2 H) 1.02 (d, J=6.96 Hz, 3 H) 2.01-2.24 (m, 1 H) 2.63-2.72 (m, 2 H) 2.72-2.81 (m, 1 H) 3.03 (t, J=6.41 Hz, 1 H) 3.08-3.36 (m, 3 H) 3.54-3.67 (m, 1 H) 3.65-3.71 (m, 2 H) 3.75-3.86 (m, 2 H) 4.57 (d, J=4.15 Hz, 0.5 H) 4.82 (d, J=4.39 Hz, 0.5 H) 7.32-8.39 (m, 1 H). MS (ESI+) for $C_{12}H_{21}N_3O_3$ m/z 256 (M+H)$^+$

Example 69

2-(4-benzylpiperidin-1-yl)-5-isopropyl-1,3-oxazol-4(5H)-one

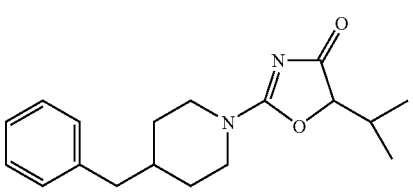

Synthesis was performed from 2-amino-5-isopropyl-1,3-oxazol-4(5H)-one and 4-benzylpiperidine according to Method G+H.
$^1$H NMR (400 MHz, DMSO-d$_6$) δ ppm 0.76-0.82 (m, 2.25 H) 0.87 (d, J=6.84 Hz, 0.75 H) 0.95-1.01 (m, 3 H) 1.07-1.35 (m, 2 H) 1.60-1.88 (m, 3 H) 2.00-2.18 (m, 1 H) 2.53 (d, J=7.08 Hz, 2 H) 2.74-2.86 (m, 0.5 H) 2.95-3.10 (m, 1.5 H) 3.23 (d, J=12.57 Hz, 0.5 H) 4.03 (d, J=13.55 Hz, 0.75 H) 4.10 (d, J=13.18 Hz, 0.75 H) 4.62 (d, J=3.78 Hz, 0.75 H) 4.84 (d, J=4.15 Hz, 0.25 H) 7.15-7.22 (m, 3 H) 7.24-7.32 (m, 2 H). MS (ESI+) for $C_{18}H_{24}N_2O_2$ m/z 301 (M+H)$^+$

Example 70

2-azocan-1-yl-5-isopropyl-1,3-oxazol-4(5H)-one

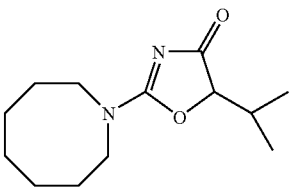

Synthesis was performed from 2-amino-5-isopropyl-1,3-oxazol-4(5H)-one and heptamethyleneimine according to Method G+H.
$^1$H NMR (400 MHz, DMSO-d$_6$) δ ppm 0.80 (d, J=6.84 Hz, 3 H) 1.00 (d, J=6.96 Hz, 3 H) 1.32-1.43 (m, 1 H) 1.47-1.56 (m, 5 H) 1.67-1.76 (m, 4 H) 2.04-2.13 (m, 1 H) 3.37-3.47 (m, 2 H) 3.58-3.71 (m, 2 H) 4.64 (d, J=3.54 Hz, 1 H). MS (ESI+) for $C_{13}H_{22}N_2O_2$ m/z 239 (M+H)$^+$

Example 71

2-[(cyclohexylmethyl)amino]-5-phenyl-1,3-oxazol-4(5H)-one

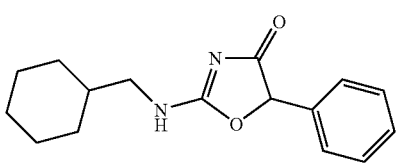

Synthesis was performed from 2-amino-5-phenyl-1,3-oxazol-4(5H)-one and aminomethylcyclohexane according to Method G+H.
$^1$H NMR (400 MHz, DMSO-d$_6$) δ ppm 0.92 (m, 2 H) 1.14 (m, 3 H) 1.57 (m, 6 H) 3.14 (m, 2 H) 5.72 (s, 0.7 H) 5.74

(s, 0.3 H) 7.28 (m, 2 H) 7.39 (m, 3 H) 9.00 (t, J=5.74 Hz, 0.7 H) 9.25 (s, 0.3 H). MS (ESI+) for C$_{16}$H$_{20}$N$_2$O$_2$ m/z 273 (M+H)$^+$ Example 72

2-(cycloheptylamino)-5-phenyl-1,3-oxazol-4(5H)-one

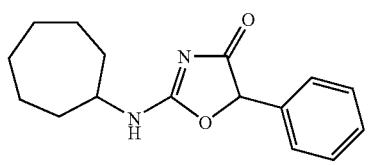

Synthesis was performed from 2-amino-5-phenyl-1,3-oxazol-4(5H)-one and cycloheptylamine according to Method G+H.

$^1$H NMR (400 MHz, DMSO-d$_6$) δ ppm 1.35-1.70 (m, 10 H) 1.92 (m, 2 H) 3.78 (m, 1 H) 5.69 (s, 0.75 H) 5.73 (s, 0.25 H) 7.28 (m, 2 H) 7.39 (m, 3 H) 8.92 (s, 1 H). MS (ESI+) for C$_{16}$H$_{20}$N$_2$O$_2$ m/z 273 (M+H)$^+$ Example 73

5-benzyl-2-[(cyclohexylmethyl)amino]-1,3-oxazol-4(5H)-one

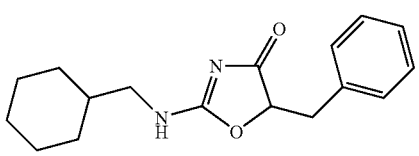

Synthesis was performed from 2-amino-5-benzyl-1,3-oxazol-4(5H)-one and aminomethylcyclohexane according to Method G+H.

$^1$H NMR (400 MHz, DMSO-d$_6$) δ ppm 0.7-1.7 (m, 11 H) 2.93 (m, 3 H) 3.16 (m, 1 H) 4.95 (m, 1 H) 7.23 (m, 5 H) 8.56 (s, 1 H). MS (ESI+) for C$_{17}$H$_{22}$N$_2$O$_2$ m/z 287 (M+H)$^+$ Example 74

2-(cycloheptylamino)-5-isopropyl-1,3-oxazol-4(5H)-one

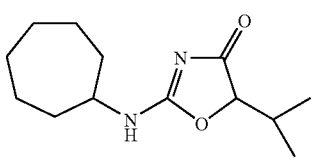

Synthesis was performed from 2-amino-5-isopropyl-1,3-oxazol-4(5H)-one and cycloheptylamine according to Method G+H.

$^1$H NMR (400 MHz, DMSO-d$_6$) δ ppm 0.77-082 (m, 3 H) 0.94-1.01 (m, 3 H) 1.32-1.67 (m, 10 H) 1.80-1.90 (m, 2 H) 2.00-2.11 (m, 1 H) 3.62-3.74 (m, 1 H) 4.53 (d, J=3.66 Hz, 0.73 H) 4.57 (d, J=3.66 Hz, 0.27 H) 8.80 (d, J=8.06 Hz, 0.73 H) 9.06 (s, 0.23 H). MS (ESI+) for C$_{13}$H$_{22}$N$_2$O$_2$ m/z 239 (M+H)$^+$ Example 75

2-(bicyclo[2.2.1]hept-2-ylamino)-5-isopropyl-1,3-oxazol-4(5H)-one

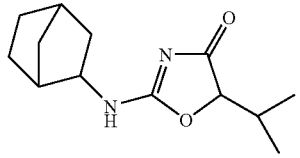

Synthesis was performed from 2-amino-5-isopropyl-1,3-oxazol-4(5H)-one and bicyclo[2.2.1]hept-2-amine according to Method G+H.

$^1$H NMR (400 MHz, DMSO-d$_6$) δ ppm 0.75-0.84 (m, 3 H) 0.93-1.02 (m, 3 H) 1.03-1.17 (m, 3 H) 1.34-1.52 (m, 4 H) 1.60-1.71 (m, 1 H) 1.98-2.25 (m, 3 H) 3.46-3.53 (m, 1 H) 4.50-4.58 (m, 1 H) 8.67 (s, 1 H). MS (ESI+) for C$_{13}$H$_{20}$N$_2$O$_2$ m/z 237 (M+H)$^+$ Example 76

2-(bicyclo[2.2.1]hept-2-ylamino)-5-isobutyl-1,3-oxazol-4(5H)-one

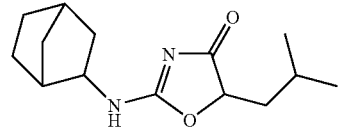

Synthesis was performed from 2-amino-5-isobutyl-1,3-oxazol-4(5H)-one and bicyclo[2.2.1]hept-2-amine according to Method G+H.

$^1$H NMR (400 MHz, CHLOROFORM-D) δ ppm 0.93-1.02 (m, 6 H) 1.08-137 (m, 3 H) 1.42-1.97 (m, 8 H) 2.28-2.41 (m, 2 H) 3.55-3.62 (m, 0.8 H) 3.75-3.83 (m, 0.2 H) 4.57-4.63 (m, 0.2 H) 4.68-4.75 (m, 0.8 H) 10.21 (s, 1 H) MS (ESI+) for C$_{14}$H$_{17}$N$_3$O$_3$ m/z 251 (M+H)$^+$ Example 77

2-(cycloheptylamino)-5-isobutyl-1,3-oxazol-4(5H)-one

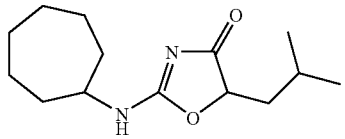

Synthesis was performed from 2-amino-5-isobutyl-1,3-oxazol-4(5H)-one and cycloheptylamine according to Method G+H.

$^1$H NMR (400 MHz, CHLOROFORM-D) δ ppm 0.93-1.01 (m, 6 H) 1.37-2.10 (m, 15 H) 3.71-3.82 (m, 0.65 H) 3.92-4.02 (m, 0.35 H) 4.60 (dd, J=10.07, 2.99 Hz, 0.35 H) 4.66 (dd, J=9.89, 3.05 Hz, 0.65 H) 9.38 (s, 1 H) MS (ESI+) for C$_{14}$H$_{17}$N$_3$O$_3$ m/z 253 (M+H)$^+$

Example 78

5-isobutyl-2-[(2-methylphenyl)amino]-1,3-oxazol-4(5H)-one

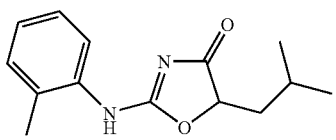

Synthesis was performed from 2-amino-5-isopropyl-1,3-oxazol-4(5H)-one and 2-methylphenylamine according to Method G+H.

$^1$H NMR (400 MHz, CHLOROFORM-D) δ ppm 0.93-1.03 (m, 6 H) 1.64-1.76 (m, 1 H) 1.81-1.95 (m, 2 H) 2.35 (s, 3 H) 4.82-4.89 (m, 1 H) 7.22-7.31 (m, 4 H)

MS (ESI+) for $C_{14}H_{17}N_3O_3$ m/z 247 (M+H)$^+$

Example 79

2-(bicyclo[2.2.1]hept-2-ylamino)-5-isopropyl-5-methyl-1,3-thiazol-4(5H)-one

To a solution of 2-amino-2,3-dimethylbutanoic acid (400 mg, 3.05 mmol) and potassium bromide (1.190 g, 10.00 mmol) in H$_2$O (4 mL) and concentrated H$_2$SO$_4$ (345 μL) at 0° C. under stirring was added via a syringe over 50 min a solution of NaNO$_2$ (295 mg, 4.27 mmol) in H$_2$O (900 μL). The reaction was allowed to slowly reach ambient temperature, and was then stirred overnight. The resulting solution was extracted with diethyl ether (2×15 mL), and the combined organic phases were washed with brined and dried over MgSO$_4$. The solvent was removed to give a transparent oil (290 mg), which was used without any further purification. A mixture of the crude oil (250 mg) and N-bicyclo[2.2.1]hept-2-ylthiourea (F18616001) (100 mg, 0.587 mmol) in 1,4-dioxane (600 μL) was stirred at 100° C. in a sealed tube for 3 days. The solvent was removed, and the residue was purified by preparative reverse-phase HPLC chromatography to give the product as a white solid.

$^1$H NMR (400 MHz, CDCl$_3$) δ 0.85-0.88 (m, 3 H), 0.99-1.04 (m, 3 H), 1.10-1.27 (m, 4 H), 1.46-1.58 (m, 2 H), 1.61-1.65 (m, 3 H), 1.71-1.88 (m, 2 H), 2.12-2.23 (m, 1 H), 2.27-2.42 (m, 2 H), 3.35 (m, 0.8 H, major isomer), 4.03 (m, 0.2 H, minor isomer). MS (ESI+) for $C_{14}H_{22}N_2OS$ m/z 267 (M+H)$^+$.

General Methodologies K-PP

Methodologies for Synthesis of Starting Materials: Carboxylic Acids, Esters, Acid Chlorides, Acyl Isothiocyanates:

Method K

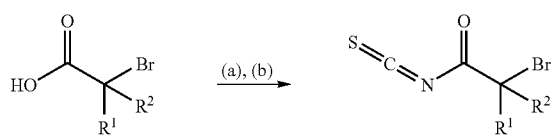

The thioisocyante intermediates can be prepared by the method K. Formation of the acid chloride, such as by treatment with oxalyl chloride and DMF, or thionyl chloride, followed by treatment with KNCS provides the thioisocyantes. Alternatively, treatment of the carboxylic acid with thionyl chloride, then bromination, such as with Br$_2$ and PBr$_3$, followed by treatment with KNCS also provides the thioisocyantes.

Method L

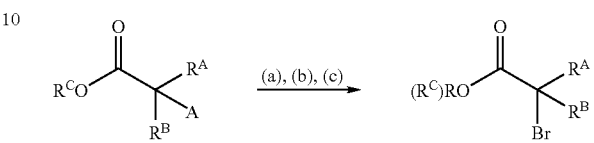

Preparation of bromo substituted esters and carboxylic acids is described in Method L. Bromination of the carboxylic acid, such as with Br$_2$, PCl$_3$ (cat.), followed by formation of the acid chloride, such as by treatment with oxalyl chloride or thionyl chloride, and treatment with alcohols, TMSCHN$_2$ or CH$_2$N$_2$, yields the desired compounds. Alternatively, the acid chloride can be formed first, followed by bromination step. Starting from esters, treatment with strong base, e.g. LDA, and a leaving group supplier such as TMSC1, followed by bromination provides the desired esters. Using amino acid starting materials (A=NH$_2$), bromination, such as by reaction with HBr in the presence of NaNO$_2$, yields the desired bromo acids.

Method M

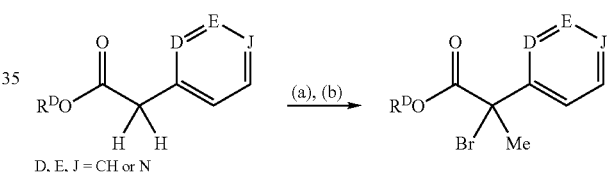

D, E, J = CH or N

Methylation of various substituted acids and esters, such as by treatment with base and an methyl halide, followed by bromination, yields the desired α-bromo-α-methyl compounds.

Method N

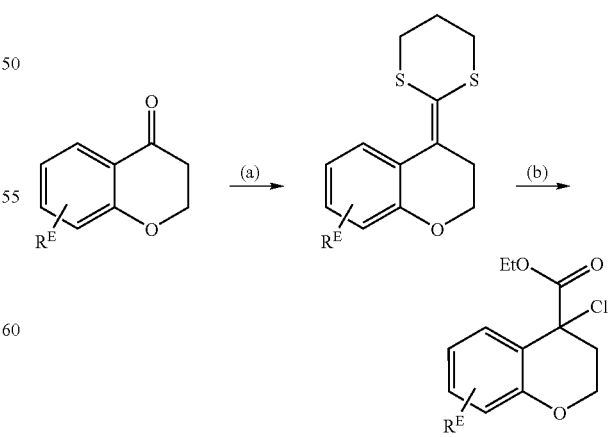

Conversion of various ketones to the esters is accomplished by Method N. Treatment with an appropriate dithiane, such as 2-trimethylsilyl-1,3-dithiane, in the presence of base, e.g. n-BuLi, followed by chlorination, such as with N-chlorosuccinimide, yields the desired compounds.

Methodologies for Synthesis of Starting Materials: Thioureas and Amines:

Method O

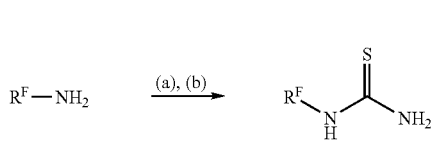

Formation of the desired thioureas is detailed in Method O. Treatment of amines with BzNCS, followed by deprotection, such as with base, yields the thioureas. Alternatively, the thiourea is formed through treatment with 1,1-thiocarbonyldiimidazole in the presence of base, e.g. $NEt_3$, followed by treatment with ammonia.

Method P

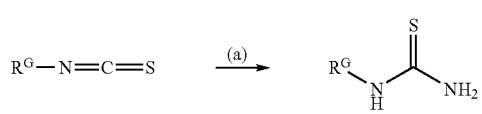

Alternatively, the thiourea is formed as described in Method P. Treatment of a substituted thioisocyanate with ammonia yields the desired thioureas.

Method Q

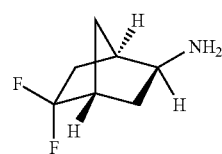

Preparation of substituted bicyclo[2.2.1]heptane amines is described in the synthetic scheme in shown in Example 97.

Method R

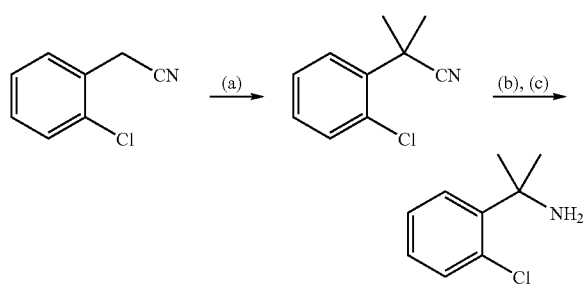

Preparation of 1-amino-1-methylethyl benzenes is described in Method R. Methylation of cyanomethylbenzenes, such as with treatment with methyl halides in the presence of non-nucleophilic base, e.g. KHMDS, yields the 1-cyano-1-methylethyl benzenes. Oxidation of the cyano compounds, such as with $H_2O_2$, in the presence of base, e.g. $K_2CO_3$, yields the amides. Hofmann rearrangement of the amides, such as by treatment with $(O_2CCF_3)_2IPh$, yields the desired amines.

Method S

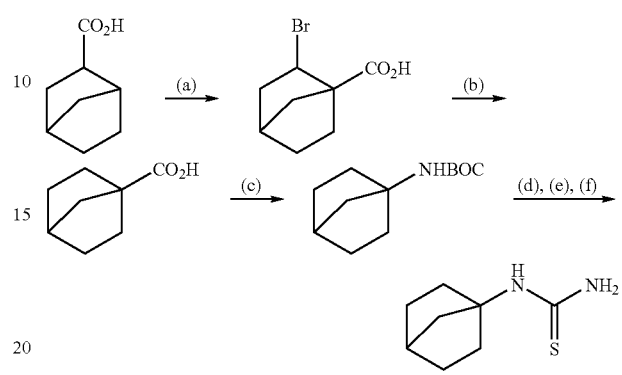

Bicyclo[2.2.1]heptanyl thioureas are provided via Method S. Bromination of carboxylic acids, such as with $Br_2$, $PCl_3$, and the resulting rearrangement provides the 2-bromo-1-carboxylic acids. Dehalogenation, such as with Zn in AcOH, yields the 1-carboxylic acids. The Curtius rearrangement such as by treatment with DPPA and a base, e.g. $NEt_3$, and an alcohol provides the protected amine. Deprotection, such as with acid, followed by formation of the thiourea and deprotection, as described above, provides the desired thioureas.

Method T

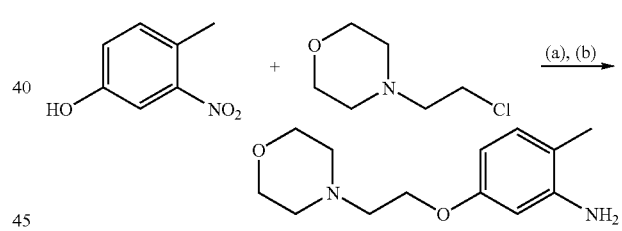

Base mediated substitution of a nitrophenol with a alkyl halide, provides the nitophenyl ether. For example $Cs_2CO_3$ can be used in the presence of NaI. Reduction of the nitro group, such as with $H_2$ in the presence of a catalyst, e.g. Pd/C, yields the desired amines.

Method U

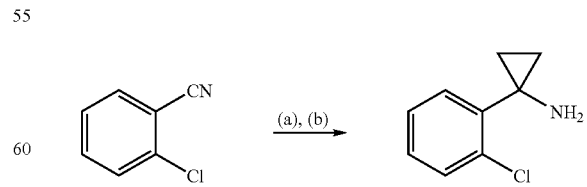

Method U describes the formation of cyclopropanamines from benzonitriles is accomplished by treatment with EtMgBr in the presence of $Ti(Oi-Pr)_4$, followed by treatment with $BF_3.OEt_2$.

Method V

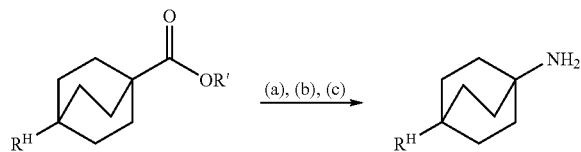

Formation of bicyclo[2.2.2]octanyl amines is described in Method V. De-esterification of the esters, such as with base, e.g. LiOH, followed the Curtius rearrangement as described previously and deprotection, e.g. acid, provides the desired amines.

Method W

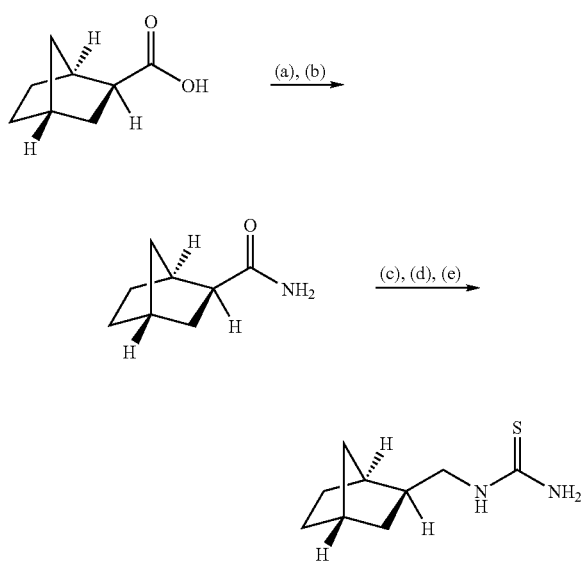

Formation of (bicyclo[2.2.1]heptanylmethyl)-thioureas from the carboxylic acids is described in Method W. Formation of the acid chloride, such as by treatment with oxalyl chloride and DMF (cat.), followed by treatment with ammonia or ammonium hydroxide, provides the amide. Reduction of the amide, such as with treatment with LiAlH$_4$, to the amine, followed by chemistry previously described, yields the desired thioureas.

Methodologies for Synthesis of Final Products:

Method X

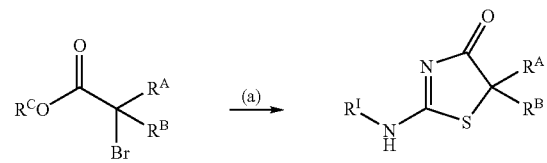

Thiazolones can be prepared by many methods, including that described in Method X. Treatment of a bromo-substituted carboxylic acid or ester with thiourea in the presence of base, such as DIEA provides the condensation/ring closure to the desired 2-amino-thiazolones.

Method Y

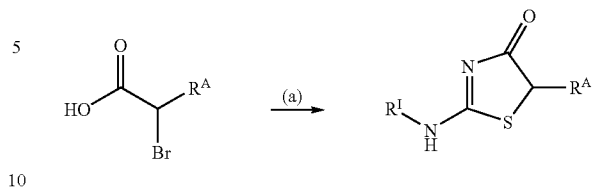

Alternatively, as shown in Method Y, treatment of a bromo-substituted carboxylic acid with thiourea in the presence of base, such as NaOAc provides the condensation/ring closure to the desired 2-amino-thiazolones.

Method Z

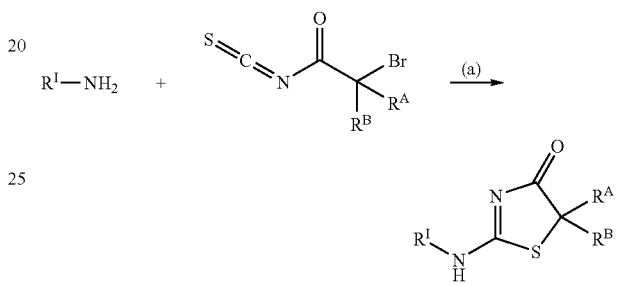

Thiazolones also can be prepared from amines by the method described in Method Z. Coupling of an amine with an isothiocyante, e.g. in the presence of base, such as NEt$_3$, provides the condensation/ring closure to the desired 2-amino-thiazolones.

Method AA

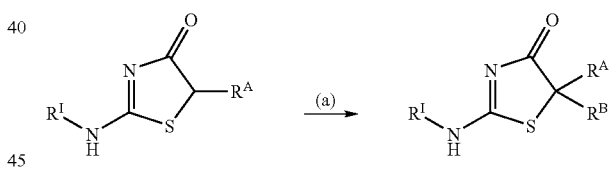

5,5-Disubstituted thiazolones can be prepared from thiazolones via the method described in Method AA. Treatment first with strong base, e.g. LDA or NaHMDS, then with a compound comprising an appropriate leaving group, such as R$^B$-LG, provides the desired compounds.

Method BB

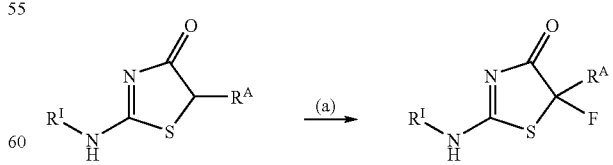

Similarly, formation of 5-fluoro-thiazolones can be prepared as described in Method BB. Treatment first with strong base, e.g. LDA or NaHMDS, and TMSCl, followed by fluorination, e.g. with Selectfluor, provides the desired compounds.

Method CC

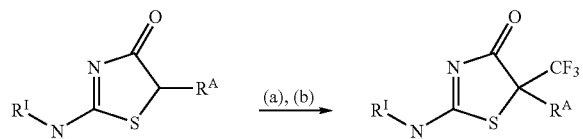

Similarly, formation of 5-trifluoromethyl-thiazolones can be prepared as described in Method CC. Treatment first with strong base, e.g. LDA or NaHMDS, and TMSCl, followed by trifluoromethylation, e.g. with S-(trifluoromethyl)dibenzothiophenium salt, provides the desired compounds.

Method DD

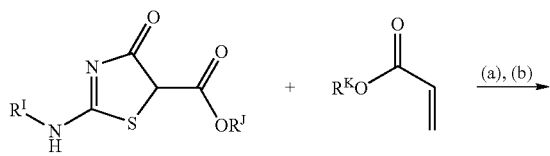

Formation of 5-carboxymethyl-thiazolones or the corresponding esters can be prepared as described in Method DD. Coupling of carboxylic acids with a substituted alkene, such as in the presence of DBU, followed by treatment with base, e.g. LiOH, provides the desired compounds.

Method EE

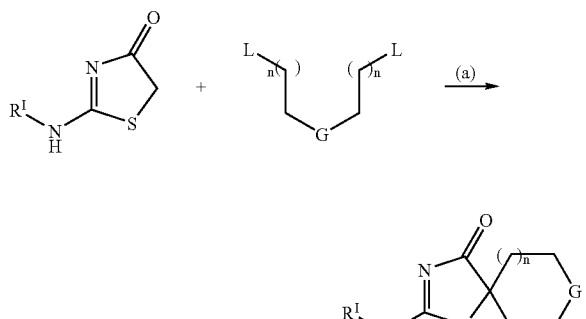

G = O, N, S, CH$_2$
L = Cl, Br, I, OSO$_2$R

Formation of 5-spiro-thiazolones can be prepared as described in Method EE. Coupling of the thiazolone in the presence of strong base, e.g. LDA or NaHMDS, provides the desired compounds. Alternatively, the cyclization can be achieved in two steps, alkylation first with base, e.g. HMDS, in the presence of TMSCl; followed by further treatment with base, e.g. LDA, in the presence of a bis-electrophile.

Method FF

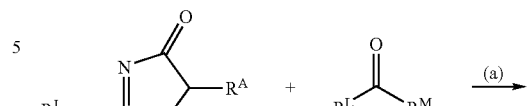

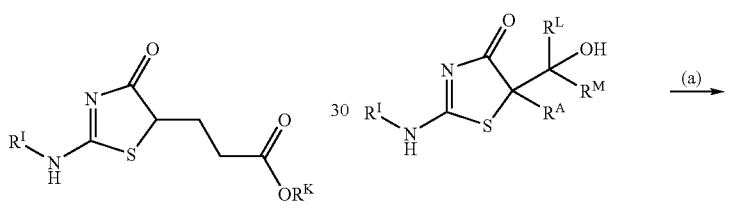

Formation of 5-hydroxymethyl-thiazolones can be prepared as described in Method FF. Treatment of a thiazolone with a ketone in the presence of strong base, e.g. LDA or NaHMDS, provides the desired compounds.

Method GG

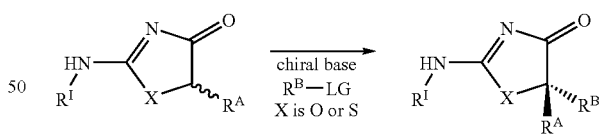

Formation of 5-fluoromethyl-thiazolones can be prepared as described in Method GG. Fluorination of 5-hydroxymethyl-thiazolones e.g. with DAST or Deoxo-Fluor, provides the desired compounds.

Method HH

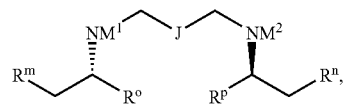

The compounds of the invention can be prepared by the method described in this scheme. Alkylation of the racemic thiazalone with a chiral base, such as where $R^m$ and $R^n$ are independently selected from alkyl, aryl, and heterocyclyl, where $R^o$ and $R^p$ are independently selected from aryl, where J is alkyl, O, NH or S, and where $M^1$ and $M^2$ are independently selected from Li, Na, K, Cs, Cu, Zn, and Mg, e.g. a chiral lithium base, more specifically

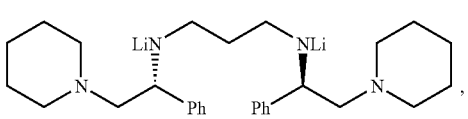

and an appropriate alkylating agent, such as a alkyl halide (e.g. an alkyl iodide) or sulfonate (e.g., mesylate, triflate), [LG is halide, tosylate, mesylate, triflate, or the like] provides the desired chiral di-substituted thiazolone. Preferably, the alkylation is performed in the presence of amine base, such as TMEDA. Treatment with the R,R form of the base provides the stereochemistry shown when $R^3$ is methyl. Treatment with the S,S form provides the opposite stereochemistry to that shown when $R^3$ is methyl. The reaction is maintained at a temperature below about RT, preferably below about 0° C., more preferably at or below about −15° C. An aprotic solvent, e.g. toluene is acceptable.

Method II

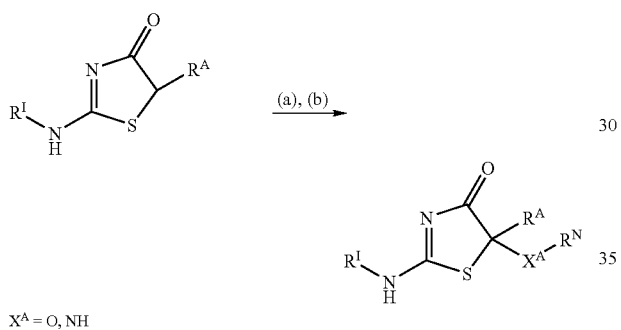

$X^A$ = O, NH

Formation of thiazolone amines and ethers can be prepared as described in Method II. Bromination of thiazolones e.g. with NBS or other techniques known to one skilled in the art, followed by treatment with an amine or alcohol, provides the desired compounds.

Method JJ

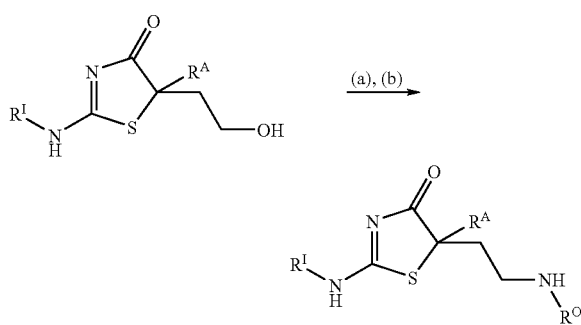

Formation of thiazolone amines can be prepared from the alcohols as described in Method JJ. Following the procedure for the Dess-Martin Periodinane or Swern reactions, followed reductive amidation, such as with reacting with an amine together with $NaBH(OAc)_3$ or $NaBH_3CN$, provides the desired compounds.

Method KK

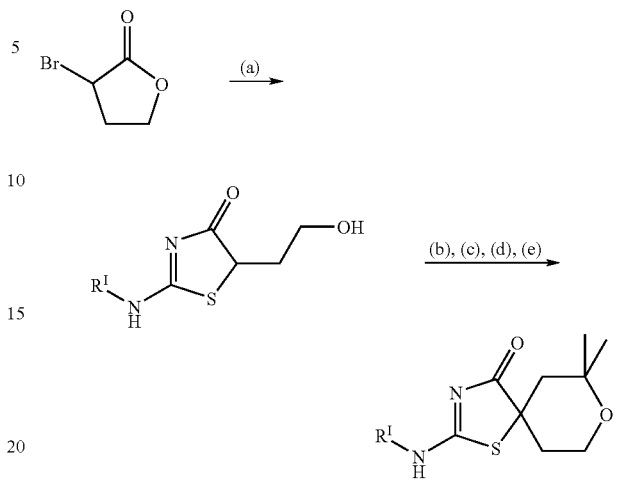

Alternatively, formation of 5-spiro-thiazolones can be prepared from the furanone as described in Method KK. Treatment of the furanone with a thiourea provides thiazolone alcohol. Protection of the alcohol, such as with dihydropyran in the presence of acid, followed by treatment with strong base, e.g. LDA, and 3-bromo-2-methylprop-1-ene, and deprotection, e.g. with PTSA, and cyclization, such as with acid, provides the desired compounds.

Method LL

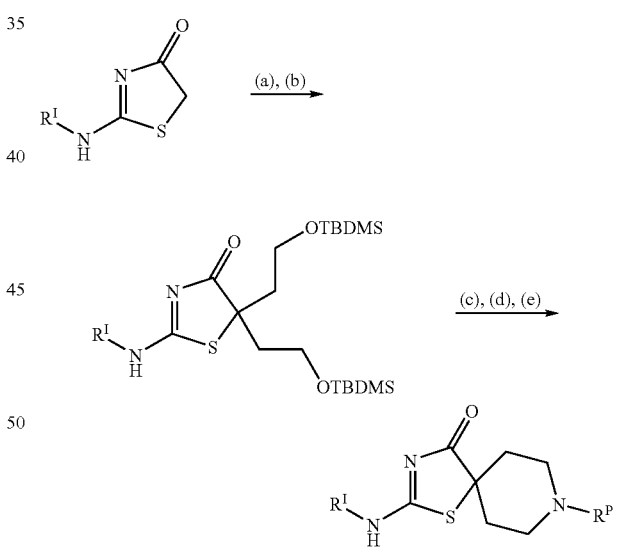

Further, formation of 5-spiro-thiazolones can be prepared from the thiazolone as described in Method LL. Treatment of the thiazolone with strong base, e.g. LDA or NaHMDS and alkylation, such as with (2-bromoethoxy)(tert-butyl)dimethylsilane provides the protected thiazolone alcohol. A subsequent round of base and silane provides the disubstituted thiazolone. Deprotection, e.g. with acid, followed with addition of a compound containing an appropriate leaving group, e.g. MsCl, in the presence of base, e.g. DIEA, and cyclization, such as with a substituted amine, provides the desired spiro piperidine compounds.

Method MM

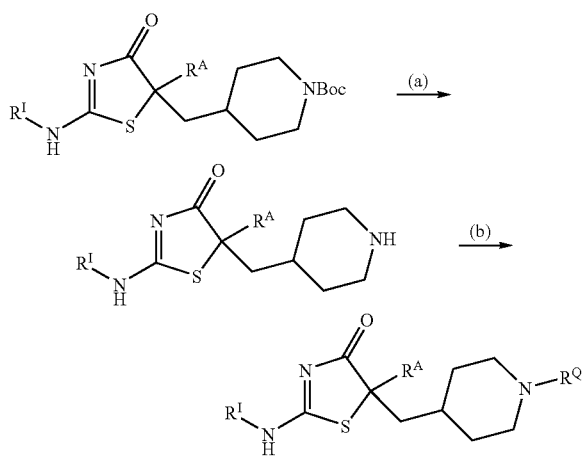

1-Substituted piperidinemethylthiazolones can be prepared by method MM. After deprotection, such as by treatment with acid, treatment with sulfonyl chlorides ($R^{12}SO_2Cl$) in the presence of base, e.g. $NEt_3$, provides compounds where $R^Q=SO_2R^S$. Alternatively, after deprotection, treatment with carboxylic acid ($R^RCO_2H$) with standard coupling chemistry, e.g. EDCI, and HOBt, provides compounds where $R^Q=COR^R$. Alternatively, after deprotection, treatment with active carbonyl compounds, e.g. acid anhydrides ($R^RCO—O—COR^R$) in the presence of base, e.g. DIEA, provides compounds where $R^Q=COR^R$.

Method NN

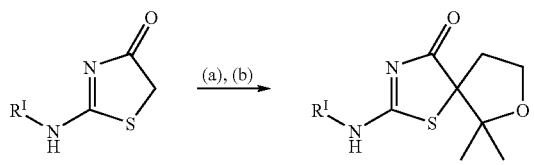

Formation of 5-spiro-thiazolones can be prepared from the thiazolone as described in Method NN. Treatment of the thiazolone with strong base, e.g. LDA and alkylation, such as with $BrCH_2CH_2Br$ provides the thiazolone bromoethyl compound. Further treatment with strong base, e.g. LDA, and dimethylketone, provides the desired spiro tetrahydrofuryl compounds.

Method OO

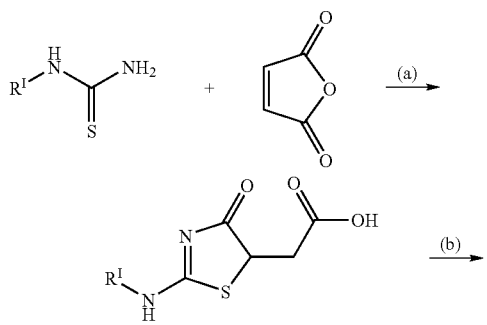

Substituted amidomethylthiazolones can be prepared by method OO. Treatment of a substituted thioureas and with active carbonyl compounds, e.g. maleic anhydride in the presence of acid, e.g. AcOH, provides the thiazolone carboxylic acids. Treatment of the acid with an amine, such as in the presence of a coupling reagent, e.g. HATU and base such as DIEA provides the desired amides.

Method PP

D, E, J = N or CH

Substituted thiazolone esters can be prepared from the alcohol by method PP. Treatment of an alcohol-substituted thiourea with active carbonyl compounds, e.g. an acid chloride, in the presence of base, e.g. DIEA, provides the desired esters.

Separation Methods

Many of the final compounds were separated by two main chromatographic methods. Normal phase liquid chromatography (NPLC) and supercritical fluid chromatography (SFC) were the two techniques utilized. NPLC was performed with Chiralpak AD/AD-H and Chiralcel OJ-H columns. The mobile phase consisted of hexane (0.2% diethylamine (DEA)) and/or methanol, ethanol (0.2% DEA), or isopropanol (0.2% DEA). All separations were conducted at ambient temperatures. Columns used with SFC were the Chiralpak AD-H and AS-H, the Chiralcel OD-H, and the Astec (R,R) P-CAP. The mobile phased was comprised of liquid carbon dioxide and an organic modifier such as methanol (with or without 0.2% DEA), ethanol (with or without 0.2% DEA), isopropanol (with or without 0.2% DEA), or acetonitrile (with or without 0.2% DEA). Organic modifiers were used individually with liquid carbon dioxide or in combinations with each other and the liquid carbon dioxide. Column/oven temperature was between 35 and 40° C., and the outlet pressure was either 100 or 120 bar.

Illustrative Method for Separating Enantiomers of Thioureas:

Stationary phase: ChiralPAK-AD, 20u, from Chiral Technology

Column: MODCOL spring load column, 4"×30 cm containing of 2.0 kg of stationary phase.

Mobile phase: 100% MeOH
Flow rate: 500 ml/min
Temperature: 30° C.
Detection wavelength: 230 nm Abbreviations AIBN, 2,2'-Azobisisobutyronitrile
aq., aqueous
brine, a saturated solution of NaCl in water
conc., concentrated
DAST, Diethylaminosulfur trifluoride
DBU, 1,8-Diazabicyclo[5.4.0]undec-7-ene
DCM, dichloromethane
DEAD, diethyl azodicarboxylate
Deoxo-Fluor, Bis(2-methoxyethyl)aminosulfur trifluoride
Dess-Martin Periodinane, 1,1,1-Tris(acetyloxy)-1,1-dihydro-1,2-benziodoxol-3(1H)-one
DIEA, N,N-Diisopropylethylamine
DMF, N,N-Dimethylformamide
DPPA, Diphenylphosphoryl azide
EDCI, 1-Ethyl-3-(3-dimethylaminopropyl)carbodiimide hydrochloride
EtOAc, ethyl acetate
EtOH, ethanol
HOBT, 1-Hydroxy-1H-benzotriazole
Hunig's base, N,N-Diisopropylethylamine
KHMDS, Potassium bis(trimethylsilyl)amine
LDA, Lithium diisopropylamide
LiHMDS, Lithium bis(trimethylsilyl)amine
MeOH, methanol
(R)-MOP, (R)-(+)-2-(diphenylphosphino)-2'-methoxy-1,1'-binaphthyl
MS; Mass Spectrum
MsCl, Methanesulfonyl chloride
MTBE, methyl tert-butyl ether
MW, microwave
NaHMDS, Sodium bis(trimethylsilyl)amine
NBS, N-Bromosuccinimide
n-BuLi, n-Butyllithium
PCC, Pyridinium chlorochromate
i-PrOH, iso-propanol
PTSA, p-toluenesulfonic acid
r.t., room temperature
sat'd, saturated solution in water
Selectfluor™, N-Fluoro-N'-chloromethyltriethylenediamine bis(tetrafluoroborate)
TBDMS, tert-butyl dimethylsilyl
THF, Tetrahydrofuran
TLC, thin layer chromatography
TMSCl, chlorotrimethylsilane Synthesis of Starting Materials: Carboxylic Acids, Esters, Acid Chlorides, and Acyl Isothiocyanates (Procedures Method-L, Method-M, Method-N, Method-K).

Unless otherwise noted, all materials were obtained from commercial suppliers and used without further purification. All parts are by weight and temperatures are in degrees centigrade unless otherwise indicated. All microwave-assisted reactions were conducted with a Smith Synthesizer from Personal Chemistry, Uppsala, Sweden or a Discover Instrument from CEM, Matthews, N.C. All compounds showed NMR spectra consistent with their assigned structures. Melting points were determined on a Buchi apparatus and are uncorrected. Mass spectral data was determined by electrospray ionization technique. All examples were purified to >95% purity as determined by high-performance liquid chromatography. Unless otherwise stated, reactions were run at RT.

Example 80

(S)-2-Bromo-3-methylbutanoic acid

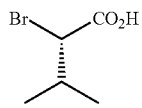

METHOD L

A 2 L jacketed reactor was charged with toluene (150 mL), water (150 mL) and 48% hydrobromic acid (260 mL, 2.30 mol). To this stirred, two-phase solution at 0° C., was added L-valine (96.2 g, 0.82 mol) in one portion (a mild exotherm was observed, temperature rose to 3.5° C.). The mixture was further cooled to −5° C., whereupon an aqueous solution of sodium nitrite (73.7 g, 1.07 mol) was added drop-wise over 6 h. The solution turned dark brown. Once the sodium nitrite was completely added, the reaction mixture was stirred for an additional 3 h at −5° C. Then, the reaction mixture was diluted with toluene (250 mL), warmed to 20° C., and stirred for 12 h. The organic layer was separated and the aqueous layer was extracted with toluene (300 mL). The toluene layers were combined and washed with a 20% sodium thiosulfate solution (200 mL) (virtually all color disappeared) followed by a 20% NaCl solution (200 mL). The organic layer was separated, and the solvent was concentrated in vacuo, and then placed on the high vacuum pump for 4 h to afford the title compound (107 g) as a pale yellow crystalline solid. MS (ESI, pos. ion) m/z: 179.1/180.9.

Example 81

1-Bromocyclopentanecarboxylic acid

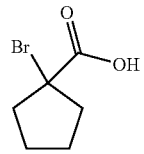

METHOD L

Phosphorus trichloride (0.54 mL, 6.20 mmol) was added drop-wise to the mixture of cyclopentanecarboxylic acid (14.2 g, 124 mmol) and bromine (7.35 mL, 143 mmol). The mixture was then gradually heated to 85° C. and stirred at this temperature in a sealed vessel for 12 h. After cooling to ambient temperature, the mixture was partitioned between EtOAc and water. The organic portion was separated, washed with water and brine, and conc. in vacuo to give the title compound as a white solid.

Example 82

Ethyl 1-bromocyclopentanecarboxylate

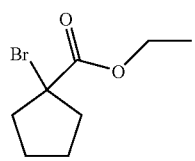

DMF (a few drops) was added to a mixture of 1-bromocyclopentanecarboxylic acid (23.9 g, 124 mmol) and oxalyl chloride (11.6 mL, 130 mmol) in 250 mL of $CH_2Cl_2$. The mixture was stirred at ambient temperature for 2 h. After removing the low-boiling solvents in vacuo, ethanol (50 mL) was added to the residue followed by the addition of N,N-diisopropylethylamine (22.7 mL, 130 mmol). The mixture was stirred at ambient temperature for 20 min. After removing the low-boiling solvents in vacuo, the residue was partitioned between diethyl ether and water. The organic portion was washed with water and brine, and conc. in vacuo. The crude product was filtered through a plug of silica gel using 0 to 10% EtOAc in hexanes as the eluant. The title compound was obtained as a pale oil.

Example 83

Methyl 2-bromo-2-cyclohexylacetate

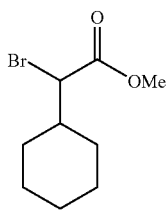

METHOD L

A 100 mL round-bottomed flask was charged with cyclohexylacetic acid (5.0 g, 0.035 mol) and thionyl chloride (4.92 g, 3.0 mL, 0.041 mol). This solution was heated to reflux during which time gas evolution occurred. After 1 h at 80° C., bromine (7.03 g, 2.25 mL, 0.044 mol) and phosphorus tribromide (0.350 mL) were added. The reaction temperature was maintained at 80° C. until the color faded from dark red to a light pink (~2 h) after which time MeOH (5.0 mL) was added, and the reaction mixture was refluxed for 30 min more. After cooling to room temperature, sodium thiosulfate was added, the suspension was filtered, and then concentrated in vacuo to provide the title compound. This bromo-ester was used without any further purification.

Example 84

Methyl 2-bromo-2-(tetrahydro-2H-pyran-4-yl)acetate

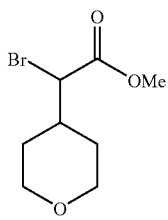

METHOD L

A 250 mL round-bottomed flask was charged with 2-(tetrahydro-2H-pyran-4-yl) acetic acid (5.0 g, 0.035 mol) and 100 mL of MeOH. To this solution was added 5 drops of conc. $H_2SO_4$. This mixture was heated at reflux for 12 h, after which time the MeOH was removed in vacuo. The remaining residue was dissolved in EtOAc, washed with saturated aqueous $NaHCO_3$, dried, and concentrated in vacuo to give the desired methyl ester. This compound was used directly in the next step without further purification.

To a dry 250 mL round-bottomed flask was added 2.20 g of methyl 2-(tetrahydro-2H-pyran-4-yl)acetate (0.014 mol) and 100 mL of dry THF. This solution was cooled to −78° C. and LDA (2.0 M in THF/heptane/ethyl benzene, 10.4 mL, 0.021 mol) was added. The resulting brown solution was stirred at −78° C. for 45 min. TMSCl (3.22 g, 3.5 mL, 0.028 mol) was then added at −78° C., and the reaction mixture was then warmed to room temperature. After being re-cooled to −78° C., N-bromosuccinimide (4.94 g, 0.028 mol) was added to the reaction mixture, and the resulting suspension was allowed to slowly warm to room temperature where it continued to stir for an additional 1.5 h. The suspension was then filtered thru a pad of $SiO_2$ using diethyl ether as the eluant. Purification of the filtrate by column chromatography ($SiO_2$ gel, 10:1 to 4:1 hexanes/ethyl acetate) delivered the desired α-bromo ester, which was used in subsequent steps without further purification.

Example 85

Ethyl 2-(pyridin-4-yl)propanoate

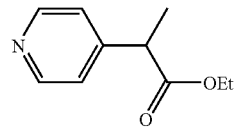

METHOD M

To a solution of $LiN(TMS)_2$ (Aldrich, 1.0 M solution in THF, 30 mL, 30 mmol) in THF (30 mL) was added ethyl 4-pyridylacetate (Aldrich, 4.7 mL, 30 mmol)) at 0° C. Methyl iodide (Aldrich, 2.4 mL, 38 mmol) was added 30 min later. After 1 h, the reaction mixture was concentrated in vacuo. The crude product was purified by silica gel chromatography. Mass Spec. m/z+ion 180 (M+1).

Example 86

Ethyl 2-bromo-2-(pyridin-4-yl)propanoate

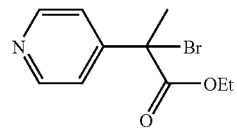

The above compounds were prepared according to the procedure reported in the literature: see D. Yang, J. Org. Chem. 2002, 67, 7429. MS: 258, 260 (M+1). To a solution of ethyl 2-(pyridin-4-yl)propanoate (5.3 g, 30 mmol), $Mg(ClO_4)_2$ (Aldrich, 2.0 g, 9.0 mmol) in $CH_3CN$ (60 mL) was added N-bromosuccinimide (Aldrich, 5.9 g, 33 mmol) at room temperature. After 2 h, the reaction mixture was diluted with ether (200 mL), and 10% $Na_2CO_3$. The organic phase was separated, dried over $Na_2SO_4$, filtered, and concentrated in vacuo. The crude product was purified by silica gel chromatography. Mass Spec. m/z+ion 258, 260 (M+1).

Example 87

Ethyl 2-bromo-2-(pyridin-3-yl)propanoate

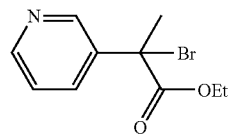

To a stirred mixture of ethyl 2-(pyridin-3-yl)propanoate (4.2 g, 23 mmol), CCl$_4$ (100 mL), and N-bromosuccinimide (Aldrich, 4.6 g, 26 mmol) was added 2,2'-azobisisobutyronitrile (Aldrich, 0.8 g, 5 mmol) under N$_2$ at room temperature. The mixture was gradually heated to reflux. After 7 h, the reaction mixture was concentrated in vacuo. The crude was purified by silica gel chromatography. Mass Spec. m/z+ion 258, 260 (M+1).

Example 88

4-(1,3-Dithian-2-ylidene)-6-fluoro-3,4-dihydro-2H-chromene

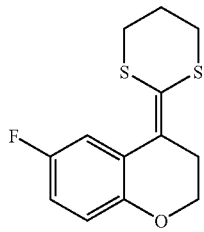

METHOD N

To a solution of 2-trimethylsilyl-1,3-dithiane (5.10 g, 26.5 mmol) in 50 mL of anhydrous THF at −60° C. under N$_2$ was added drop-wise n-BuLi (1.6 M solution in hexanes, 16.6 mL, 26.5 mmol). The mixture was left to warm slowly to 0° C. over 3 h and subsequently cooled to −60° C. A solution of 6-fluoro-2,3-dihydrochromen-4-one (4.40 g, 26.5 mmol) in 25 mL of THF was added drop-wise. The mixture was slowly warmed to ambient temperature overnight, then poured into water, and extracted with EtOAc. The combined organic portions were washed with brine, and conc. in vacuo. The crude product was purified by flash column chromatography (0 to 10% of EtOAc in hexanes). The title compound was obtained as a pale oil.

Example 89

Ethyl 4-chloro-6-fluoro-3,4-dihydro-2H-chromene-4-carboxylate

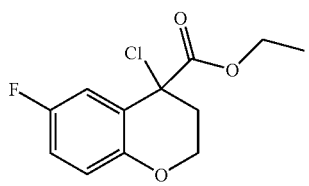

A solution of 4-(1,3-dithian-2-ylidene)-6-fluoro-3,4-dihydro-2H-chromene (4.60 g, 17.1 mmol) in 45 mL of anhydrous THF in an addition funnel was added drop-wise to a stirring solution of N-chlorosuccinimide (11.7 g, 85.7 mmol) in 100 mL of CH$_3$CN and 50 mL of EtOH at r.t. After 3 h, 50 mL of water was added. The mixture was partitioned between EtOAc and water. The combined organic portions were washed with brine, and conc. in vacuo. The residue was purified by flash column chromatography (0 to 10% of EtOAc in hexanes). The title compound was obtained as a colorless oil.

Example 90

(R)-2-Bromo-3-methylbutanoyl chloride

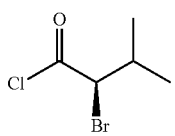

METHOD K

To a 500 mL round-bottom flask was added 5.0 g (27.6 mmol) of (R)-2-bromo-3-methylbutanoic acid and 200 mL CH$_2$Cl$_2$. The resulting solution was cooled to 0° C. in an ice bath and then 3 mL of oxalyl chloride (34.4 mmol) was added in one portion. After 5 min, 0.2 mL of DMF (2.59 mmol) was added drop-wise. Once the addition was completed, the mixture was warmed to room temperature and stirred for 4 h. The mixture was then concentrated, triturated with hexanes (50 mL), and filtered. The residual solid was washed with hexane (2×10 mL) and the combined supernatant liquids were concentrated to afford the title compound as a pale yellow oil.

Example 91

(R)-2-Bromo-3-methylbutanoyl isothiocyanate

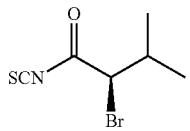

A 100 mL round-bottom flask was charged with KNCS (0.786 g, 8.08 mmol). Acetone (24 mL) was added and the mixture stirred at room temperature until the solid was completely dissolved. A solution of (R)-2-bromo-3-methylbutanoyl chloride (1.51 g, 7.55 mmol, 1.0 equiv) in acetone (2 mL) was added drop-wise resulting in the formation of a white precipitate with concomitant color change of the solution from clear to pink to reddish orange. Once addition was complete, the mixture was stirred for 30 min at room temperature. The reaction mixture was then filtered through Celite in a sintered glass (medium porosity) funnel, and washed twice with acetone (10 mL each wash). The deep red solution was concentrated, taken up in hexanes (40 mL), and re-filtered. Concentration afforded the title compound as an orange oil.

Synthesis of Starting Materials: Thioureas and Amines (procedures: Method-O, Method-P, Method-Q, Method-R, Method-S, Method-T, Method-U, Method-V, Method-W).

Example 92

(±)-endo-1-(Bicyclo[2.2.1]heptan-2-yl)thiourea

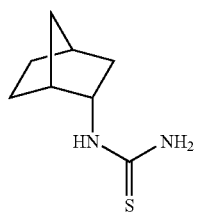

METHOD O

To a stirred solution of 1,1-thiocarbonyldiimidazole (1.94 g, 10.9 mmol) and triethylamine (3.0 mL, 21.8 mmol) in dichloromethane (22.0 mL) under nitrogen was added (±)-endo-2-aminonorborane HCl (1.21 g, 10.9 mmol) over 10 min at ambient temperature for 3 h. The solvent was then evaporated in vacuo, and the residue was dissolved in a 0.5M solution of ammonia in dioxane. After stirring at room temperature under nitrogen for 16 h, the resulting solid was filtered off, and the filtrate was evaporated in vacuo. Upon scratching the glass, the residue crystallized. The solid was placed on the high vacuum pump overnight to afford the title compound (1.16 g) as a brown crystalline solid. MS (ESI, pos. ion) m/z: 171.2 (M+H).

Example 93

1-Benzoyl-3-cyclooctylthiourea

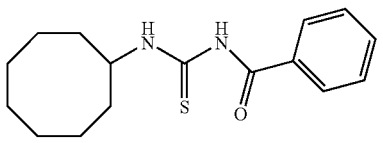

METHOD O

Benzoyl isothiocyanate (7.40 mL, 54.0 mmol) was added to a solution of cyclooctanamine (6.25 g, 49.1 mmol) in 200 mL of chloroform. The mixture was stirred at ambient temperature overnight. The solvents were removed in vacuo to give the title compound as a viscous light yellowish oil. MS m/z: 291.0 (M+H)$^+$.

Example 94

1-Cyclooctylthiourea

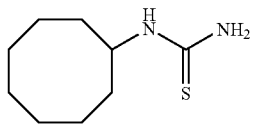

A mixture of 1-benzoyl-3-cyclooctylthiourea (14.3 g, 49.1 mmol) and potassium carbonate (34.6 g, 250 mmol) in methanol (200 mL), water (100 mL), and THF (100 mL) was stirred at ambient temperature overnight. The low boiling solvents were removed in vacuo, and the residue was partitioned between EtOAc and water. The organic portion was washed with brine, and concentrated in vacuo. The title compound was obtained as a white solid after flash column chromatography (0 to 100% of ethyl acetate in hexanes). MS m/z: 187.1 (M+H)$^+$.

Example 95

(±)-exo-1-(Bicyclo[2.2.1]heptan-2-yl)thiourea

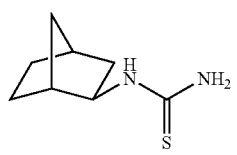

METHOD P

A solution of exo-2-norbornylisothiocyanate (32.2 mL, 326 mmol) in 0.5M solution of ammonia in dioxane (1.3 L, 652 mmol) in a 2 L round-bottomed flask was stirred at room temperature for 16 h. The solvent was then evaporated in vacuo, and the solid was further dried under high vacuum to afford the title compound (39.0 g) as a white amorphous solid. MS (ESI, pos. ion) m/z: 171.2 (M+H).

Example 96

1-Adamantylthiourea

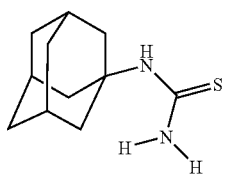

METHOD-P

A mixture of 1-adamantyl isothiocyanate (4.83 g, 25.0 mmol, Aldrich) and ammonia (0.5 M solution in 1,4-dioxane, 100 mL, 50 mmol) was stirred at ambient temperature for 48 h. The solvents were removed in vacuo to give the title compound as a white solid. MS m/z: 211.1 (M+H)$^+$.

Example 97

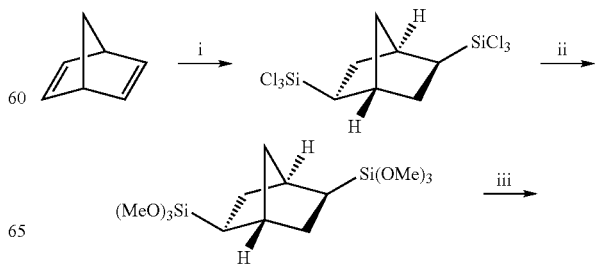

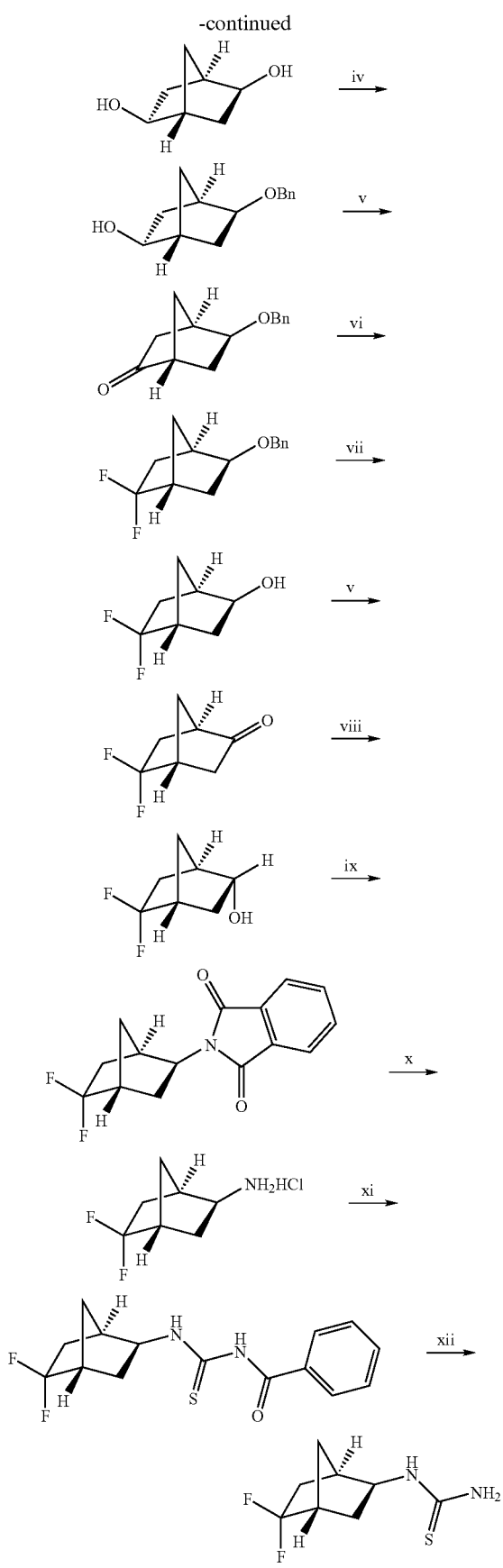

(i) HSiCl₃, allyl palladium(II) chloride, (R)-MOP, −3° C., 3 days; (ii) MeOH, Et₃N, Et₂O, 0° C. to r.t., overnight; (iii) KHF₂, urea-H₂O₂, MnO₂, MeOH, 60° C., overnight; (iv) PhCH₂Br, NaOH, 15-Crown-5, THF, 10° C., 3 h; (v) PCC, CH₂Cl₂, 0° C.-r.t., overnight; (vi) Deoxo-Fluor, BF₃-Et₂O (0.1 eq), 55° C., 33 h; (vii) H₂, Pd/C, MeOH, r.t., 3 h; (viii) L-Selectride, THF, −78° C., 3 h; H₂O₂, NaOH, 65° C., 10 h; (ix) Phthalimide, Ph₃P, DEAD, THF, r.t., 70 h; (x) H₂NNH2, EtOH, reflux, 5 h; HCl(aq), 60° C., 1.5 h; (xi) PhC(O)NCS, Et₃N, CHCl₃, r.t.; (xii) K₂CO₃, MeOH/THF/H₂O, r.t.

(1R,2S,4R,5S)-2,5-Bis(trichlorosilyl)-bicyclo[2.2.1]heptane

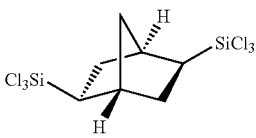

METHOD Q

A solution of allylpalladium(II) chloride (0.0180 g, 0.0492 mmol) and (R)-(+)-2-(diphenylphosphino)-2'-methoxy-1,1'-binaphthyl (0.105 g, 0.223 mmol) in benzene (2.5 mL) was placed into a double-jacketed 250-mL three-neck flask equipped with a mechanical stirrer under nitrogen atmosphere. Trichlorosilane (20.0 mL, 198 mmol) was added, and the mixture was cooled to −3° C. Bicyclo[2.2.1]hepta-2,5-diene (8.3 mL, 76.9 mmol) was added slowly with mechanical stirring. After stirring at −3° C. for 69 h, the color of the mixture turned into a pale yellowish solid. The reaction mixture was dissolved in toluene (anhydrous, 60 mL), and then concentrated in vacuo to give a pale solid, which was used in the following reaction without further purification.

Example 98

(1R,2S,4R,5S)-2,5-Bis(trimethoxysilyl)bicyclo[2.2.1]heptane

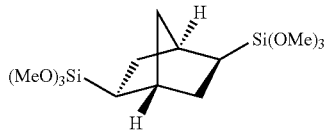

A mixture of methanol (anhydrous, 60 mL), triethylamine (anhydrous, 80 mL), and diethyl ether (anhydrous, 50 mL) was added slowly to (1R,2S,4R,5S)-2,5-bis(trichlorosilyl)-bicyclo[2.2.1]heptane (crude from the previous reaction, 76.9 mmol) in diethyl ether (anhydrous, 50 mL) at 0° C. under a nitrogen atmosphere. After the mixture was stirred at ambient temperature overnight, the precipitated salts were removed by filtration. The solids were washed with diethyl ether (50 mL×3). The combined filtrates were concentrated in vacuo to yield a light yellow slurry which was used in the next reaction without further purification.

Example 99

(1R,2S,4R,5S)-Bicyclo[2.2.1]heptane-2,5-diol

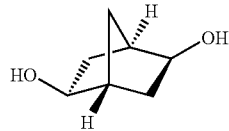

To (1R,2S,4R,5S)-2,5-bis(trimethoxysilyl)bicyclo[2.2.1]heptane (76.9 mmol) was added potassium hydrogen fluoride (33.0 g, 423 mmol), tetrahydrofuran (80.0 mL), methanol (80.0 mL), and urea hydrogen peroxide addition compound (65.0 g, 691 mmol, Aldrich). The resulting white slurry was stirred overnight at 60° C. After cooling to ambient temperature, $MnO_2$ (0.56 g, 6.4 mmol) was added, and the mixture was stirred at this temperature for 4 h. The solids were removed by filtration, and the filter cake was washed with methanol. The combined filtrates were concentrated in vacuo. The residue was dissolved in water (100 mL) and extracted with a $CHCl_3$/i-PrOH mixture (3/1, v/v, 5×100 mL). The combined organic portions were dried over $MgSO_4$ and conc. in vacuo. After triturating the residue with $CH_2Cl_2$ and EtOAc, the white solid was collected by filtration. This material was the title compound. A second crop of desired product was obtained by flash column chromatography (0-5% MeOH in EtOAc) from the concentrated filtrate.

Example 100

(1R,2S,4R,5S)-5-(Benzyloxy)bicyclo[2.2.1]heptan-2-ol

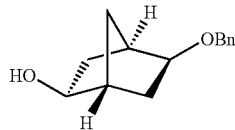

To a stirred solution of (1R,2S,4R,5S)-bicyclo[2.2.1]-heptane-2,5-diol (1.15 g, 8.97 mmol) and 15-crown-5 (0.054 mL, 0.269 mmol) in tetrahydrofuran (30.0 mL, 8.97 mmol) were added at 10° C. (ice/water bath) finely ground sodium hydroxide (2.15 g, 53.8 mmol) and 1-(bromomethyl)benzene (1.07 mL, 8.97 mmol). After stirring at 10° C. for 3 h, the mixture was stirred at ambient temperature overnight. The mixture was partitioned between EtOAc and water, and the organic portions were washed with brine, and conc. in vacuo. The crude product was purified by flash column chromatography (0 to 80% of ethyl acetate in hexanes). The title compound was obtained as a colorless oil.

Example 101

(1R,4R,5S)-5-(Benzyloxy)bicyclo[2.2.1]heptan-2-one

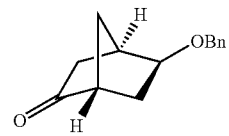

Silica gel 60 (particle size, 0.040-0.063 mm, CAS # 63231-67-4, from EMD Chemical Inc. 9.0 g) was added to a solution of (1R,2S,4R,5S)-5-(benzyloxy)bicyclo[2.2.1]heptan-2-ol (2.79 g, 12.8 mmol) in anhydrous dichloromethane (60.0 ml). The mixture was cooled to 0° C., and pyridinium chlorochromate (4.40 g, 20.4 mmol) was added. The reaction mixture was warmed to ambient temperature and stirred at this temperature for 5 h. After this time, the mixture was diluted with dichloromethane (60 mL) and then filtered through a pad of Celite. The solvent was removed in vacuo, and the residue was purified by flash column chromatography (0 to 25% of ethyl acetate in hexanes) to give the title compound as a colorless oil.

Example 102

(1R,4R,5S)-5-(Benzyloxy)-2,2 difluorobicyclo-[2.2.1]heptane

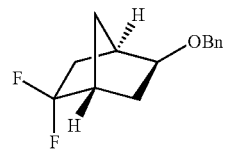

Deoxo-Fluor (50% in THF, 17.7 g, 40.0 mmol) was added to (1R,4R,5S)-5-(benzyloxy)bicyclo[2.2.1]heptan-2-one (2.45 g, 11.3 mmol) in a 250 mL round-bottom flask. The mixture was heated to 85° C. (oil bath temperature) and stirred at this temperature under nitrogen for 16.5 h. After cooling to ambient temperature, the mixture was diluted with ethyl acetate, then poured into sat'd $NaHCO_3$ in ice. The organic portion was separated, washed with brine, dried over $MgSO_4$, filtered, and conc. in vacuo. The crude product was purified by flash column chromatography (0 to 5% of ethyl acetate in hexanes) to give the title compound as a colorless oil.

Example 103

(1R,2S,4R)-5,5-Difluorobicyclo[2.2.1]heptan-2-ol

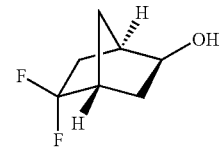

Palladium (10 wt. % on activated carbon, 0.28 g) was added to a solution of (1R,4R,5S)-5-(benzyloxy)-2,2-difluorobicyclo[2.2.1]-heptane (1.43 g, 6.0 mmol) in methanol (15 mL), and the mixture was placed under a balloon full of hydrogen. After stirring at ambient temperature for 4 h, the mixture was filtered through a pad of Celite, and the filtrate was concentrated in vacuo. The residue was adsorbed onto a small pad of silica gel, and eluted with 20% of ethyl acetate in hexanes. The solvents were removed in vacuo to give the title compound as a white solid.

Example 104

(1R,4R)-5,5-Difluorobicyclo[2.2.1]heptan-2-one

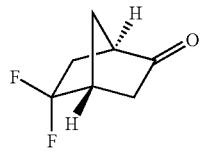

Silica gel 60 (particle size, 0.040-0.063 mm, CAS # 63231-67-4, from EMD Chemical Inc. 4.0 g) was added to a solution of (1R,2S,4R)-5,5-difluorobicyclo[2.2.1]heptan-2-ol (0.800 g, 5.40 mmol) in anhydrous dichloromethane (20.0 ml). The mixture was cooled to 0° C., and pyridinium chlorochromate (1.86 g, 8.64 mmol) was added. The reaction mixture was warmed to ambient temperature and stirred at this temperature overnight. After this time, the mixture was diluted with dichloromethane (30 mL) and then filtered through a pad of silica gel. Removal of the solvents gave the title compound as a white solid.

Example 105

(1R,2R,4R)-5,5-Difluorobicyclo[2.2.1]heptan-2-ol

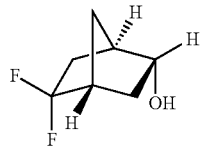

To a solution of (1R,4R)-5,5-difluorobicyclo[2.2.1]heptan-2-one (0.540 g, 3.7 mmol) in anhydrous tetrahydrofuran (8.00 mL) at −78° C. under nitrogen was added drop-wise L-Selectride (1.0 M solution in tetrahydrofuran, 7.40 mL). After stirring at −78° C. for 3 h, 30% $H_2O_2$ (6.0 mL) and 10% NaOH (aq., 110.0 mL) were added. The mixture was warmed to r.t. and then stirred at 65° C. for 10 h. After cooling to ambient temperature, the mixture was extracted with EtOAc (50 mL×2). The combined organic portions were washed with brine, and conc. in vacuo. Flash column chromatography (0 to 30% of ethyl acetate in hexanes) gave the title compound as a white solid.

Example 106

2-((1R,2S,4R)-5,5-Difluorobicyclo[2.2.1]heptan-2-yl)isoindoline-1,3-dione

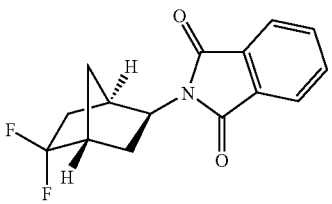

A solution of diethyl azodicarboxylate (0.56 mL, 3.6 mmol) in anhydrous THF (3.0 mL) was added drop-wise to a mixture of (1R,2R,4R)-5,5-difluorobicyclo[2.2.1]heptan-2-ol (0.44 g, 3.0 mmol), phthalimide (0.50 g, 3.4 mmol), and triphenyl phosphine (0.78 mL, 3.4 mmol) in anhydrous tetrahydrofuran (15.0 mL) at r.t. under nitrogen. After stirring at ambient temperature for 66 h, the solvents were removed in vacuo. The residue was partitioned between ethyl acetate and water, and the organic portion was separated, washed with brine, and conc. in vacuo. Flash column chromatography (0 to 35% of ethyl acetate in hexanes) gave the title compound as an off-white solid.

Example 107

(1R,2S,4R)-5,5-Difluorobicyclo[2.2.1]heptan-2-amine hydrochloride

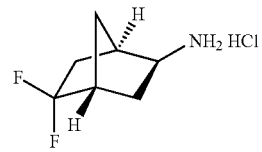

To a suspension of 2-((1R,2S,4R)-5,5-difluorobicyclo[2.2.1]-heptan-2-yl)isoindoline-1,3-dione (0.58 g, 2.09 mmol) in ethanol (anhydrous, 30 mL) was added hydrazine (0.10 mL, 3.14 mmol). After refluxing this mixture under nitrogen for 5 h, it was cooled in an ice bath, and hydrochloric acid (37%, 0.50 mL) was added. After stirring at 60° C. for 1.5 h, the mixture was cooled to ambient temperature. After the white solid was removed by filtration, the filter cake was washed with methanol, and the filtrate was conc. in vacuo. The resulting residue was diluted in ~50 mL of water, filtered, and the filtrate was washed with diethyl ether (30 mL×3). The filtrate was then treated with sodium carbonate monohydrate to saturation, and the aqueous layer was extracted with diethyl ether (50 mL×3). These organic layers were combined, dried over potassium carbonate (solid), and filtered. The solution was treated with hydrochloric acid (1M aqueous, 4 mL), stirred for 5 min, and then concentrated in vacuo to give the title compound as a white solid.

Example 108

1-Benzoyl-3-((1R,2S,4R)-5,5-difluorobicyclo-[2.2.1]heptan-2-yl)thiourea

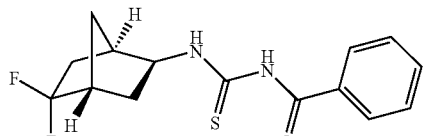

Benzoyl isothiocyanate (0.32 mL, 2.34 mmol) was added to the mixture of (1R,2S,4R)-5,5-difluorobicycle-[2.2.1]heptan-2-amine hydrochloride (0.33 g, 1.80 mmol) and triethylamine (0.38 mL, 2.70 mmol) in anhydrous chloroform (25.0 mL) at ambient temperature under nitrogen. After stirring overnight, the reaction mixture was concentrated in vacuo. Water (50 mL) was added to the residue, and it was extracted with diethyl ether (2×50 mL). The organic portions were combined, washed with brine, and conc. in vacuo to give a light yellowish oil as the title compound that was used in the following reaction without purification. Mass Spec m/z: 311.1 (M+H)+.

Example 109

1-((1R,2S,4R)-5,5-difluorobicyclo[2.2.1]heptan-2-yl)thiourea

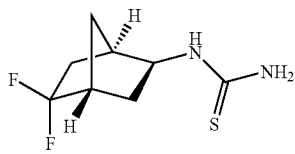

A mixture of 1-benzoyl-3-((1R,2S,4R)-5,5-difluorobicyclo-[2.2.1]heptan-2-yl)thiourea (~1.80 mmol) and potassium carbonate (1.49 g, 10.8 mmol) in methanol (5.0 mL), water (2.5 mL), and tetrahydrofuran (2.5 mL) was stirred at ambient temperature for 2 h. The reaction mixture was concentrated in vacuo, and the residue was partitioned between EtOAc and water. The organic portion was washed with brine, conc. in vacuo, and purified by flash column chromatography (0 to 65% of ethyl acetate in hexanes) to give the title compound as a white solid. MS m/z: 207.0 (M+H)+.

Example 110

2-(2-Chlorophenyl)-2-methylpropanenitrile

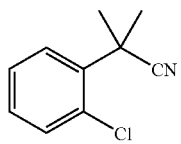

METHOD R

A 500 mL round-bottomed flask was charged with 2-(2-chlorophenyl)acetonitrile (6.82 g, 0.045 mol) and 30 mL of THF. This solution was cooled to −40° C., and KHMDS (0.5 M in toluene, 200 mL, 0.100 mol) was added at such a rate that the internal temperature did not rise above −40° C. This solution was allowed to stir between −40 to −50° C. for an additional 1 h. After that time, MeI (14.2 g, 6.25 mL, 0.100 mol) was added and the solution was warmed to room temperature (a thick solid formed). The reaction was stirred for 1 h at room temperature then quenched by the addition of saturated aqueous NaHCO₃. The layers were separated, and the aqueous phase was extracted with CH₂Cl₂. The combined organic extracts were dried and concentrated in vacuo to give an oil that was purified by column chromatography (SiO₂, 100% hexanes to 90% hexanes/ethyl acetate) to provide 2-(2-chlorophenyl)-2-methylpropanenitrile as a colorless oil.

Example 111

2-(2-Chlorophenyl)propan-2-amine

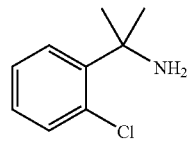

2-(2-Chlorophenyl)-2-methylpropanenitrile (5.0 g, 0.028 mol) along with 50 mL of EtOH was added into a 250 mL round-bottomed flask. To this was added 50 mL of saturated aqueous $K_2CO_3$. This mixture was cooled to 0° C. then 85 mL of 30% aqueous $H_2O_2$ was slowly added. The reaction mixture was allowed to warm to room temperature, and then it was stirred at that temperature for 12 h. The mixture was extracted with $CH_2Cl_2$ (3×150 mL), and the combined organic extracts were dried over $MgSO_4$, filtered, and concentrated in vacuo to give a viscous oil. To this oil was added 40 mL of $CH_3CN$, 40 mL $H_2O$, and 13.2 g (0.031 mol) of $PhI(O_2CCF_3)_2$. This mixture was stirred at r.t. for 12 h, diluted with 300 mL of $H_2O$, and then stirred for an additional 4 h at room temperature. The aqueous phase was extracted using MTBE (1×200 mL) follow by diethyl ether (2×100 mL). The aqueous layer was basified with 1N NaOH (pH=13) and then extracted with $CH_2Cl_2$ (3×100 mL). The organic extracts were dried and concentrated in vacuo to give the desired product as a colorless oil that was used in subsequent steps without further purification.

Example 112

2-Bromobicyclo[2.2.1]heptane-1-carboxylic acid

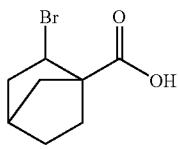

METHOD S

To a 50 mL round-bottomed flask was added (1S,4R)-bicyclo[2.2.1]heptane-2-carboxylic acid (9.84 g, 70 mmol) and bromine (4.10 ml, 80 mmol). The suspension was stirred at room temperature until dissolution. Trichlorophosphine (0.30 ml, 3.4 mmol) was then added slowly and drop wise (significant exotherm observed). A reflux condenser was fitted to the flask with a nitrogen gas inlet and gas outlet (Tygon tubing) running into a scrubber solution of sodium sulfite (1 M, 200 mL). After the addition was complete, the reaction mixture was heated in a silicone oil bath at 80° C. for 4 h. After this time, the reaction was cooled to 10° C. and phosphorus-trichloride (4.23 ml, 48.3 mmol) was added drop-wise. The reaction was then heated to 80° C. During this time the color intensity of the reaction decreased, and after 8 h, the reaction mixture appeared dark orange. The reaction was then cooled to room temperature and diluted with ether (1 L). The ethereal solution was transferred to a separation funnel and washed with 1M sodium sulfite (2×500 mL), water (1×500 mL), and brine (1×500 mL). The organic layer was dried over MgSO₄, filtered, and concentrated in vacuo to afford an oil. Ice cold pentane (50 mL) was then added to the crude product, and the mixture was stirred vigorously. After 20 min, a fine white precipitate formed, which was filtered and washed with pentane (20 mL) and then air dried under a gentle vacuum to afford (4S)-2-bromobicyclo[2.2.1]heptane-1-carboxylic acid (100.2 g, 457 mmol) as a white solid material.

Example 113

Bicyclo[2.2.1]heptane-1-carboxylic acid

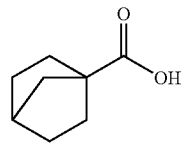

A 2-L reactor equipped with an overhead mechanical stirrer, condenser, nitrogen gas inlet port, temperature probe and reagent charging port, was placed under an atmosphere of nitrogen. The reactor was charged with zinc powder (<10 micron) (298 g, 4560 mmol) and acetic acid (500 mL). While vigorously stirring the heterogeneous mixture, (4S)-2-bromobicyclo[2.2.1]heptane-1-carboxylic acid (100 g, 456 mmol) was then added. A second portion of acetic acid (500 mL) was then used to rinse the walls of the reactor. The reaction mixture was brought to a gentle reflux (ca. 30 min) and then held at this temperature for 5 h. The cooled (room temperature) reaction mixture was passed through a pad of Celite, which was washed with acetic acid (1×300 mL) and ethyl acetate (1 (500 mL). The filtrate was concentrated, water (300 mL) was added, and then the mixture was stirred vigorously to induce precipitation. The precipitate was collected by filtration, washed with water, and dried under vacuum at 35° C. overnight. Pentane (50 mL) was then added, and the mixture was stirred vigorously for 20 min during which time a fine white precipitate formed. The resulting precipitate was filtered, washed with pentane (20 mL), and air dried to afford bicyclo[2.2.1]heptane-1-carboxylic acid (52 g) as a white solid.

Example 114 tert-Butyl bicyclo[2.2.1]heptan-1-ylcarbamate

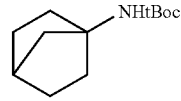

A 100 mL round-bottomed flask equipped with a condenser and nitrogen inlet was charged with bicyclo[2.2.1]heptane-1-carboxylic acid (2.00 g, 14.3 mmol), toluene (35 mL), triethylamine (2.18 ml, 15.7 mmol) and diphenylphosphoryl azide (3.38 ml, 15.7 mmol) at room temperature under an atmosphere of nitrogen. The reaction mixture was stirred at room temperature for 1 h before being heated to 50° C. for 3 h. Gas evolved from the reaction mixture for approximately 2-3 h. After 3 h at 50° C., the temperature of the reaction mixture was increased to 70° C. and stirring continued for another 2 h until no further gas evolution occurred. The reaction mixture was then cooled and then concentrated in vacuo. The resulting oil was dissolved in anhydrous t-BuOH (10 mL, 99.9% anhydrous packed under argon; Alfa Aesar), placed under and atmosphere of nitrogen, and refluxed in a 90° C. bath for 14 h. After this time, the reaction mixture was cooled and concentrated under reduced pressure to afford an off-white solid which was then dissolved in ether (50 mL), washed with water (20 mL), 1M NaOH (20 mL), water (20 mL) and brine (20 mL). After being dried over MgSO4, the mixture was filtered and concentrated in vacuo to afford 2.2 g of an off-white solid. Pentane (20 mL) was added, and solution was stirred vigorously until the majority of the material dissolved. The light orange colored precipitate that did not dissolve was removed through a fine grade sintered glass filter funnel. The mother liquor was concentrated to afford the title compound (2.2 g) as an off white solid.

Example 115

1-(Bicyclo[2.2.1]heptan-1-yl)thiourea

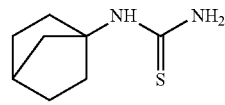

A 100 mL RBF was purged with nitrogen gas before being charged with tert-butyl bicyclo[2.2.1]heptan-1-ylcarbamate (6.60 g, 31.0 mmol) and dichloromethane (66 mL). The solution was cooled in a 0° C. a bath, and then trifluoroacetic acid (12 mL, 18 g, 156 mL) was added. The cooling bath was removed, and the reaction mixture was allowed to warm to room temperature during which time a gas evolved from the reaction mixture. After 3 h at room temperature the reaction mixture was concentrated in vacuo to afford a viscous oil. This material was dissolved in dichloromethane (82 mL), and triethylamine (13.0 mL, 94 mmol) and benzoyl isothiocyanate (4.6 mL, 34 mmol) were added. After stirring at room temperature under an atmosphere of nitrogen for 14 h, the reaction mixture was concentrated in vacuo, and the resulting residue was dissolved in MeOH/THF/H$_2$O (2:1:1, ca. 0.3 M). Potassium carbonate (22 g, 156 mmol) was added, and the biphasic solution was vigorously stirred for 3 h. The organic solvents were removed under reduced pressure during which time a yellow precipitate formed. The precipitate was filtered, washed with water (30 ml) and cold (−20° C.) diethyl ether to provide a white precipitate. This material was allowed to air dry for 10 min and then dried under high vacuum at room temperature for ca. 18 h to afford the title compound (3.8 g) as a fine white powder.

Example 116

4-(2-(4-Methyl-3-nitrophenoxy)ethyl)morpholine

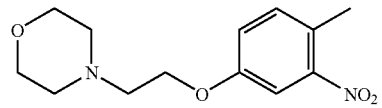

METHOD T

A mixture of 4-methyl-3-nitrophenol (1.53 g, 10 mmol.), 4-(2-chloroethyl)morpholine (2.79 g, 15 mmol), Cs$_2$CO$_3$ (9.78 g, 30 mmol) and NaI (145 mg, 1 mmol) in DMF (15 mL) was stirred for 3 h at 80° C. The reaction mixture was then cooled to room temperature, diluted with water, and extracted with EtOAc. The organic layer was dried over MgSO₄, filtered and concentrated in vacuo. The crude residue was purified by flash chromatography (4:1:0.05 CH₂Cl₂/EtOAc/MeOH) to give the title compound as an oil.

Example 117

2-Methyl-5-(2-morpholinoethoxy)benzenamine

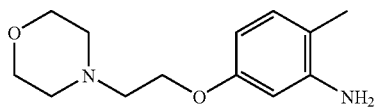

To the mixture of 4-(2-(4-methyl-3-nitrophenoxy)ethyl) morpholine (532 mg, 2 mmol) in MeOH (50 mL) was added 10% Pd/C (250 mg). The mixture was stirred under an atmosphere of H₂ (balloon) overnight. The contents of the reaction mixture were then filtered and concentrated in vacuo to give the title product, which was used without further purification.

Example 118

1-(2-Chlorophenyl)cyclopropanamine

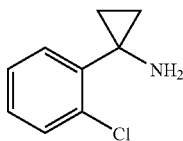

METHOD U

This compound was prepared using the method described by Bertus and Szymoniak; *J. Org. Chem.* 2003, 68, 7133.

Example 119 tert-Butyl 4-(4-(methylsulfonyl)phenyl)bicyclo[2.2.2]octan-1-ylcarbamate

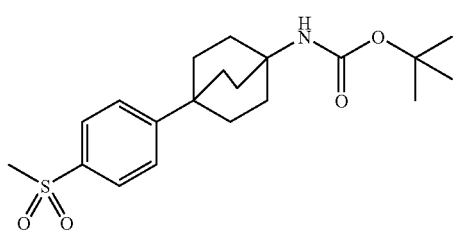

METHOD V

To a flame-dried 100 mL round-bottomed flask equipped with magnetic stirring and argon inlet/outlet was added 4-(4-(methylsulfonyl)phenyl)bicyclo[2.2.2]octane-1-carboxylic acid (200 mg, 649 μmol, prepared by the method described in US Patent Application: 2004/0133011 and 5 mL of toluene. Triethylamine (0.10 mL, 713 μmol) was added followed by diphenylphosphoryl azide (0.2 mL, 713 μmol), and the reaction mixture warmed in a 50° C. oil bath for 30 min, then to 70° C. for 5 h. tert-Butanol (5 mL, 53 mmol) was then added, and the reaction mixture continued to stir in the 70° C. bath. After 20 h, copper (I) chloride (10 mg, 101 μmol) was added, and the reaction continued to stir for ca 1.5 d at 70° C. The reaction was removed from the oil bath and then poured thru a 1 cm pad of Celite. The Celite pad was washed with CH₂Cl₂, and the filtrate was concentrated in vacuo. CH₂Cl₂ (50 mL) was added to the filtrate, and the organic layer was washed with 1M NaOH (2×), sat'd NH₄Cl, sat'd NaHCO₃, and brine. The organic layer was then dried over MgSO₄, filtered and concentrated in vacuo to give tert-butyl 4-(4-(methylsulfonyl)phenyl)bicyclo[2.2.2]octan-1-ylcarbamate (mass=170 mg). The crude reaction product was taken onto the next step without further purification.

Example 120

4-(4-(Methylsulfonyl)phenyl)bicyclo[2.2.2]octan-1-amine

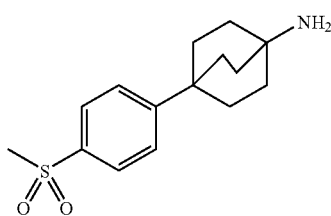

To a 100 mL round-bottomed flask equipped with magnetic stirring was added tert-butyl 4-(4-(methylsulfonyl)phenyl)bicyclo[2.2.2]octan-1-ylcarbamate (170 mg, 448 μmol), 2 mL of CH₂Cl₂, ca. 5 drops of water, and trifluoroacetic acid (2 mL, 27 mmol). The reaction mixture was stirred at ambient temperature for 3.5 h, after which time the mixture was concentrated in vacuo. NaOH (ca. 50 mL of a 1M aq. solution) was added to the mixture, and the aqueous layer was extracted with CH₂Cl₂ (3×15 mL). The organic layers were combined, dried over K₂CO₃, filtered, and concentrated in vacuo to give 4-(4-(methylsulfonyl)phenyl)bicyclo[2.2.2]octan-1-amine (mass=120 mg, Mass Spec. m/z+ion=280.2) The crude reaction product was taken onto the next step without further purification.

Example 121

1-Benzoyl-3-(4-(4-(methylsulfonyl)phenyl)bicyclo[2.2.2]octan-1-yl)thiourea

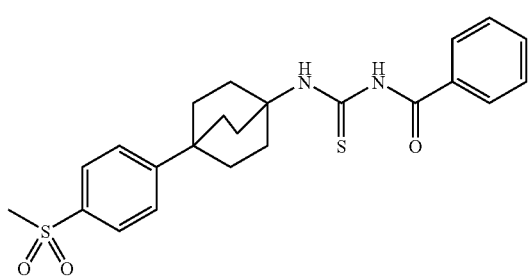

To a 100 mL round-bottomed flask equipped with magnetic stirring was added 4-(4-(methylsulfonyl)phenyl)bicyclo[2.2.2]octan-1-amine (120 mg, 429 µmol) in 2 mL of $CH_2Cl_2$, and benzoyl isothiocyanate (63.6 µl, 472 µmol). The reaction was stirred at ambient temperature for ca. 26 h, and then it was concentrated in vacuo to give 1-benzoyl-3-(4-(4-(methylsulfonyl)phenyl)bicyclo[2.2.2]octan-1-yl)thiourea (mass=185 mg, Mass spec. m/z+ion=443.2). The crude reaction product was taken onto the next step without further purification.

Example 122

1-(4-(4-(Methylsulfonyl)phenyl)bicyclo[2.2.2]octan-1-yl)thiourea

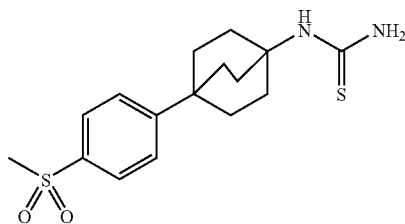

To a 100 mL round-bottomed flask equipped with magnetic stirring was added a solution of 1-benzoyl-3-(4-(4-(methylsulfonyl)phenyl)bicyclo[2.2.2]octan-1-yl)thiourea (185 mg, 418 µmol) suspended in THF (1.5 mL) and methanol (3 mL). A solution of potassium carbonate (289 mg, 2090 µmol) in 1.5 mL of water was added, and the reaction mixture was stirred at ambient temperature. After 3.5 h, 3 mL more of THF was added. Then after 22.5 h, the lower boiling solvents of the reaction mixture were removed in vacuo. Water was added, and the aqueous layer was extracted with EtOAc (1×10 mL), $CH_2Cl_2$ (3×10 mL), and EtOAc (1×20 mL). The aqueous layer was the saturated with solid NaCl, and it was extracted with THF (3×10 mL). All organic layers were combined along with 30 mL more THF and dried over $K_2CO_3$, filtered, and concentrated in vacuo. The residue was absorbed onto silica gel and purified on a 40 g silica gel column using 1:2 hexanes-EtOAc+2% MeOH as the eluant followed by 1:2 hexanes-EtOAc+4.5% MeOH. Purified 1-(4-(4-(methylsulfonyl)phenyl)bicyclo[2.2.2]octan-1-yl)thiourea was isolated from the chromatography (43 mg, white solid, Mass spec. m/z+ion=339.2).

Example 123

Bicyclo[2.2.1]heptane-2-carboxamide

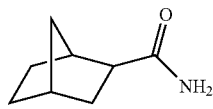

METHOD W

A round-bottomed flask was charged with 450 g exo-2-norbornyl carboxylic acid (3200 mmol) in 100 mL of $CH_2Cl_2$. To the solution was added 0.23 mL of DMF (3.21 mmol) followed by the drop-wise addition of 325 mL of oxalyl chloride (3700 mmol). The reaction was stirred for 1 h at ambient temperature then warmed to 45° C. for an additional 30 min. The reaction was allowed to cool to ambient temperature and 2.5 L of 28% $NH_4OH$ was slowly added. The reaction was stirred for 1 h at ambient temperature. The desired product was isolated by filtration.

Example 124

1-Benzoyl-3-(bicyclo[2.2.1]heptan-2-ylmethyl)thiourea

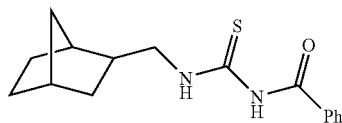

A dry 500 mL round-bottomed flask equipped with a magnetic stir bar under an atmosphere of $N_2$ was charged with 3.96 g (28.5 mmol) of bicyclo[2.2.1]heptane-2-carboxamide in 30 mL of anhydrous THF. The mixture was cooled to 0° C. and 57 mL (57 mmol) of lithium aluminum hydride (1.0 M in THF) were added via syringe. The reaction was stirred for 10 min. at 0° C. then allowed to warm to ambient temperature and stirred an additional 15 h. The reaction solution was then cooled to 0° C., and 2.2 mL of $H_2O$ were added drop-wise followed by the addition of 2.2 mL of 15% aq. NaOH. Water (6.6 mL) was then added and the reaction was allowed to stir for 0.5 h at ambient temperature. The solids were removed by filtration through a Celite pad. Trifluoroacetic acid (2.6 mL) was then added to the filtrate, and the mixture stirred for 1 h at ambient temperature. The solvent was removed in vacuo providing amine salt as a white solid.

A dry 150 mL round-bottomed flask equipped with a magnetic stir bar under an atmosphere of $N_2$ was charged with 5.46 g (22.8 mmol) of amine salt in 50 mL of $CH_2Cl_2$. To the solution was added 6.5 mL (46.6 mmol) of triethylamine followed by the drop-wise addition of 3.05 mL (22.7 mmol) of benzoyl isothiocyanate. After stirring the reaction mixture for 1.3 h at ambient temperature, the organic layer was washed with $H_2O$ (2×25 mL), 1M KOH (2×25 mL), 1M HCl (2×25 mL), and brine. The organic phase was dried over $MgSO_4$, filtered, and concentrated in vacuo to provide the desired N-acylthiourea. MS (ESI, pos. ion) m/z: 289.2 (M+H).

Example 125

1-(Bicyclo[2.2.1]heptan-2-ylmethyl)thiourea

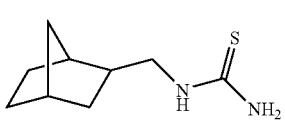

A 250 mL round-bottomed flask equipped with a magnetic stir bar was charged with 6.17 g (22.4 mmol) of 1-benzoyl-3-(bicyclo[2.2.1]heptan-2-ylmethyl)thiourea in 30 mL of MeOH. KOH was added (2.55 g, 45.4 mmol) and the reaction was stirred at ambient temperature for 4 h. Water (150 mL) was then added to the reaction mixture, and the solid was removed by filtration. The flask and filter cake were rinsed with 40 mL of H$_2$O. The collected solid was then suspended in 15 mL of MTBE, and the solid was collected by filtration providing the desired thiourea. MS (ESI, pos. ion) m/z: 185.2 (M+H).

Synthesis of Final Products. (Procedures: Method-X, Method-Y, Method-Z, Method-AA, Method-BB, Method-CC, Method-DD, Method-EE, Method-FF, Method-GG, Method-II, Method-JJ, Method-KK, Method-LL Method-MM, Method-NN, Method-OO, Method-PP).

Example 126

6-(Cycloheptylamino)-5-thia-7-azaspiro[3.4]oct-6-en-8-one

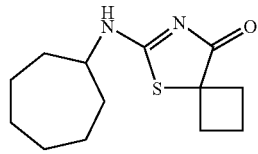

METHOD X

A mixture of 1-cycloheptylthiourea (0.255 g, 1.48 mmol) and ethyl 1-bromocyclobutanecarboxylate (0.25 mL, 1.48 mmol, Aldrich) in N,N-diisopropylethylamine (0.5 mL) and ethanol (1.0 mL) was heated in a sealed tube in a microwave oven (Emrys Optimizer from Personal Chemistry) at 155° C. for 2 h, then at 170° C. for 1.5 h. After removing the low-boiling solvents in vacuo, the residue was partitioned between EtOAc and water. The organic portion was separated, washed with brine, and conc. in vacuo. The residue was purified by flash column chromatography (0 to 35% of EtOAc in hexanes) to give the title compound as a tan solid. MS m/z: 253.2 (M+H)$^+$

Example 127

Ethyl 4-oxo-2-(2-(trifluoromethyl)phenylamino)-4,5-dihydrothiazole-5-carboxylate

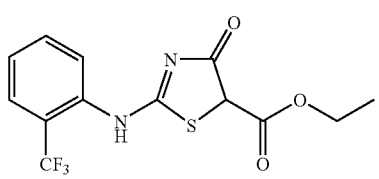

Method X

To a stirred solution of 2-(trifluoromethyl)phenylthiourea (Menai Organics, 2.36 g, 10.7 mmol), Hunig's base (Aldrich, 1.9 mL, 10.7 mmol) in EtOH (10 mL) was added diethyl bromomalonate (2.0 mL, 10.7 mmol). After 1.5 h at room temperature, the reaction mixture was diluted with EtOAc, washed with saturated NaHCO$_3$ and brine, dried over Na$_2$SO$_4$, filtered, and concentrated in vacuo. The crude product was purified by silica gel chromatography. MS: 333 (M+1).

Example 128

(5R)-(±)-endo-2-(Bicyclo[2.2.1]heptan-2-ylamino)-5-isopropylthiazol-4(5H)-one

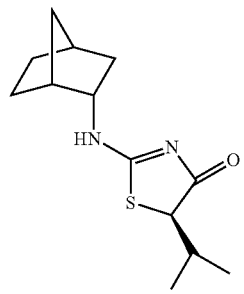

METHOD Y

To a stirred solution of (±)-endo-1-(bicyclo[2.2.1]heptan-2-yl)thiourea (314 mg, 1.84 mmol) and (S)-2-bromo-3-methylbutanoic acid (334 mg, 1.84 mmol) in anhydrous ethanol (10 mL) under nitrogen, was added sodium acetate (182 mg, 2.21 mmol, 1.2 equ.) at room temperature. After refluxing the reaction mixture for 3 h, the solvent was evaporated in vacuo, and the residue was taken up in ethyl acetate (20 mL). The organic layer was washed with water (20 mL) followed by brine (20 mL), then dried over sodium sulfate, filtered and concentrated in vacuo. The residue was purified by flash chromatography (SiO$_2$ 4:1 hexane/acetone) to afford the title compound (90 mg). MS (ESI, pos. ion) m/z: 253.1 (M+H).

Example 129

(S)-2-((rel-1R,2R,4S)-bicyclo[2.2.1]heptan-2-ylamino)-5-isopropylthiazol-4(5H)-one

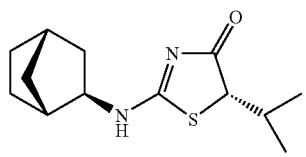

METHOD Z

To a solution of (R)-2-bromo-3-methylbutanoyl isothiocyanate (734 mg, 3.30 mmol) in CH$_2$Cl$_2$ at 0° C. was added drop-wise exo-2-aminonorbornane (0.4 mL, 3.37 mmol). The mixture was allowed to stir for 30 min at 0° C. Triethylamine (0.47 mL, 3.38 mmol, 1.02 equiv) was then added, and the mixture allowed to warm to room temperature and stirred overnight. The mixture was concentrated and the resulting oil triturated with THF (26 mL), filtered, and concentrated in vacuo. Flash chromatography (gradient of hexanes:acetone gradient—automated, hexanes:acetone 4:1—manual) furnished the title compound as a sticky white solid. Material was foamed by dissolution in CH$_2$Cl$_2$ followed by re-concentration.

Example 130

5-Isopropyl-5-methyl-2-(pyridin-2-ylmethylamino)thiazol-4(5H)-one

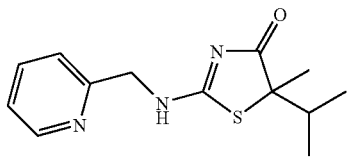

METHOD Z

Pyridin-2-ylmethanamine (0.22 mL, 2.1 mmol) was added to 2-bromo-2,3-dimethylbutanoyl isothiocyanate (240 mg, 1.1 mmol) at room temperature. The reaction was exothermic, and was stirred at room temperature for 15 min. CH$_2$Cl$_2$ (2 ml) was added, and the resulting precipitate was removed by filtration. The CH$_2$Cl$_2$ solution was concentrated, and the mixture was purified by silica gel column (gradient 1% (10% NH$_3$ in MeOH) to 30% (10% NH$_3$ in MeOH) in CH$_2$Cl$_2$) to give the title compound as an off-white solid (123 mg). Mass Spec.=m/z+ion 264.1 (M+H)

Example 131

5-Cyclopentyl-5-fluoro-2-(2-fluorophenylamino)thiazol-4(5H)-one

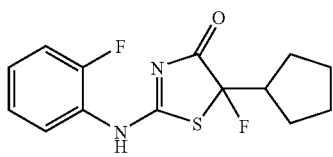

METHOD BB

A dry 100 mL round-bottomed flask was charged with 5-cyclopentyl-2-(2-fluorophenylamino)thiazol-4(5H)-one (0.200 g, 0.717 mmol) and 6.0 mL of THF. This solution was cooled to −78° C., and LDA (2.0 M in THF/heptane/ethyl benzene, 1.43 mL, 2.86 mmol) was added. The resulting brown solution was allowed to stir at that temperature for 1 h, then TMSCl (0.623 g, 0.725 mL, 5.74 mmol) was added. The solution was warmed to room temperature and allowed to stir for an additional 1 h. The solution was concentrated in vacuo to remove the volatiles and then redissolved in 10 mL of CH$_3$CN. Selectfluor (0.508 g, 1.43 mmol) was added at room temperature, and the resulting solution was stirred for 2 h. The reaction was quenched with saturated aqueous NaHCO$_3$, and the resulting mixture was thoroughly extracted with CH$_2$Cl$_2$. This combined organic extracts were dried and concentrated in vacuo to give an oil which was purified by column chromatography (100% to 70% hexanes/30% ethyl acetate) to give the title compound as a colorless oil. Mass Spec (M+H)$^+$; 297.1.

Example 132

2-(Bicyclo[2.2.1]heptan-2-ylamino)-5-methyl-5-(trifluoromethyl)thiazol-4(5H)-one

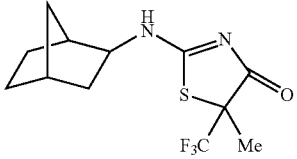

METHOD CC

A dry 100 mL round-bottomed flask equipped with a magnetic stir bar under an atmosphere of N$_2$ was charged with 528 mg (2.35 mmol) of 2-(bicyclo[2.2.1]heptan-2-ylamino)-5-methylthiazol-4(5H)-one in 5 mL of anhydrous THF. The reaction was cooled to −20° C. and 5.0 mL (5.0 mmol) of NaHMDS (11.0M in THF) were added drop-wise via syringe. The resulting reaction mixture was stirred at −20° C. for 30 min then 0.86 mL (6.78 mmol) of TMSCl was added drop-wise via syringe. The reaction mixture was held at −20° C. for 15 min, and then the mixture was allowed to warm to ambient temperature. After stirring the reaction mixture for an additional 1 h, the mixture was concentrated in vacuo. The reaction flask was again equipped with a magnetic stir bar and placed under an N$_2$ atmosphere. Anhydrous CH$_3$CN was added, and 978 mg (2.58 mmol) of S-(trifluoromethyl)dibenzothiophenium-3-sulfonate C$_2$H$_5$OH was added to the reaction mixture in one portion, and the resulting suspension was stirred at ambient temperature for 19 h. The solids were then removed by filtration through a Celite pad, and the reaction flask and pad were rinsed with CH$_2$Cl$_2$. The organic layer was washed with 20 mL of 1:1 H$_2$O/sat'd NH$_4$Cl, and the aqueous layer was extracted with an additional portion of CH$_2$Cl$_2$. The combined organic layers were washed with brine, dried over MgSO$_4$, filtered, and concentrated in vacuo. Flash chromatography (SiO$_2$, CH$_2$Cl$_2$ to 5% MeOH/CH$_2$Cl$_2$) provided the desired compound. MS (ESI, pos. ion) m/z: 293.1 (M+H).

Example 133

Ethyl 5-(3-tert-butoxy-3-oxopropyl)-4-oxo-2-(2-(trifluoromethyl)phenylamino)-4,5-dihydrothiazole-5-carboxylate

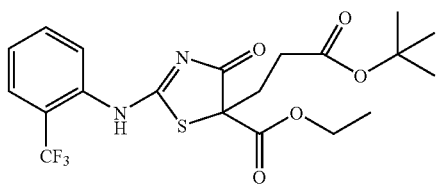

METHOD DD

The above compounds were prepared according to the procedure reported in the literature: see S. Muthusamy Synth. Commun. 2002, 32, 3247. To a stirred solution of ethyl 4-oxo-2-(2-(trifluoromethyl)phenylamino)-4,5-dihydrothiazole-5-carboxylate (1.1 g, 3.3 mol), tert-butyl acrylate (Aldrich, 2.5 mL, 16.5 mmol) in EtOH (10 mL) was added DBU (Aldrich, 0.25 mL, 1.6 mmol). The mixture was stirred at r.t. overnight and concentrated in vacuo. The crude product was purified by silica gel chromatography. MS: 461 (M+1).

Example 134 tert-Butyl 3-(4-oxo-2-(2-(trifluoromethyl)phenylamino)-4,5-dihydrothiazol-5-yl)propanoate

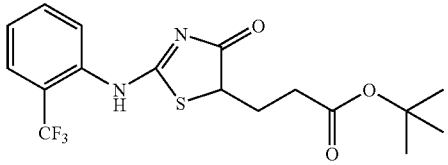

To a mixture of ethyl 5-(3-tert-butoxy-3-oxopropyl)-4-oxo-2-(2-(trifluoromethyl)phenylamino)-4,5-dihydrothiazole-5-carboxylate (88.7 mg, 0.19 mmol), THF (1 mL), MeOH (0.3 mL), and water (0.3 mL) was added LiOH.H₂O (Aldrich, 20 mg, 0.47 mmol) at room temperature. After 3 h, 1N HCl (0.7 mL) was added to the reaction mixture at 0° C. The mixture was extracted with EtOAc, and the organic phase was dried over Na₂SO₄, filtered, and concentrated in vacuo. The crude material was purified by silica gel chromatography. MS: 389 (M+1).

Example 135

2-((1S,2S,4R-Bicyclo[2.2.1]hept-2-ylamino)-8-oxa-1-thia-3-azaspiro[4.5]dec-2-en-4-one

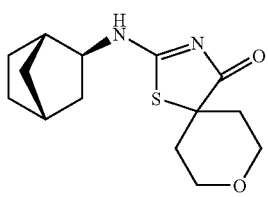

METHOD EE

To the mixture of 2-((1S,2S,4R)-bicyclo[2.2.1]heptan-2-ylamino)thiazol-4(5H)-one (840 mg, 4.0 mmol) in THF (5.0 mL) was added LDA (2.0 M, 20 mL) at −78° C. The resulting mixture was stirred for 10 min at −78° C., and then 1-bromo-2-(2-bromoethoxy)ethane (3.71 g, 16 mmol) was added. The mixture was allowed to warm to room temperature and then stirred overnight. A sat'd solution of NaH₂PO₄ was added, and it was extracted with EtOAc. The organic layer was washed with sat'd NH₄Cl, dried over MgSO₄, filtered, and concentrated in vacuo. The crude residue was purified through flash chromatography (4:1:0.05; CH₂Cl₂/EtOAc/MeOH) to give the title compound as off-white solid. MS (ES⁺): 281 (M+H)⁺.

Example 136

2-((1S,2S,4R)-Bicyclo[2.2.1]heptan-2-ylamino)-5-(2-hydroxypropan-2-yl)-5-methylthiazol-4(5H)-one

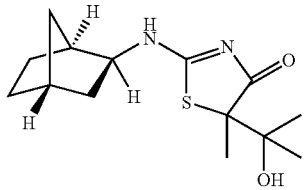

METHOD FF

To a solution of 2-((1S,2S,4R)-bicyclo[2.2.1]heptan-2-ylamino)-5-methylthiazol-4(5H)-one (1.10 g, 5.0 mmol) in THF (5 ml) at −78° C. was added LDA (2.0 M, 10 ml). After 5 min, acetone was added, and the reaction mixture was stirred for 1 h at −78° C. The resulting reaction mixture was poured into a sat'd NaH₂PO₄, and extracted with EtOAc. The organic layer was dried over MgSO₄, filtered and concentrated in vacuo. The crude residue was purified by flash chromatography (4:1; Hexane:EtOAc) to give the title compound as a white solid. MS (ES⁺): 283 (M+H)⁺. The diastereomers were separated using standard HPLC methods described within this text.

Example 137

2-((1S,2S,4R-Bicyclo[2.2.1]heptan-2-ylamino)-5-(2-fluoropropan-2-yl)-5-methylthiazol-4(5H)-one

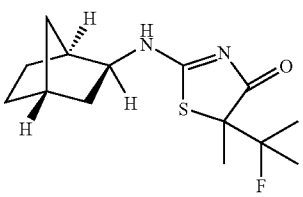

METHOD GG

To the solution of DAST (527 mg, 3.3 mmol) in CH₂Cl₂ (2 ml) at −78° C. was added a solution of 2-((1S,2S,4R)-bicyclo[2.2.1]heptan-2-ylamino)-5-(2-hydroxypropan-2-yl)-5-methylthiazol-4(5H)-one in CH₂Cl₂ (8 ml) over 10 min. After the addition, the cold bath was removed and the temperature was allowed to warm up to 0° C., and then quenched with sat'd NaHCO₃. The mixture was extracted with CH₂Cl₂, dried over Na₂SO₄, filtered, and concentrated in vacuo. The crude residue was purified by flash chromatography (4:1; Hexane:EtOAc) to give the title compound as white solid. MS (ES⁺): 285 (M+H)⁺. The diastereomers were separated using standard HPLC methods described within this text.

Example 138

5-Isopropyl-5-methoxy-2-(tricyclo[3.3.1.1$^{3,7}$]decan-1-ylamino)-thiazol-4-one

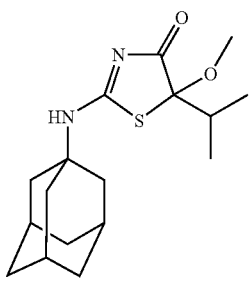

METHOD H

A mixture of 5-(1-methylethyl)-2-(tricyclo[3.3.1.1$^{3,7}$]dec-1-ylamino)-1,3-thiazol-4(5H)-one (146 mg, 0.5 mmol) and NBS (107 mg, 0.6 mmol) in CCl$_4$ (60 mL) was stirred at reflux for 30 min. The resulting mixture was cooled to 0° C., and filtered to remove the solid. The residue was then concentrated in vacuo and diluted with CH$_2$Cl$_2$ (20 mL). To this mixture was added MeOH (200 uL) and DIEA (200 uL). The mixture was stirred for 30 min, then was concentrated in vacuo and purified by flash chromatography (4:1; Hexane: EtOAc) to give the title compound as white solid. MS (ES$^+$): 323 (M+H)$^+$.

Example 139

2-(2-(1-Adamantylamino)-4-oxo-4,5-dihydrothiazol-5-yl)acetaldehyde

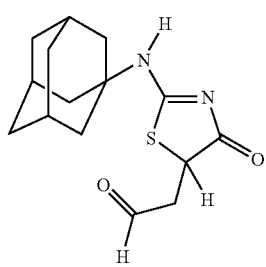

METHOD JJ

A suspension of 2-(1-adamantylamino)-5-(2-hydroxyethyl)thiazol-4(5H)-one (0.25 g, 0.85 mmol) in CH$_2$Cl$_2$ (10 mL) was added to Dess-Martin periodinane (0.56 g, 1.28 mmol, Aldrich) in CH$_2$Cl$_2$ (10 mL). After stirring at ambient temperature for 1 h, the solvent was removed in vacuo. The residue was partitioned between ethyl acetate and saturated aqueous sodium thiosulfate and aqueous sodium bicarbonate. The organic portion was separated, washed with brine, and conc. in vacuo to give the title compound as a light yellowish solid. MS m/z: 293.6 (M+H)$^+$.

Example 140

2-((1S,2S,4R)-bicyclo[2.2.1]heptan-2-ylamino)-5-(2-hydroxyethyl)thiazol-4(5H)-one

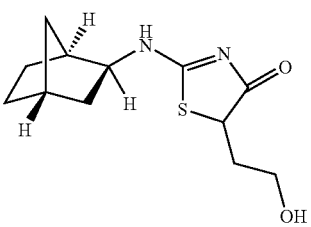

METHOD KK 1-((1S,2S,4R)-Bicyclo[2.2.1]heptan-2-yl)thiourea (887 mg, 5.25 mmol), 3-bromo-dihydrofuran-2(3 H)-one (1.65 g, 5 mmol), EtOH (10 mL) and DIEA (5.0 mL) were placed in a microwave reaction vessel. The mixture was placed in a microwave synthesizer and was irradiated at 150° C. for 30 min. The resulting mixture was poured into water and extracted with EtOAc and dried over MgSO$_4$. After being filtered and concentrated in vacuo, the title compound was obtained a brown solid. MS (ES$^+$): 255 (M+H)$^+$.

Example 141

2-((1S,2S,4R)-Bicyclo[2.2.1]heptan-2-ylamino)-5-(2-(tetrahydro-2H-pyran-2-yloxy)ethyl)thiazol-4(5H)-one

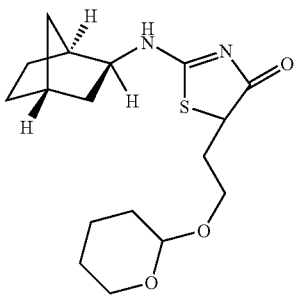

The mixture of 2-((1S,2S,4R)-bicyclo[2.2.1]heptan-2-ylamino)-5-(2-hydroxyethyl)thiazol-4(5H)-one (3.2 g, 12.6 mmol) and p-toulenesulfonic acid (500 mg) in 3,4-dihydro-2H-pyran (10 mL) was stirred for 2 h at room temperature. The resulting mixture was diluted with CH$_2$Cl$_2$ (100 mL), then washed with sat'd NaH$_2$PO$_4$, and dried over MgSO$_4$. After being filtered and concentrated in vacuo, the crude residue was purified by flash chromatography (3:2; Hexane: EtOAc) to give the title compound as an oil. MS (ES$^+$): 339 (M+H)$^+$.

Example 142

2-((1S,2S,4)-Bicyclo[2.2.1]heptan-2-ylamino)-5-(2-methylallyl)-5-(2-(tetrahydro-2H-pyran-2-yloxy)ethyl)thiazol-4(5H)-one

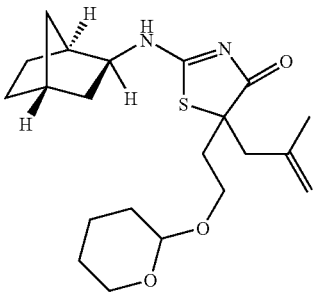

To the mixture of 2-((1S,2S,4R)-bicyclo[2.2.1]heptan-2-ylamino)-5-(2-(tetrahydro-2H-pyran-2-yloxy)ethyl)thiazol-4(5H)-one (1160 mg, 3.43 mmol) in THF (8.0 mL) cooled in a −78° C. bath was added LDA (2.0 M, 17.15 mL). The resulting mixture was stirred for 10 min at −78° C., and then 3-bromo-2-methylprop-1-ene (1.6 ml, 17.15 mmol) was added. After the reaction mixture was allowed to warm to room temperature and stirred ca. 18 h. Saturated NaH$_2$PO$_4$ was added, and the aqueous phase was extracted with EtOAc. The organic layer was washed with sat'd NH$_4$Cl, dried over MgSO$_4$, filtered, and concentrated in vacuo. The crude residue was purified by flash chromatography (4:1; Hexane:EtOAc) to give the title compound as yellow oil. MS (ES$^+$): 393 (M+H)$^+$.

Example 143

2-((1S,2S,4R)-Bicyclo[2.2.1]heptan-2-ylamino)-5-(2-hydroxyethyl)-5-(2-methylallyl)thiazol-4(5H)-one

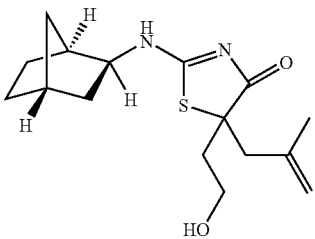

The mixture of 2-((1S,2S,4R)-bicyclo[2.2.1]heptan-2-ylamino)-5-(2-methylallyl)-5-(2-(tetrahydro-2H-pyran-2-yloxy)ethyl)thiazol-4(5H)-one (420 mg, 1.07 mmol) and p-toluenesulfonic acid (100 mg) in MeOH (5.0 mL) was stirred for 16 h at room temperature. The reaction mixture was then concentrated in vacuo, and sat'd NaH$_2$PO$_4$ was added. The mixture was then extracted with EtOAc, and the organic layer was washed with sat'd NH$_4$Cl, dried over MgSO$_4$, filtered and concentrated in vacuo. The crude residue was purified by flash chromatography (4:1; Hexane:EtOAc) to give the title compound as solid. MS (ES$^+$): 309 (M+H)$^+$.

Example 144

2-((1S,2S,4R)-Bicyclo[2.2.1]hept-2-ylamino)-7,7-dimethyl-8-oxa-1-thia-3-azaspiro[4.5]dec-2-en-4-one

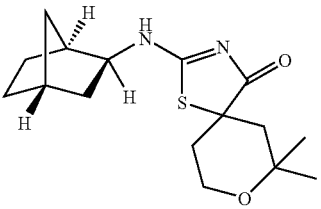

To a solution of 2-((1S,2S,4R)-bicyclo[2.2.1]heptan-2-ylamino)-5-(2-hydroxyethyl)-5-(2-methylallyl)thiazol-4(5H)-one (120 mg) in CH$_2$Cl$_2$ (3 mL) was added concentrated H$_2$SO$_4$ (200 uL). The resulting mixture was stirred for 16 h, then concentrated in vacuo. The residue was treated with sat'd NaH$_2$PO$_4$ and extracted with CH$_2$Cl$_2$. The organic layer was washed with sat'd NH$_4$Cl, dried over MgSO$_4$, filtered and concentrated in vacuo. The crude residue was purified by flash chromatography (4:1; Hexane:EtOAc) to give the title compound as solid. MS (ES$^+$): 309 (M+H)$^+$. The diastereomers were separated using standard HPLC methods described within this text.

Example 145

2-(Bicyclo[2.2.1]heptan-2-ylamino)-5-(2-(tert-butyldimethylsilyloxy)ethyl)thiazol-4(5H)-one

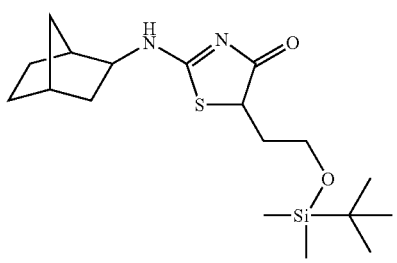

METHOD LL

The title compound was prepared according to the procedure described in the preparation of tert-butyl 4-((2-((2S)-bicyclo[2.2.1]heptan-2-ylamino)-5-methyl-4-oxo-4,5-dihydrothiazol-5-yl)methyl)piperidine-1-carboxylate by using 2-(bicyclo[2.2.1]heptan-2-ylamino)thiazol-4(5H)-one (1.00 g, 4.76 mmol), lithium diisopropylamide (Aldrich, 2.0 M in heptane/THF/ethylbenzene, 8.5 mL, 19.0 mmol), and (2-bromoethoxy)(tert-butyl)dimethylsilane (Aldrich, 6.83 g, 28.5 mmol). The title compound was obtained as an off-white solid (950 mg). MS (ESI, pos. ion) m/z: 369 (M+H).

Example 146

2-(Bicyclo[2.2.1]heptan-2-ylamino)-5,5-bis(2-(tert-butyldimethylsilyloxy)ethyl)thiazol-4(5H)-one

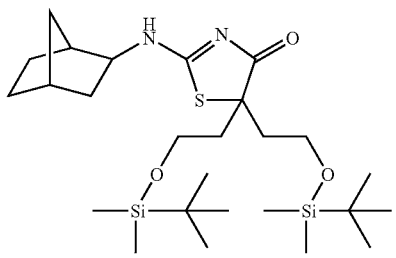

The title compound was prepared according to the procedure described in the preparation of tert-butyl 4-((2-((2S)-bicyclo[2.2.1]heptan-2-ylamino)-5-methyl-4-oxo-4,5-dihydrothiazol-5-yl)methyl)piperidine-1-carboxylate by using 2-(bicyclo[2.2.1]heptan-2-ylamino)-5-(2-(tert-butyldimethylsilyloxy)ethyl)thiazol-4(5H)-one (630 mg, 1.71 mmol), lithium diisopropylamide (Aldrich, 2.0 M in heptane/THF/ethylbenzene, 4.27 mL, 8.55 mmol), and (2-bromoethoxy)(tert-butyl)dimethylsilane (Aldrich, 2.46 g, 10.25 mmol). The title compound was obtained as a sticky orange solid (771 mg). MS (ESI, pos. ion) m/z: 413 (M-TBDMS+2H).

Example 147

2-(Bicyclo[2.2.1]heptan-2-ylamino)-5,5-bis(2-hydroxyethyl)thiazol-4(5H)-one

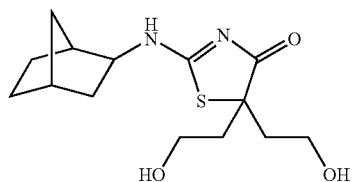

A mixture of 2-(bicyclo[2.2.1]heptan-2-ylamino)-5,5-bis(2-(tert-butyldimethylsilyloxy)ethyl)thiazol-4(5H)-one (771 mg, 1.46 mmol) in 15 mL of a 1% HCl solution in ethanol was stirred at room temperature for 3 h. The reaction mixture was then concentrated in vacuo. Flash column chromatography (silica gel, 0-8% MeOH—CH$_2$Cl$_2$) afforded the title compound as a colorless thin film (390 mg). MS (ESI, pos. ion) m/z: 299 (M+H).

Example 148

Methanesulfonic acid 2-[2-(bicyclo[2.2.1]hept-2-ylamino)-5-(2-methanesulfonyloxy-ethyl)-4-oxo-4,5-dihydro-thiazol-5-yl]-ethyl ester

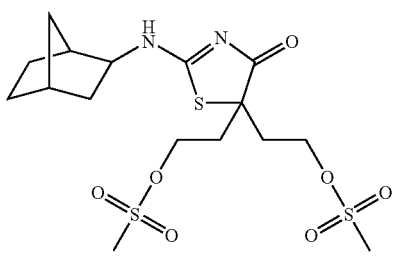

To a mixture of 2-(bicyclo[2.2.1]heptan-2-ylamino)-5,5-bis(2-hydroxyethyl)thiazol-4(5H)-one (280 mg, 0.94 mmol) and diisopropylethylamine (Aldrich, 412 mg, 3.19 mmol) in CH$_2$Cl$_2$ (5 mL) was added methanesulfonyl chloride (344 mg, 3.00 mmol, 3.2 eq), and the reaction mixture was stirred at room temperature for 18 h. The reaction mixture was then concentrated in vacuo to provide the title compound which was used without further purification. MS (ESI, pos. ion) m/z: 455 (M+H).

Example 149

2-(Bicyclo[2.2.1]hept-2-ylamino)-8-cyclopentyl-1-thia-3,8-diaza-spiro[4.5]dec-2-en-4-one

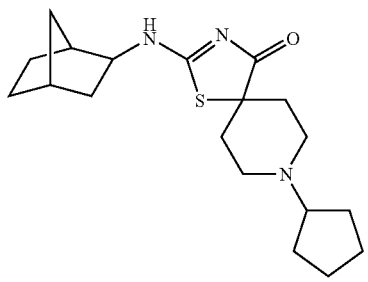

A mixture of methanesulfonic acid 2-[2-(bicyclo[2.2.1]hept-2-ylamino)-5-(2-methanesulfonyloxy-ethyl)-4-oxo-4,5-dihydro-thiazol-5-yl]-ethyl ester (half of the crude product from above) and cyclopentylamine (799 mg, 9.38 mmol) in CH$_2$Cl$_2$ (1.5 mL) was stirred at room temperature for 4 d. Flash column chromatography (silica gel, 0-10% MeOH in CH$_2$Cl$_2$) afforded the title compound as an off-white solid (52 mg). MS (ESI, pos. ion) m/z: 348 (M+H).

Example 150 tert-Butyl 4-((2-((2S)-bicyclo[2.2.1]heptan-2-ylamino)-5-methyl-4-oxo-4,5-dihydrothiazol-5-yl)methyl)piperidine-1-carboxylate

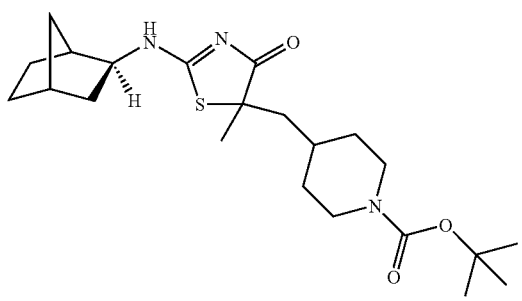

METHOD AA

To a solution of 2-((2S)-bicyclo[2.2.1]heptan-2-ylamino)-5-methylthiazol-4(5H)-one in anhydrous THF (30 mL) at −78° C. under N$_2$ was added lithium diisopropylamide (Aldrich, 2.0 M in heptane/THF/ethylbenzene, 9.2 mL, 18.4 mmol). After stirring the reaction mixture at −78° C. for 1 h, a solution of 4-bromomethyl-piperidine-1-carboxylic acid tert-butyl ester (Pharma Core, 5.12 g, 18.4 mmol, 4.0 eq) in anhydrous THF (10 mL) was added under N$_2$. The resulting reaction mixture was stirred at −78° C. for 4 h. The cooling bath was removed, and the reaction mixture was stirred at ambient temperature for ca. 18 h. Saturated NH₄Cl was then added, and the THF was removed in vacuo. The residue was extracted with EtOAc (3×180 mL), and the combined organic layers were washed with saturated NaCl, dried over Na₂SO₄, filtered, and concentrated in vacuo. Flash column chromatography (silica gel, 0-60% EtOAc in hexane) afforded the title compound as an off-white solid (1.42 g). MS (ESI, neg. ion) m/z: 420 (M–H).

Example 151

2-((2S)-Bicyclo[2.2.1]heptan-2-ylamino)-5-methyl-5-(piperidin-4-ylmethyl)thiazol-4(5H)-one

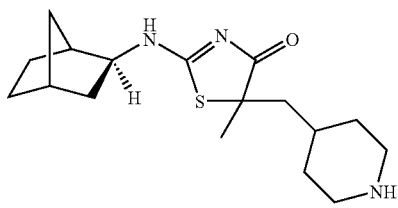

METHOD MM

A mixture of tert-butyl 4-((2-((2S)-bicyclo[2.2.1]heptan-2-ylamino)-5-methyl-4-oxo-4,5-dihydrothiazol-5-yl)methyl)piperidine-1-carboxylate (1.42 g, 3.37 mmol, 1.0 eq) in 50 mL of a 4.7 M HCl solution in EtOAc was stirred at room temperature. After 4 h, the reaction mixture was concentrated in vacuo. Aqueous Na₂CO₃ (2.0 M, 20 mL) was then added, and water was removed in vacuo. The residue was then triturated with 10% MeOH—CH₂Cl₂ (6×100 mL), and the combined triturating solution were concentrated in vacuo. The crude product was dissolved in CH₂Cl₂, filtered, and concentrated in vacuo to afford the title compound as a light orange solid (1.08 g). MS (ESI, pos. ion) m/z: 322 (M+H).

Example 152 tert-Butyl 2-(3-(4-((2-((2S)-bicyclo[2.2.1]heptan-2-ylamino)-5-methyl-4-oxo-4,5-dihydrothiazol-5-yl)methyl)piperidine-1-carbonyl)phenoxy)ethylcarbamate

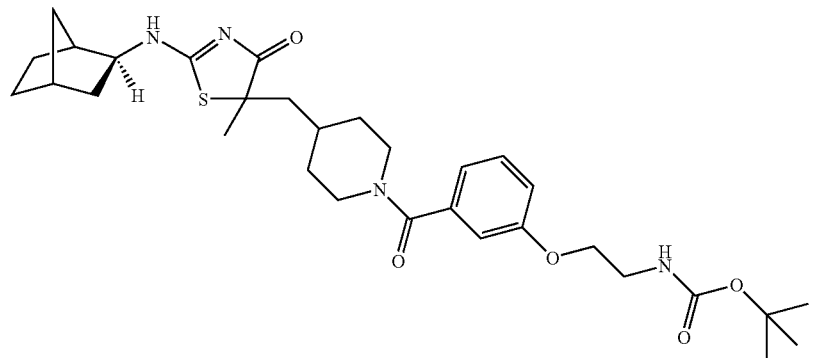

A mixture of 2-((2S)-bicyclo[2.2.1]heptan-2-ylamino)-5-methyl-5-(piperidin-4-ylmethyl)thiazol-4(5H)-one (534 mg, 1.66 mmol), 4-[2-(Boc-amino)ethyloxy]-benzoic acid (NeoMPS, 701 mg, 2.49 mmol), EDCI (Aldrich, 637 mg, 3.32 mmol, 2.0 eq), HOBt (Aldrich, 45 mg, 0.332 mmol, 0.2 eq) and triethylamine (Aldrich, 336 mg, 3.32 mmol, 2.0 eq) in CH₂Cl₂ (10 mL) was stirred at room temperature for ca. 18 h. The reaction was quenched with saturated NaHCO₃ (100 mL), and the crude product was extracted with CH₂Cl₂ (3×100 mL). The combined organic extracts were washed with brine, dried over Na₂SO₄, filtered, and concentrated. Flash column chromatography (silica gel, 0-5% MeOH in CH₂Cl₂) afforded the title compound as a white solid (800 mg). MS (ESI, pos. ion) m/z: 585 (M+H).

Example 153

5-((1-Acetylpiperidin-4-yl)methyl)-2-((2S))-bicyclo[2.2.1]heptan-2-ylamino)-5-methylthiazol-4(5H)-one

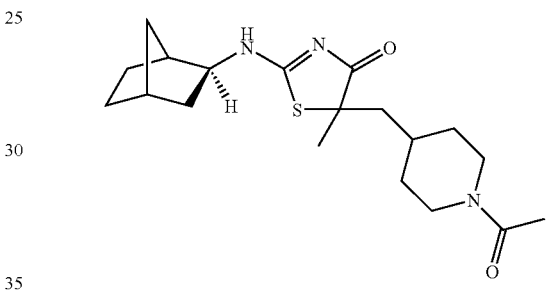

A mixture of 2-((2S)-bicyclo[2.2.1]heptan-2-ylamino)-5-methyl-5-(piperidin-4-ylmethyl)thiazol-4(5H)-one (130 mg, 0.41 mmol), acetic anhydride (Aldrich, 83 mg, 0.81 mmol) and diisopropylethylamine (157 mg, 1.22 mmol) in CH₂Cl₂ (3 mL) was stirred at room temperature for ca. 18 h. Brine was then added, and the mixture was extracted with CH₂Cl₂ (4×60 mL). The combined organic extracts were washed with brine, dried over Na₂SO₄, filtered, and concentrated in vacuo. Flash column chromatography (silica gel, 0-3.5% MeOH in CH₂Cl₂) afforded the title compound as a colorless thin film (116 mg). MS (ESI, pos. ion) m/z: 364 (M+H).

Example 154

2-((2S)-Bicyclo[2.2.1]heptan-2-ylamino)-5-methyl-5-((1-(methylsulfonyl)piperidin-4-yl)methyl)thiazol-4(5H)-one

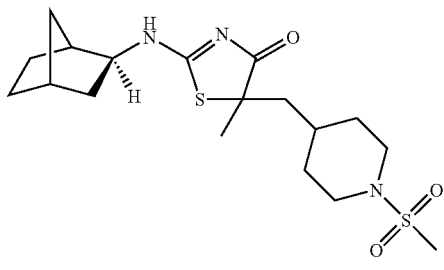

To a solution of 2-((2S)-bicyclo[2.2.1]heptan-2-ylamino)-5-methyl-5-(piperidin-4-ylmethyl)thiazol-4(5H)-one (64 mg, 0.20 mmol) in $CH_2Cl_2$ (1.5 mL) was added methanesulfonyl chloride (Aldrich, 34 mg, 0.30 mmol) and triethylamine (60 mg, 0.60 mmol), and the reaction mixture was stirred at room temperature for ca. 18 h. Water (30 mL) was then added, and the crude product was extracted with $CH_2Cl_2$ (3×60 mL). The combined organic extracts were washed with brine, dried over $Na_2SO_4$, filtered, and concentrated in vacuo. Flash column chromatography (silica gel, 0-3% MeOH in $CH_2Cl_2$) afforded the title compound as a white solid (34 mg). MS (ESI, pos. ion) m/z: 400 (M+H).

Example 155

2-((1S,2S,4R)-Bicyclo[2.2.1]heptan-2-ylamino)-5-(2-bromoethyl)thiazol-4(5H)-one

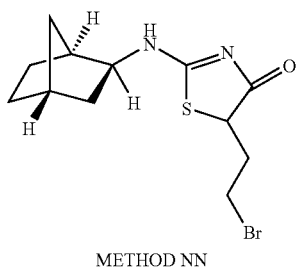

METHOD NN

To a solution of 2-((1S,2S,4R)-bicyclo[2.2.1]heptan-2-ylamino)thiazol-4(5H)-one (2.98 g, 14.2 mmol) in THF (15 ml) at −78° C. was added LDA (2.0 N, 28.4 ml). After 5 min, 1,2-dibromoethane (4.87 mL, 56.8 mmol) was added, and the reaction mixture was stirred for 3 h at −78° C. The resulting reaction mixture was poured into sat'd $NaH_2PO_4$ and extracted with EtOAc. The organic layer was dried over $MgSO_4$, filtered and concentrated in vacuo. The crude residue was purified by flash chromatography (4:1; Hexane:EtOAc) to give the title compound as a white solid. MS ($ES^+$): 317 (M+H)$^+$.

Example 156

2-((1S,2S,4R)-Bicyclo[2.2.1]hept-2-ylamino)-6,6-dimethyl-7-oxa-1-thia-3-azaspiro[4.4]non-2-en-4-one and 5-((1S,2S,4R)-bicyclo[2.2.1]hept-2-ylamino)-4-thia-6-azaspiro[2.4]hept-5-en-7-one

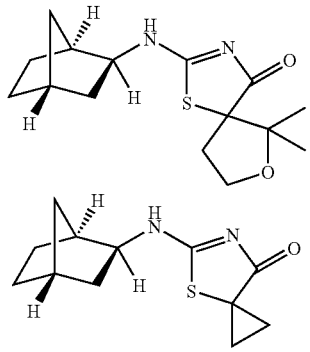

To a solution of 2-((1S,2S,4R)-bicyclo[2.2.1]heptan-2-ylamino)-5-(2-bromoethyl)thiazol-4(5H)-one (134 mg, 0.5 mmol) in THF (1 mL) at −78° C. was added LDA (2.0 N, 1.25 ml). After 5 min, acetone (500 uL) was added, and the reaction mixture was stirred for 3 h at −78° C. The resulting reaction mixture was poured into a sat'd $NaH_2PO_4$ and extracted with EtOAc. The organic layer was dried over $MgSO_4$, filtered and concentrated in vacuo. The crude residue was purified through flash chromatography (4:1; Hexane:EtOAc) to give 2-((1S,2S,4R)-bicyclo[2.2.1]hept-2-ylamino)-6,6-dimethyl-7-oxa-1-thia-3-azaspiro[4.4]non-2-en-4-one as a white solid. (MS ($ES^+$): 295 (M+H)$^+$), and 5-((1S,2S,4R)-bicyclo[2.2.1]hept-2-ylamino)-4-thia-6-azaspiro[2.4]hept-5-en-7-one as a white solid. MS ($ES^+$): 237 (M+H)$^+$.

Example 157

2-(2-(Bicyclo[2.2.1]heptan-2-ylamino)-4-oxo-4,5-dihydrothiazol-5-yl)acetic acid

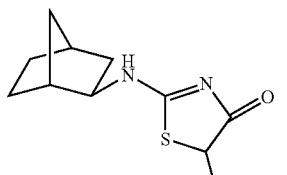

METHOD OO

A stirred mixture of (±)-exo-1-(bicyclo[2.2.1]heptan-2-yl)thiourea (1.00 g, 5.87 mmol) and maleic anhydride (576 mg, 5.87 mmol) in glacial acetic acid (20 mL) was heated to reflux. After 1 h, the solvent was evaporated in vacuo, and the residue was azeotroped from toluene (3×15 mL). The resulting solid was suspended in water, filtered, washed with water (3×15 mL) and then hexane (2×10 mL). Air drying the solid afforded the title compound (1.57 g) as a cream-colored amorphous solid.

Example 158

5-(2-(Azepan-1-yl)-2-oxoethyl)-(±)-exo-2-(bicyclo[2.2.1]heptan-2-ylamino)thiazol-4(5H)-one

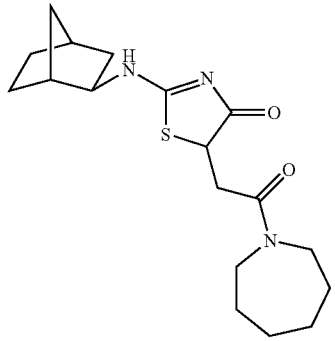

To a stirred solution of 2-(2-(bicyclo[2.2.1]heptan-2-ylamino)-4-oxo-4,5-dihydrothiazol-5-yl)acetic acid (518 mg, 1.93 mmol) in N,N-dimethylformamide (20 mL) were added N,N-diisopropylethylamine (0.404 mL, 2.32 mmol) and O-(7-azabenzotriazol-1-yl)-N,N,N',N'-tetramethyluronium hexafluorophosphate (807 mg, 2.12 mmol) at room temperature. After 20 min, hexamethyleneimine (0.218 mL, 1.93 mmol) was added. After an additional 3 h, the reaction was diluted with ethyl acetate (40 mL), washed with water (25 mL), and then brine (30 mL). The organic layer was then dried over sodium sulfate, filtered, and concentrated in vacuo. The residue was purified by flash chromatography (SiO$_2$, dichloromethane/methanol, 98:2 to 97:3) to afford the title compound (472 mg) as a cream-colored amorphous solid. MS (ESI, pos. ion) m/z: 350.2 (M+H).

Example 159

2-(2-(Bicyclo[2.2.1]heptan-2-ylamino)-5-methyl-4-oxo-4,5-dihydrothiazol-5-yl)ethyl isonicotinate

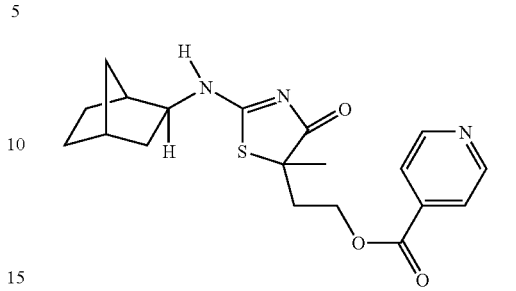

METHOD PP

A mixture of 2-(bicyclo[2.2.1]heptan-2-ylamino)-5-(2-hydroxyethyl)-5-methylthiazol-4(5H)-one (0.080 g, 0.30 mmol), isonicotinoyl chloride hydrochloride (0.056, 0.30 mmol), and N,N-diisopropylethylamine (0.13 mL, 0.75 mmol) in CH$_2$Cl$_2$ (1.0 mL) was heated in a sealed tube in a microwave oven (SmithSynthesizer from Personal Chemistry) at 120° C. for 10 min. The reaction mixture was conc. in vacuo, and the residue was partitioned between EtOAc and water. The organic portion was separated, washed with brine, conc. in vacuo, and purified by RP-HPLC to give the title compound as a white solid. MS m/z: 374.1 (M+H)$^+$.

Example 160

2-((2S)-Bicyclo[2.2.1]heptan-2-ylamino)-5-methyl-5-((1-(3-(2-morpholinoethoxy)benzoyl)piperidin-4-yl)methyl)thiazol-4(5H)-one

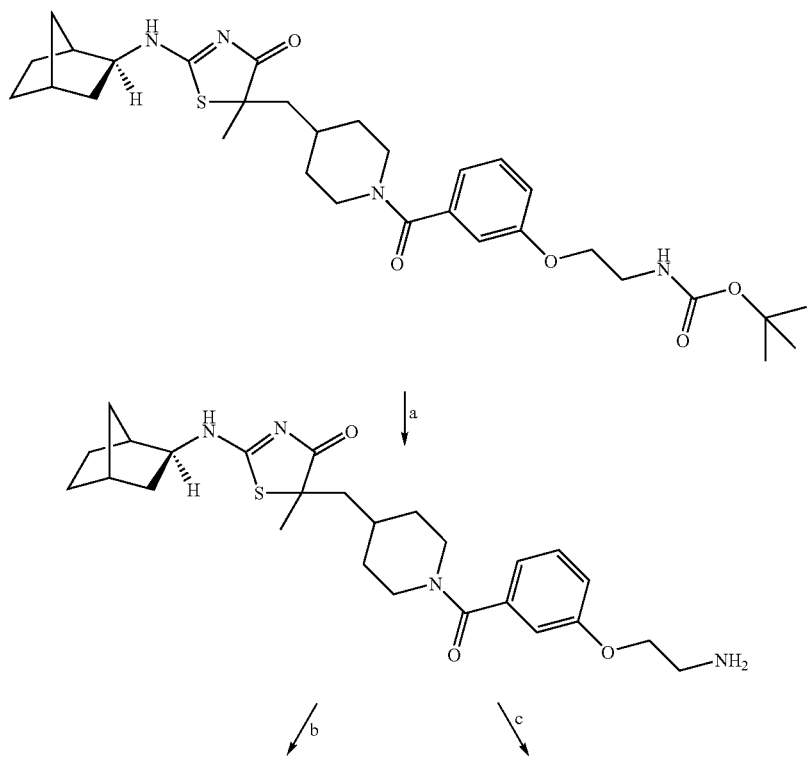

-continued

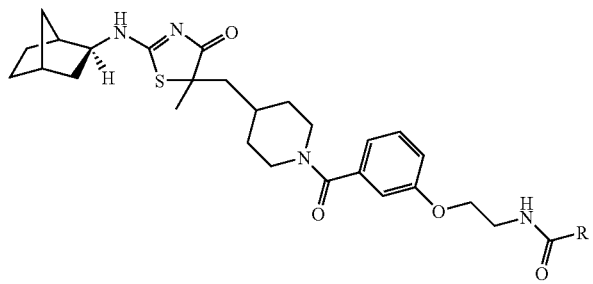

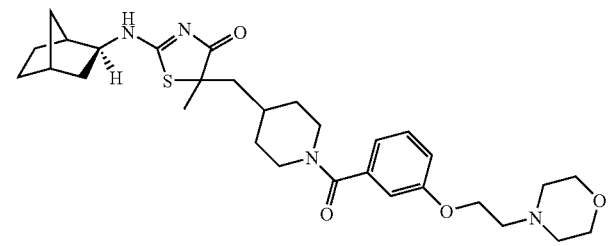

(a) 4.0-4.7 M HCl/EtOAc, room temperature; (b) RCOOH, EDCI, HOBt or (RCO)₂O, (Et)₃N; (c) (ClCH₂CH₂)₂O, KI, K₂CO₃

5-((1-(3-(2-Aminoethoxy)benzoyl)piperidin-4-yl)methyl)-2-((2S)-bicyclo[2.2.1]heptan-2-ylamino)-5-methylthiazol-4(5H)-one

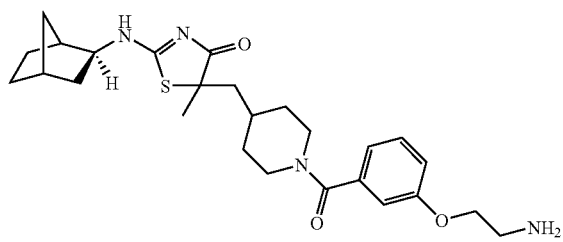

The title compound was prepared according to the procedure described in the preparation of 2-((2S)-bicyclo[2.2.1]heptan-2-ylamino)-5-methyl-5-(piperidin-4-ylmethyl)thiazol-4(5H)-one by using tert-butyl 2-(3-(4-((2-((2S)-bicyclo[2.2.1]heptan-2-ylamino)-5-methyl-4-oxo-4,5-dihydrothiazol-5-yl)methyl)piperidine-1-carbonyl)phenoxy)ethylcarbamate (689 mg, 1.18 mmol) as the starting material. The title compound was obtained as an off-white solid (531 mg). MS (ESI, pos. ion) m/z: 485 (M+H)

N-(2-(3-(4-((2-((2S)-Bicyclo[2.2.1]heptan-2-ylamino)-5-methyl-4-oxo-4,5-dihydrothiazol-5-yl)methyl)piperidine-1-carbonyl)phenoxy)ethyl)furan-3-carboxamide

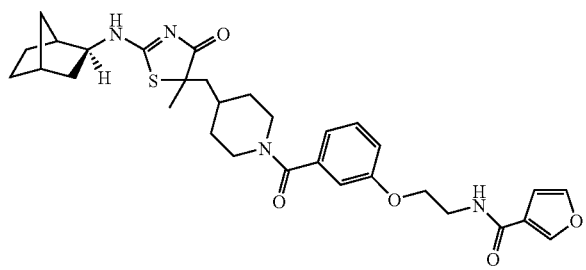

The title compound was prepared according to the procedure described in the preparation of tert-butyl 2-(3-(4-((2-((2S)-bicyclo[2.2.1]heptan-2-ylamino)-5-methyl-4-oxo-4,5-dihydrothiazol-5-yl)methyl)piperidine-1-carbonyl)phenoxy)ethylcarbamate by using 5-((1-(3-(2-aminoethoxy)benzoyl)piperidin-4-yl)methyl)-2-((2S)-bicyclo[2.2.1]heptan-2-ylamino)-5-methylthiazol-4(5H)-one (93 mg, 0.19 mmol), 3-furoic acid (Aldrich, 39 mg, 0.35 mmol), EDCI (Aldrich, 74 mg, 0.38 mmol), HOBt (Aldrich, 5.2 mg, 0.038 mmol) and triethylamine (Aldrich, 39 mg, 0.38 mmol, 2.0 eq). The title compound was obtained as an off-white solid (89 mg). MS (ESI, pos. ion) m/z: 579 (M+H).

2-((2S)-Bicyclo[2.2.1]heptan-2-ylamino)-5-methyl-5-((1-(3-(2-morpholinoethoxy)benzoyl)piperidin-4-yl)methyl)thiazol-4(5H)-one

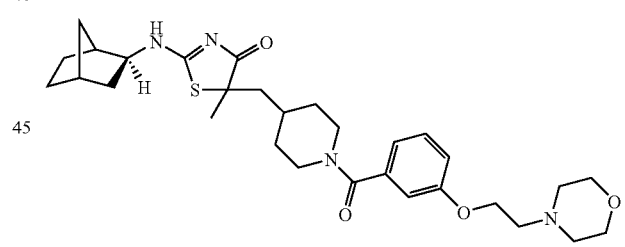

A mixture of 5-((1-(3-(2-aminoethoxy)benzoyl)piperidin-4-yl)methyl)-2-((2S)-bicyclo[2.2.1]heptan-2-ylamino)-5-methylthiazol-4(5H)-one (100 mg, 0.207 mmol), K₂CO₃ (114 mg, 0.83 mmol), KI (Aldrich, 6.9 mg, 0.041 mmol), 1-chloro-2-(2-chloroethoxy)ethane (Aldrich, 38 mg, 0.27 mmol) in CH₂Cl₂ (3 mL) was heated at reflux for 10 d. Saturated NaHCO₃ (50 mL) was added, and the crude product was extracted with CH₂Cl₂ (4×60 mL). The combined organic layers were washed with brine, dried over Na₂SO₄, filtered, and concentrated in vacuo. Flash column chromatography (silica gel, CH₂Cl₂ with 0-4% MeOH) afforded the title compound as a colorless thin film (10 mg). MS (ESI, pos. ion) m/z: 555 (M+H).

The following table of compounds were prepared using the methodologies outlined above.

TABLE 1

| Structure | Mol Wt. | Mass Spec | Name | Methods of Prep. |
|---|---|---|---|---|
| 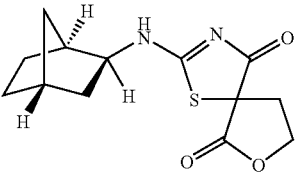 | 280.3 | 281 | 2-((1S,2S,4R)-bicyclo[2.2.1]hept-2-ylamino)-7-oxa-1-thia-3-azaspiro[4.4]non-2-ene-4,6-dione | X |
| 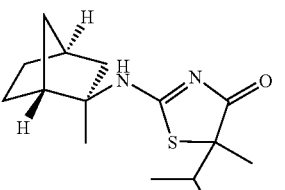 | 266.4 | 267 | 2-((1R,2R,4S)-bicyclo[2.2.1]heptan-2-ylamino)-5-isopropyl-5-methylthiazol-4(5H)-one | Y AA |
| 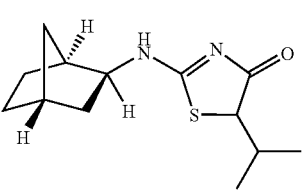 | 252.4 | 253. | 2-((1S,2S,4R)-bicyclo[2.2.1]heptan-2-ylamino)-5-isopropylthiazol-4(5H)-one | Y |
| 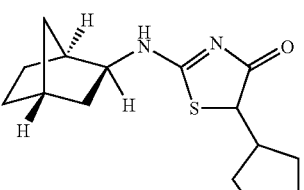 | 278.4 | 279 | 2-((1S,2S,4R)-bicyclo[2.2.1]heptan-2-ylamino)-5-cyclopentylthiazol-4(5H)-one | X |
| 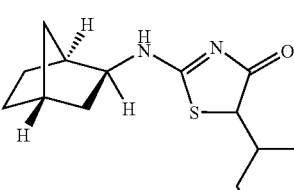 | 292.4 | 293 | 2-((1S,2S,4R)-bicyclo[2.2.1]heptan-2-ylamino)-5-cyclohexylthiazol-4(5H)-one | X |
| 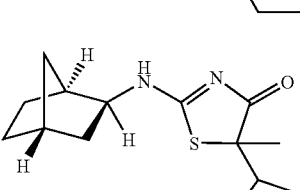 | 292.4 | 293 | 2-((1S,2S,4R)-bicyclo[2.2.1]heptan-2-ylamino)-5-cyclopentyl-5-methylthiazol-4(5H)-one | AA |
| 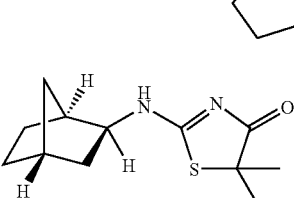 | 306.5 | 307 | 2-((1S,2S,4R)-bicyclo[2.2.1]heptan-2-ylamino)-5-cyclohexyl-5-methylthiazol-4(5H)-one | AA |

TABLE 1-continued

| Structure | Mol Wt. | Mass Spec | Name | Methods of Prep. |
|---|---|---|---|---|
| 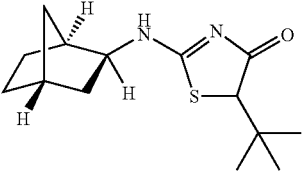 | 266.4 | 267 | 2-((1S,2S,4R)-bicyclo[2.2.1]heptan-2-ylammino)-5-tert-butylthiazol-4(5H)-one | X |
| 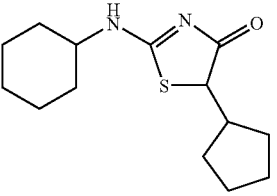 | 266.4 | 267 | 2-(cyclohexylamino)-5-cyclopentylthiazol-4(5H)-one | P X |
| 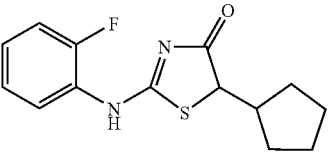 | 278.3 | 279 | 5-cyclopentyl-2-(2-fluorophenylamino)thiazol-4(5H)-one | X |
| 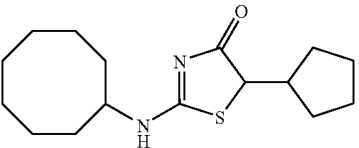 | 294.5 | 295 | 2-(cyclooctylamino)-5-cyclopentylthiazol-4(5H)-one | P X |
| 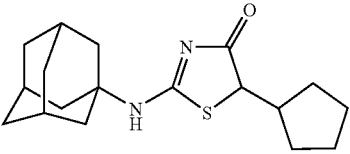 | 318.5 | 319 | 2-(adamantylamino)-5-cyclopentylthiazol-4(5H)-one | P X |
| 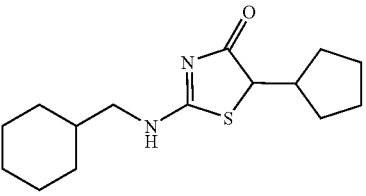 | 280.4 | 281 | 2-(cyclohexylmethylamino)-5-cyclopentylthiazol-4(5H)-one | P X |
| 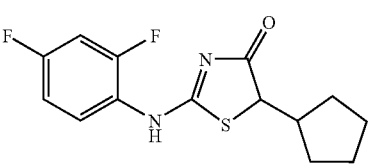 | 296.3 | 297 | 5-cyclopentyl-2-(2,4-difluorophenylamino)thiazol-4(5H)-one | X |
| 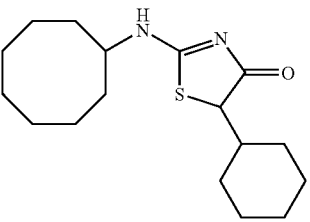 | 308.5 | 309 | 5-cyclohexyl-2-(cyclooctylamino)thiazol-4(5H)-one | P X |

TABLE 1-continued

| Structure | Mol Wt. | Mass Spec | Name | Methods of Prep. |
|---|---|---|---|---|
| 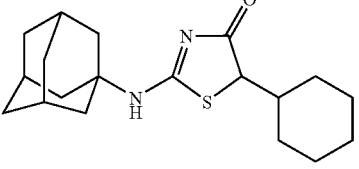 | 332.5 | 333 | 2-(adamantylamino)-5-cyclohexylthiazol-4(5H)-one | X |
| 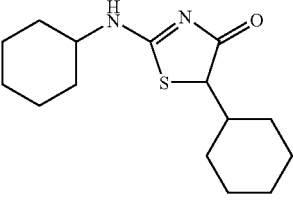 | 280.4 | 281 | 5-cyclohexyl-2-(cyclohexylamino)thiazol-4(5H)-one | P X |
| 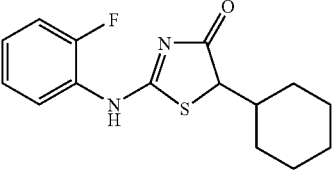 | 292.4 | 293 | 5-cyclohexyl-2-(2-fluorophhenylamino)thiazol-4(5H)-one | X |
| 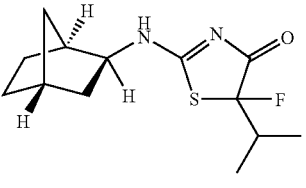 | 270.4 | 271 | 2-((1S,2S,4R)-bicyclo[2.2.1]heptan-2-ylamino)-5-fluoro-5-isopropylthiazol-4(5H)-one | Y BB |
| 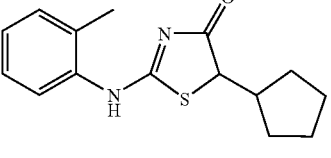 | 274.4 | 275 | 2-(o-toluidino)-5-cyclopentylthiazol-4(5H)-one | X |
| 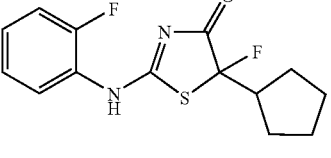 | 296.3 | 297 | 5-cyclopentyl-5-fluoro-2-(2-fluorophhenylamino)thiazol-4(5H)-one | X BB |
| 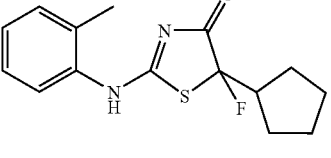 | 292.4 | 293 | 2-(o-toluidino)-5-cyclopentyl-5-fluorothiazol-4(5H)-one | X BB |
| 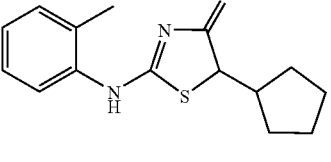 | 274.4 | 275 | 2-(o-toluidino)-5-cyclopentylthiazol-4(5H)-one | X |

TABLE 1-continued

| Structure | Mol Wt. | Mass Spec | Name | Methods of Prep. |
|---|---|---|---|---|
| 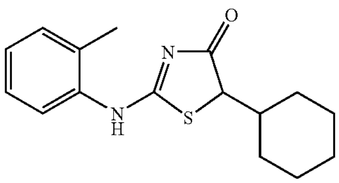 | 288.4 | 289 | 2-(o-toluidino)-5-cyclohexylthiazol-4(5H)-one | X |
| 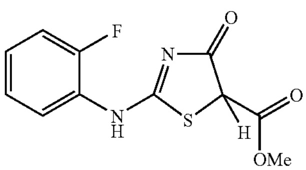 | 268.3 | 269 | methyl 2-(2-fluorophenylamino)-4-oxo-4,5-dihydrothiazole-5-carboxylate | X |
| 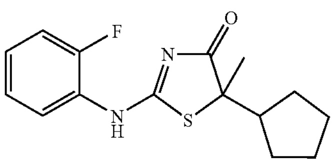 | 292.4 | 293 | 5-cyclopentyl-2-(2-fluorophenylamino)-5-methylthiazol-4(5H)-one | AA |
| 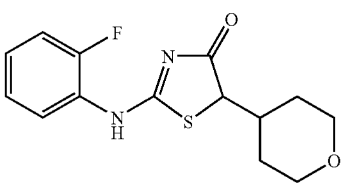 | 294.3 | 295 | 2-(2-fluorophenylamino)-5-(tetrahydro-2H-pyran-4-yl)thiazol-4(5H)-one | L X |
| 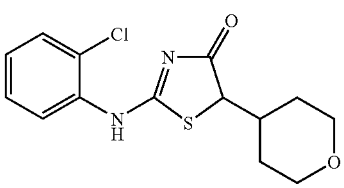 | 310.8 | 311 | 2-(2-chlorophenylamino)-5-(tetrahydro-2H-pyran-4-yl)thiazol-4(5H)-one | L X |
| 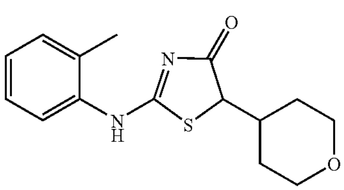 | 290.4 | 291 | 2-(o-toluidino)-5-(tetrahydro-2H-pyran-4-yl)thiazol-4(5H)-one | L X |
| 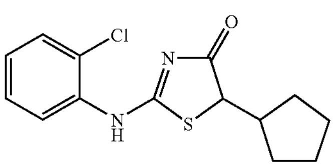 | 294.8 | 295 | 2-(2-chlorophenylamino)-5-cyclopentylthiazol-4(5H)-one | X |
| 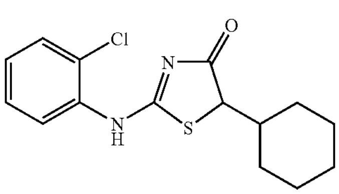 | 308.8 | 309 | 2-(2-chlorophenylamino)-5-cyclohexylthiazol-4(5H)-one | X |

TABLE 1-continued

| Structure | Mol Wt. | Mass Spec | Name | Methods of Prep. |
|---|---|---|---|---|
| 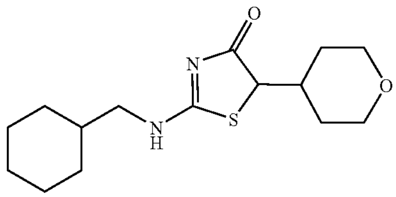 | 296.4 | 297 | 2-(cyclohexylmethylamino)-5-(tetrahydro-2H-pyran-4-yl)thiazol-4(5H)-one | P L X |
| 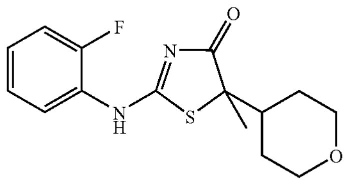 | 308.4 | 309 | 2-(2-fluorophenylamino)-5-methyl-5-(tetrahydro-2H-pyran-4-yl)thiazol-4(5H)-one | L X AA |
| 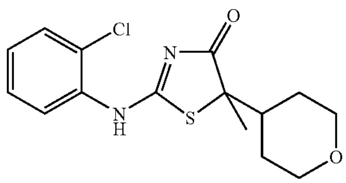 | 324.8 | 325 | 2-(2-chlorophenylamino)-5-methyl-5-(tetrahydro-2H-pyran-4-yl)thiazol-4(5H)-one | L X AA |
| 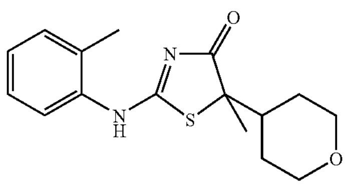 | 304.4 | 305 | 2-(o-toluidino)-5-methyl-5-(tetrahydro-2H-pyran-4-yl)thiazol-4(5H)-one | L X AA |
| 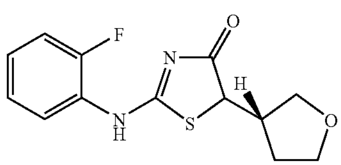 | 280.3 | 281 | 2-(2-fluorophenylamino)-5-((S)-tetrahydrofuran-3-yl)thiazol-4(5H)-one | L X |
| 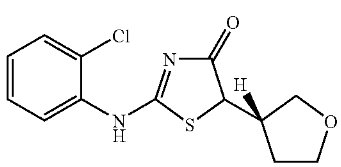 | 296.8 | 297 | 2-(2-chlorophenylamino)-5-((S)-tetrahydrofuran-3-yl)thiazol-4(5H)-one | L X |
| 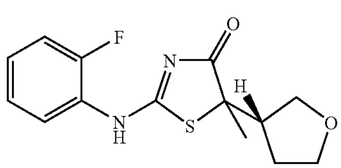 | 294.3 | 295 | 2-(2-fluorophenylamino)-5-methyl-5-((S)-tetrahydrofuran-3-yl)thiazol-4(5H)-one | L X AA |
| 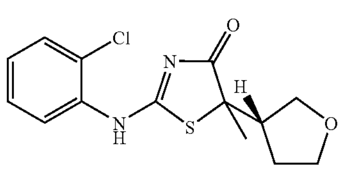 | 310.8 | 311 | 2-(2-chlorophenylamino)-5-methyl-5-((S)-tetrahydrofuran-3-yl)thiazol-4(5H)-one | L X AA |

TABLE 1-continued

| Structure | Mol Wt. | Mass Spec | Name | Methods of Prep. |
|---|---|---|---|---|
| 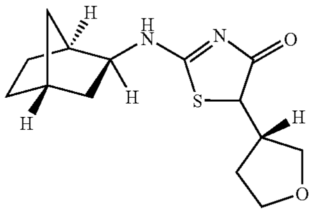 | 280.4 | 281 | 2-((1S,2S,4R)-bicyclo[2.2.1]heptan-2-ylamino)-5-((S)-tetrahydrofuran-3-yl)thiazol-4(5H)-one | L X |
| 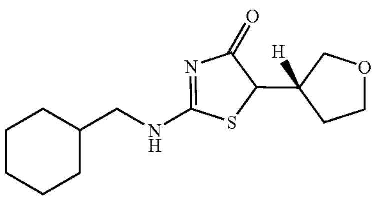 | 282.4 | 283 | 2-(cyclohexylmethylamino)-5-((S)-tetrahydrofuran-3-yl)thiazol-4(5H)-one | P L X |
| | 294.4 | 295 | 2-((1S,2S,4R)-bicyclo[2.2.1]heptan-2-ylamino)-5-methyl-5-((S)-tetrahydrofuran-3-yl)thiazol-4(5H)-one | L X AA |
| 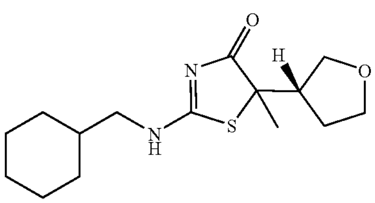 | 296.4 | 297 | 2-(cyclohexylmethylamino)-5-methyl-5-((S)-tetrahydrofuran-3-yl)thiazol-4(5H)-one | P L X AA |
| | 294.4 | 295 | 2-((1S,2S,4R)-bicyclo[2.2.1]heptan-2-ylamino)-5-(tetrahydro-2H-pyran-4-yl)thiazol-4(5H)-one | L X |
| 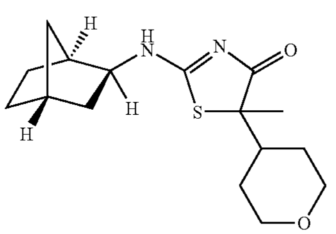 | 308.4 | 309 | 2-((1S,2S,4R)-bicyclo[2.2.1]heptan-2-ylamino)-5-methyl-5-(tetrahydro-2H-pyran-4-yl)thiazol-4(5H)-one | L X AA |
| 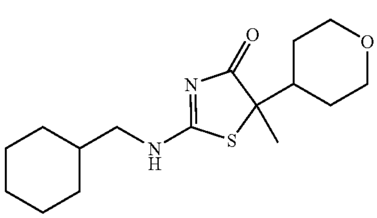 | 310.5 | 311 | 2-(cyclohexylmethylamino)-5-methyl-5-(tetrahydro-2H-pyran-4-yl)thiazol-4(5H)-one | P L X AA |

TABLE 1-continued

| Structure | Mol Wt. | Mass Spec | Name | Methods of Prep. |
|---|---|---|---|---|
| 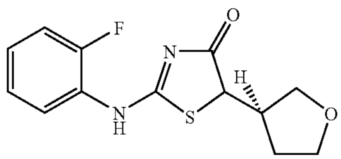 | 280.3 | 281 | 2-(2-fluorophenylamino)-5-((R)-tetrahydrofuran-3-yl)thiazol-4(5H)-one | L X |
| 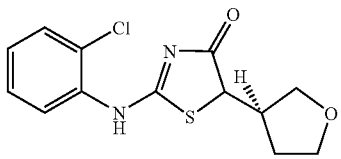 | 296.8 | 297 | 2-(2-chlorophenylamino)-5-((R)-tetrahydrofuran-3-yl)thiazol-4(5H)-one | L X |
| 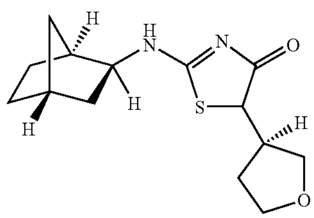 | 280.4 | 281 | 2-((1S,2S,4R)-bicyclo[2.2.1]heptan-2-ylamino)-5-((R)-tetrahydrofuran-3-yl)thiazol-4(5H)-one | L X |
| 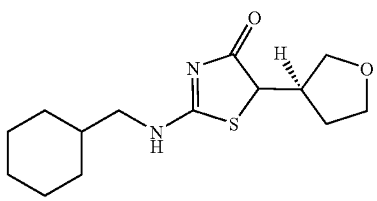 | 282.4 | 283 | 2-(cyclohexylmethylamino)-5-((R)-tetrahydrofuran-3-yl)thiazol-4(5H)-one | P L X |
| 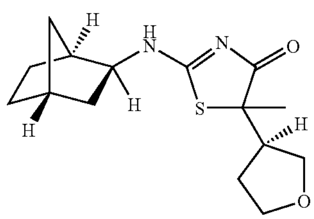 | 294.4 | 295 | 2-((1S,2S,4R)-bicyclo[2.2.1]heptan-2-ylamino)-5-methyl-5-((R)-tetrahydrofuran-3-yl)thiazol-4(5H)-one | L X AA |
| 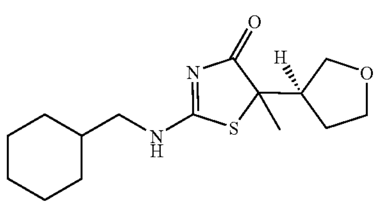 | 296.4 | 297 | 2-(cyclohexylmethylamino)-5-methyl-5-((R)-tetrahydrofuran-3-yl)thiazol-4(5H)-one | P L X AA |
| 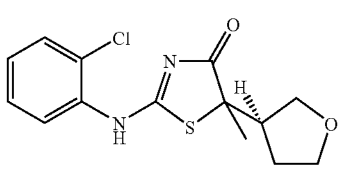 | 310.8 | 311 | 2-(2-chlorophenylamino)-5-methyl-5-((R)-tetrahydrofuran-3-yl)thiazol-4(5H)-one | L X AA |
| 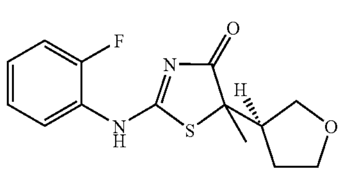 | 294.3 | 295 | 2-(2-fluorophenylamino)-5-methyl-5-((R)-tetrahydrofuran-3-yl)thiazol-4(5H)-one | L X AA |

TABLE 1-continued

| Structure | Mol Wt. | Mass Spec | Name | Methods of Prep. |
|---|---|---|---|---|
| 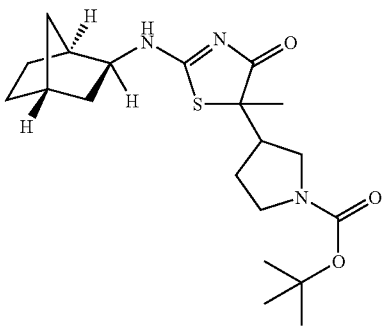 | 393.5 | 338; (M-t-Bu)+ | tert-butyl 3-(2-((1S,2S,4R)-bicyclo[2.2.1]heptan-2-ylamino)-5-methyl-4-oxo-4,5-dihydrothiazol-5-yl)pyrrolidine-1-carboxylate | L X AA |
| 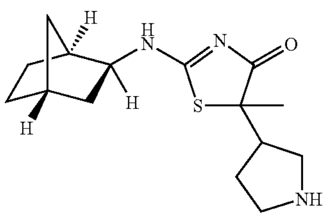 | 293.4 | 294 | 2-((1S,2S,4R)-bicyclo[2.2.1]heptan-2-ylamino)-5-methyl-5-(pyrrolidin-3-yl)thiazol-4(5H)-one | L X AA MM |
| 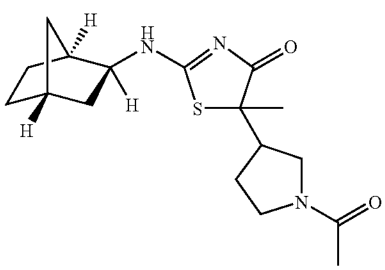 | 335.5 | 336 | 5-(1-acetylpyrrolidin-3-yl)-2-((1S,2S,4R)-bicyclo[2.2.1]heptan-2-ylamino)-5-methylthiazol-4(5H)-one | L X AA MM |
| 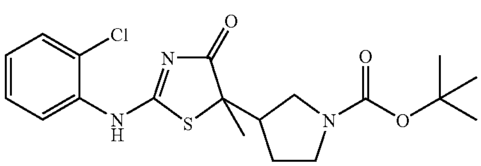 | 409.9 | 354; (M-t-Bu)+ | tert-butyl 3-(2-(2-chlorophenylamino)-5-methyl-4-oxo-4,5-dihydrothiazol-5-yl)pyrrolidine-1-carboxylate | L X AA |
| 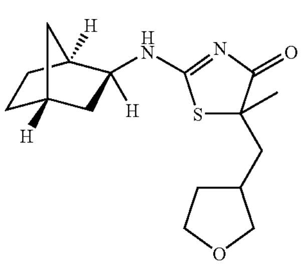 | 308.4 | 309 | 2-((1S,2S,4R)-bicyclo[2.2.1]heptan-2-ylamino)-5-methyl-5-((tetrahydrofuran-3-yl)methyl)thiazol-4(5H)-one | X AA |
| 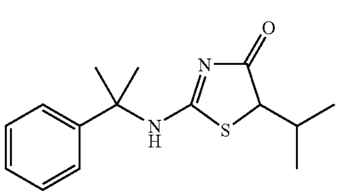 | 276.4 | 277 | 5-isopropyl-2-(2-phenylpropan-2-ylamino)thiazol-4(5H)-one | O X |

TABLE 1-continued

| Structure | Mol Wt. | Mass Spec | Name | Methods of Prep. |
|---|---|---|---|---|
| 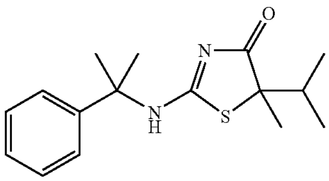 | 290.4 | 291 | 5-isopropyl-5-methyl-2-(2-phenylpropan-2-ylamino)thiazol-4(5H)-one | O X AA |
| 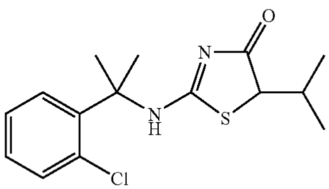 | 282.3 | 283 | 2-(2-chlorobenzylamino)-5-isopropylthiazol-4(5H)-one | O X |
| 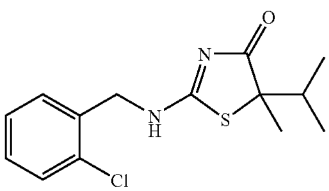 | 296.8 | 297 | 2-(2-chlorobenzylamino)-5-isopropyl-5-methylthiazol-4(5H)-one | O X AA |
| 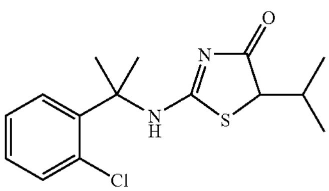 | 310.8 | 311 | 2-(2-(2-chlorophenyl)propan-2-ylamino)-5-isopropylthiazol-4(5H)-one | R O X |
| 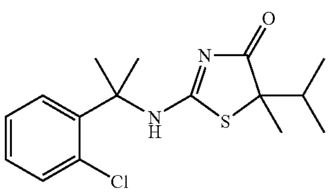 | 324.9 | 325 | 2-(2-(2-chlorophenyl)propan-2-ylamino)-5-isopropyl-5-methylthiazol-4(5H)-one | R O X AA |
| 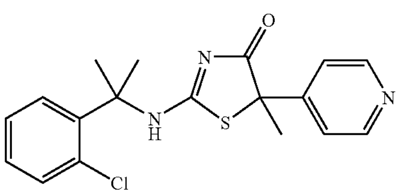 | 359.9 | 360 | 2-(2-(2-chlorophenyl)propan-2-ylamino)-5-methyl-5-(pyridin-4-yl)thiazol-4(5H)-one | R L O X |
| 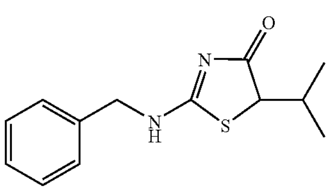 | 248.3 | 285 | 2-(benzylamino)-5-isopropylthiazol-4(5H)-one | O X |
| 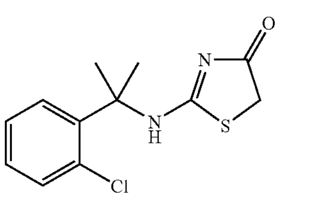 | 268.8 | 269 | 2-(2-(2-chlorophenyl)propan-2-ylamino)thiazol-4(5H)-one | O X |

TABLE 1-continued

| Structure | Mol Wt. | Mass Spec | Name | Methods of Prep. |
|---|---|---|---|---|
| | 262.4 | 263 | 2-(benzylamino)-5-isopropyl-5-methylthiazol-4(5H)-one | O X AA |
| 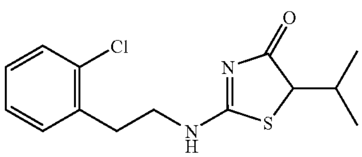 | 296.8 | 297 | 2-(2-chlorophenethylamino)-5-isopropylthiazol-4(5H)-one | O X |
| 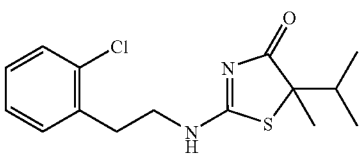 | 310.8 | 311 | 2-(2-chlorophenethylamino)-5-isopropyl-5-methylthiazol-4(5H)-one | O X AA |
| | 262.4 | 263 | 5-isopropyl-2-((R)-1-phenethylamino)thiazol-4(5H)-one | O X |
| | 262.4 | 263 | 5-isopropyl-2-((S)-1-phenethylamino)thiazol-4(5H)-one | O X |
| 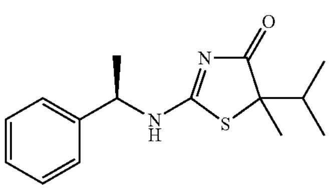 | 276.4 | 277 | 5-isopropyl-5-methyl-2-((R)-1-phenylethylamino)thiazol-4(5H)-one | O X AA |
| 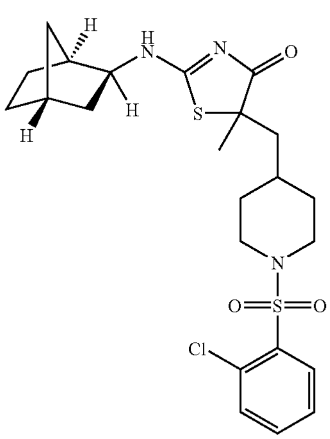 | 496.1 | 496 | 2-((1S,2S,4R)-bicyclo[2.2.1]heptan-2-ylamino)-5-((1-(2-chlorophenylsulfonyl)piperidin-4-yl)methyl)-5-methylthiazol-4(5H)-one | O X AA MM |

TABLE 1-continued

| Structure | Mol Wt. | Mass Spec | Name | Methods of Prep. |
|---|---|---|---|---|
| 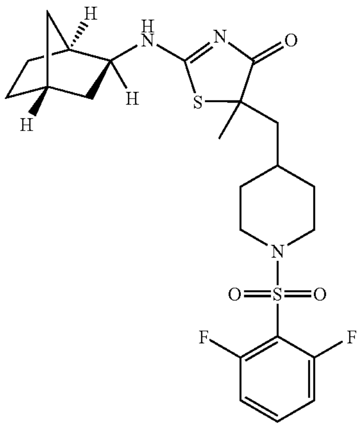 | 497.6 | 498 | 2-((1S,2S,4R)-bicyclo[2.2.1]heptan-2-ylamino)-5-((1-(2,6-difluorophenylsulfonyl)piperidin-4-yl)methyl)-5-methylthiazol-4(5H)-one | O X AA MM |
| 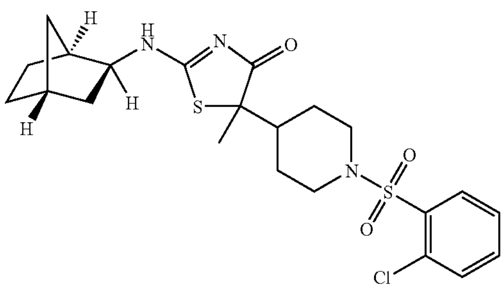 | 482.1 | 482 | 2-((1S,2S,4R)-bicyclo[2.2.1]heptan-2-ylamino)-5-(1-(2-chlorophenylsulfonyl)piperidin-4-yl)-5-methylthiazoil-4(5H)-one | O X L MM |
| 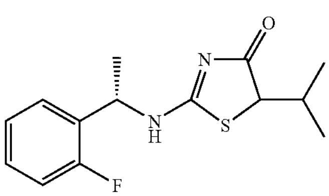 | 280.4 | 281 | 2-((S)-1-(2-fluorophenyl)ethylamino)-5-isopropylthiazol-4(5H)-one | Z |
| 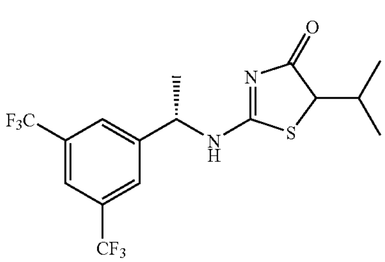 | 398.4 | 399 | 2-((S)-1-(3,5-bis(trifluoromethyl)phenyl)ethylamino)-5-isopropylthiazol-4(5H)-one | Z |
| 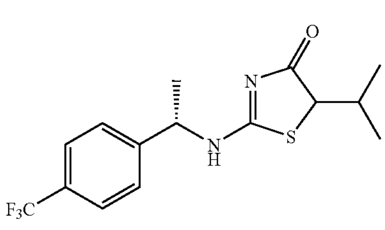 | 330.4 | 331 | 5-isopropyl-2-((S)-1-(4-(trifluoromethyl)phenyl)ethylamino)thiazol-4(5H)-one | Z |

TABLE 1-continued

| Structure | Mol Wt. | Mass Spec | Name | Methods of Prep. |
|---|---|---|---|---|
| 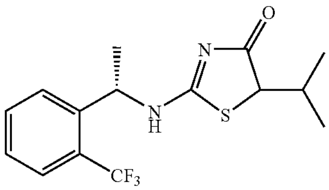 | 330.1 | 331 | 5-isopropyl-2-((S)-1-(2-(trifluoromethyl)phenyl)ethyl-amino)thiazol-4(5H)-one | Z |
| 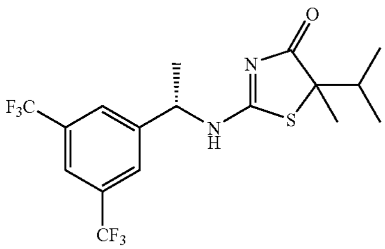 | 412.4 | 413 | 2-((S)-1-(3,5-bis(trifluoromethyl)phenyl)ethyl-amino)-5-isopropyl-5-methylthiazol-4(5H)-one | Z |
| 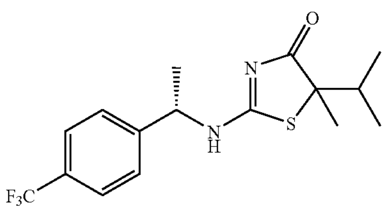 | 344.4 | 345 | 5-isopropyl-5-methyl-2-((S)-1-(4-(trifluoromethyl)phenyl)ethyl-amino)thiazol-4(5H)-one | Z |
| 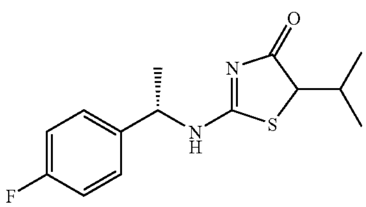 | 280.4 | 281 | 2-((S)-1-(4-fluorophenyl)ethylamino)-5-isopropylthiazol-4(5H)-one | Z |
| | 276.4 | 277 | (R)-5-isopropyl-5-methyl-2-((S)-1-phenylethylamino)thiazol-4(5H)-one | Z AA |
| | 276.4 | 277 | (S)-5-isopropyl-5-methyl-2-((S)-1-phenylethylamino)thiazol-4(5H)-one | Z AA |
| 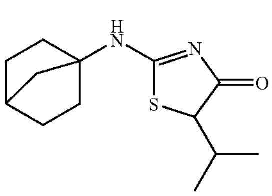 | 252.4 | 253 | 2-(bicyclo[2.2.1]heptan-1-ylamino)-5-isopropylthiazol-4(5H)-one | S X |

TABLE 1-continued

| Structure | Mol Wt. | Mass Spec | Name | Methods of Prep. |
|---|---|---|---|---|
| 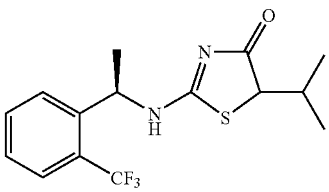 | 330.4 | 331 | 5-isopropyl-2-((R)-1-(2-(trifluoromethyl)phenyl)ethyl-amino)thiazol-4(5H)-one | Z |
| | 280.4 | 281 | 2-((R)-1-(2-fluorophenyl)ethylamino)-5-isopropylthiazol-4(5H)-one | Z |
| | 280.4 | 281 | 2-((R)-1-(4-fluorophenyl)ethylamino)-5-isopropylthiazol-4(5H)-one | Z |
| 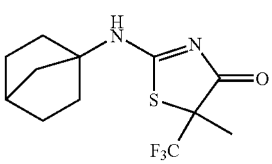 | 292.3 | 293 | 2-(bicyclo[2.2.1]heptan-1-ylamino)-5-methyl-5-(trifluoromethyl)thiazol-4(5H)-one | S X CC |
| 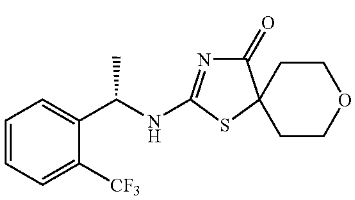 | 358.4 | 359 | 2-((S)-1-(2-(trifluoromethyl)phenyl)ethyl-amino))-8-oxa-1-thia-3-azaspiro[4.5]non-2-ene-4-one | O X EE |
| | 344.4 | 345 | (S)-5-isopropyl-5-methyl-2-((S)-1-(2-(trifluoromethyl)phenyl)ethyl-amino)thiazol-4(5H)-one | Z AA |
| | 344.4 | 345 | (R)-5-isopropyl-5-methyl-2-((S)-1-(2-(trifluoromethyl)phenyl)ethyl-amino)thiazol-4(5H)-one | Z AA |

TABLE 1-continued

| Structure | Mol Wt. | Mass Spec | Name | Methods of Prep. |
|---|---|---|---|---|
| | 266.4 | 267 | (S)-2-(bicyclo[2.2.1]heptan-1-ylamino)-5-isopropyl-5-methylthiazol-4(5HH)-one | S X AA |
| | 266.4 | 267 | (R)-2-(bicyclo[2.2.1]heptan-1-ylamino)-5-isopropyl-5-methylthiazol-4(5H)-one | S X AA |
| | 294.4 | 295 | (S)-2-((S)-1-(2-fluorophenyl)ethylamino)-5-isopropyl-5-methylthiazol-4(5H)-one | Z AA |
| | 294.4 | 295 | (R)-2-((S)-1-(2-fluorophenyl)ethylamino)-5-isopropyl-5-methylthiazol-4(5H)-one | Z AA |
| 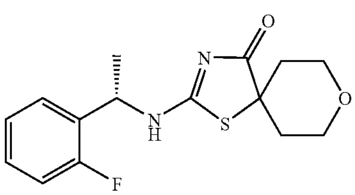 | 308.4 | 309 | 2-((S)-1-(2-fluorophenyl)ethylamino))-8-oxa-1-thia-3-azaspiro[4.5]non-2-ene-4-one | O X EE |
| 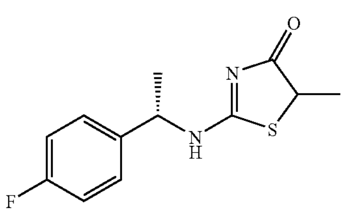 | 252.3 | 253 | 2-((S)-1-(4-fluorophenyl)ethylamino)-5-methylthiazol-4(5H)-one | O X |
| | 292.3 | 293 | (R)-2-((1S,2S,4R)-bicyclo[2.2.1]heptan-2-ylamino)-5-methyl-5-(trifluoromethyl)thiazol-4(5H)-one | O Y CC |
| | 292.3 | 293 | (S)-2-((1S,2S,4R)-bicyclo[2.2.1]heptan-2-ylamino)-5-methyl-5-(trifluoromethyl)thiazol-4(5H)-one | O Y CC |

TABLE 1-continued

| Structure | Mol Wt. | Mass Spec | Name | Methods of Prep. |
|---|---|---|---|---|
| 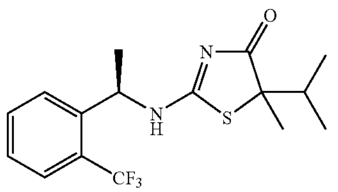 | 344.4 | 345 | 5-isopropyl-5-methyl-2-((R)-1-(2-(trifluoromethyl)phenyl)ethyl-amino)thiazol-4(5H)-one | Z AA |
| | 294.4 | 295 | 2-((R)-1-(2-fluorophenyl)ethylamino)-5-isopropyl-5-methylthiazol-4(5H)-one | Z AA |
| | 294.4 | 295 | 2-((R)-1-(4-fluorophenyl)ethylamino)-5-isopropyl-5-methylthiazol-4(5H)-one | Z AA |
| 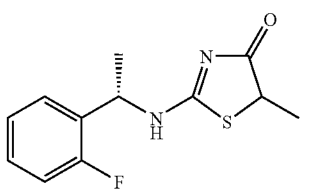 | 252.3 | 253 | 2-((S)-1-(2-fluorophenyl)ethylamino)-5-methylthiazol-4(5H)-one | Z |
| 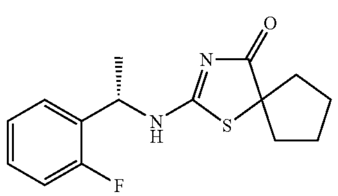 | 292.4 | 293 | 2-((S)-1-(2-fluorophenyl)ethylamino))-1-thia-3-azaspiro[4.4]non-2-ene-4-one | O X |
| 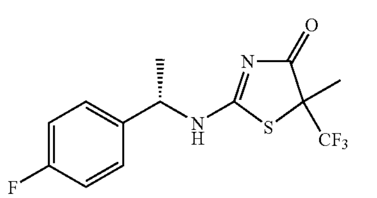 | 320.3 | 321 | 2-((S)-1-(4-fluorophenyl)ethylamino)-5-methyl-5-(trifluoromethyl)thiazol-4(5H)-one | O X CC |
| | 294.4 | 295 | (S)-2-((S)-1-(4-fluorophenyl)ethylamino)-5-isopropyl-5-methylthiazol-4(5H)-one | X AA |

TABLE 1-continued

| Structure | Mol Wt. | Mass Spec | Name | Methods of Prep. |
|---|---|---|---|---|
| 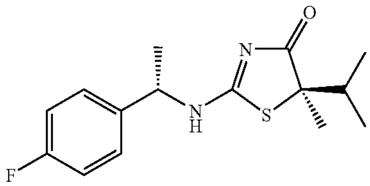 | 294.4 | 295 | (R)-2-((S)-1-(4-fluorophenyl)ethylamino)-5-isopropyl-5-methylthiazol-4(5H)-one | X<br>AA |
| 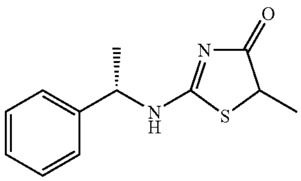 | 234.3 | 235 | 5-methyl-2-((S)-1-phenylethylamino)thiazol-4(5H)-one | O<br>X |
| 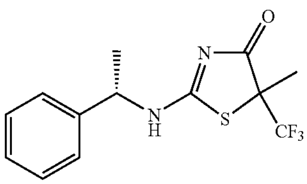 | 302.3 | 303 | 5-methyl-2-((S)-1-phenylethylamino)-5-(trifluoromethyl)thiazol-4(5H)-one | O<br>X<br>CC |
| 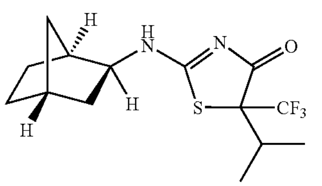 | 320.4 | 321 | 2-((1S,2S,4R)-bicyclo[2.2.1]heptan-2-ylamino)-5-isopropyl-5-(trifluoromethyl)thiazol-4(5H)-one | O<br>X<br>CC |
| 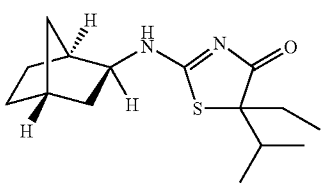 | 280.4 | 281 | 2-((1S,2S,4R)-bicyclo[2.2.1]heptan-2-ylamino)-5-ethyl-5-isopropylthiazol-4(5H)-one | O<br>X<br>AA |
| | 320.3 | 321 | (R)-2-((S)-1-(2-fluorophenyl)ethylamino)-5-methyl-5-(trifluoromethyl)thiazol-4(5H)-one | O<br>Y<br>CC |
| | 320.3 | 321 | (S)-2-((S)-1-(2-fluorophenyl)ethylamino)-5-methyl-5-(trifluoromethyl_thiazol-4(5H)-one | O<br>Y<br>CC |
| 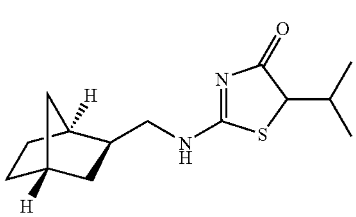 | 266.4 | 267 | 2-((1S,2S,4R)-bicyclo[2.2.1]heptan-2-ylmethylamino)-5-isopropylthiazol-4(5H)-one | W<br>O<br>X |

TABLE 1-continued

| Structure | Mol Wt. | Mass Spec | Name | Methods of Prep. |
|---|---|---|---|---|
| 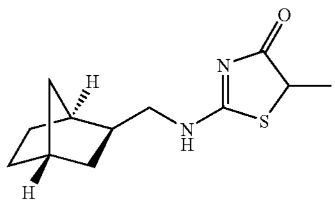 | 238.3 | 239 | 2-((1S,2S,4R)-bicyclo[2.2.1]heptan-2-ylmethylamino)-5-methylthiazol-4(5H)-one | W O Y |
| 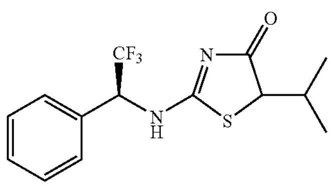 | 316.3 | 317 | 5-isopropyl-2-((S)-2,2,2-trifluoro-1-phenylethylamino)thiazol-4(5H)-one | Z |
| 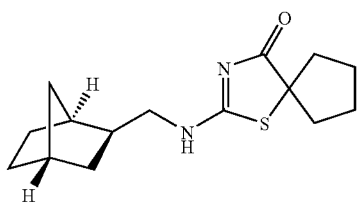 | 278.4 | 279 | 2-((1S,2S,4R)-bicyclo[2.2.1]hept-2-ylmethylamino)-1-thia-3-azaspiro[4.4]non-2-ene-4-one | W O X |
| 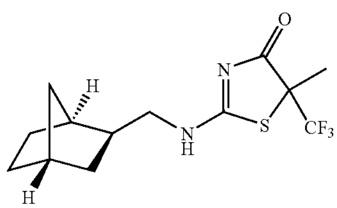 | 306.3 | 307 | 2-((1S,2S,4R)-bicyclo[2.2.1]heptan-2-ylmethylamino)-5-methyl-5-(trifluoromethyl)thiazol-4(5H)-one | W O Y CC |
| 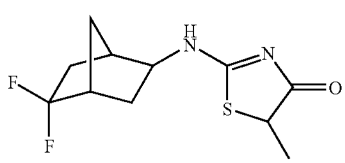 | 260.3 | 261 | 2-(5,5-difluorobicyclo[2.2.1]heptan-2-ylamino)-5-methylthiazol-4(5H)-one | W O Y |
| 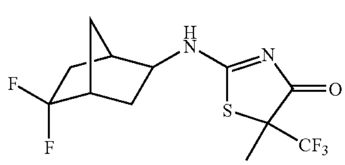 | 328.3 | 329 | 2-(5,5-difluorobicyclo[2.2.1]heptan-2-ylamino)-5-methyl-5-(trifluoromethyl)thiazol-4(5H)-one | Q O Y CC |
| 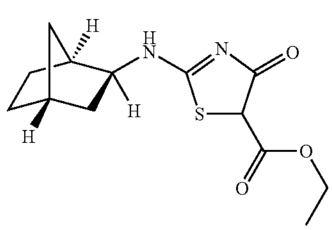 | 282.4 | 283 | ethyl 2-((1S,4R)-bicyclo[2.2.1]heptan-2-ylammino)-4-oxo-4,5-dihydrothiazol-5-carboxylate | X |

TABLE 1-continued

| Structure | Mol Wt. | Mass Spec | Name | Methods of Prep. |
|---|---|---|---|---|
| 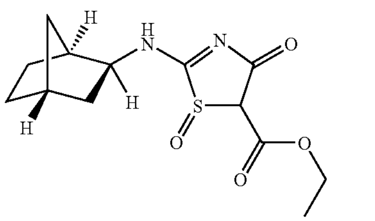 | 298.4 | 299 | 2-((1S,4R)-Bicyclo[2.2.1]hept-2-ylamino)-1,4-dioxo-4,5-dihydro-1H-1λ⁴-thiazole-5-carboxylic acid ethyl ester | X |
| 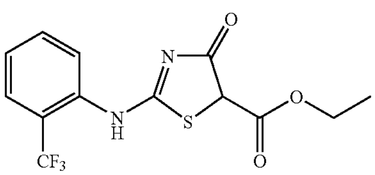 | 332.3 | 333 | ethyl 4-oxo-2-(2-(trifluoromethyl)phenylamino)-4,5-dihydrothiazole-5-carboxylate | X |
| 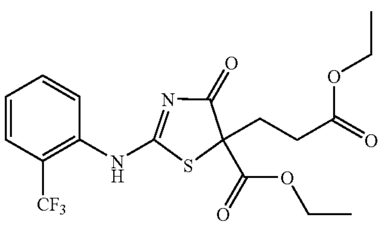 | 432.4 | 433 | ethyl 5-(3-ethoxy-3-oxopropyl)-4-oxo-2-(2-(trifluoromethyl)phenylamino)-4,5-dihydrothiazole-5-carboxylate | X DD |
| 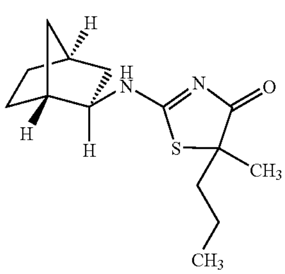 | 266.4 | 267 | 2-((1R,2R,4S)-bicyclo[2.2.1]heptan-2-ylamino)-5-methyl-5-propylthiazol-4(5H)-one | X |
| 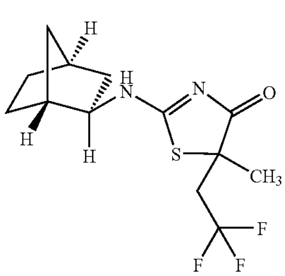 | 306.4 | 307 | 2-((1R,2R,4S)-bicyclo[2.2.1]heptan-2-ylamino)-5-methyl-5-(2,2,2-trifluoroethyl)thiazol-4(5H)-one | X |
| 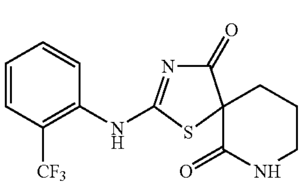 | 343.3 | 344 | 2-(2-Trifluoromethyl-phenylamino)-1-thia-3,7-diaza-spiro[4.5]dec-2-ene-4,6-dione | M X |

TABLE 1-continued

| Structure | Mol Wt. | Mass Spec | Name | Methods of Prep. |
|---|---|---|---|---|
| | 293.4 | 294 | 2-((1R,2R,4S)-Bicyclo[2.2.1]hept-2-ylamino)-1-thia-3,7-diaza-spiro[4.5]dec-2-ene-4,6-dione | M X |
| 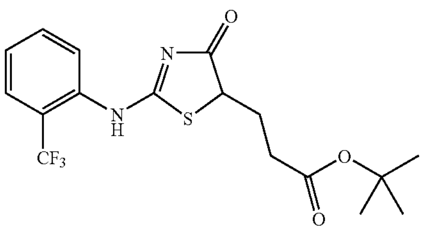 | 388.4 | 389 | tert-butyl 3-(4-oxo-2-(2-(trifluoromethyl)phenylamino)-4,5-dihydrothiazol-5-yl)propanoate | X DD |
| | 293.4 | 294 | 2-((1S,2S,4R)-Bicyclo[2.2.1]hept-2-ylamino)-1-thia-3,7-diaza-spiro[4.5]dec-2-ene-4,6-dione | M X |
| 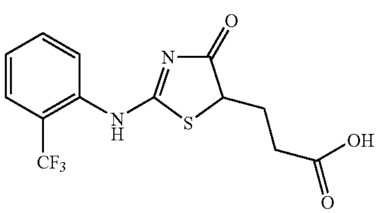 | 332.3 | 333 | 3-(4-oxo-2-(2-(trifluoromethyl)phenylamino)-4,5-dihydrothiazol-5-yl)propanoic acid | X DD |
| 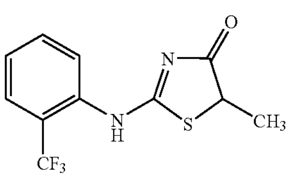 | 240.7 | 241 | 2-(2-chlorophenylamino)-5-methylthiazol-4(5H)-one | X |
| 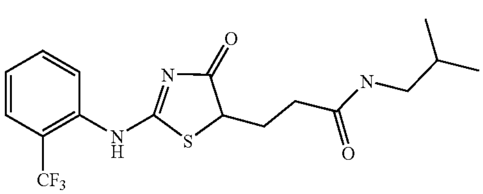 | 387.4 | 388 | N-isobutyl-3-(4-oxo-2-(2-(trifluoromethyl)phenylamino)-4,5-dihydrothiazol-5-yl)propanamide | X DD MM |
| 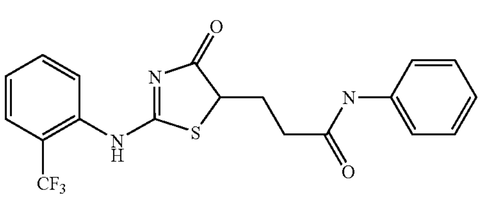 | 407.4 | 408 | 3-(4-oxo-2-(2-(trifluoromethyl)phenylamino)-4,5-dihydrothiazol-5-yl)-N-phenylpropanamide | X DD MM |

TABLE 1-continued

| Structure | Mol Wt. | Mass Spec | Name | Methods of Prep. |
|---|---|---|---|---|
| 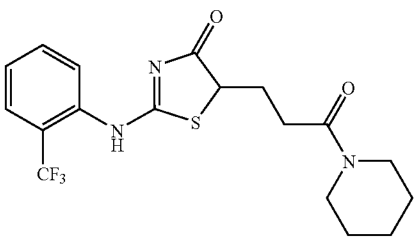 | 399.4 | 400 | 5-(3-oxo-3-(piperidin-1-yl)propyl)-2-(2-(trifluoromethyl)phenylamino)thiazol-4(5H)-one | X DD MM |
| 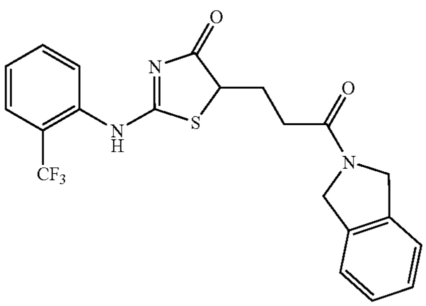 | 433.4 | 434 | 5-(3-isoindolin-2-yl)-3-oxopropyl)-2-(2-(trifluoromethyl)phenylamino)-thiazol-4(5H)-one | X DD MM |
| 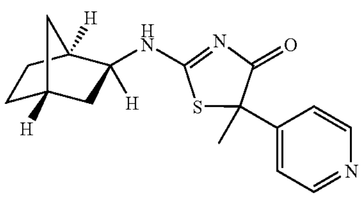 | 301.4 | 302 | 2-((1S,2S,4R)-bicyclo[2.2.1]heptan-2-ylamino)-5-methyl-5-(pyridin-4-yl)thiazol-4(5H)-one | M X |
| 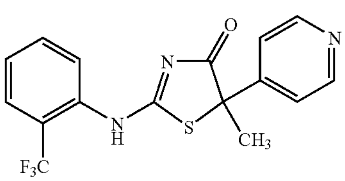 | 351.4 | 352 | 5-methyl-5-(pyridin-4-yl)-2-(2-(trifluoromethyl)phenylamino)thiazol-4(5H)-one | M X |
| 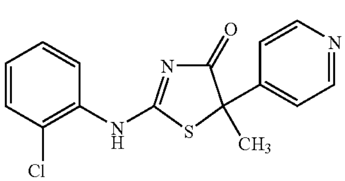 | 317.8 | 318 | 2-(2-chlorophenylamino)-5-methyl-5-(pyridin-4-yl)thiazol-4(5H)-one | M X |
| 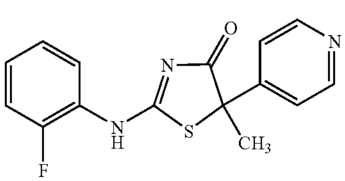 | 301.3 | 302 | 2-(2-fluorophenylamino)-5-methyl-5-(pyridin-4-yl)thiazol-4(5H)-one | M X |

TABLE 1-continued

| Structure | Mol Wt. | Mass Spec | Name | Methods of Prep. |
|---|---|---|---|---|
| 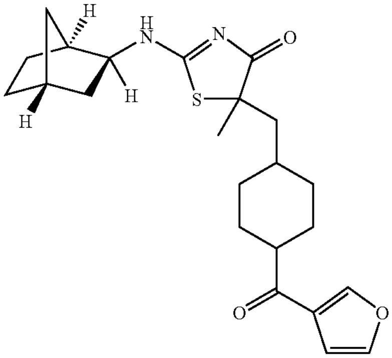 | 415.6 | 416 | 2-((1S,2S,4R)-bicyclo[2.2.1]heptan-2-ylamino)-5-((1-(furan-4-carbonyl)piperidin-4-yl)methyl)-5-methylthiazol-4(5H)-one | X AA MM |
| 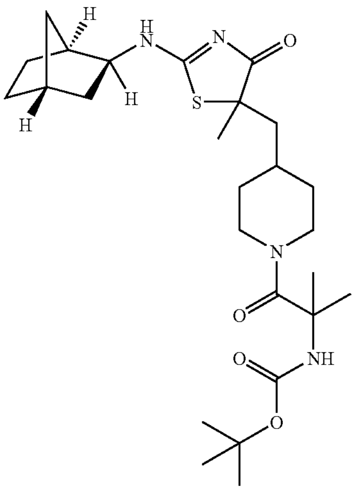 | 506.7 | 507 | tert-butyl 1-(4-((2-((1S,2S,4R)-bicyclo[2.2.1]heptan-2-ylamino)-5-methyl-4-oxo-4,5-dihydrothiazol-5-yl)methyl)piperidin-1-yl)-2-methyl-1-oxopropan-2-ylcarbamate | X AA MM |
| 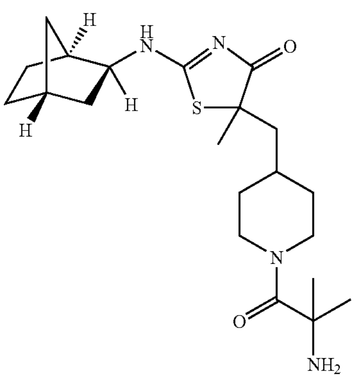 | 406 | 407 | 5-((1-(2-amino-2-methylpropanoyl)piperidin-4-yl)methyl)-2-((1S,2S,4R)-bicyclo[2.2.1]heptan-2-ylamino)-5-methylthiazol-4(5H)-one | X AA MM |
| 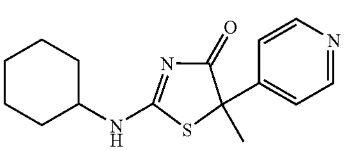 | 289.4 | 290 | 2-(cyclohexylamino)-5-methyl-5-(pyridin-4-yl)thiazol-4(5H)-one | M X |
| 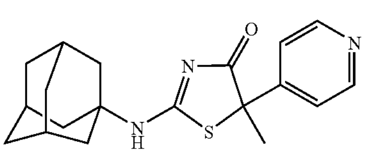 | 341.5 | 342 | 2-(Adamantyl-1-ylamino)-5-methyl-5-pyridin-4-yl-thiazol-4-one | M X |

TABLE 1-continued

| Structure | Mol Wt. | Mass Spec | Name | Methods of Prep. |
|---|---|---|---|---|
| 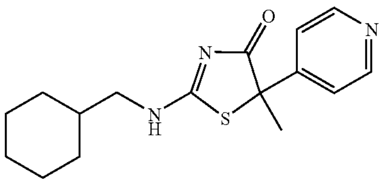 | 303.4 | 304 | 2-(cyclohexylmethylamino)-5-methyl-5-(pyridin-4-yl-thiazol-4(5H)-one | M X |
| | 301.4 | 302 | 2-((1S,2S,4R)-bicyclo[2.2.1]heptan-2-ylamino)-5-methyl-5-(pyridin-3-yl)thiazol-4(5H)-one | M X |
| | 317.8 | 318 | 2-(2-chlorophenylamino)-5-methyl-5-(pyridin-3-yl)thiazol-4(5H)-one | M X |
| | 317.8 | 318 | 2-(2-chlorophenylamino)-5-methyl-5-(pyridin-2-yl)thiazol-4(5H)-one | M X |
| | 301.4 | 302 | 2-((1S,2S,4R)-bicyclo[2.2.1]heptan-2-ylamino)-5-methyl-5-(pyridin-2-yl)thiazol-4(5H)-one | M X |
| 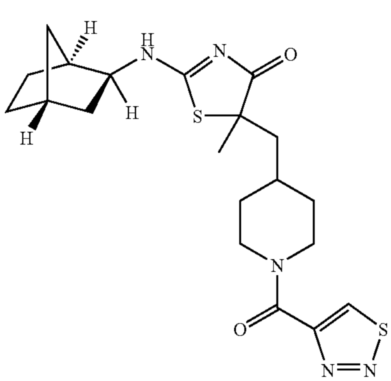 | 433.6 | 434 | 5-((1-(1,2,3-thiadiazole-4-carbonyl)piperidin-4-yl)methyl)-2-((1S,2S,4R)-bicyclo[2.2.1]heptan-2-ylamino)-5-methylthiazol-4(5H)-one | X AA MM |

TABLE 1-continued

| Structure | Mol Wt. | Mass Spec | Name | Methods of Prep. |
|---|---|---|---|---|
| 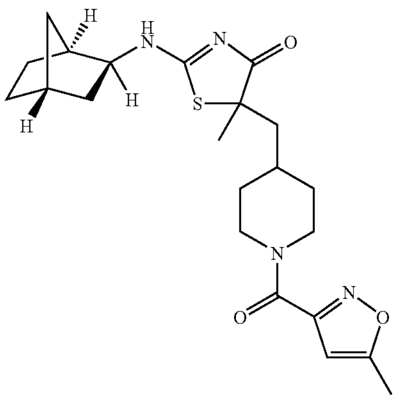 | 430.6 | 431 | 2-((1S,2S,4R)-bicyclo[2.2.1]heptan-2-ylamino)-5-methyl-5-((1-(5-methylisoxazole-3-carbonyl)piperidin-4-yl)methyl)thiazol-4(5H)-one | X AA MM |
| 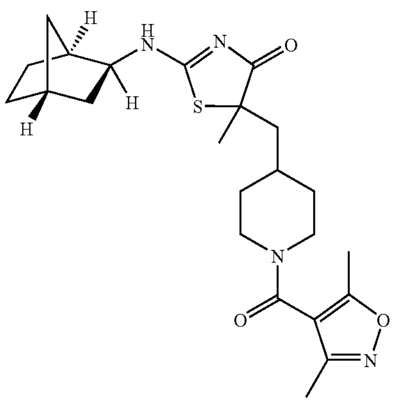 | 444.6 | 445 | 2-((1S,2S,4R)-bicyclo[2.2.1]heptan-2-ylamino)-5-((1-(3,5-dimethylisoxazole-4-carbonyl)piperidin-4-yl)methyl)-5-methylthiazol-4(5H)-one | X AA MM |
| 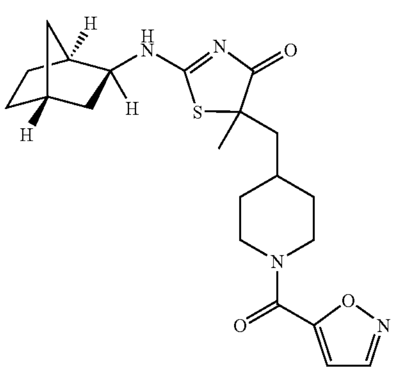 | 416.5 | 417 | 2-((1S,2S,4R)-bicyclo[2.2.1]heptan-2-ylamino)-5-((1-(isoxazole-5-carbonyl)piperidin-4-yl)methyl)-5-methylthiazol-4(5H)-one | X AA MM |
| 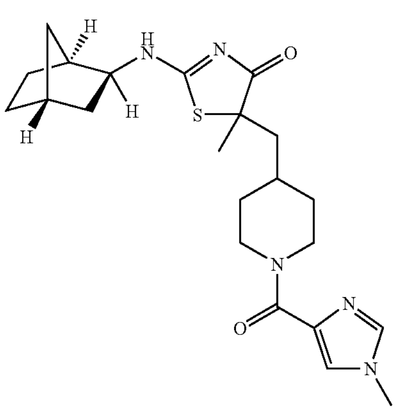 | 429.6 | 430 | 2-((1S,2S,4R)-bicyclo[2.2.1]heptan-2-ylamino)-5-methyl-5-((1-(1-methyl-1H-imidazole-4-carbonyl)piperidin-4-yl)methyl)thiazol-4(5H)-one | X AA MM |

TABLE 1-continued

| Structure | Mol Wt. | Mass Spec | Name | Methods of Prep. |
|---|---|---|---|---|
| | 464.6 | 465 | 5-((1-(1H-indole-3-carbonyl)piperidin-4-yl)methyl)-2-((1S,2S,4R)-bicyclo[2.2.1]heptan-2-ylamino)-5-methylthiazol-4(5H)-one | X AA MM |
| | 464.6 | 465 | 5-((1-(1H-indole-2-carbonyl)piperidin-4-yl)methyl)-2-((1S,2S,4R)-bicyclo[2.2.1]heptan-2-ylamino)-5-methylthiazol-4(5H)-one | X AA MM |
| 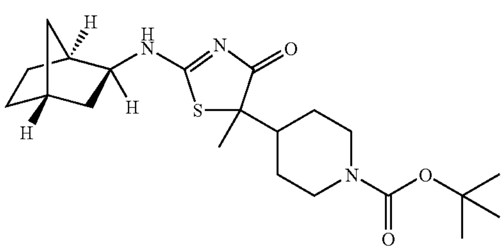 | 407.6 | 408 | tert-butyl 4-(2-((1S,2S,4R)-bicyclo[2.2.1]heptan-2-ylamino)-5-methyl-4-oxo-4,5-dihydrothiazol-5-yl)piperidine-1-carboxylate | L X AA |
| 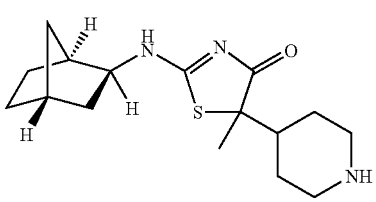 | 307.2 | 308 | 2-((1S,2S,4R)-bicyclo[2.2.1]heptan-2-ylamino)-5-methyl-5-(piperidin-4-yl)thiazol-4(5H)-one | L X AA MM(a) |
| 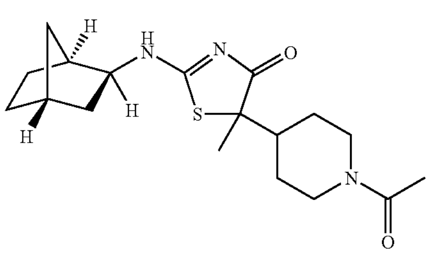 | 349.5 | 350 | 5-(1-acetylpiperidin-4-yl)-2-((1S,2S,4R)-bicyclo[2.2.1]heptan-2-ylamino)-5-methylthiazol-4(5H)-one | L X AA MM |

TABLE 1-continued

| Structure | Mol Wt. | Mass Spec | Name | Methods of Prep. |
|---|---|---|---|---|
| 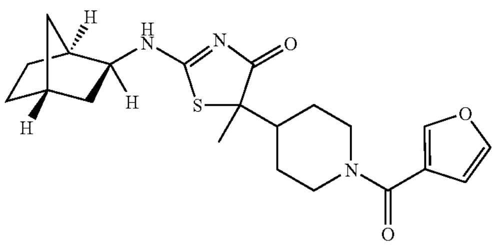 | 401.5 | 402 | 2-((1S,2S,4R)-bicyclo[2.2.1]heptan-2-ylamino)-5-(1-(furan-4-carbonyl)piperidin-4-yl)-5-methylthiazol-4(5H)-one | L X AA MM |
| | 412.6 | 413 | 2-((1S,2S,4R)-bicyclo[2.2.1]heptan-2-ylamino)-5-(1-isonicotinoylpiperidin-4-yl)-5-methylthiazol-4(5H)-one | L X AA MM |
| | 412.6 | 413 | 2-((1S,2S,4R)-bicyclo[2.2.1]heptan-2-ylamino)-5-methyl-5-(1-nicotinoylpiperidin-4-yl)thiazol-4(5H)-one | L X AA MM |
| | 412.6 | 413 | 2-((1S,2S,4R)-bicyclo[2.2.1]heptan-2-ylamino)-5-methyl-5-(1-picolinoylpiperidin-4-yl)thiazol-4(5H)-one | L X AA MM |
| | 426.6 | 427 | 2-((1S,2S,4R)-bicyclo[2.2.1]heptan-2-ylamino)-5-methyl-5-(1-(2-(pyridin-4-yl)acetyl)piperidin-4-yl)thiazol-4(5H)-one | L X AA MM |
| | 426.6 | 427 | 2-((1S,2S,4R)-bicyclo[2.2.1]heptan-2-ylamino)-5-methyl-5-(1-(2-(pyridin-2-yl)acetyl)piperidin-4-yl)thiazol-4(5H)-one | L X AA MM |

TABLE 1-continued

| Structure | Mol Wt. | Mass Spec | Name | Methods of Prep. |
|---|---|---|---|---|
| 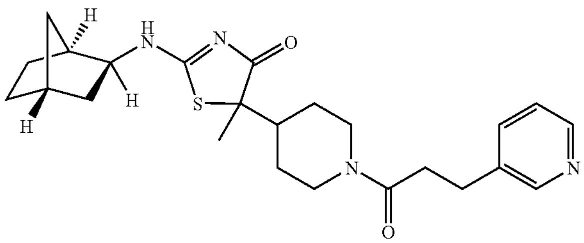 | 440.6 | 441 | 2-((1S,2S,4R)-bicyclo[2.2.1]heptan-2-ylamino)-5-methyl-5-(1-(3-(pyridin-3-yl)propanoyl)piperidin-4-yl)thiazol-4(5H)-one | L X AA MM |
| 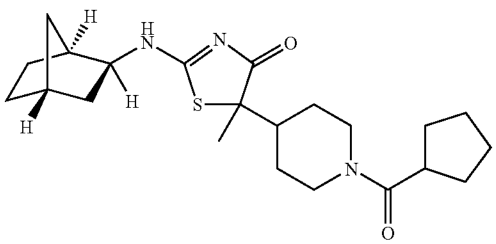 | 403.6 | 404 | 2-((1S,2S,4R)-bicyclo[2.2.1]heptan-2-ylamino)-5-(1-(cyclopentanecarbonyl)piperidin-4-yl)-5-methylthiazol-4(5H)-one | L X AA MM |
| 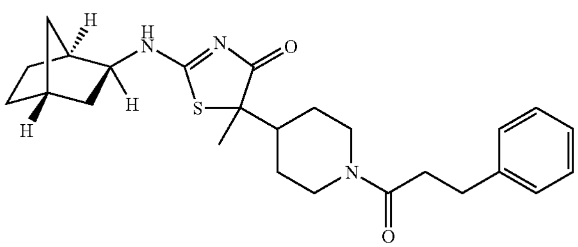 | 439.6 | 440 | 2-((1S,2S,4R)-bicyclo[2.2.1]hepten-2-ylamino)-5-methyl-5-(1-(3-phenylpropanoyl)piperidin-4-yl)thiazol-4(5H)-one | L X AA MM |
| 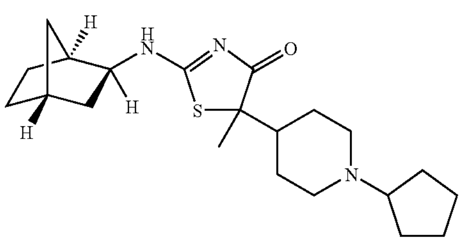 | 375.6 | 376 | 2-((1S,2S,4R)-bicyclo[2.2.1]heptan-2-ylamino)-5-(1-cyclopentylpiperidin-4-yl)-5-methylthiazol-4(5H)-one | L X AA JJ |
| 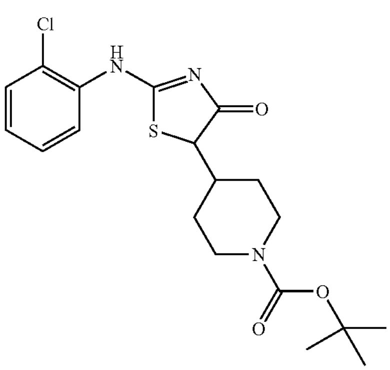 | 409.9 | 408 | tert-butyl 4-(2-(2-chlorophenylamino)-4-oxo-4,5-dihydrothiazol-5-yl)piperidine-1-carboxylate | L X |
| 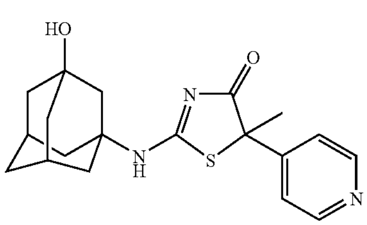 | 357.5 | 358 | 2-(3-Hydroxy-adamantan-1-ylamino)-5-methyl-5-pyridin-4-yl-thiazol-4-one | O M X |

TABLE 1-continued

| Structure | Mol Wt. | Mass Spec | Name | Methods of Prep. |
|---|---|---|---|---|
| 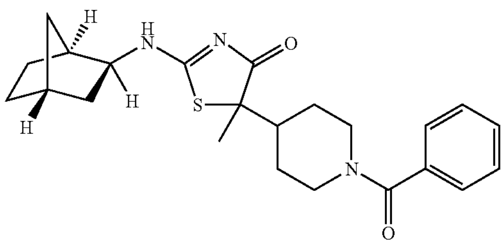 | 411.6 | 412 | 5-(1-benzoylpiperidin-4-yl)-2-((1S,2S,4R)-bicyclo[2.2.1]heptan-2-ylamino)-5-methylthiazol-4(5H)-one | L X AA MM |
| 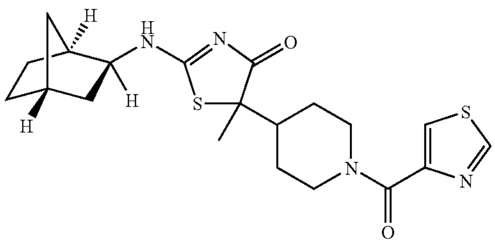 | 418.6 | 419 | 2-((1S,2S,4R)-bicyclo[2.2.1]heptan-2-ylamino)-5-methyl-5-(1-(thiazole-4-carbonyl)piperidin-4-yl)thiazol-4(5H)-one | L X AA MM |
| 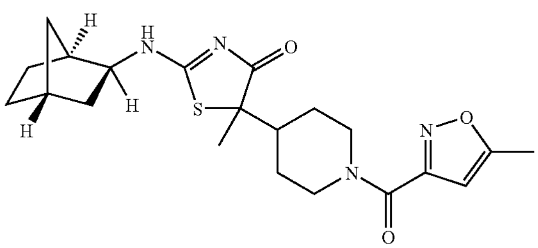 | 416.5 | 417 | 2-((1S,4R)-bicyclo[2.2.1]heptan-2-ylamino)-5-methyl-5-(1-(5-methylisoxazole-3-carbonyl)piperidin-4-yl-yl)thiazol-4(5H)-one | L X AA MM |
| 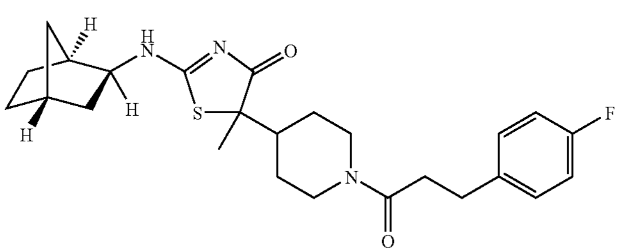 | 457.6 | 458 | 2-((1S,4R)-bicyclo[2.2.1]heptan-2-ylamino)-5-(1-(3-(4-fluorophenyl)propanoyl)piperidin-4-yl)-5-methylthiazol-4(5H)-one | L X AA MM |
| 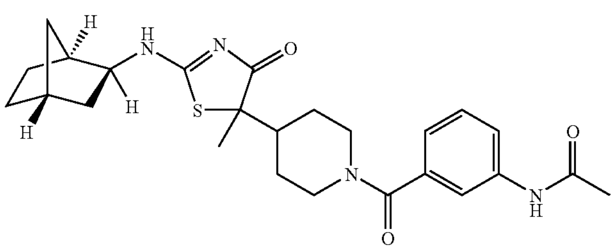 | 468.6 | 469 | N-(3-(4-(2-((1S,4R)-bicyclo[2.2.1]heptan-2-ylamino)-5-methyl-4-oxo-4,5-dihydrothiazol-5-yl)piperidine-1-carbonyl)phenyl)acetamide | L X AA MM |
| 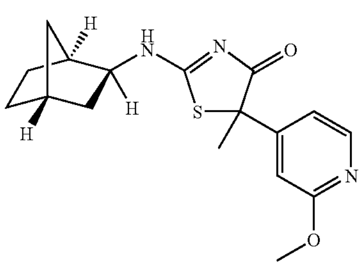 | 317.4 | 318 | 2-((1S,4R)-bicyclo[2.2.1]heptan-2-ylamino)-5-(2-methoxypyridin-4-yl)thiazol-4(5H)-one | L X AA |

TABLE 1-continued

| Structure | Mol Wt. | Mass Spec | Name | Methods of Prep. |
|---|---|---|---|---|
| 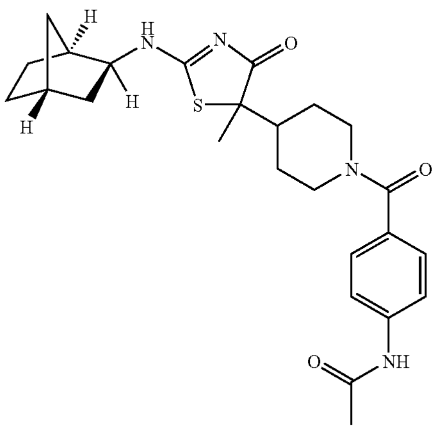 | 468.6 | 469 | N-(4-(4-(2-((1S,4R)-bicyclo[2.2.1]heptan-2-ylaminoi)-5-methyl-4-oxo-4,5-dihydrothiazol-5-yl)piperidine-1-carbonyl)phenyl)acetamide | L X AA MM |
| 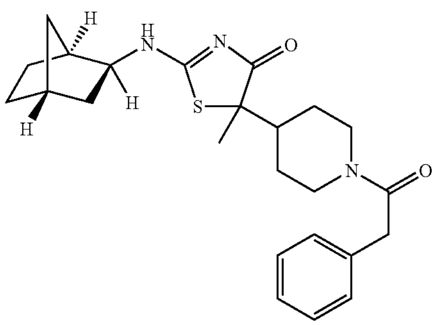 | 425.6 | 426 | 2-((1S,2S,4R)-bicyclo[2.2.1]heptan-2-ylamino)-5-methyl-5-(1-(2-phenylacetyl)piperidin-4-yl)thiazol-4(5HH)-one | L X AA MM |
| 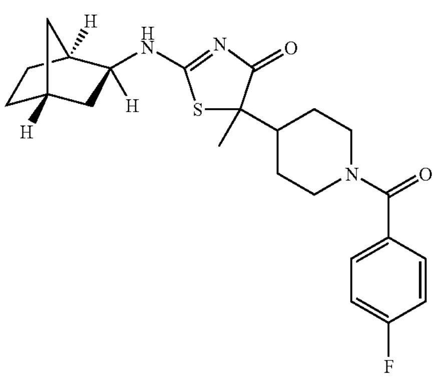 | 429.6 | 430 | 2-((1S,2S,4R)-bicyclo[2.2.1]heptan-2-ylamino)-5-(1-(4-fluorobenzoyl)piperidin-4-yl)-5-methylthiazol-4(5H)-one | L X AA MM |
| 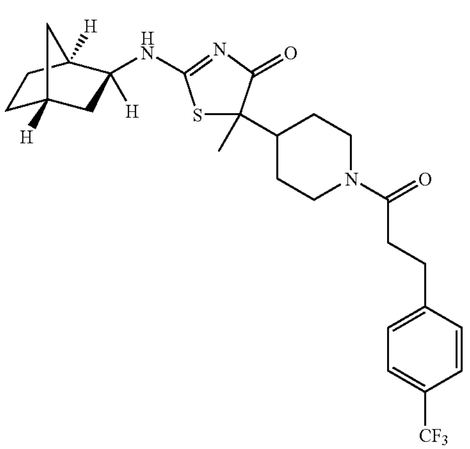 | 507.6 | 508 | 2-((1S,2S,4R)-bicyclo[2.2.1]heptan-22-ylamino)-5-methyl-5-(1-(3-(4-(trifluoromethyl)phenyl)propanoyl)piperidin-4-yl)thiazol-4(5H)-one | L X AA MM |

TABLE 1-continued

| Structure | Mol Wt. | Mass Spec | Name | Methods of Prep. |
|---|---|---|---|---|
| 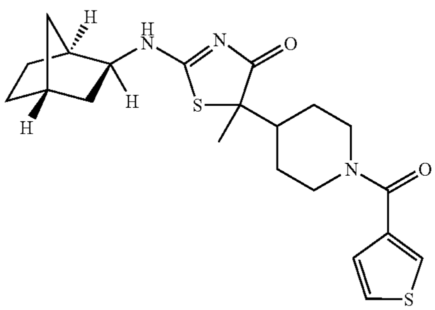 | 417.6 | 418 | 2-((1S,2S,4R)-bicyclo[2.2.1]heptan-2-ylamino)-5-methyl-5-(1-(thiophene-4-carbonyl)piperidin-4-yl)thiazol-4(5H)-one | L X AA MM |
| 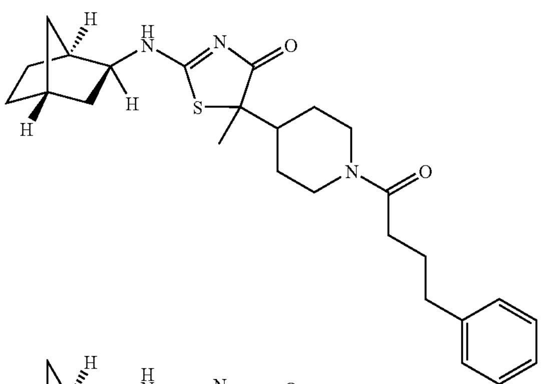 | 453.6 | 454 | 2-((1S,2S,4R)-bicyclo[2.2.1]heptan-2-ylamino)-5-methyl-5-(1-(4-phenylbutanoyl)piperidin-4-yl)thiazol-4(5H)-one | L X AA MM |
| 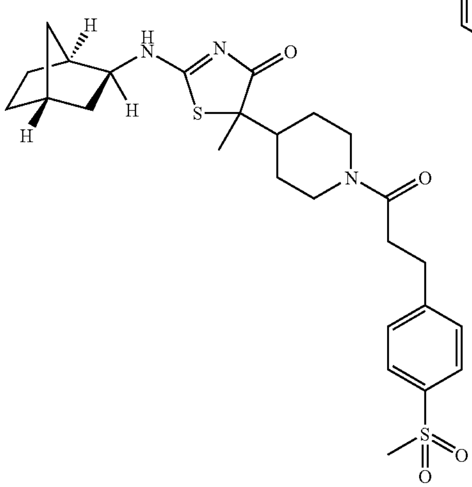 | 517.7 | 518 | 2-((1S,2S,4R)-bicyclo[2.2.1]heptan-2-ylamino)-5-methyl-5-(1-(3-(4-(methylsulfonyl)phenyl)propanoyl)piperidin-4-yl)thiazol-4(5H)-one | L X AA MM |
| 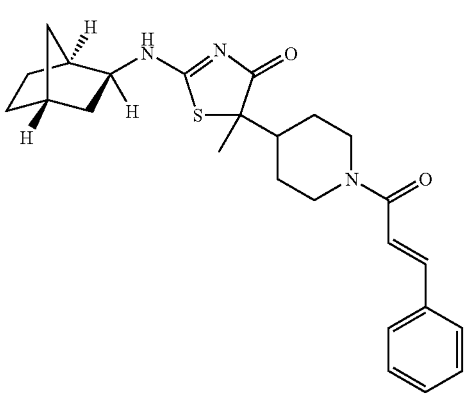 | 437.6 | 438 | 2-((1S,2S,4R)-bicyclo[2.2.1]heptan-2-ylamino)-5-(1-cinnamoylpiperidin-4-yl)-5-methylthiazol-4(5H)-one | L X AA MM |

TABLE 1-continued

| Structure | Mol Wt. | Mass Spec | Name | Methods of Prep. |
|---|---|---|---|---|
| 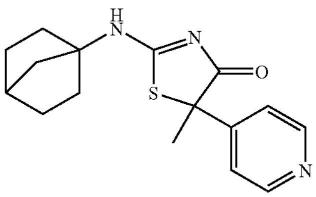 | 301.4 | 302 | 2-(bicyclo[2.2.1]heptan-1-ylamino)-5-methyl-5-(pyridin-4-yl)thiazol-4(5H)-one | M X |
| | 329.4 | 330 | 2-((S)-1-(4-fluorophenyl)ethylamino)-5-methyl-5-(pyridin-4-yl)thiazol-4(5H)-one | O M X |
| | 329.4 | 330 | 2-((S)-1-(2-fluorophenyl)ethylamino)-5-methyl-5-(pyridin-4-yl)thiazol-4(5H)-one | O M X |
| 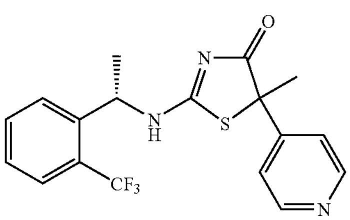 | 379.4 | 380 | 5-methyl-5-(pyridin-4-yl)-2-((S)-1-(2-(trifluoromethyl)phenyl)ethyl-amino)thiazol-4(5H)-one | O M X |
| 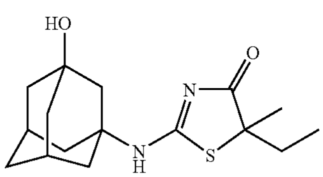 | 308.4 | 309 | 5-Ethyl-2-(3-hydroxy-adamantan-1-ylamino)-5-methyl-thiazol-4-one | O X |
| 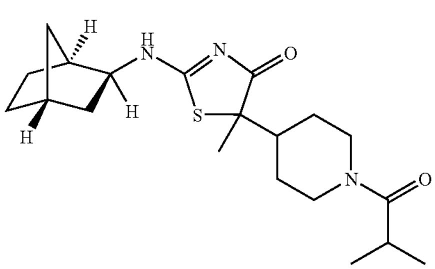 | 377.6 | 378 | 2-((1S,2S,4R)-bicyclo[2.2.1]heptan-2-ylamino)-5-(1-isobutyrylpiperidin-4-yl)-5-methylthiazol-4(5H)-one | L X AA MM |

TABLE 1-continued

| Structure | Mol Wt. | Mass Spec | Name | Methods of Prep. |
|---|---|---|---|---|
| 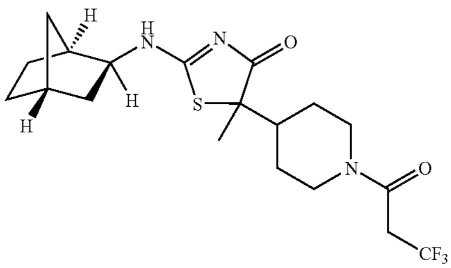 | 417.5 | 418 | 2-((1S,2S,4R)-bicyclo[2.2.1]heptan-2-ylamino)-5-methyl-5-(1-(3,3,3-trifluoropropanoyl)piperidin-4-yl)thiazol-4(5H)-one | L X AA MM |
| 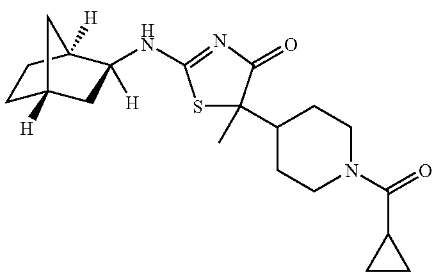 | 375.5 | 376 | 2-((1S,2S,4R)-bicyclo[2.2.1]heptan-2-ylamino)-5-(1-(cyclopropanecarbonyl)piperidin-4-yl)-5-methylthiazol-4(5H)-one | L X AA MM |
| 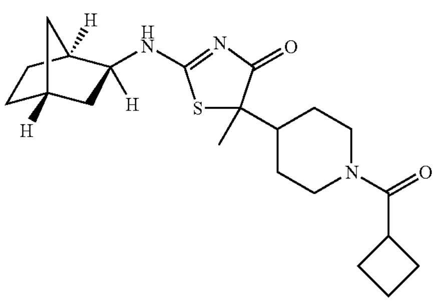 | 389.6 | 390 | 2-((1S,2S,4R)-bicyclo[2.2.1]heptan-2-ylamino)-5-(1-(cyclobutanecarbonyl)piperidin-4-yl)-5-methylthiazol-4(5H)-one | L X AA MM |
| 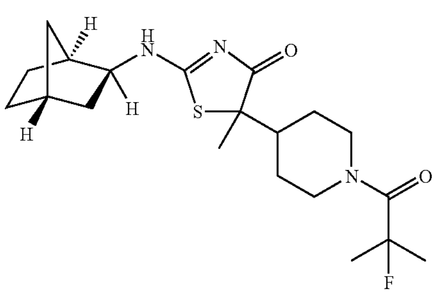 | 395.5 | 396 | 2-((1S,2S,4R)-bicyclo[2.2.1]heptan-2-ylamino)-5-(1-(2-fluoro-2-methylpropanoyl)piperidin-4-yl)-5-methylthiazol-4(5H)-one | L X AA MM |
| 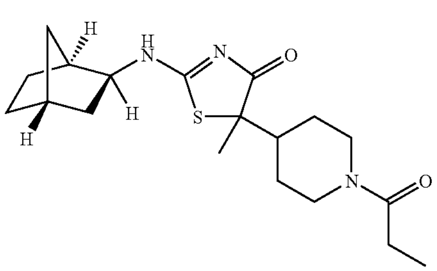 | 363.5 | 364 | 2-((1S,2S,4R)-bicyclo[2.2.1]heptan-2-ylamino)-5-methyl-5-(1-propionylpiperidin-4-yl)thiazol-4(5H)-one | L X AA MM |

TABLE 1-continued

| Structure | Mol Wt. | Mass Spec | Name | Methods of Prep. |
|---|---|---|---|---|
| 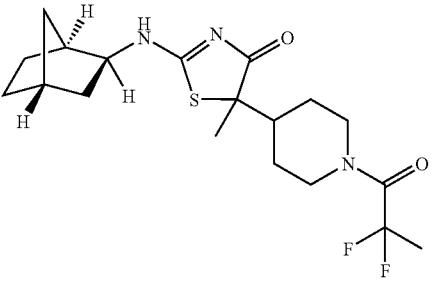 | 399.5 | 400 | 2-((1S,2S,4R)-bicyclo[2.2.1]heptan-2-ylamino)-5-(1-(2,2-difluoropropanoyl)piperidin-4-yl)-5-methylthiazol-4(5H)-one | L X AA MM |
| 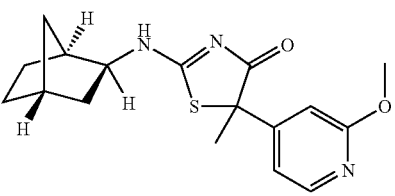 | 331.4 | 332 | 2-((1S,2S,4R)-bicyclo[2.2.1]heptan-2-ylamino)-5-(2-methoxypyridin-4-yl)-5-methylthiazol-4(5H)-one | L X AA |
| 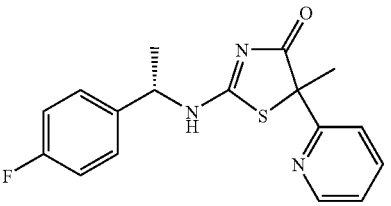 | 329.4 | 330 | 2-((S)-1-(4-fluorophhenyl)ethylamino)-5-methyl-5-(pyridin-2-yl)thiazol-4(5H)-one | O M X |
| 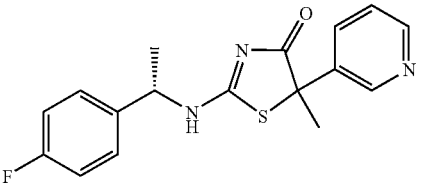 | 329.4 | 330 | 2-((S)-1-(4-fluorophenyl)ethylamino)-5-methyl-5-(pyridin-3-yl)thiazol-4(5H)-one | O M X |
| 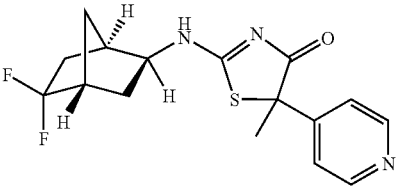 | 337.4 | 338 | 2-((1R,2S,4R)-5,5-difluorobicyclo[2.2.1]heptan-2-ylamino)-5-methyl-5-(pyridin-4-yl)thiazol-4(5H)-one | Q O M X |
| 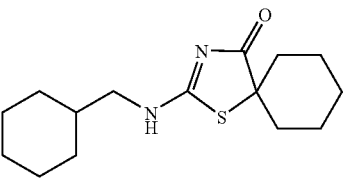 | 280.4 | 281 | 2-((cyclohexylmethyl)amino)-1-thia-3-azaspiro[4.5]dec-2-en-4-one | P X |
| 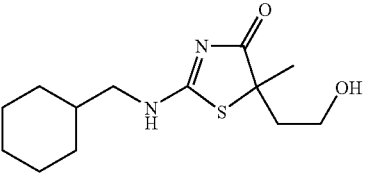 | 270.1 | 271 | 2-(cyclohexylmethylamino)-5-(2-hydroxyethyl)-5-methylthiazol-4(5H)-one | P X |

TABLE 1-continued

| Structure | Mol Wt. | Mass Spec | Name | Methods of Prep. |
|---|---|---|---|---|
| 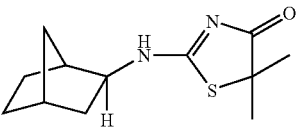 | 238.4 | 239 | 2-(bicyclo[2.2.1]heptan-2-ylamino)-5,5-dimethylthiazol-4(5H)-one | X |
| 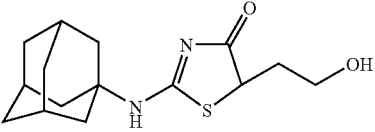 | 294.4 | 295 | 5-(2-hydroxyethyl)-2-(tricyclo[3.3.1.1~3,7~]dec-1-ylamino)-1,3-thiazol-4(5H)-one | P X |
| 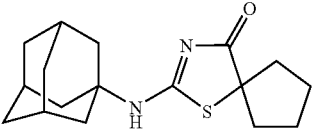 | 304.5 | 305 | 2-(tricyclo[3.3.1.1~3,7~]dec-1-ylamino)-1-thia-3-azaspiro[4.4]non-2-en-4-one | P L X |
| 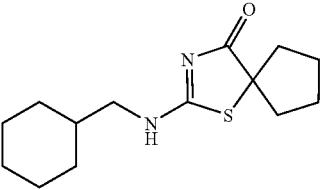 | 266.4 | 267 | 2-((cyclohexylmethyl)amino)-1-thia-3-azaspiro[4.4]non-2-en-4-one | P L X |
| 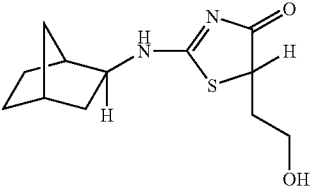 | 254.4 | 255 | 2-(bicyclo[2.2.1]heptan-2-ylamino)-5-(2-hydroxyethyl)thiazol-4(5H)-one | X |
| 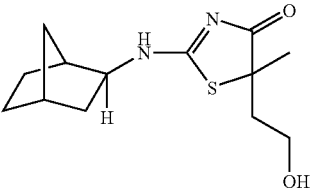 | 268.4 | 279 | 2-(Bicyclo[2.2.1]heptan-2-ylamino)-5-(2-hydroxyethyl)-5-methylthiazol-4(5H)-one | X |
| 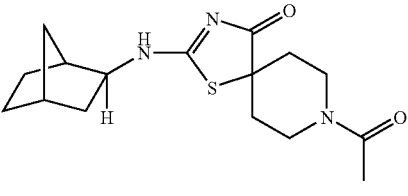 | 321.4 | 322 | 8-acetyl-2-bicyclo[2.2.1]hept-2-ylamino)-1-thia-3,8-diazaspiro[4.5]dec-2-en-4-one | L X |
| 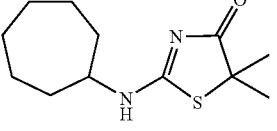 | 240.4 | 241 | 2-(cycloheptylamino)-5,5-dimethylthiazol-4(5H)-one | P X |

TABLE 1-continued

| Structure | Mol Wt. | Mass Spec | Name | Methods of Prep. |
|---|---|---|---|---|
| 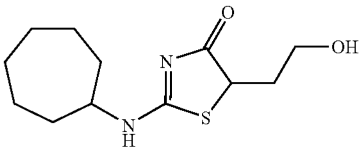 | 256.4 | 257 | 2-(cycloheptylamino)-5-(2-hydroxyethyl)thiazol-4(5H)-one | P X |
| 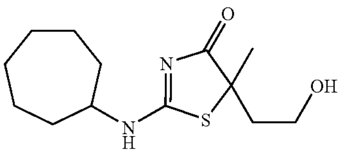 | 270.4 | 271 | 2-(cyclopentylamino)-5-(2-hydroxyethyl)-5-methylthiazol-4(5H)-one | P X |
| 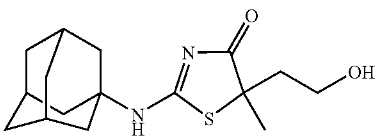 | 308.4 | 309 | 5-(2-Hydroxyethyl)-5-methyl-2-(tricyclo[3.3.1.1~3.7~]dec-1-ylamino)-1,3-thiazol-4(5H)-one | P X |
| | 290.4 | 291 | 1-methyl-5-(tricyclo[3.3.1.1~3.7~]dec-1-ylamino)-4-thia-6-azaspiro[2.4]hept-5-en-7-one | P L X |
| 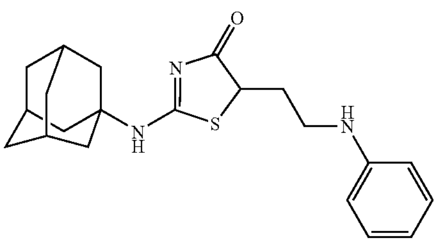 | 369.5 | 370 | 2-(1-adamantylamino)-5-(2-(phenylamino)ethyl)thiazol-4-(5H)-one | P X JJ |
| | 290.4 | 291 | 6-(tricyclo[3.3.1.1~3,7~]dec-1-ylamino)-5-thia-7-azaspiro[3.4]oct-6-en-8-one | P X |
| 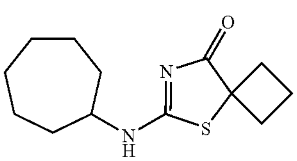 | 252.4 | 253 | 6-(cycloheptylamino)-6-thia-7-azaspiro[3.4]oct-6-en-8-one | P X |
| 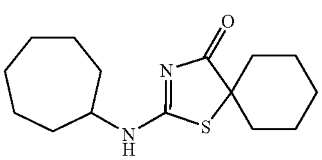 | 280.4 | 281 | 2-(cycloheptylamino)-1-thia-3-azaspiro[4.5]dec-2-en-4-one | P X |
| 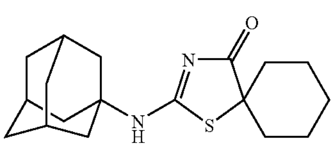 | 318.5 | 319 | 2-(tricyclo[3.3.1.1~3,7~]dec-1-ylamino)-1-thia-3-azaspiro[4.5]dec-2-en-4-one | P X |

TABLE 1-continued

| Structure | Mol Wt. | Mass Spec | Name | Methods of Prep. |
|---|---|---|---|---|
| | 252.4 | 253 | 5-((cyclohexylmethyl)amino)-1-methyl-4-thia-6-azaspiro[2.4]hept-5-en-7-one | P L X |
| | 308.4 | 309 | 2-(cyclohexylmethylamino)-5-methyl-5-(2,2,2-trifluoromethyl)-thiazol-4(5H)-one | P L X |
| | 254.4 | 255 | 2-(cyclohexylmethylamino)-5-propylthiazol-4(5H)-one | P X |
| 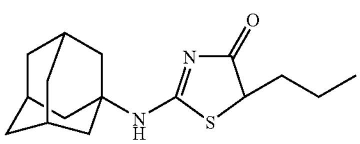 | 292.4 | 293 | 5-propyl-2-(tricyclo[3.3.1.1~3,7~]dec-1-ylamino)-1,3-thiazol-4(5H)-one | P X |
| | 308.4 | 309 | 2-(cycloheptylamino)-5-methyl-5-(2,2,2-trifluoroethyl)-thiazol-4(5H)-one | P L X |
| 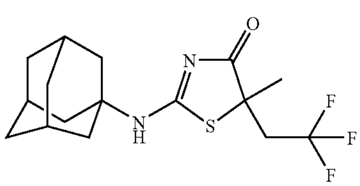 | 346.4 | 347 | 5-methyl-2-(tricyclo[3.3.1.1~3,7~]dec-1-ylamino)-5-(2,2,2-trifluoroethyl)-1,3-thiazol-4(5H)-one | P L X |
| | 252.4 | 253 | 2-bicyclo[2.2.1]heptan-2-ylamino-5-propylthiazol-4(5H)-one | X |
| | 254.4 | 255 | 2-(cycloheptylamino)-5-propylthiazol-4(5H)-one | X |

TABLE 1-continued

| Structure | Mol Wt. | Mass Spec | Name | Methods of Prep. |
|---|---|---|---|---|
| | 268.4 | 269 | 2-(cyclohexylmethylamino)-5,5-diethylthiazol-4(5H)-one | P L X |
| | 268.4 | 269 | 2-(cycloheptylamino)-5,5-diethylthiazol-4(5H)-one | P L X |
| | 268.4 | 269 | 2-(cyclohexylmethylamino)-5-methyl-5-propylthiazol-4(5H)-one | P L X |
| | 306.5 | 307 | 5-methyl-5-propyl-2-(tricyclo[3.3.1.1~3,7]]dec-1-ylamino)-1,3-thiazol-4(5H)-one | P L X |
| | 254.4 | 255 | 2-(cyclohexylamino)-5-methyl-5-propylthiazol-4(5H)-one | P L X |
| | 254.4 | 255 | 2-(cyclohexylamino)-5,5-diethylthiazol-4(5H)-one | P L X |
| 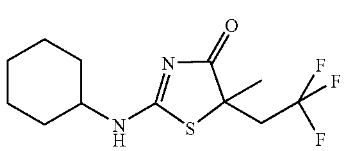 | 294.3 | 295 | 2-(cyclohexylamino)-5-methyl-5-(2,2,2-trifluoroethyl)thiazol-4(5H)-one | P L X |
| | 306.5 | 307 | 5,5-diethyl-2-(tricyclo[3.3.1.1~3,7~]dec-1-ylamino)-1,3-thiazol-4(5H)-one | P L X |

TABLE 1-continued

| Structure | Mol Wt. | Mass Spec | Name | Methods of Prep. |
|---|---|---|---|---|
| 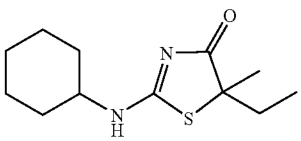 | 240.4 | 241 | 2-(cyclohexylammino)-5-ethyl-5-methylthiazol-4(5H)-one | P L X |
| 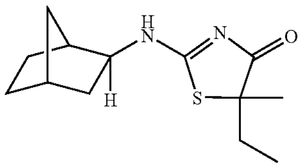 | 252.4 | 253 | 2-bicyclo[2.2.1]heptan-2-ylamino)-5-ethyl-5-methylthiazol-4(5H)-one | L X |
| 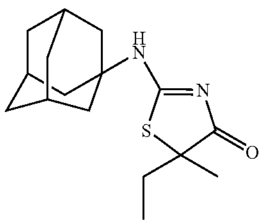 | 292.4 | 293 | 5-ethyl-5-methyl-2-(tricyclo[3.3.1.1~3,7~]dec-1-ylamino)_1,3-thiazol-4(5H)-one | P L X |
| 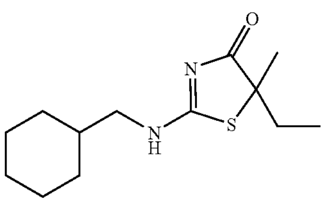 | 254.4 | 255 | 2-(cyclohexylmethylamino)-5-ethyl-5-methylthiaol-4(5H)-one | P L X |
| | 264.4 | 265 | 2-((1S,2S,4R)-bicyclo[2.2.1]hept-2-ylamino)-1-thia-3-azaspiro[4.4]non-2-en-4-one | L X |
| 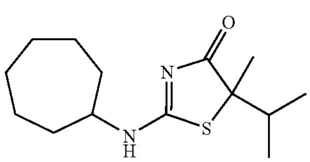 | 268.4 | 269 | 2-(cycloheptylamino)-5-isopropyl-5-methylthiazol-4(5H)-one | P X AA |
| 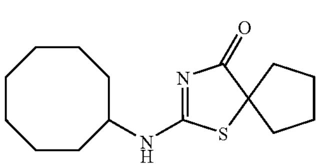 | 280.4 | 281 | 2-(cyclooctylamino)-1-thia-3-azaspiro[4.49 non-2-en-4-one | O L X |
| | 264.4 | 265 | 2-((1R,2R,4S)-bicyclo[2.2.1]hept-2-ylamino)-1-thia-3-azaspiro[4.4]non-2-en-4-one | L X |

TABLE 1-continued

| Structure | Mol Wt. | Mass Spec | Name | Methods of Prep. |
|---|---|---|---|---|
| 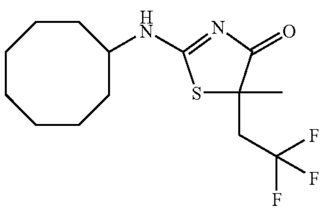 | 322.4 | 323 | 2-(cyclooctylamino)-5-methyl-5-(2,2,2-trifluoroethyl)thiazol-4(5H)-one | O L X |
| | 278.4 | 279 | 2-((1S,2S,4R)-bicyclo[2.2.1]hept-2-ylamino)-1-thia-3-azaspiro[4.5]dec-2-en-4-one | X |
| | 278.4 | 279 | 2-((1R,2R,4S)-cicyclo[2.2.1]hept-2-ylamino)-1-thia-3-azaspiro[4.5]dec-2-en-4-one | X |
| 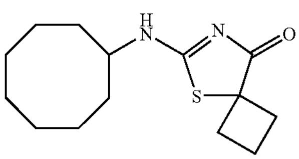 | 266.4 | 267 | 6-(cyclooctylamino)-5-thia-7-azaspiro[3.4]oct-6-en-8-one | O X |
| 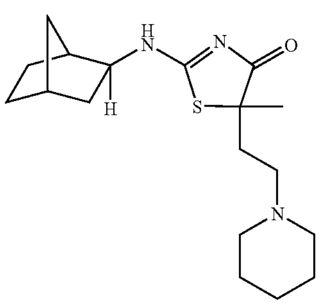 | 335.5 | 336 | 2-(bicyclo[2.2.1]heptan-2-ylamino)-5-methyl-5-(2-(piperidin-1-yl)ethyl)thiazol-4(5H)-one | X JJ |
| 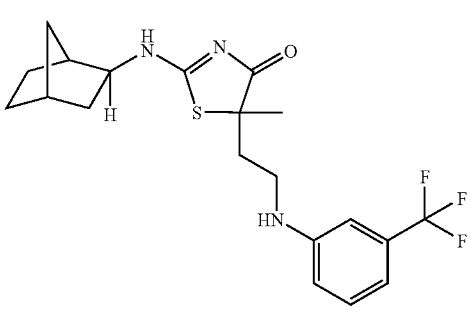 | 411.5 | 412 | 2-(bicyclo[2.2.1]heptan-2-ylamino)-5-methyl-5-(2-(3-(trifluoromethyl)phenylamino)ethyl)thiazol-4(5H)-one | X JJ |

TABLE 1-continued

| Structure | Mol Wt. | Mass Spec | Name | Methods of Prep. |
|---|---|---|---|---|
| 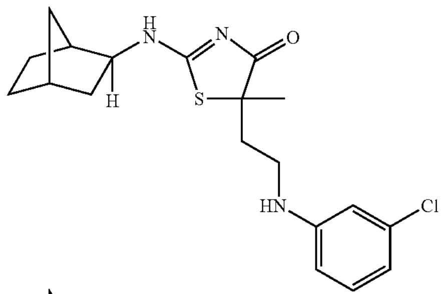 | 377.9 | 378 | 2-(bicyclo[2.2.1]heptan-2-ylamino)-5-(2-(3-chlorophenylamino)ethyl)-5-methylthiazol-4(5H)-one | X JJ |
| 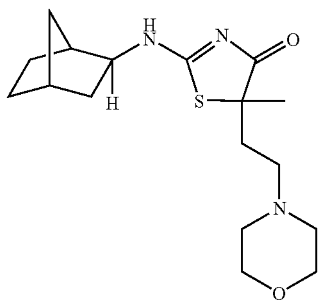 | 337.5 | 338 | 2-(bicyclo[2.2.1]heptan-2-ylamino)-5-methyl-5-(2-morpholinoethyl)thiazol-4(5H)-one | X JJ |
| 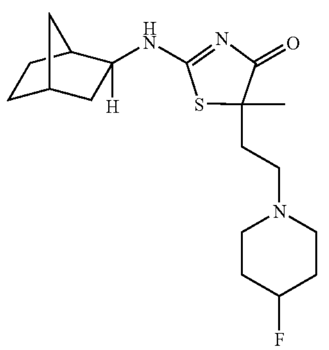 | 353.5 | 354 | 2-(bicyclo[2.2.1]heptan-2-ylamino)-5-(2-(4-fluoropiperidin-1-yl)ethyl)-5-methylthiazol-4(5H)-one | X JJ |
| 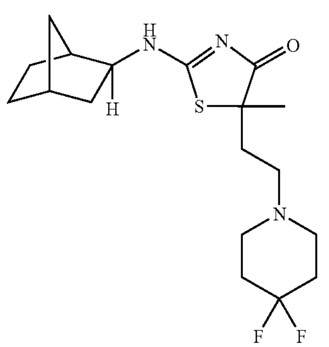 | 371.5 | 372 | 2-(bicyclo[2.2.1]heptan-2-ylamino)-5-(2-(4,4-difluoropiperidin-1-yl)ethyl)-5-methylthiazol-4(5H)-one | X JJ |
| 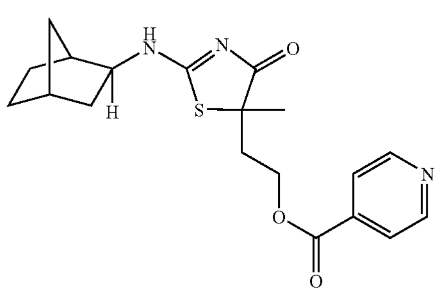 | 373.5 | 374 | 2-(2-(bicyclo[2.2.1]heptan-2-ylamino)-5-methyl-4-oxo-4,5-dihydrothiazol-5-yl)ethyl isonicotinate | X |

TABLE 1-continued

| Structure | Mol Wt. | Mass Spec | Name | Methods of Prep. |
|---|---|---|---|---|
| 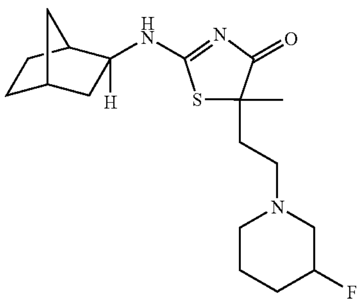 | 353.5 | 354 | 2-(bicyclo[2.2.1]heptan-2-ylamino)-5-(2-(3-fluoropiperidin-1-yl)ethyl)-5-methylthiazol-4(5H)-one | X<br>JJ |
| | 306.4 | 307 | (S)-2-((1S,2S,4R)-bicyclo[2.2.1]heptan-2-ylamino)-5-methyl-(2,2,2-trifluoroethyl)thiazol-4(5H)-one | L<br>X |
| | 306.4 | 307 | (R)-2-((1S,2S,4R)-bicyclo[2.2.1]heptan-2-ylamino)-5-methyl-5-(2,2,2-trifluoroethyl)thiazol-4(5H)-one | L<br>X |
| | 266.4 | 267 | (S)-2-((1S,2S,4R)-bicyclo[2.2.1]heptan-2-ylamino)-5-methyl-5-propylthiazol-4(5H)-one | L<br>X |
| | 266.4 | 267 | (R)-2-((1S,2S,4R)-bicyclo[2.2.1]heptan-2-ylamino)-5-methyl-5-propylthiazol-4(5H)-one | L<br>X |
| 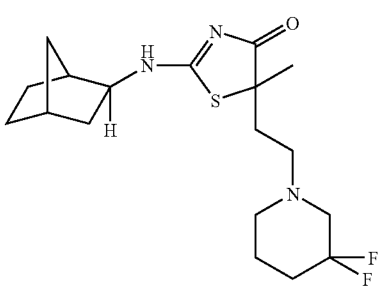 | 371.5 | 372 | 2-(bicyclo[2.2.1]heptan-2-ylamino)-5-(2-(3,3-difluoropiperidin-1-yl)ethyl)-5-methylthiazol-4(5H)-one | X<br>JJ |

TABLE 1-continued

| Structure | Mol Wt. | Mass Spec | Name | Methods of Prep. |
|---|---|---|---|---|
| 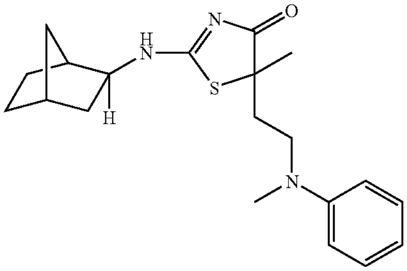 | 357.5 | 358 | 2-(bicyclo[2.2.1]heptan-2-ylamino)-5-methyl-5-(2-(methyl(phenyl)amino)ethyl)thiazol-4(5H)-one | X JJ |
| 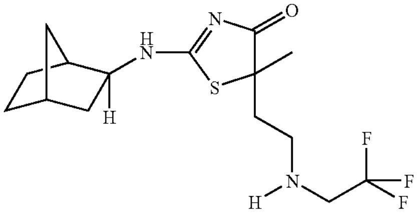 | 349.4 | 350 | 2-(bicyclo[2.2.1]heptan-2-ylamino)(-5-methyl-5-(2-(2,2,2-trifluoroethylamino)ethyl)thiazol-4(5H)-one | X JJ |
| 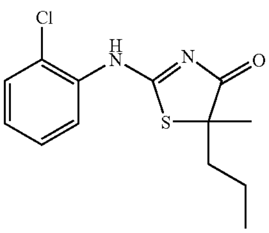 | 282.80 | 283/285 | 2-(2-chlorophenylamino)-5-methyl-5-propylthiazol-4(5H)-one | L X |
| 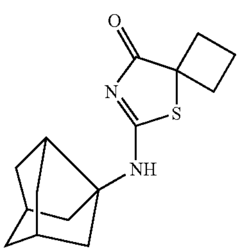 | 276.4 | 277 | 6-(tricyclo[3.3.1.0~3,7~]non-3-ylamino)-5-thia-7-azaspiro[3.4]oct-6-en-8-one | O X |
| 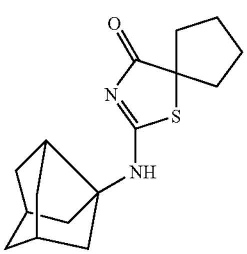 | 290.4 | 291 | 2-(tricyclo[3.3.1.0~3,7~]non-3-ylamino)-1-thia-3-azaspiro[4.4]non-2-en-4-one | O L X |
| 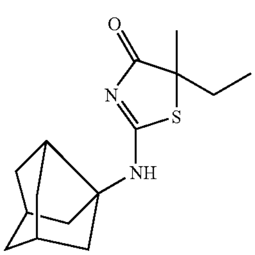 | 278.4 | 279 | 5-ethyl-5-methyl;-2-(tricyclo[3.3.1.0~3,7]non-3-ylamino)-1,3-thiazol-4(5H)-one | O L X |

TABLE 1-continued

| Structure | Mol Wt. | Mass Spec | Name | Methods of Prep. |
|---|---|---|---|---|
| 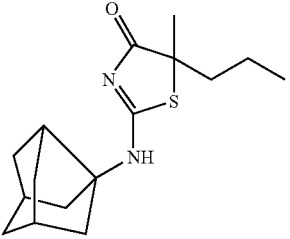 | 292.4 | 293 | 5-methyl-5-propyl-2-(tricyclo[3.3.1.0~3,7~]non-3-ylamino)-1,3-thiazol-4(5H)-one | O L X |
| 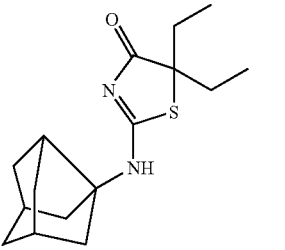 | 292.4 | 293 | 5,5-diethyl-2-(tricyclo[3.3.1.0~3,7]non-3-ylamino)-1,3-thiazol-4(5H)-one | O L X |
| 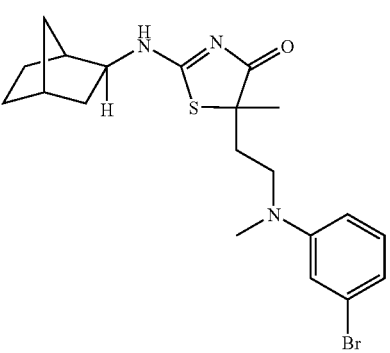 | 436.4 | 436/438 | 2-(bicyclo[2.2.1]heptan-2-ylamino)-5-(2-((3-bromophenyl)(methyl)amino)ethyl)-5-methylthiazol-4(5H)-one | X JJ |
| 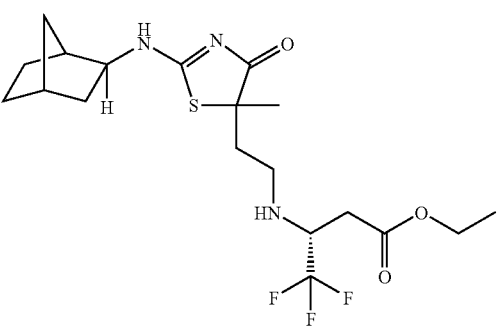 | 435.5 | 436 | (3R)-ethyl 3-(2-(2-(bicyclo[2.2.1]heptan-2-ylamino)-5-methyl-4-oxo-4,5-dihydrothiazol-5-yl)ethylamino)-4,4,4-trifluorobutanoate | X JJ |
| 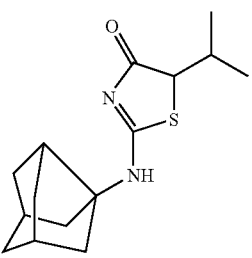 | 278.4 | 279 | 5-(1-methylethyl)-2-(tricyclo[3.3.1.0~3,7]non-3-ylamino)-1,3-thiazol-4(5H)-one | O X |

TABLE 1-continued

| Structure | Mol Wt. | Mass Spec | Name | Methods of Prep. |
|---|---|---|---|---|
| 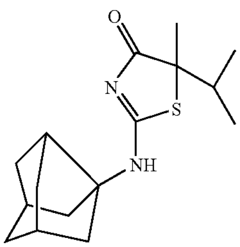 | 292.4 | 293 | 5-methyl-5-(1-methylethyl)-2-(tricyclo[3.3.1.0~3,7~]non-3-ylamino)-1,3-thiazol-4(5H)-one | O X AA |
| | 308.4 | 309 | (7R)-2-((1S,2S,4R)-bicyclo[2.2.1]hept-2-ylamino)-7-(methyloxy)-1-thia-3-azaspiro[4.5]dec-2-en-4-one | L X |
| | 308.4 | 309 | 2-((1S,2S,4R)-bicyclo[2.2.1]hept-2-ylamino)-8-(methyloxy)-1-thia-3-azaspiro[4.5]dec-2-en-4-one | L X |
| 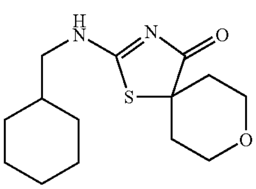 | 2282.4 | 283 | 2-((cyclohexylmethyl)amino)-8-oxa-1-thia-3-azaspiro[4.5]dec-2-en-4-one | P X EE |
| 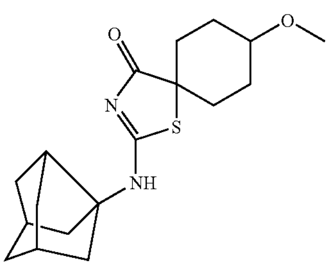 | 348.5 | 349 | 8-(methyloxy)-2-(tricyclo[3.3.1.1~3,7~]dec-1-ylaminoi)-1-thia-3-azaspiro[4.5]dec-2-en-4-one | P L X |
| 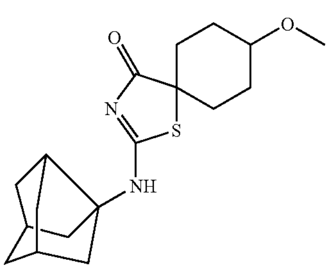 | 334.5 | 335 | 8-(methyloxy)-2-(tricyclo[3.3.1.0~3,7~]non-3-ylamino)-1-thia-3-azaspiro[4.5]dec-2-en-4-one | O L X |

TABLE 1-continued

| Structure | Mol Wt. | Mass Spec | Name | Methods of Prep. |
|---|---|---|---|---|
| | 310.5 | 311 | 2-((cyclohexylmethyl)amino)-8-(methyloxy)-1-thia-3-azaspiro[4.5]dec-2-en-4-one | P L X |
| | 296.4 | 297 | 2-(cyclohexylamino)-8-(methyloxy)-1-thia-3-azaspiro[4.5]dec-2-en-4-one | P L X |
| | 310.5 | 311 | 2-(cyclopentylamino)-8-(methyloxy)-1-thia-3-azaspiro[4.5]dec-2-en-4-one | P L X |
| 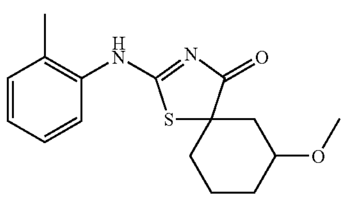 | 304.4 | 305 | 7-(methyloxy)-2-((2-methylphenyl)amino)-1-thia-03-azaspiro[4.5]dec-2-en-4-one | L X |
| | 296.4 | 297 | 2-(cyclohexylamino)-7-(methyloxy)-1-thia-3-azaspiro[4.5]dec-2-en-4-one | P L X |
| | 310.5 | 311 | 2-((cyclohexylmethyl)amino)-7-(methyloxy)-1-thia-3-azaspiro[4.5]dec-2-en-4-one | P L X |
| | 310.5 | 311 | 2-(cycloheptylamino)-7-(methyloxy)-1-thia-3-azaspiro[4.5]dec-2-en-4-one | P L X |

TABLE 1-continued

| Structure | Mol Wt. | Mass Spec | Name | Methods of Prep. |
|---|---|---|---|---|
| 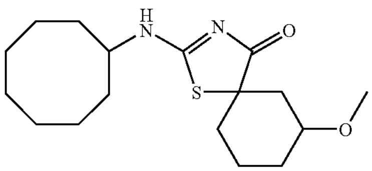 | 324.5 | 325 | 2-(cyclooctylamino)-7-(methyloxy)-1-thia-3-azaspiro[4.5]dec-2-en-4-one | O L X |
| 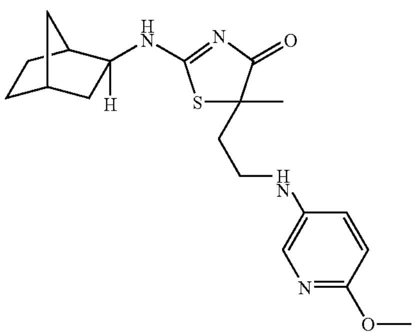 | 374.5 | 375 | 2-(bicyclo[2.2.1]hept-2-ylamino)-5-methyl-5-(2-((6-(methyloxy)-3-pyridinyl)amino)ethyl)-1,3-thiazol-4(5H)-one | X JJ |
| 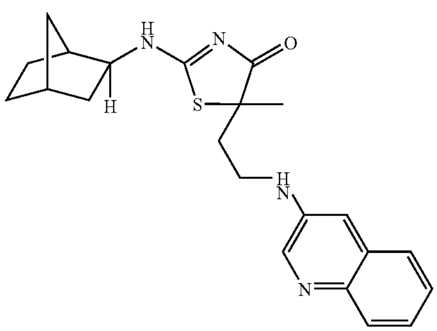 | 394.5 | 395 | 2-(bicyclo[2.2.1]hept-2-ylamino)-5-(2-(4-isoquinolinylamino)ethyl)-5-methyl-1,3-thiazol-4(5H)-one | X JJ |
| 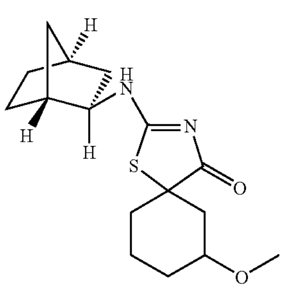 | 308.4 | 309 | 2-bicyclo[2.2.1]hept-2-ylamino)-7-(methyloxy)-1-thia-3-azaspiro[4.5]dec]dec-2-en-4-one | L X |
| 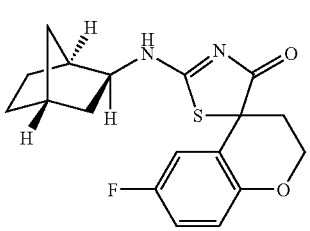 | 346.4 | 347 | 2'-((1S,2S,4R)-bicyclo[2.21]heptan-2-ylamino-6-fluoro-2,3-dihydro-spiro[4H-1-benzopyran-4,5'(4'H)-thiazol]-4'-one | N X |

TABLE 1-continued

| Structure | Mol Wt. | Mass Spec | Name | Methods of Prep. |
|---|---|---|---|---|
| 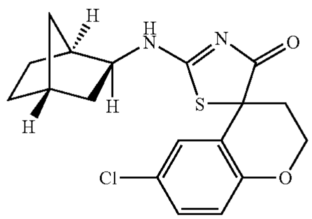 | 362.9 | 363/365 | 2'-((1S,2S,4R)-bicyclo[2.2.1]heptan-2-ylamino-6-chloro-2,3-dihydro-spiro[4H-1-benzopyran-4,5'(4'H)-thiazol]-4'-one | N X |
| 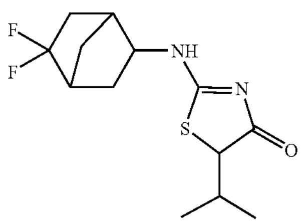 | 288.4 | 289 | 2-(5,5-difluorobicyclo[2.2.1]heptan-2-ylamino)-5-isopropylthiazol-4(5H)-one/ 2-(6,6-difluorobicyclo[2.2.1]heptan-2-ylamino)-5-isopropyltrhiazol-4(5H)-one | X |
| 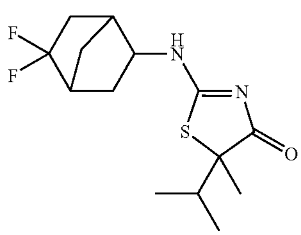 | 302.4 | 303 | 3-(5,5-difluorobicyclo[2.2.1]heptan-2-ylamino)-5-isopropyl-5-methylthiazol-4(5H)-one/ 2-(6,6-difluorobicyclo[2.2.1]heptan-2-ylamino)-5-isopropyl-5-methylthiazol-4(5H)-one | X AA |
| 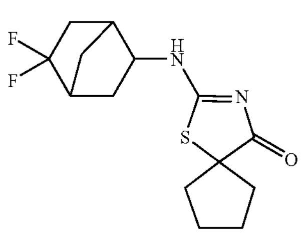 | 300.4 | 301 | 2-((5,5-difluorobicyclo[2.2.1]hept-2-yl)amino)-1-thia-3-azaspiro[4.4]none-2-en-4-one/ 2-((6,6-difluorobicyclo[2.2.1]hept-2-yl)amino)-1-thia-3-azaspiro[4.4]non-2-en-4-one | L X |

TABLE 1-continued

| Structure | Mol Wt. | Mass Spec | Name | Methods of Prep. |
|---|---|---|---|---|
| | | | | |
| 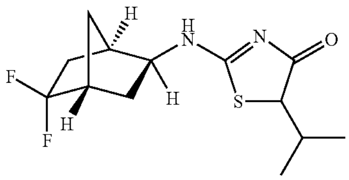 | 288.4 | 289 | 2-((1R,2S,4R)-5,5-difluorobicyclo[2.2.1]heptan-2-ylamino)-5-isopropylthiazol-4(5H)-one | Q X |
| 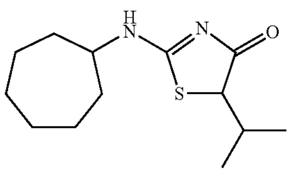 | 254.4 | 255 | 2-(cycloheptylamino)-5-isopropylthiazol-4(5H)-one | P X |
| | 302.4 | 303 | (R)-2-((1R,2S,4R)-5,5-difluorobicyclo[2.2.1]heptan-2-ylamino)-5-isopropyl-5-methylthiazol-4(5H)-one | Q X AA |
| | 302.4 | 303 | (S)-2-((1R,2S,4R)-5,5-difluorobicyclo[2.2.1]heptan-2-ylamino)-5-isopropyl-5-methylthiazol-4(5H)-one | Q X AA |
| 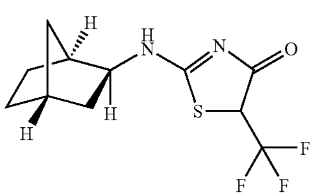 | 2278.3 | 279 | 2-((1S,2S,4R)-bicyclo[2.2.1]heptan-2-ylamino)-5-(trifluoromethyyl)thiazol-4(5H)-one | X |
| 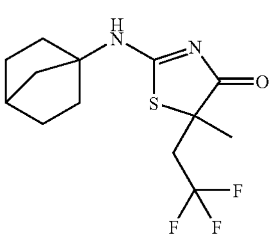 | 306.4 | 307 | 2-(bicyclo[2.2.1]heptan-1-ylamino)-5-methyl-5-(2,2,2-trifluorometrhyl)thiazol-4(5H)-one | S L X |

TABLE 1-continued

| Structure | Mol Wt. | Mass Spec | Name | Methods of Prep. |
|---|---|---|---|---|
| 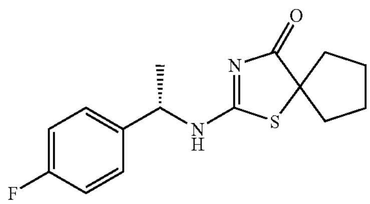 | 292.4 | 293 | 2-(S)-2-(1-(4-fluorophenyl)ethylamino)-1-thia-3-azaspiro[4.4]non-2-en-4-one | O L X |
| 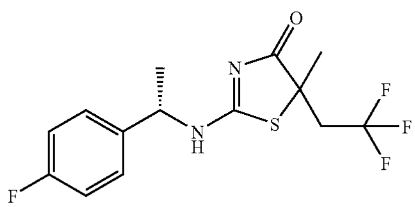 | 334.3 | 335 | 2-((S)-1-(4-fluorophenyl)ethylamino)-5-methyl-5-(2,2,2-trifluoroethyl)thiazol-4(5H)-one | O L X |
| 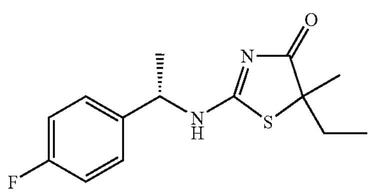 | 280.4 | 281 | 5-ethyl-2-((S)-1-(4-fluorophenyl)ethylamino)-5-methyylthiazol-4(5H)-one | O L X |
| 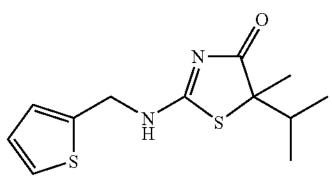 | 268.4 | 269 | 5-isopropyl-5-methyl-2-(thiophen-2-ylmethylamino)thiazol-4(5H)-one | Z |
| | 263.4 | 264 | 5-isopropyl-5-methyl-2-(pyridin-2-ylmethylamino)thiazol-4(5H)-one | Z |
| | 263.4 | 264 | 5-isopropyl-5-methyl-2-(pyridin-3-ylmethylamino)thiazol-4(5H)-one | Z |
| | 263.4 | 264 | 5-isopropyl-5-methyl-2-(pyridin-4-ylmethylamino)thiazol-4(5H)-one | Z |

TABLE 1-continued

| Structure | Mol Wt. | Mass Spec | Name | Methods of Prep. |
|---|---|---|---|---|
| | 249.3 | — | 5-isopropyl-2-(pyridin-4-ylmethylamino)thiazol-4(5H)-one | Z |
| | 249.3 | 250 | 5-isopropyl-2-(pyridin-2-ylmethylamino)thiazol-4(5H)-one | Z |
| 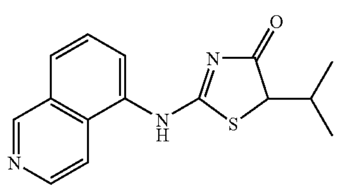 | 285.4 | 286 | 5-isopropyl-2-(isoquinolin-5-ylamino)thiazol-4(5H)-one | Z |
| | 277.4 | 278 | 5-isopropyl-5-methyl-2-(1-(pyridin-2-yl)ethylamino)thiazol-4(5H)-one | Z |
| | 277.4 | 278 | 5-isopropyl-5-methyl-2-(1-(pyridin-4-yl)ethylamino)thiazol-4(5H)-one | Z |

TABLE 1-continued

| Structure | Mol Wt. | Mass Spec | Name | Methods of Prep. |
|---|---|---|---|---|
| 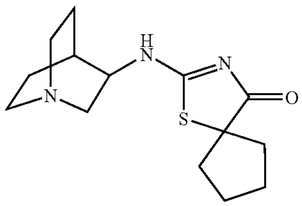 | 279.4 | 280 | 2-(1-azabicyclo[2.2.2]oct-3-ylamino)-1-thia-3-azaspiro[4.4]non-2-en-4-one | O X |
| 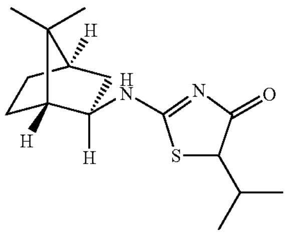 | 294.4 | 295 | 5-isopropyl-2-((1R,2R,4R)-1,7,7-trimethylbicyclo[2.2.1]heptan-2-ylamino)thiazol-4(5H)-one | O X |
| 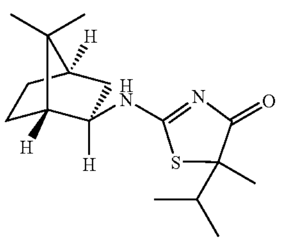 | 308.5 | 309 | 5-isopropyl-5-methyl-2-((1R,2R,4R)-1,7,7-trimethylbicyclo[2.2.1]heptan-2-ylamino)thiazol-4(5H)-one | O X AA |
| 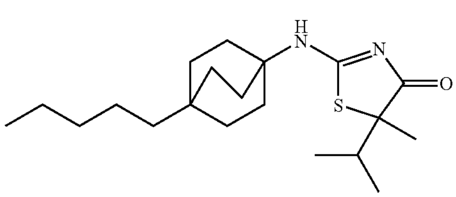 | 350.5 | 351 | 5-isopropyl-5-methyl-2-(4-pentylbicyclo[2.2.2]octan-1-ylamino)thiazol-4(5H)-one | O X AA |
| 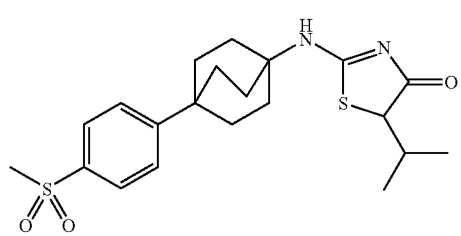 | 420.6 | 421 | 5-isopropyl-2-(4-(4-(methylsulfonyl)phenyl)bicyclo[2.2.2]octan-1-ylamino)thiazol-4(5H)-one | V O X |

TABLE 1-continued

| Structure | Mol Wt. | Mass Spec | Name | Methods of Prep. |
|---|---|---|---|---|
| 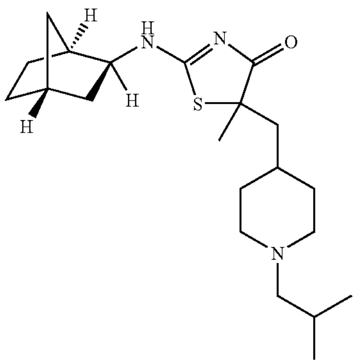 | 377.6 | 378 | 2-((1S,2S,4R)-bicyclo[2.2.1]heptan-2-ylamino)-5-((1-isobutylpiperidin-4-yl)methyl)-5-methylthiazol-4(5H)-one | Y<br>LL<br>JJ(b)<br>MM(a) |
| 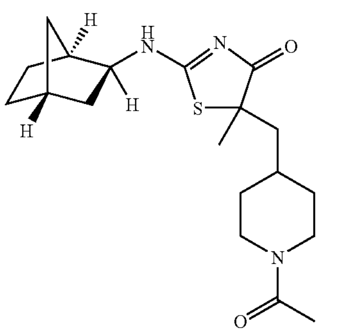 | 363.5 | 364 | 5-((1-acetylpiperidin-4-yl)methyl)-2-((1S,2S,4R)-bicyclo[2.2.1]heptan-2-ylamino)-5-methylthiazol-4(5H)-one | Y<br>LL<br>MM |
| 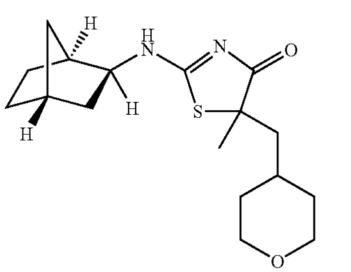 | 322.5 | 323 | 2-((1S,2S,4R)-bicyclo[2.2.1]heptan-2-ylamino)-5-methyl-5-((tetrahydro-2H-pyran-4-yl)methyl)thiazol-4(5H)-one | Y<br>LL |
| 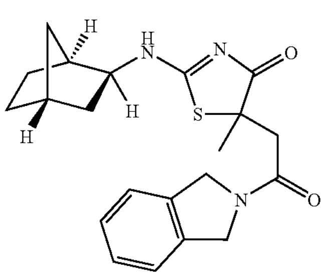 | 383.5 | 384 | 2-((1S,2S,4R)-bicyclo[2.2.1]heptan-2-ylamino)-5-(2-(isoindolin-2-yl)-2-oxoethyl)-5-methylthiazol-4(5H)-one | Y<br>LL<br>DD(b)<br>OO(b) |

| Structure | Mol Wt. | Mass Spec | Name | Methods of Prep. |
|---|---|---|---|---|
| 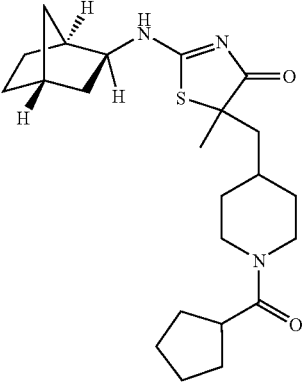 | 417.6 | 418 | 2-((1S,2S,4R)-bicyclo[2.2.1]heptan-2-ylamino)-5-((1-(cyclopentanecarbonyl)piperidin-4-yl)methyl)-5-methylthiazol-4(5H)-one | Y LL MM |
| 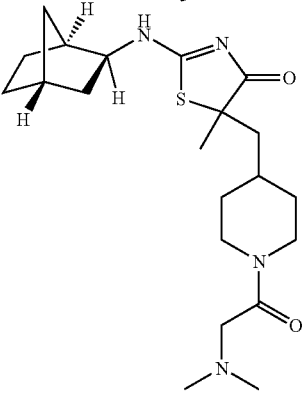 | 406.6 | 408 | 2-((1S,2S,4R)-bicyclo[2.2.1]heptan-2-ylamino)-5-((1-(2-(dimethylamino)acetyl)piperidin-4-yl)methyl)-5-methylthiazol-4(5H)-one | Y LL MM |
| 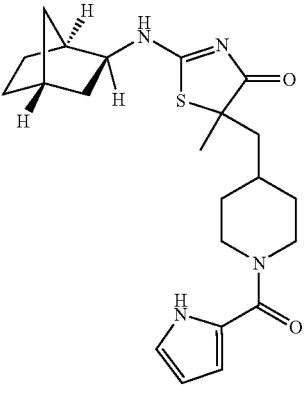 | 414.6 | 415 | 5-((1-(1H-pyrrole-2-carbonyl)piperidin-4-yl)methyl)-2-((1S,2S,4R)-bicyclo[2.2.1]heptan-2-ylamino)-5-methylthiazol-4-(5H)-one | Y LL MM |
| 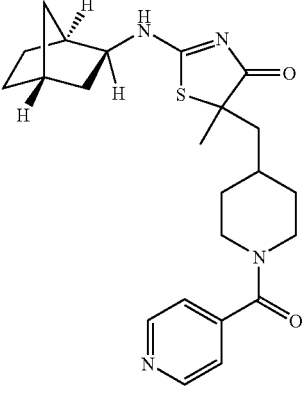 | 426.6 | 427 | 2-((1S,2S,4R)-bicyclo[2.2.1]heptan-2-ylamino)-5-((1-isonicotinoylpiperidin-4-yl)methyl)-5-methylthiazol-4(5H)-one | Y LL MM |

-continued

| Structure | Mol Wt. | Mass Spec | Name | Methods of Prep. |
|---|---|---|---|---|
| 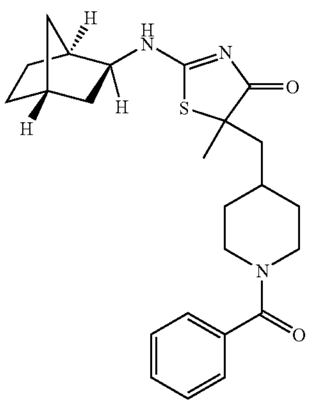 | 425.6 | 426 | 5-((1-benzoylpiperidin-4-yl)methyl)-2-((1S,2S,4R)-bicyclo[2.2.1]heptan-2-ylammino)-5-methylthiazol-4(5H)-one | Y LL MM |
| 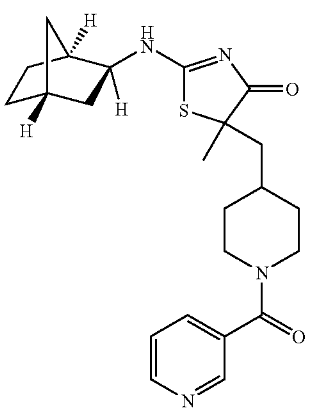 | 426.6 | 427 | 2-((1S,2S,4R)-bicyclo[2.2.1]heptan-2-ylamino)-5-mewthyl-5-((1-nictinoylpiperidin-4-yl)methyl)thiazol-4(5H)-one | Y LL MM |
| 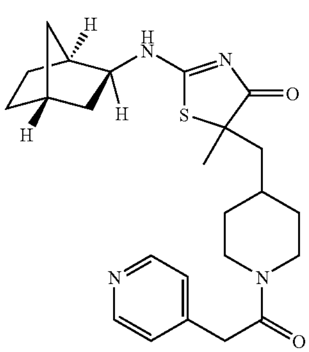 | 440.6 | 441 | 2-((1S,2S,4R)-bicyclo[2.2.1]heptan-2-ylamino)-5-methyl-5-((1-(2-(pyridin-4-yl)acetyl)piperidin-4-yl)methyl)thiazol-4(5H)-one | Y LL MM |
| 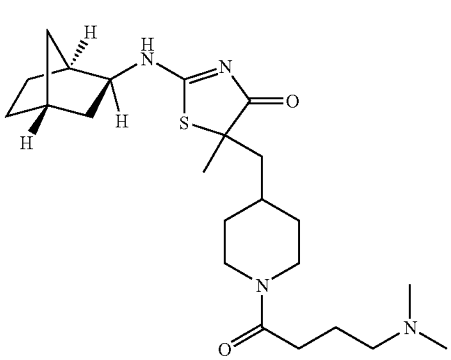 | 434.6 | 435 | 2-((1S,2S,4R)-bicyclo[2.2.1]heptan-2-ylamino)-5-((1-(4-(dimethylamino)butanoyl)piperidin-4-yl)methyl)-5-methylthiazol-4(5H)-one | Y LL MM |

-continued

| Structure | Mol Wt. | Mass Spec | Name | Methods of Prep. |
|---|---|---|---|---|
| 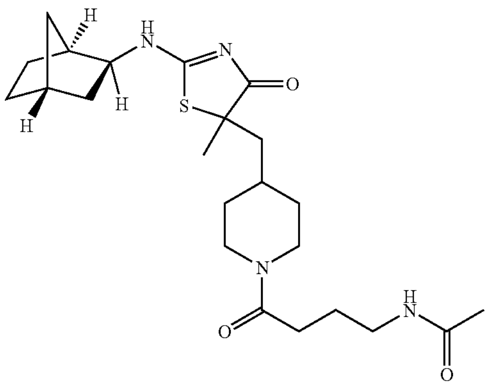 | 448.6 | 449 | N-(4-(4-((2-(1S,2S,4R)-bicyclo[2.2.1]heptan-2-ylamino)-5-methyl-4-oxo-4,5-dihydrothiazol-5-yl)methyl)piperidin-1-yl)-4-oxobutyl)acetamide | Y LL MM |
| 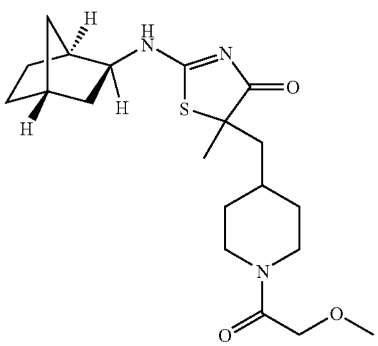 | 393.5 | 394 | 2-((1S,2S,4R)-bicyclo[2.2.1]heptan-2-ylamino)-5-((1-(2-methoxyacetyl)piperidin-4-yl)methyl)-5-methylthiazzol-4(5H)-one | Y LL MM |
| 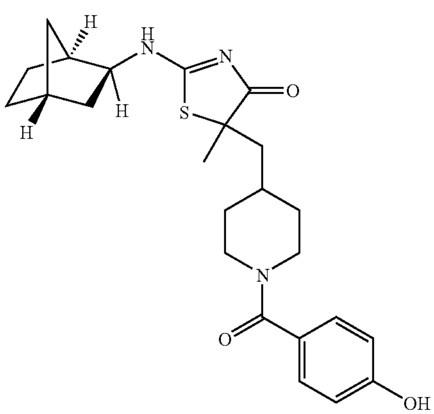 | 441.6 | 442 | 2-((1S,2S,4R)-bicyclo[2.2.1]heptan-2-ylamino)-5-((1-(4-hydroxybenzoyl)piperidin-4-yl)methyl)-5-methylthiazol-4(5H)-one | Y LL MM |
| 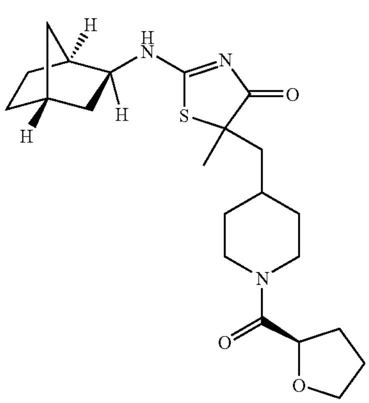 | 419.6 | 420 | 2-((1S,2S,4R)-bicyclo[2.2.1]heptan-2-ylamino)-5-methyl-5-((1-((R)-tetrahydrofuran-2-carbonyl)piperidin-4-yl)methyl)thiazol-4(5H)-one | Y LL MM |

-continued

| Structure | Mol Wt. | Mass Spec | Name | Methods of Prep. |
|---|---|---|---|---|
|  | 419.6 | 420 | 2-((1S,2S,4R)-bicyclo[2.2.1]heptan-2-ylamino)-5-methyl-5-((1-((S)-tetrahydrofuran-2-carbonyl)piperidin-4-yl)methyl)thiazol-4(5H)-one | Y LL MM |
|  | 419.6 | 420 | 2-((1S,2S,4R)-bicyclo[2.2.1]heptan-2-ylamino)-5-methyl-5-((1-(tetrahydrofuran-2-carbonyl)piperidin-4-yl)methyl)thiazol-4(5H)-one | Y LL MM |
| 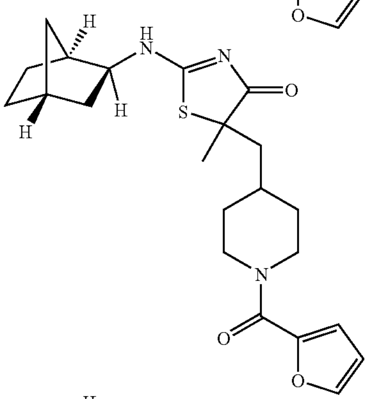 | 415.6 | 416 | 2-((1S,2S,4R)-bicyclo[2.2.1]heptan-2-ylamino)-5-((1-(furan-2-carbonyl)piperidin-4-yl)methyl)-5-methylthiazol-4(5H)-one | Y LL MM |
| 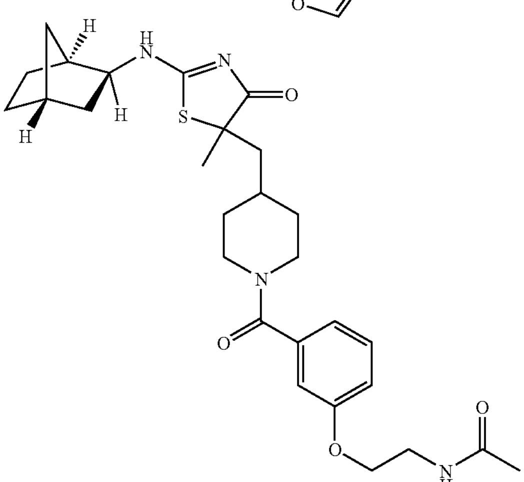 | 526.7 | 527 | N-(2-(3-(4-((2-((1S,2S,4R)-bicyclo[2.2.1]heptan-2-ylamino)-5-methyl-4-oxo-4,5-dihydrothiazol-5-yl)methyl)piperidine-1-carbonyl)phenooxy)ethyl)acetamide | Y LL MM |

-continued

| Structure | Mol Wt. | Mass Spec | Name | Methods of Prep. |
|---|---|---|---|---|
| 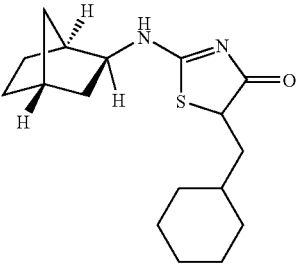 | 306.5 | 307 | 2-((1S,2S,4R)-bicyclo[2.2.1]heptan-2-ylamino)-5-(cyclohexylmethyl)thiazol-4(5H)-one | Y LL |
| 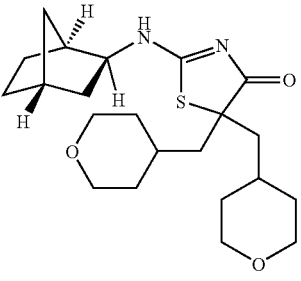 | 406.6 | 407 | 2-((1S,2S,4R)-bicyclo[2.2.1]heptan-2-ylamino)-5,5-bis((tetrahydro-2H-pyran-4-yl)methyl)thiazol-4(5H)-one | Y LL |
| 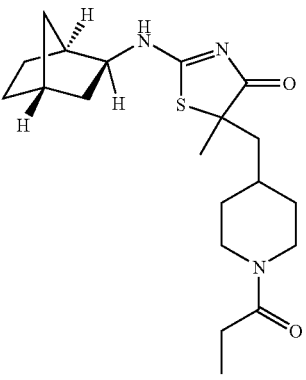 | 377.6 | 378 | 2-((1S,2S,4R)-bicyclo[2.2.1]heptan-2-ylamino)-5-methyl-5-((1-propionylpiperidin-4-yl)methyl)thiazol-4(5H)-one | Y LL MM |
| 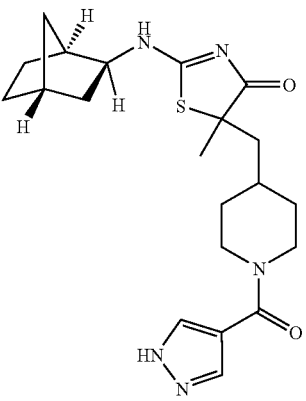 | 415.6 | 416 | 5-((1-(1H-pyrazole-4-carbonyl)piperidin-4-yl)methyl)-2-((1S,2S,4R)-bicyclo[2.2.1]heptan-2-ylamino)-5-methylthiazol-4(5H)-one | Y LL MM |

-continued

| Structure | Mol Wt. | Mass Spec | Name | Methods of Prep. |
|---|---|---|---|---|
| 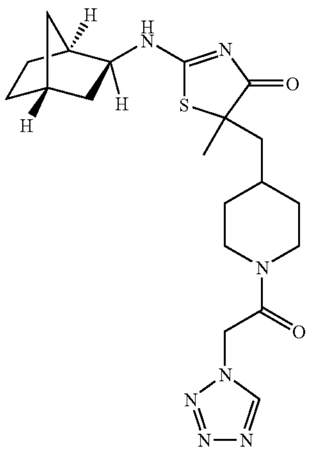 | 432.6 | 432 | 5-((1-(2-(1H-tetrazol-1-yl)acetyl)piperidin-4-yl)methyl)-2-((1S,2S,4R)-bicyclo[2.2.1]heptan-2-ylamino)-5-methylthiazol-4(5H)-one | Y LL MM |
| 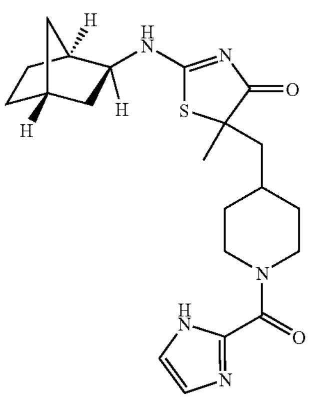 | 415.6 | 416 | 5-((1-(1H-imidazole-2-carbonyl)piperidin-4-yl)methyl)-2-((1S,2S,4R)-bicyclo[2.2.1]heptan-2-ylamino)-5-methylthiazol-4(5H)-one | Y LL MM |
| 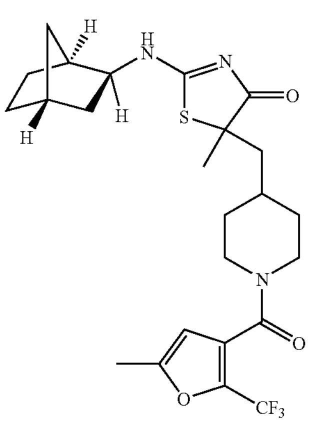 | 497.6 | 498 | 2-((1S,2S,4R)-bicyclo[2.2.1]heptan-2-ylamino)-5-methyl-5-((1-(2-methyl-5-(trifluoromethyl)furan-4-carbonyl)piperidin-4-yl)methyl)thiazol-4(5H)-one | Y LL MM |

-continued

| Structure | Mol Wt. | Mass Spec | Name | Methods of Prep. |
|---|---|---|---|---|
| 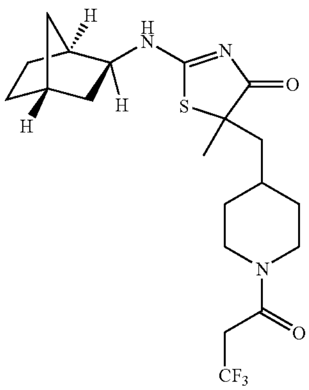 | 431.5 | 432 | 2-((1S,2S,4R)-bicyclo[2.2.1]heptan-2-ylamino)-5-methyl-5-((1-(3,3,3-trifluoropropanoyl)piperidin-4-yl)methyl)thiazol-4(5H)-one | Y LL MM |
| 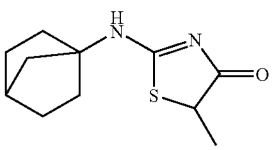 | 224.3 | 225 | 2-(bicyclo[2.2.1]heptan-1-ylamino)-5-methylthiazol-4(5H)-one | Y |
| 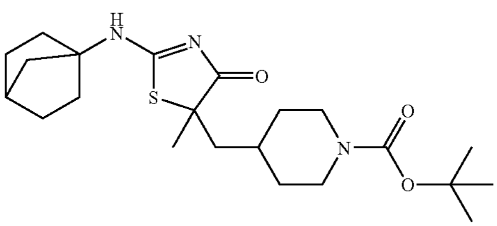 | 421.6 | 422 | tert-butyl 4-((2-(bicyclo[2.2.1]heptan-1-ylamino)-5-methyl-4-oxo-4,5-dihydrothiazol-5-yl)methyl)piperidine-1-carboxylate | Y LL |
| 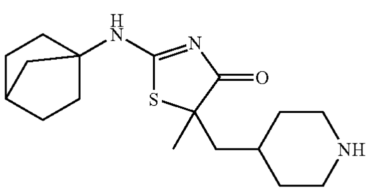 | 321.5 | 322 | 2-(bicyclo[2.2.1]heptan-1-ylamino)-5-methyl-5-(piperidin-4-ylmethyl)thiazol-4(5H)-one | Y LL MM(a) |
| 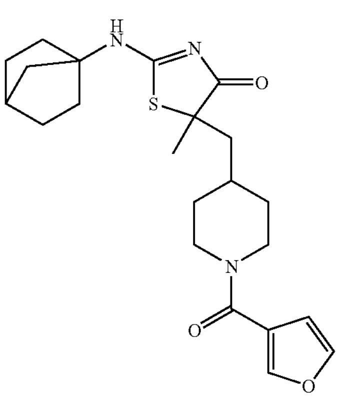 | 415.6 | 416 | 2-(bicyclo[2.2.1]heptan-1-ylamino)-5-((1-(furan-3-carbonyl)piperidin-4-yl)methyl)-5-methylthiazol-4(5H)-one | Y LL MM |

-continued

| Structure | Mol Wt. | Mass Spec | Name | Methods of Prep. |
|---|---|---|---|---|
| 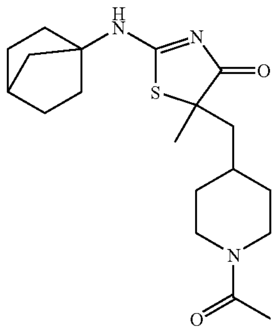 | 363.5 | 364 | 5-((1-acetylpiperidin-4-yl)methyl)-2-(bicyclo[2.2.1]heptan-1-ylammino)-5-methylthiazol-4(5H)-one | Y LL MM |
| 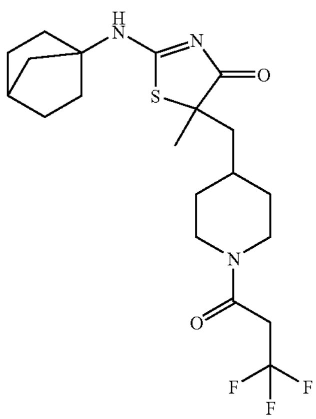 | 431.5 | 432 | 2-(bicyclo[2.2.1]heptan-1-ylamino)-5-methyl-5-((1-(3,3,3-trifluoropropanoyl)piperidin-4-yl)methyl)thiazol-4(5H)-one | Y LL MM |
| 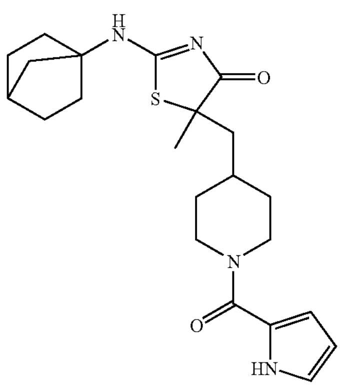 | 414.6 | 415 | 5-((1-(1H-pyrrole-2-carbonyl)piperidin-4-yl)methyl)-2-(bicyclo[2.2.1]heptan-1-ylamino)-5-methylthiazol-4(5H)-one | Y LL MM |
| 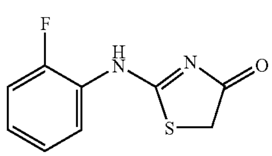 | 210.2 | 211 | 2-(2-fluorophenylamino)thiazol-4(5H)-one | Y |
| 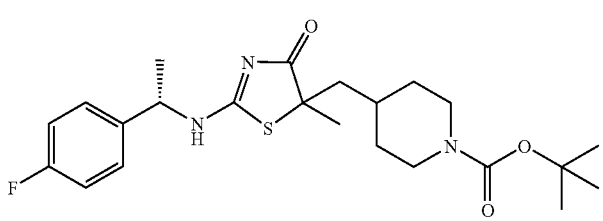 | 449.6 | 450 | tert-butyl 4-((2-((S)-1-(4-fluorophenyl)ethylamino)-5-methyl-4-oxo-4,5-dihydrothiazol-5-yl)methyl)piperidine-1-carboxylate | Y LL |

| Structure | Mol Wt. | Mass Spec | Name | Methods of Prep. |
|---|---|---|---|---|
| 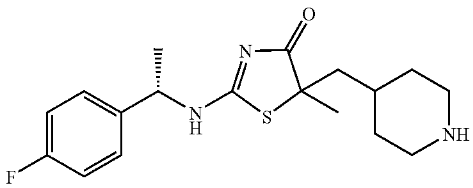 | 349.5 | 350 | 2-((S)-1-(4-fluorophenyl)ethylamino)-5-methyl-5-(piperidin-4-ylmethyl)thiazol-4(5H)-one | Y LL MM(a) |
| 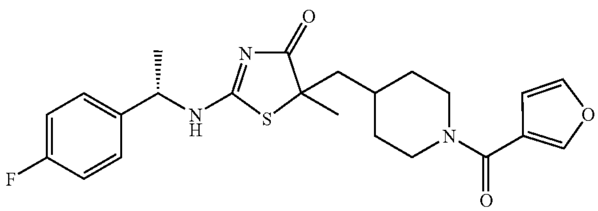 | 443.5 | 444 | 2-((S)-1-(4-fluorophenyl)ethylamino)-5-((1-furan-3-carbonyl)piperidin-4-yl)methyl)-5-methylthiazol-4(5H)-one | Y LL MM |
| 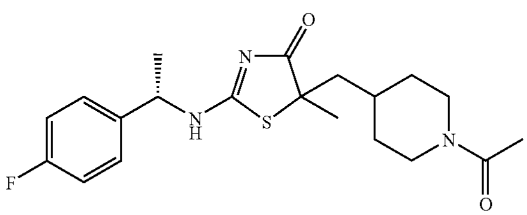 | 391.5 | 392 | 5-((1-acetylpiperidin-4-yl)methyl)-2-((S)-1-(4-fluorophenyl)ethylamino)-5-methylthiazol-4(5H)-one | Y LL MM |
| 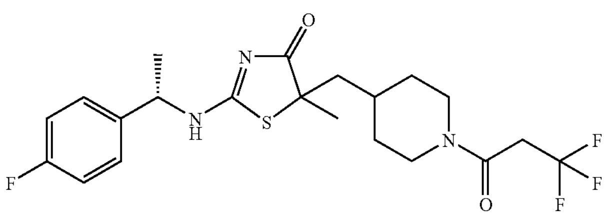 | 459.5 | 460 | 2-((S)-1-(4-fluorophenyl)ethylamino)-5-methyl-5-((1-(3,3,3-trifluoropropanoyl)piperidin-4-yl)methyl)thiazol-4(5H)-one | Y LL MM |
| 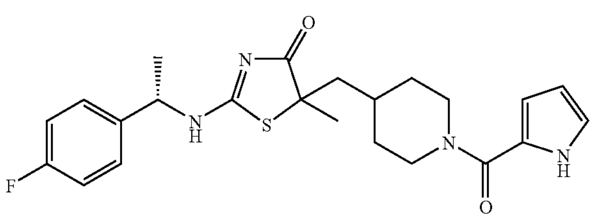 | 442.6 | 443 | 5-((1-(1H-pyrrole-2-carbonyl)piperidin-4-yl)methyl)-2-((S)-1-(4-fluorophenyl)ethylamino)-5-methylthiazol-4(5H)-one | Y LL MM |
| 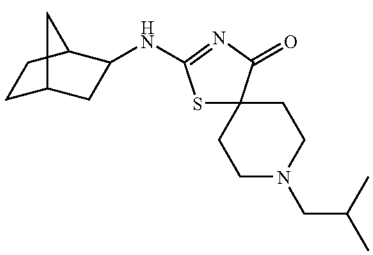 | 335.5 | 336 | 2-(Bicyclo[2.2.1]hept-2-ylamino)-8-isobutyl-1-thia-3,8-diaza-spiro[4.5]dec-2-en-4-one | Y LL |

-continued

| Structure | Mol Wt. | Mass Spec | Name | Methods of Prep. |
|---|---|---|---|---|
| 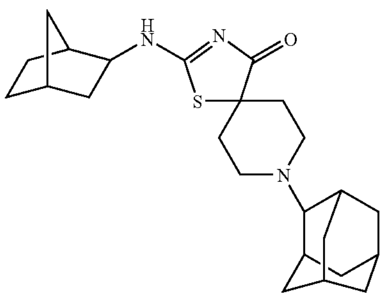 | 413.6 | 414 | 8-Adamantan-2-yl-2-(bicyclo[2.2.1]hept-2-ylamino)-1-thia-3,8-diaza-spiro[4.5]dec-2-en-4-one | Y LL |
| 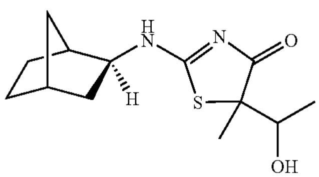 | 268.4 | 269 | 2-((2S)-bicyclo[2.2.1]heptan-2-ylamino)-5-(1-hydroxyethyl)-5-methylthiazol-4(5H)-pne | Y FF |
| 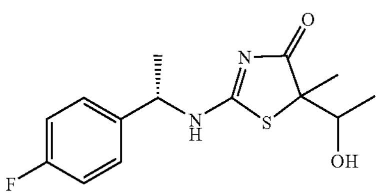 | 296.4 | 297 | 2-((S)-1-(4-fluorophenyl)ethylamino)-5-(1-hydroxyethyl)-5-methylthiazol-4(5H)-one | Y FF |
| 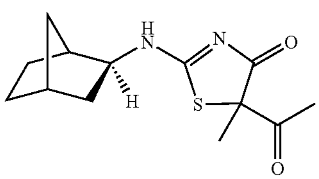 | 266.4 | 267 | 5-acetyl-2-((2S)-bicyclo[2.2.1]heptan-2-ylamino)-5-methylthiazol-4(5H)-one | Y FF JJ(a) |
| 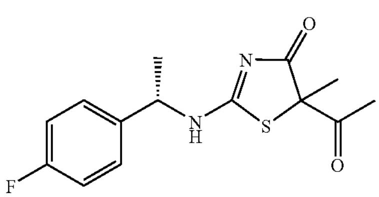 | 294.4 | 295 | 5-acetyl-2-((S)-1-(4-fluorophenyl)ethylamino)-5-methylthiazol-4(5H)-one | Y FF JJ(a) |
| 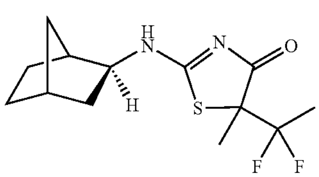 | 288.4 | 289 | 2-((2S)-bicyclo[2.2.1]heptan-2-ylamino)-5-(1,1-difluoroethyl)-5-methylthiazol-4(5H)-one | Y FF JJ(a) GG |
| 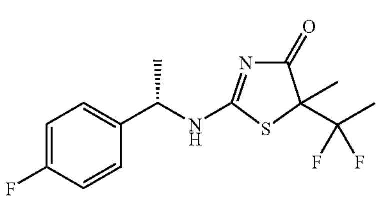 | 316.4 | 317 | 5-(1,1-difluoroethyl)-2-((S)-1-(4-fluorophenyl)ethylamino)-5-methylthiazol-4(5H)-one | Y FF JJ(a) GG |

| Structure | Mol Wt. | Mass Spec | Name | Methods of Prep. |
|---|---|---|---|---|
| 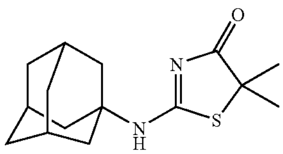 | 278.4 | 279 | 5,5-dimethyl-2-(tricyclo[3.3.1.1~3,7~]dec-1-ylamino)-1,3-thiazol-4(5H)-one | X |
| 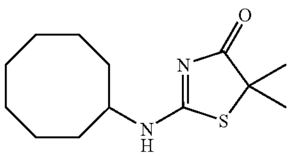 | 254.4 | 255 | 2-(cyclooctylamino)-5,5-dimethyl-1,3-thiazol-4(5H)-one | X |
| 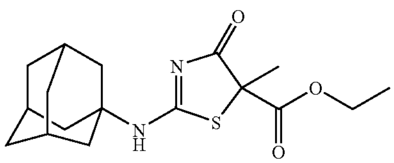 | 336.5 | 337 | ethyl 5-methyl-4-oxo-2-(tricyclo[3.3.1.1~3,7~]dec-1-ylamino)-4,5-dihydro-1,3-thiazole-5-carboxylate | X |
| 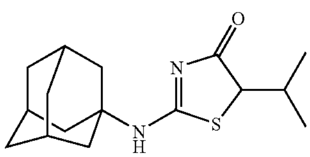 | 292.4 | 293 | 5-(1-methylethyl)-2-(tricyclo[3.3.1.1~3,7~]dec-1-ylamino)-1,3-thiazol-4(5H)-one | X |
| 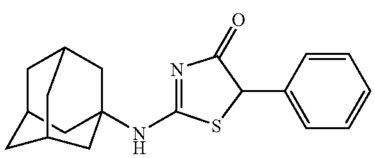 | 326.5 | 327 | 5-phenyl-2-(tricyclo[3.3.1.1~3,7~]dec-1-ylamino)-1,3-thiazol-4(5H)-one | X |
| 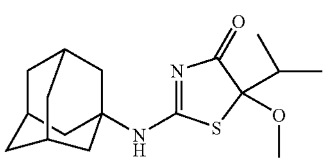 | 322.5 | 323 | 5-(1-methylethyl)-5-(methyloxy)-2-(tricyclo[3.3.1.1~3,7~]dec-1-ylamino)-1,3-thiazol-4(5H)-one | II |
| 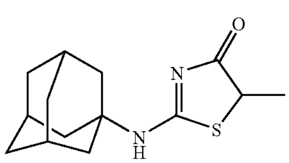 | 264.4 | 265 | 5-methyl-2-(tricyclo[3.3.1.1~3,7~]dec-1-ylamino)-1,3-thiazol-4(5H)-one | X |
| 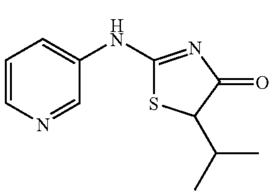 | 235.3 | 236 | 5-(1-methylethyl)-2-(3-pyridinylamino)-1,3-thiazol-4(5H)-one | X |
| 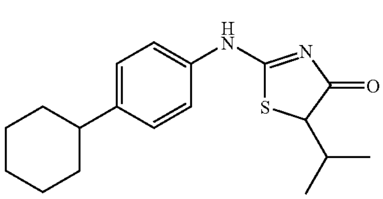 | 316.5 | 317 | 2-((4-cyclohexylphenyl)amino)-5-(1-methylethyl)-1,3-thiazol-4(5H)-one | X |

-continued

| Structure | Mol Wt. | Mass Spec | Name | Methods of Prep. |
|---|---|---|---|---|
| 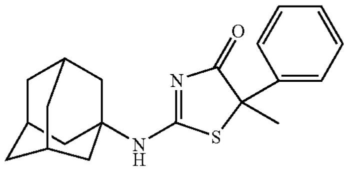 | 340.5 | 341 | 5-methyl-5-phenyl-2-(tricyclo[3.3.1.1~3,7~]dec-1-ylamino)-1,3-thiazol-4(5H)-one | X |
| 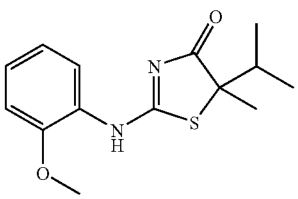 | 264.3 | 265 | 5-(1-methylethyl)-2-((2-(methyloxy)phenyl)amino)-1,3-thiazol-4(5H)-one | X |
| 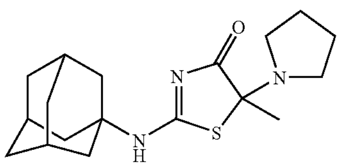 | 333.5 | 334 | 5-methyl-5-(1-pyrrolidinyl)-2-(tricyclo[3.3.1.1~3,7~]dec-1-ylamino)-1,3-thiazol-4(5H)-one | II |
| 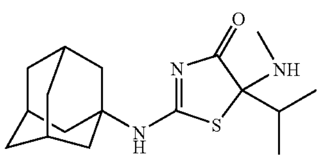 | 321.5 | 322 | 5-(methylamino)-5-(1-methylethyl)-2-(tricyclo[3.3.1.1~3,7~]dec-1-ylamino)-1,3-thiazol-4(5H)-one | II |
| | 235.3 | 236 | 5-(1-methylethyl)-2-(2-pyridinylamino)-1,3-thiazol-4(5H)-one | X |
| 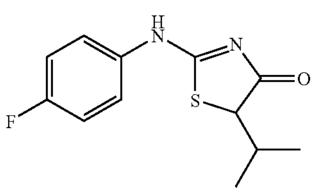 | 252.3 | 253 | 2-((4-fluorophenyl)amino)-5-(1-methylethyl)-1,3-thiazol-4(5H)-one | X |
| | 235.3 | 236 | 5-(1-methylethyl)-2-(4-pyridinylamino)-1,3-thiazol-4(5H)-one | X |
| 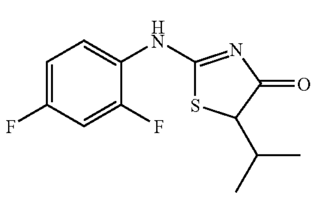 | 270.3 | 271 | 2-((2,4-difluorophenyl)amino)-5-(1-methylethyl)-1,3-thiazol-4(5H)-one | X |

-continued

| Structure | Mol Wt. | Mass Spec | Name | Methods of Prep. |
|---|---|---|---|---|
| 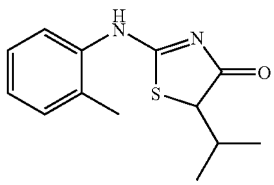 | 248.4 | 249 | 5-(1-methylethyl)-2-((2-methylphenyl)amino)-1,3-thiazol-4(5H)-one | X |
| 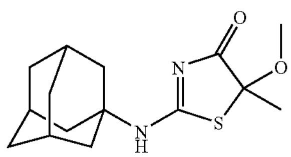 | 294.4 | 295 | 5-methyl-5-(methyloxy)-2-(tricyclo[3.3.1.1~3,7~]dec-1-ylamino)-1,3-thiazol-4(5H)-one | X II |
| 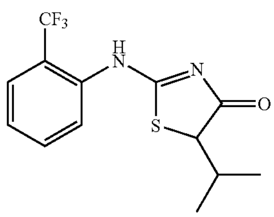 | 302.3 | 303 | 5-(1-methylethyl)-2-((2-(trifluoromethyl)phenyl)amino)-1,3-thiazol-4(5H)-one | X |
| 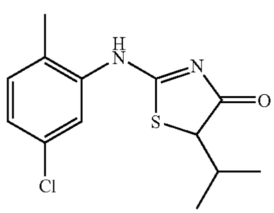 | 282.8 | 283 | 2-((5-chloro-2-methylphenyl)amino)-5-(1-methylethyl)-1,3-thiazol-4(5H)-one | X |
| 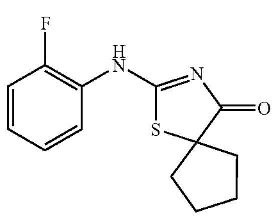 | 264.3 | 265 | 2-((2-fluorophenyl)amino)-1-thia-3-azaspiro[4.4]non-2-en-4-one | X |
| 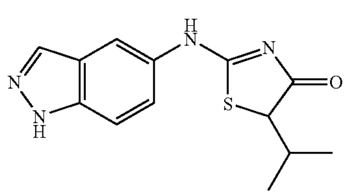 | 274.4 | 275 | 2-(1H-indazol-5-ylamino)-5-(1-methylethyl)-1,3-thiazol-4(5H)-one | X |
| 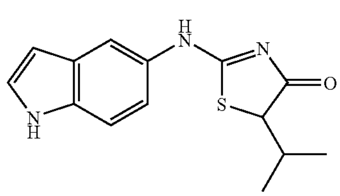 | 273.4 | 274 | 2-(1H-indol-4-ylamino)-5-(1-methylethyl)-1,3-thiazol-4(5H)-one | X |

| Structure | Mol Wt. | Mass Spec | Name | Methods of Prep. |
|---|---|---|---|---|
| | 268.4 | 269 | 2-(((1S)-1-cyclohexylethyl)amino)-5-(1-methylethyl)-1,3-thiazol-4(5H)-one | X |
| | 268.4 | 269 | 2-(((1R)-1-cyclohexylethyl)amino)-5-(1-methylethyl)-1,3-thiazol-4(5H)-one | X |
| | 268.4 | 269 | 2-(cyclooctylamino)-5-(1-methylethyl)-1,3-thiazol-4(5H)-one | X |
| | 266.3 | 267 | 2-((5-fluoro-2-methylphenyl)amino)-5-(1-methylethyl)-1,3-thiazol-4(5H)-one | X |
| 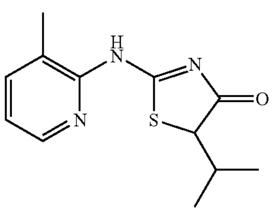 | 249.3 | 250 | 5-(1-methylethyl)-2-((3-methyl-2-pyridinyl)amino)-1,3-thiazol-4(5H)-one | X |
| 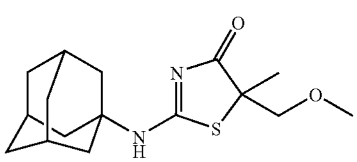 | 308.4 | 309 | 5-methyl-5-((methyloxy)methyl)-2-(tricyclo[3.3.1.1~3,7~]dec-1-ylamino)-1,3-thiazzol-4(5H)-one | AA |
| | 266.3 | 267 | 2-((2-fluorophenyl)amino)-5-methyl-5-(1-methylethyl)-1,3-thiazol-4(5H)-one | AA |
| 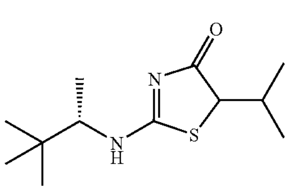 | 242.4 | 243 | 5-(1-methylethyl)-2-(((1S)-1,2,2-trimethylpropyl)amino)-1,3-thiazol-4(5H)-one | X |

-continued

| Structure | Mol Wt. | Mass Spec | Name | Methods of Prep. |
|---|---|---|---|---|
| 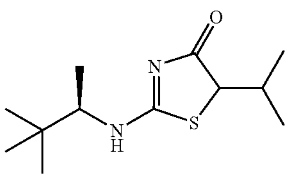 | 242.4 | 243 | 5-(1-methylethyl)-2-(((1R)-1,2,2-trimethylpropyl)amino)-1,3-thiazol-4(5H)-one | X |
| 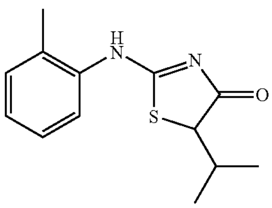 | 262.4 | 263 | 5-methyl-5-(1-methylethyl)-2-((2-methylphenyl)amino)-1,3-thiazol-4(5H)-one | AA |
| 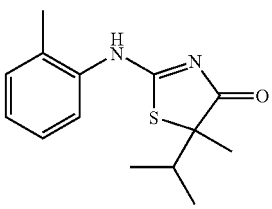 | 252.3 | 253 | 5-ethyl-2-((2-fluorophenyl)amino)-5-methyl-1,3-thiazol-4(5H)-one | X |
| 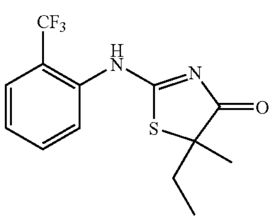 | 302.3 | 303 | 5-ethyl-5-methyl-2-((2-trifluoromethyl)phenyl)amino)-1,3-thiazol-4(5H)-one | X |
| | 266.3 | 267 | (5S)-2-((2-fluorophenyl)amino)-5-methyl-5-(1-methylethyl)-1,3-thiazol-4(5H)-one | AA |
| | 266.3 | 267 | (5R)-2-((2-fluorophenyl)amino)-5-methyl-5-(1-methylethyl)-1,3-thiazol-4(5H)-one | AA |
| 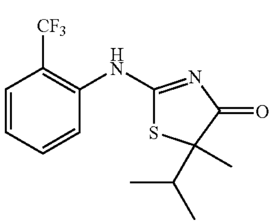 | 316.4 | 317 | 5-methyl-5-(1-methylethyl)-2-((2-(trifluoromethyl)phenyl)amno)-1,3-thiazol-4(5H)-one | AA |

-continued

| Structure | Mol Wt. | Mass Spec | Name | Methods of Prep. |
|---|---|---|---|---|
| | 300.4 | 301 | 2-((2-fluorophenyl)amino)-5-methyl-5-phenyl-1,3-thiazol-4(5H)-one | X |
| 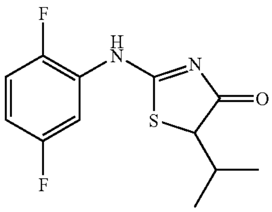 | 270.3 | 271 | 2-((2,5-difluorophenyl)amino)-5-(1-methylethyl)-1,3-thiazol-4(5H)-one | X |
| 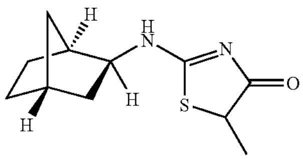 | 224.3 | 225 | 2-((1S,2S,4R)-bicyclo[2.2.1]hept-2-ylamino)-5-methyl-1,3-thiazol-4(5H)-one | X |
| | 300.4 | 301 | 2-((1S,2S,4R)-bicyclo[2.2.1]hept-2-ylamino)-5-methyl-5-phenyl-1,3-thiazol-4(5H)-one | X |
| 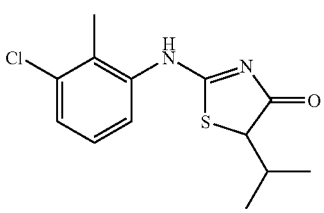 | 282.8 | 283 | 2-((3-chloro-2-methylphenyl)amino)-5-(1-methylethyl)-1,3-thiazol-4(5H)-one | X |
| 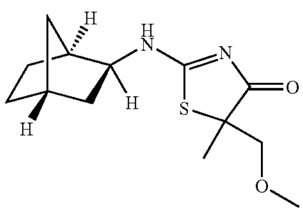 | 268.4 | 269 | 2-((1S,2S,4R)-bicyclo[2.2.1]hept-2-ylamino)-5-methyl-5-((methyloxy)methyl)-1,3-thiazol-4(5H)-one | AA |
| 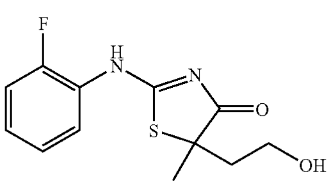 | 268.3 | 269 | 2-((2-fluorophenyl)amino)-5-(2-hydroxyethyl)-5-methyl-1,3-thiazol-4(5H)-one | KK |

-continued

| Structure | Mol Wt. | Mass Spec | Name | Methods of Prep. |
|---|---|---|---|---|
| 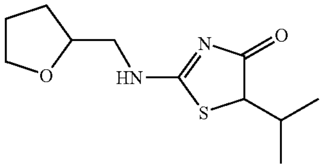 | 242.3 | 243 | 5-(1-methylethyl)-2-(((2R)-tetrahydro-2-furanylmethyl)amino)-1,3-thiazol-4(5H)-one | X |
| 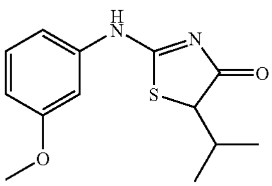 | 264.4 | 265 | 5-(1-methylethyl)-2-((3-(methyloxy)phenyl)amino)-1,3-thiazol-4(5H)-one | X |
| 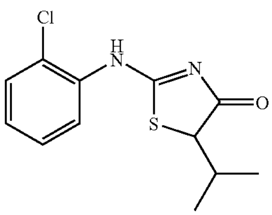 | 268.8 | 269 | 2-((2-chlorophenyl)amino)-5-(1-methylethyl)-1,3-thiazol-4(5H)-one | X |
| 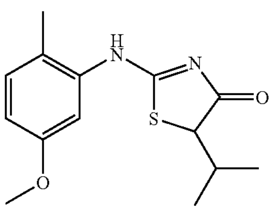 | 278.4 | 279 | 5-(1-methylethyl)-2-((2-methyl-5-(methyloxy)phenyl)amino)-1,3-thiazol-4(5H)-one | X |
| 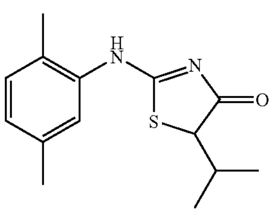 | 262.4 | 263 | 2-((2,5-dimethylphenyl)amino)-5-(1-methylethyl)-1,3-thiazol-4(5H)-one | X |
| 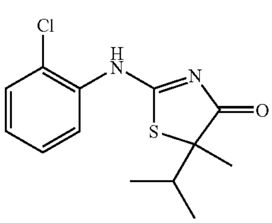 | 282.8 | 283 | 2-((2-chlorophenyl)amino)-5-methyl-5-(1-methylethyl)-1,3-thiazol-4(5H)-one | AA |
| 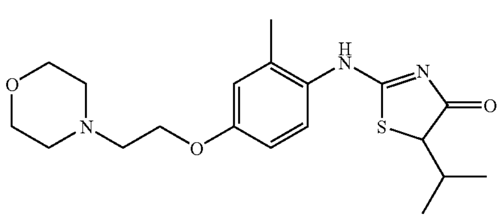 | 377.5 | 378 | 5-(1-methylethyl)-2-((2-methyl-5-((2-(4-morpholinyl)ethyl)oxy)phenyl)amino)-1,3-thiazol-4(5H)-one | T Z |

-continued

| Structure | Mol Wt. | Mass Spec | Name | Methods of Prep. |
|---|---|---|---|---|
| 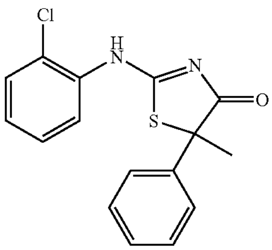 | 316.8 | 317 | 2-((2-chlorophenyl)amino)-5-methyl-5-phenyl-1,3-thiazol-4(5H)-one | X |
| 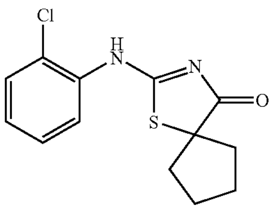 | 280.8 | 281 | 2-((2-chlorophenyl)amino)-1-thia-3-azaspiro[4.4]non-2-en-4-one | X |
| 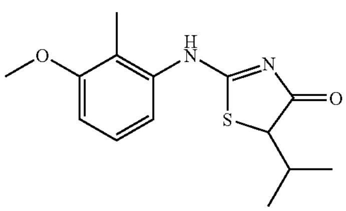 | 278.4 | 279 | 5-(1-methylethyl)-2-((2-methyl-3-(methyloxy)phenyl)amino)-1,3-thiazol-4(5H)-one | X |
| 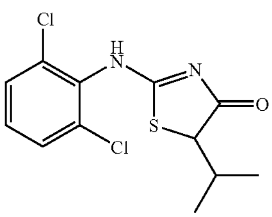 | 303.2 | 304 | 2-((2,6-dichlorophenyl)amino)-5-(1-methylethyl)-1,3-thiazol-4(5H)-one | X |
| 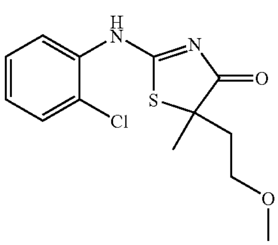 | 298.8 | 299 | 2-((2-chlorophenyl)amino)-5-methyl-5-(2-(methyloxy)ethyl)-1,3-thiazol-4(5H)-one | AA |
| 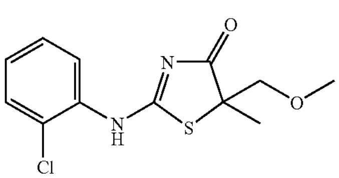 | 284.8 | 285 | 2-((2-chlorophenyl)amino)-5-methyl-5-((methyloxy)methyl)-1,3-thiazol-4(5H)-one | AA |
| 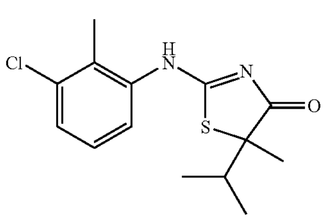 | 296.8 | 297 | 2-((3-chloro-2-methylphenyl)amino)-5-methyl)-5-(1-methylethyl)-1,3-thiazol-4(5H)-one | AA |

-continued

| Structure | Mol Wt. | Mass Spec | Name | Methods of Prep. |
|---|---|---|---|---|
| 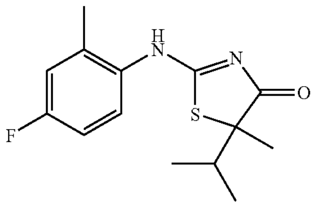 | 280.4 | — | 2-((4-fluoro-2-methylphenyl)amino)-5-methyl-5-(1-methylethyl)-1,3-thiazol-4(5H)-one | AA |
| 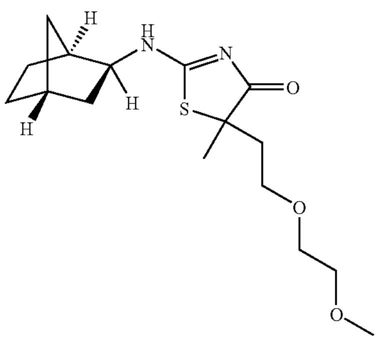 | 326.5 | — | 2-((1S,2S,4R)-bicyclo[2.2.1]heptan-2-ylamino)-5-(2-(2-methoxyethoxy)ethyl)-5-methylthiazol-4(5H)-one | AA |
| | 316.8 | 317 | (5S)-2-((2-chlorophenyl)amino)-5-methyl-5-phenyl-1,3-thiazol-4(5H)-one | X |
| | 316.8 | 317 | (5R)-2-((2-chlorophenyl)amino)-5-methyl-5-phenyl-1,3-thiazol-4(5H)-one | X |
| | 282.8 | 283 | (5R)-2-((2-chlorophenyl)amino)-5-methyl-5-(1-methylethyl)-1,3-thiazol-4(5H)-one | X |
| | 282.8 | 283 | 2-((2-chlorophenyl)amino)-5-methyl-5-(1-methylethyl)-1,3-thiazol-4(5H)-one | X |

-continued

| Structure | Mol Wt. | Mass Spec | Name | Methods of Prep. |
|---|---|---|---|---|
| 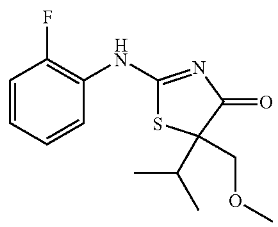 | 296.4 | 297 | 2-((2-fluorophenyl)amino)-5-(1-methylethyl)-5-((methyloxy)methyl)-1,3-thiazol-4(5H)-one | AA |
| 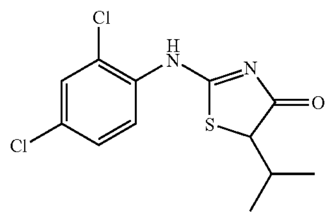 | 303.2 | 304 | 2-((2,4-dichlorophenyl)amino)-5-(1-methylethyl)-1,3-thiazol-4(5H)-one | X |
| | 280.4 | 281 | 2-((1R,2R,4S)-bicyclo[2.2.1]hept-2-ylamino)-8-oxa-1-thia-3-azaspiro[4.5]dec-2-en-4-one | EE |
| | 280.4 | 281 | 2-((1S,2S,4R)-bicyclo[2.2.1]hept-2-ylamino)-8-oxa-1-thia-3-azaspiro[4.5]dec-2-en-4-one | EE |
| 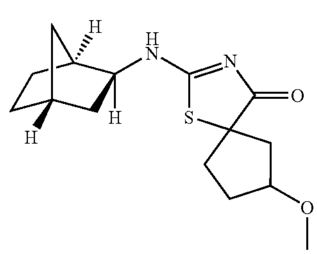 | 294.4 | 295 | 2-((1S,2S,4R)-bicyclo[2.2.1]hept-2-ylamino)-7-(methyloxy)-1-thia-3-azaspiro[4.4]non-2-en-4-one | EE |
| 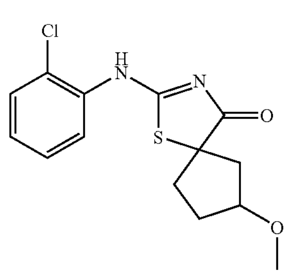 | 310.8 | 311 | 2-((2-chlorophenyl)amino)-7-(methyloxy)-1-thia-3-azaspiro[4.4]non-2-en-4-one | EE |

-continued

| Structure | Mol Wt. | Mass Spec | Name | Methods of Prep. |
|---|---|---|---|---|
| 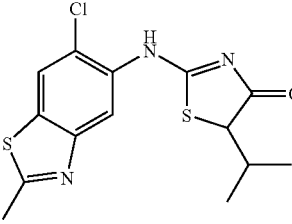 | 305.4 | 306 | 2-((2-methyl-1,3-benzothiazol-5-yl)amino)-5-(1-methylethyl)-1,3-thiazol-4(5H)-one | X |
| 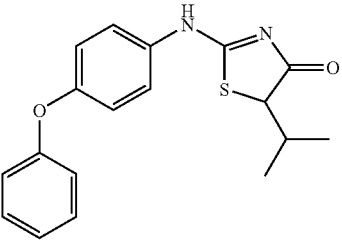 | 326.4 | 327 | 5-(1-methylethyl)-2-((4-(phenyloxy)phenyl)amino)-1,3-thiazol-4(5H)-one | X |
| 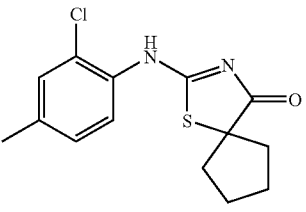 | 294.8 | 295 | 2-((2-chloro-4-methylphenyl)amino)-1-thia-3-azaspiro[4.4]non-2-en-4-one | X |
| 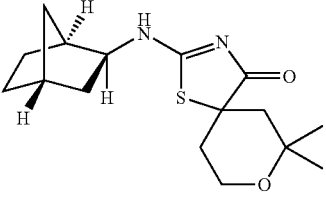 | 308.4 | 309 | 2-((1S,2S,4R)-bicyclo[2.2.1]hept-2-ylamino)-7,7-dimethyl-8-oxa-1-thia-3-azaspiro[4.5]dec-2-en-4-one | KK |
| 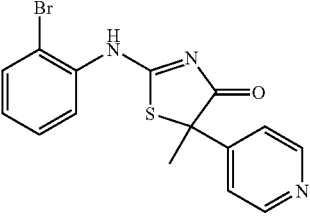 | 362.3 | 363 | 2-((2-bromophenyl)amino)-5-methyl-5-(4-pyridinyl)-1,3-thiazol-4(5H)-one | M X |
| 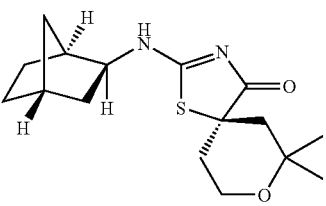 | 308.4 | 309 | (5R)-2-((1S,2S,4R)-bicyclo[2.2.1]hept-2-ylamino)-7,7-dimethyl-8-oxa-1-thia-3-azaspiro[4.5]dec-2-en-4-one | KK |

-continued

| Structure | Mol Wt. | Mass Spec | Name | Methods of Prep. |
|---|---|---|---|---|
| 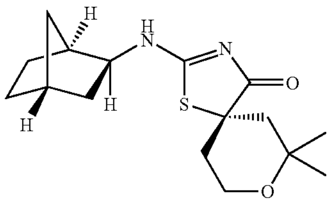 | 308.4 | 309 | (5S)-2-((1S,2S,4R)-bicyclo[2.2.1]hept-2-ylamino)-7,7-dimethyl-8-oxa-1-thia-3-azaspiro[4.5]dec-2-en-4-one | KK |
| 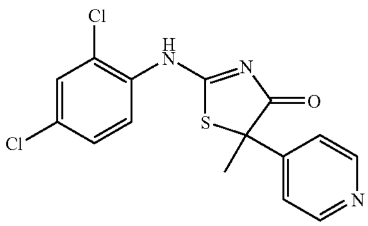 | 352.2 | 353 | 2-((2,4-dichlorophenyl)amino)-5-methyl-5-(4-pyridinyl)-1,3-thiazol-4(5H)-one | M X |
| 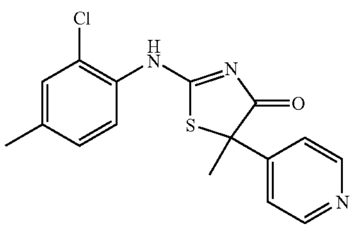 | 331.8 | 332 | 2-((2-chloro-4-methylphenyl)amino)-5-methyl-5-(4-pyridinyl)-1,3-thiazol-4(5H)-one | M X |
| 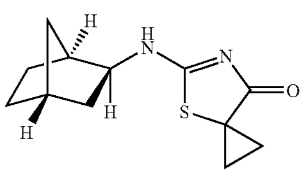 | 236.3 | 237 | 5-((1S,2S,4R)-bicyclo[2.2.1]hept-2-ylamino)-4-thia-6-azaspiro[2.4]hept-5-en-7-one | AA |
| 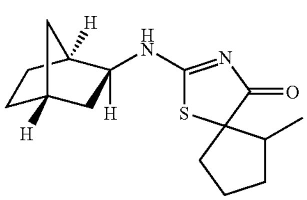 | 278.4 | 279 | 2-((1S,2S,4R)-bicyclo[2.2.1]hept-2-ylamino)-6-methyl-1-thia-3-azaspiro[4.4]non-2-en-4-one | EE |
| 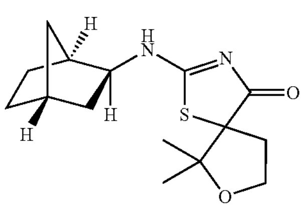 | 294.4 | 295 | 2-((1S,2S,4R)-bicyclo[2.2.1]hept-2-ylamino)-6,6-dimethyl-7-oxa-1-thia-3-azaspiro[4.4]non-2-en-4-one | NN |
| 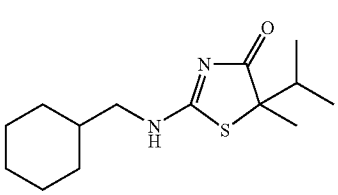 | 282.5 | 283 | 2-((S)-1-cyclohexylethylamino)-5-isopropyl-5-methylthiazol-4(5H)-one | AA |

-continued

| Structure | Mol Wt. | Mass Spec | Name | Methods of Prep. |
|---|---|---|---|---|
| 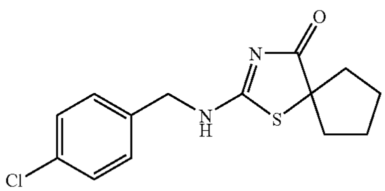 | 294.8 | 295 | 2-(((4-chlorophenyl)methyl)amino)-1-thia-3-azaspiro[4.4]non-2-en-4-one | X |
| 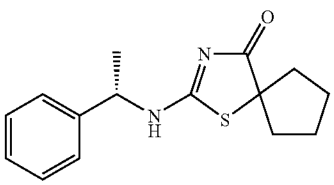 | 274.4 | 275 | 2-(((1S)-1-phenylethyl)amino)-1-thia-3-azaspiro[4.4]non-2-en-4-one | X |
| 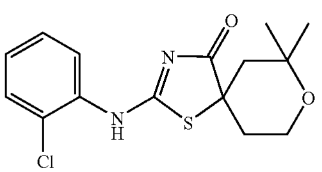 | 324.8 | 325 | 2-((2-chlorophenyl)amino)-7,7-dimethyl-8-oxa-1-thia-3-azaspiro[4.5]dec-2-en-4-one | KK |
| 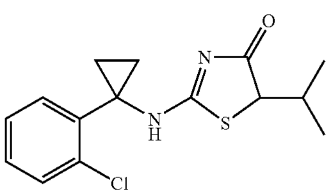 | 308.8 | 309 | 2-((1-(2-chlorophenyl)cyclopropyl)amino)-5-(1-methylethyl)-1,3-thiazol-4(5H)-one | U O X |
| 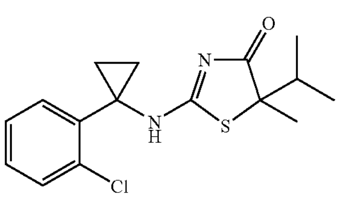 | 322.9 | 323 | 2-((1-(2-chlorophenyl)cyclopropyl)amino)-5-methyl-5-(1-methylethyl)-1,3-thiazol-4(5H)one | AA |
| 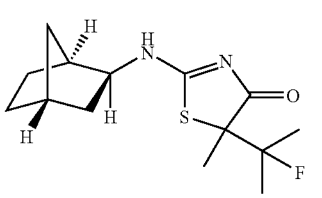 | 284.4 | 285 | 2-(((1S,2S,4R)-bicyclo[2.2.1]hept-2-ylamino)-5-(1-fluoro-1-methylethyl)-5-methyl-1,3-thiazol-4(5H)-one | FF GG |
| 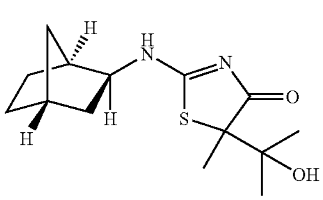 | 282.4 | 283 | 2-(((1S,2S,4R)-bicyclo[2.2.1]hept-2-ylamino)-5-(1-hydroxy-1-methylethyl)-5-methyl-1,3-thiazol-4(5H)-one | FF |

-continued

| Structure | Mol Wt. | Mass Spec | Name | Methods of Prep. |
|---|---|---|---|---|
| 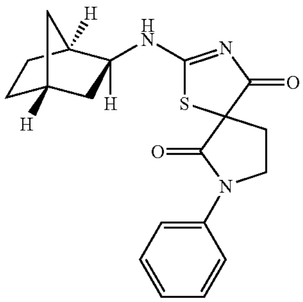 | 355.5 | 356 | 2-((1S,2S,4R)-bicyclo[2.2.1]hept-2-ylamino)-7-phenyl-1-thia-3,7-diazaspiro[4.4]non-2-ene-4,6-dione | X |
| 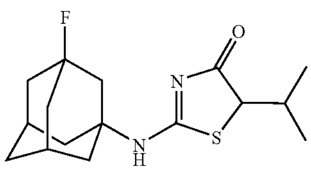 | 310.4 | 311 | 2-((3-fluorotricyclo[3.3.1.1~3,7~]dec-1-yl)amino)-5-(1-methylethyl)-1,3-thiazol-4(5H)-one | GG |
| | 324.4 | 325 | 2-((3-fluorotricyclo[3.3.1.1~3,7~]dec-1-yl)amino)-5-methyl-5-(1-methylethyl)-1,3-thiazol-4(5H)-one | GG |
| 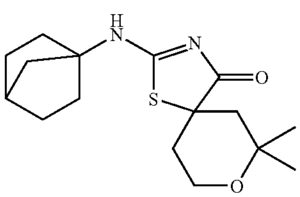 | 308.4 | 309 | 2-(bicyclo[2.2.1]hept-1-ylamino)-7,7-dimethyl-8-oxa-1-thia-3-azaspiro[4.5]dec-2-en-4-one | KK |
| | 284.4 | 285 | (5S)-2-((1S,2S,4R)-bicyclo[2.2.1]hept-2-ylamino)-5-(1-fluoro-1-methylethyl)-5-methyl-1,3-thiazol-4(5H)-one | FF GG |
| | 284.4 | 285 | (5R)-2-((1S,2S,4R)-bicyclo[2.2.1]hept-2-ylamino)-5-(1-fluoro-1-methylethyl)-5-methyl-1,3-thiazol-4(5H)-one | FF GG |
| | 324.4 | 325 | 2-((1S,2S,4R)-bicyclo[2.2.1]hept-2-ylamino)-5-(4-hydroxytetrahydro-2H-pyran-4-yl)-5-methyl-1,3-thiazol-4(5H)-one | FF |

| Structure | Mol Wt. | Mass Spec | Name | Methods of Prep. |
|---|---|---|---|---|
| 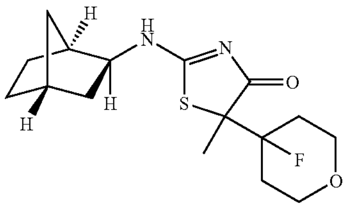 | 326.4 | 327 | 2-((1S,2S,4R)-bicyclo[2.2.1]hept-2-ylamino)-5-(4-fluorotetrahydro-2H-pyran-4-yl)-5-methyl-1,3-thhiazol-4(5H)-one | GG |
| 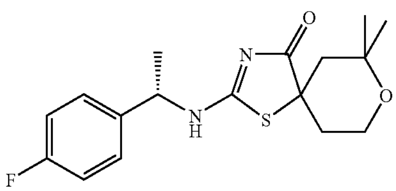 | 336.4 | 337 | 2-(((1S)-1-(4-fluorophenyl)ethyl)amino)-7,7-dimethyl-8-oxa-1-thia-3-azaspiro[4.5]dec-2-en-4-one | KK |
| 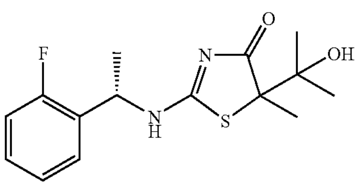 | 310.4 | 311 | 2-(((1S)-1-(2-fluorophenyl)ethyl)amino)-5-(1-hydroxcy-1-methylethyl)-5-methyl-1,3-thiazol-4(5H)-one | FF |
| 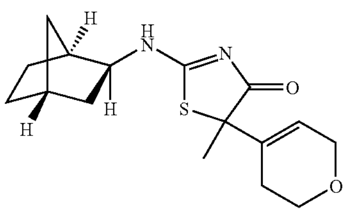 | 306.4 | 307 | 2-((1S,2S,4R)-bicyclo[2.2.1]hept-2-ylamino)-5-(3,6-dihydro-2H-pyran-4-yl)-5-methyl-1,3-thiazol-4(5H)-one | GG |
| 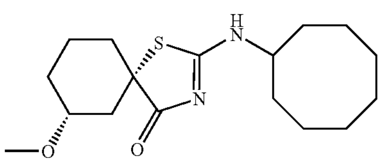 | 324.5 | 325 | (5S,7R)-2-(cyclooctylamino)-7-(methyloxy)-1-thia-3-azaspiro[4.5]dec-2-en-4-one | O L X |

The following compounds are encompassed by the present invention and are prepared by one of the methodologies described herein:

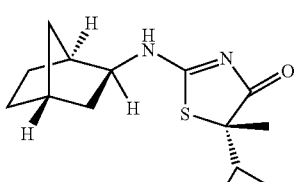

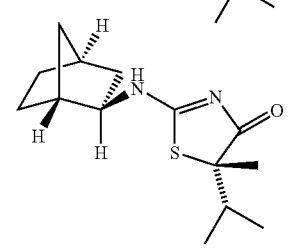

-continued

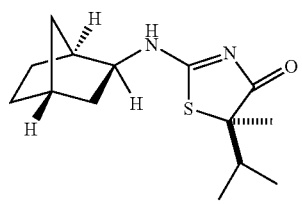

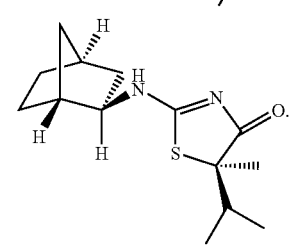

| MOLSTRUCTURE |
|---|
| 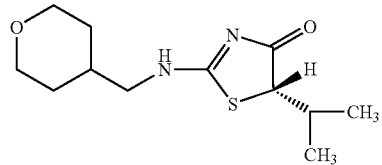 |
| 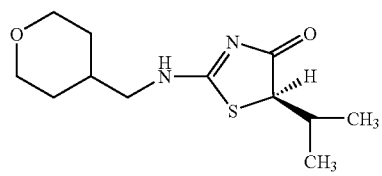 |
| 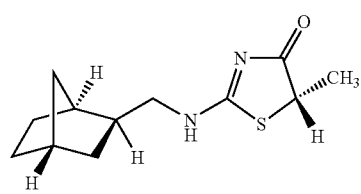 |
| 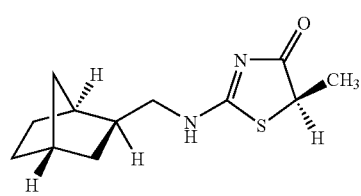 |
| 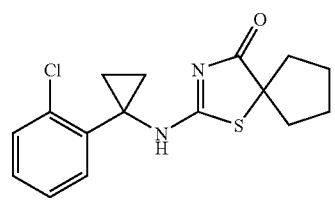 |
| 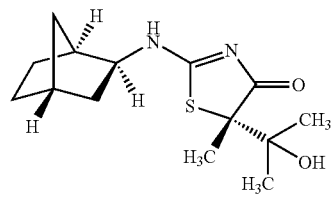 |
| 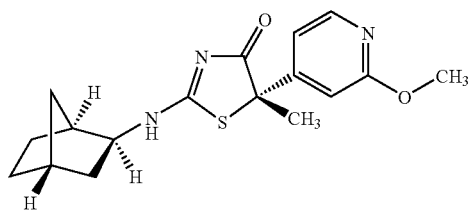 |
-continued
| MOLSTRUCTURE |
|---|
| 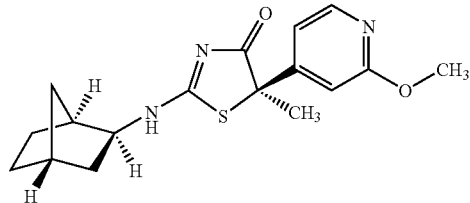 |
| 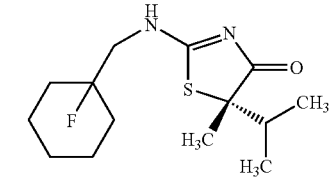 |
| 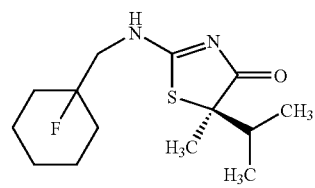 |
| 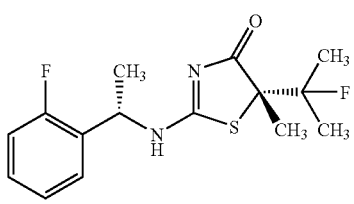 |
| 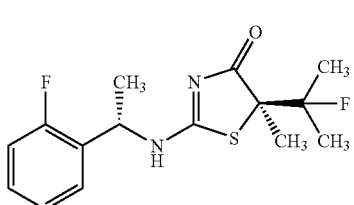 |
| 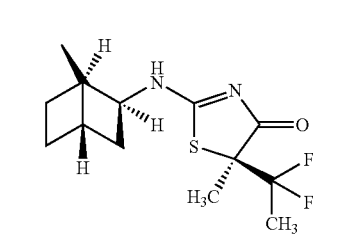 |
| 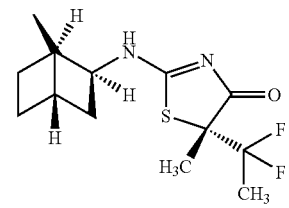 |

-continued
| MOLSTRUCTURE |
|---|
| 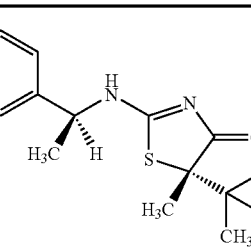 |
| 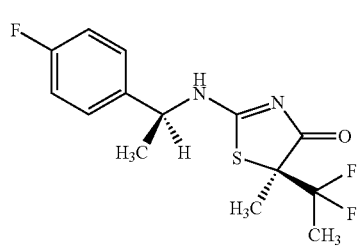 |
| 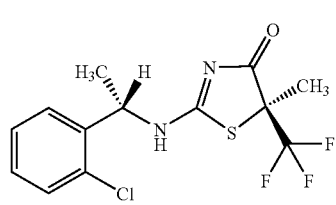 |
| 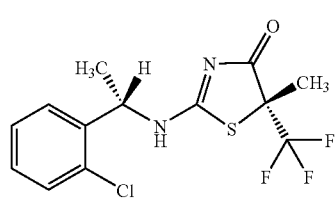 |
| 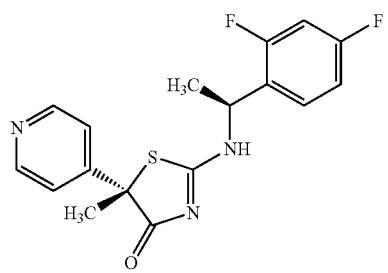 |
| 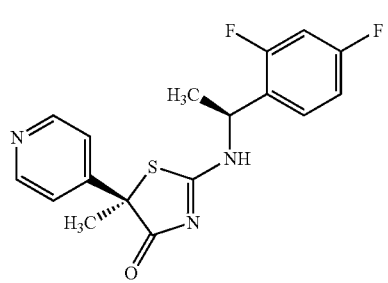 |
-continued
| MOLSTRUCTURE |
|---|
| 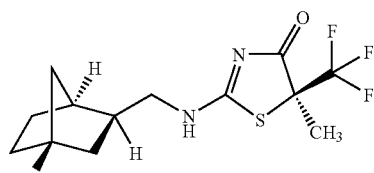 |
| 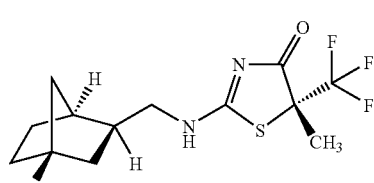 |
| 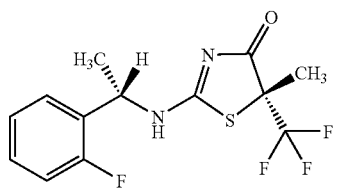 |
| 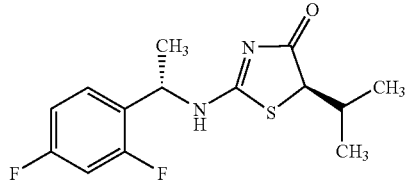 |
| 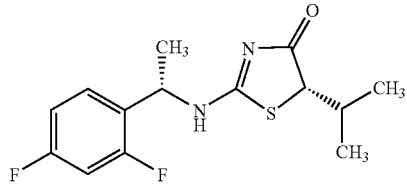 |
| 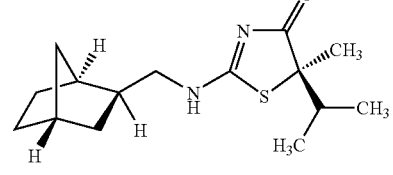 |
| 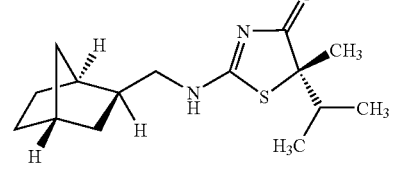 |
| 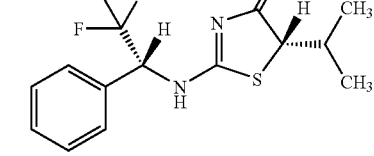 |

-continued
| MOLSTRUCTURE |
|---|
| 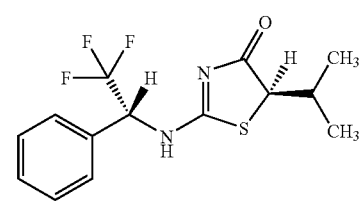 |
| 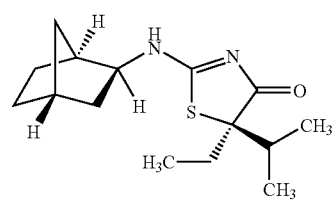 |
| 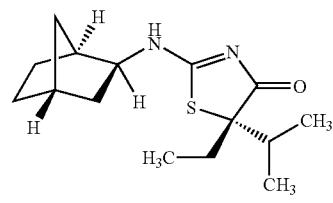 |
| 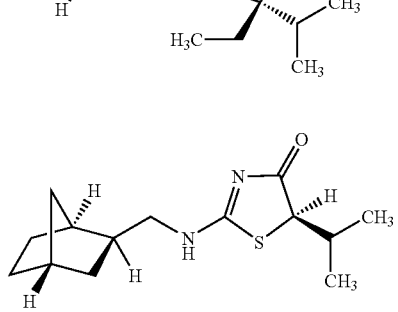 |
| 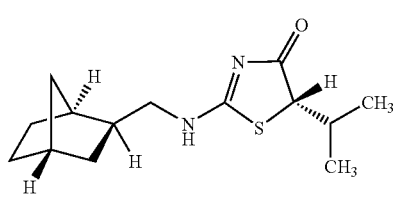 |
| 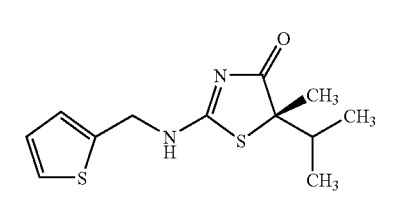 |
| 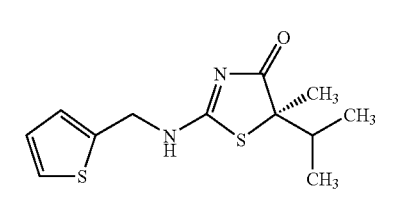 |
-continued
| MOLSTRUCTURE |
|---|
| 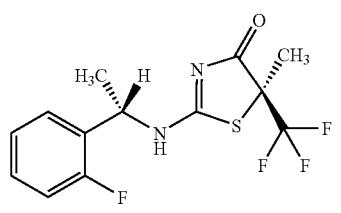 |
| 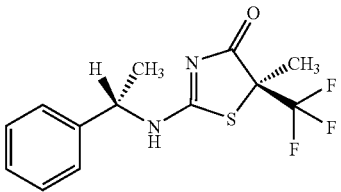 |
| 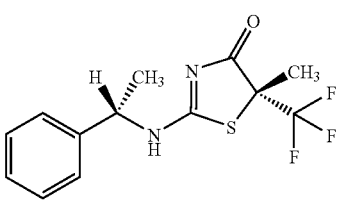 |
| 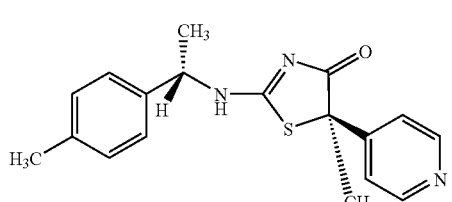 |
| 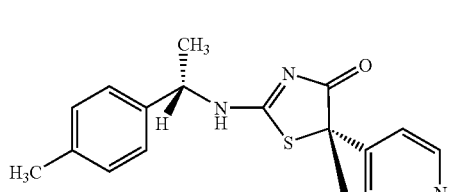 |
| 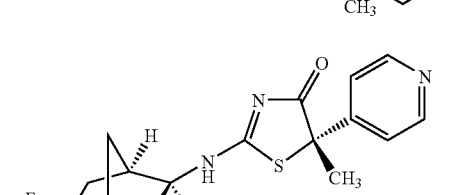 |
| 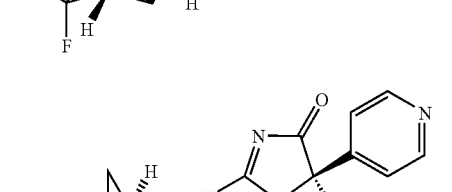 |

| 271 | 272 |
|---|---|
| -continued | -continued |
| MOLSTRUCTURE | MOLSTRUCTURE |
| 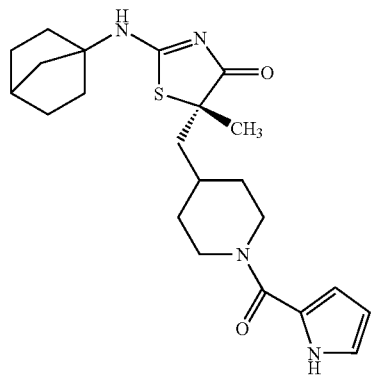 | 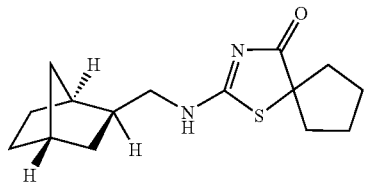 |
| 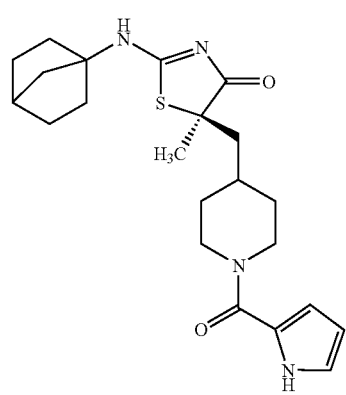 | 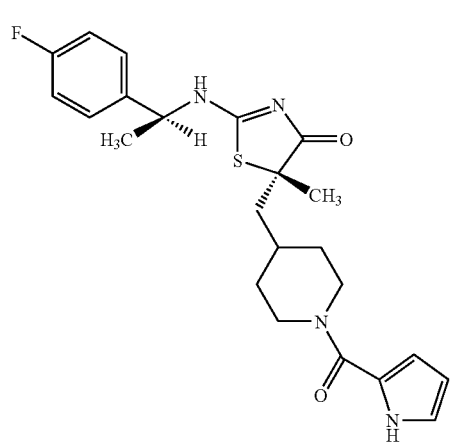 |
| 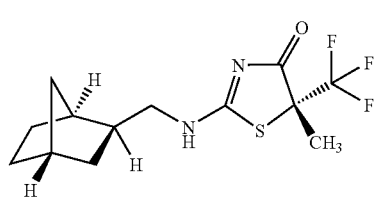 | 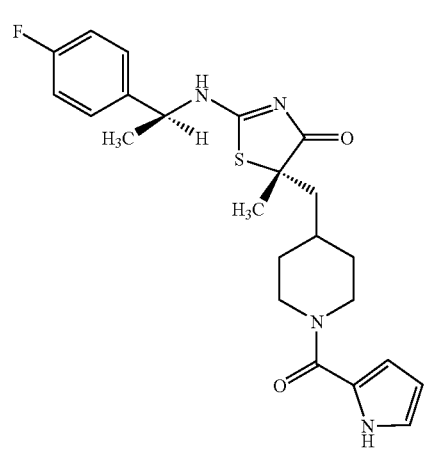 |
| 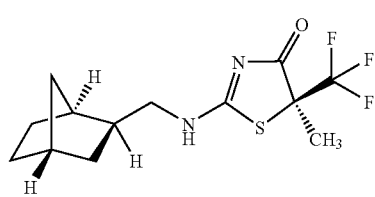 | 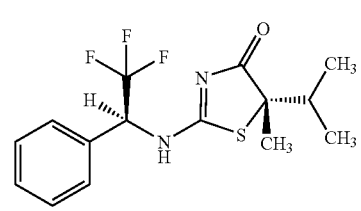 |
| 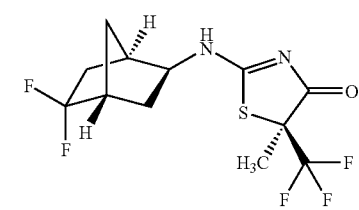 | 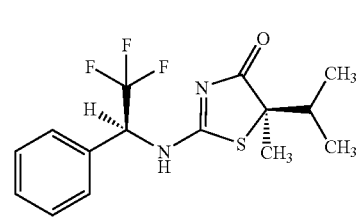 |
| 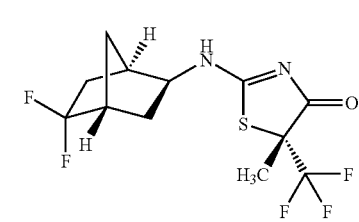 | |

| 273 | 274 |
|---|---|
| -continued | -continued |
| MOLSTRUCTURE | MOLSTRUCTURE |
| 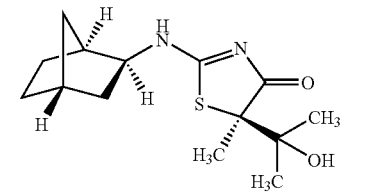 | 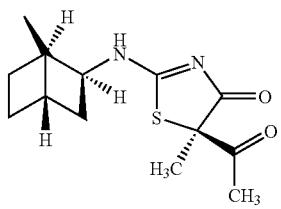 Chiral |
| 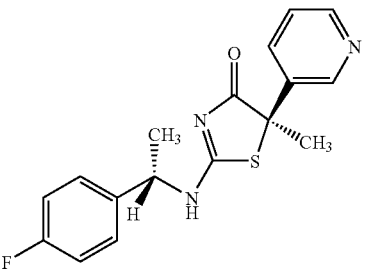 | 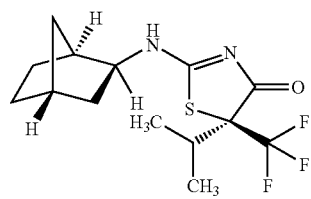 |
| 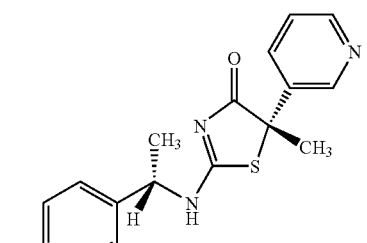 | 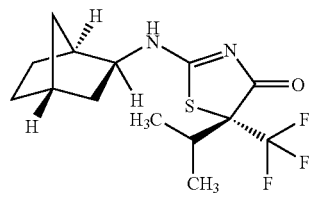 |
| 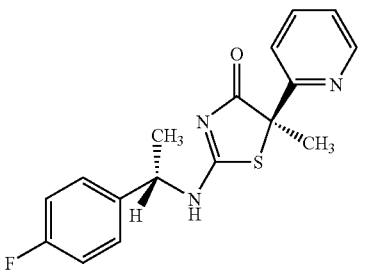 | 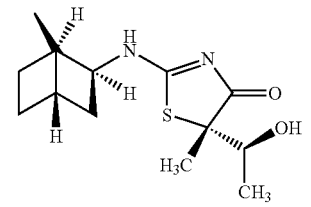 |
| 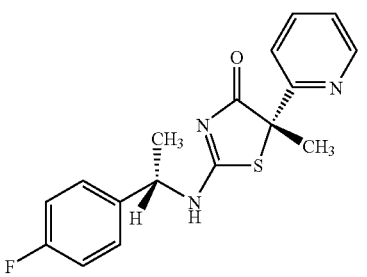 | 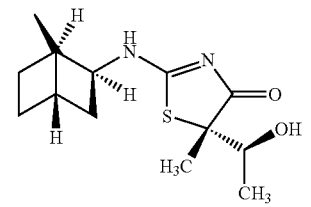 |
| 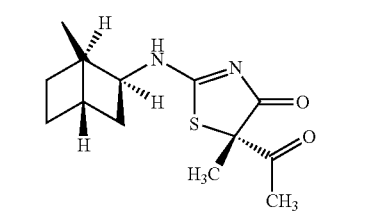 | 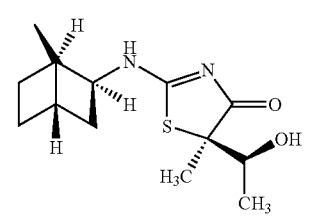 |

-continued
MOLSTRUCTURE
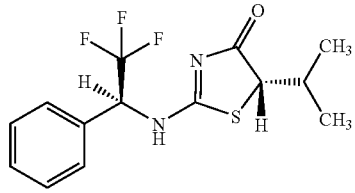
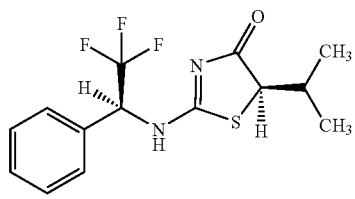
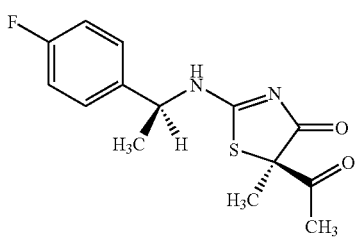
Chiral
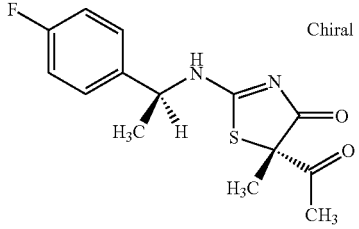
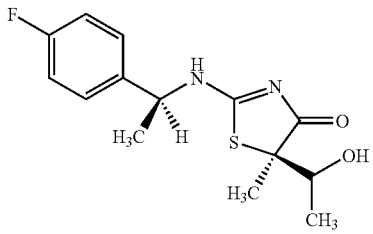
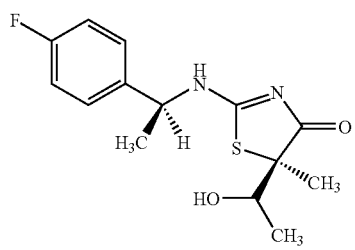
-continued
MOLSTRUCTURE
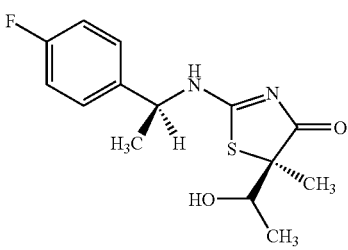
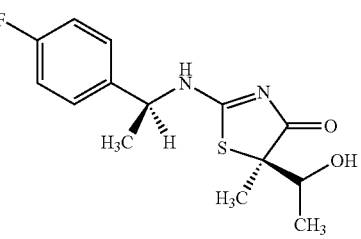
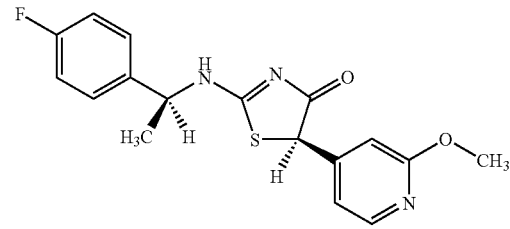
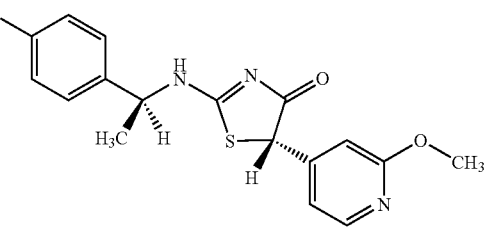
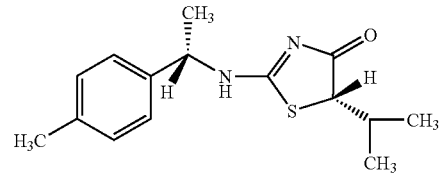
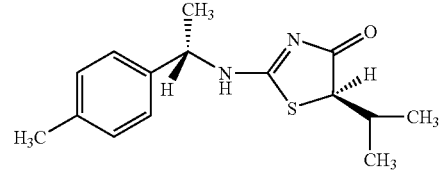
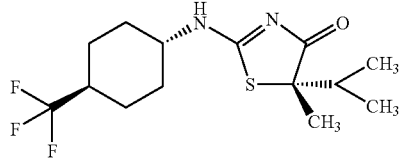

-continued
| MOLSTRUCTURE |
|---|
| 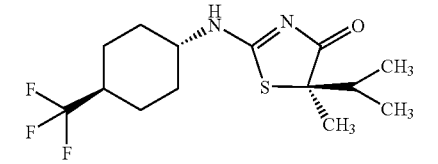 |
| 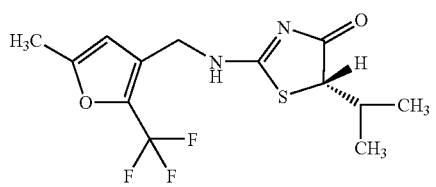 |
| 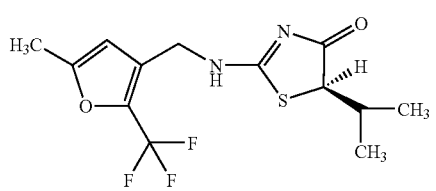 |
| 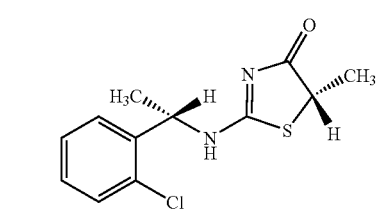 |
| 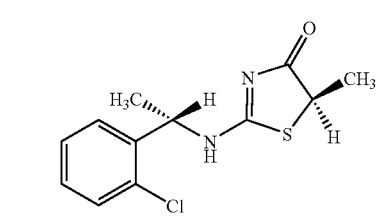 |
| 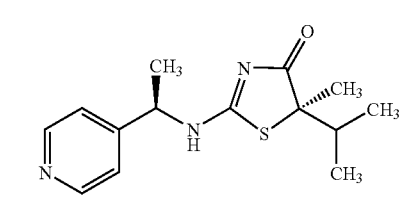 |
| 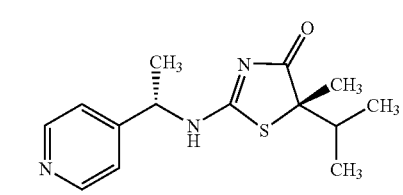 |
| 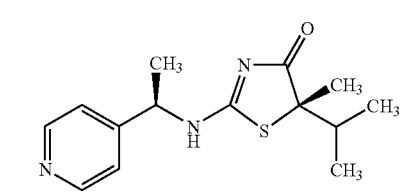 |
-continued
| MOLSTRUCTURE |
|---|
| 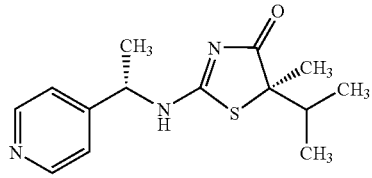 |
| 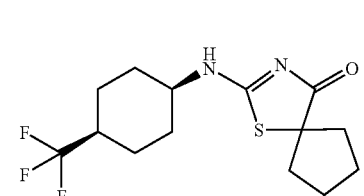 |
| 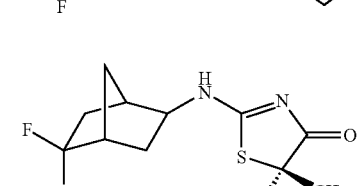 |
| 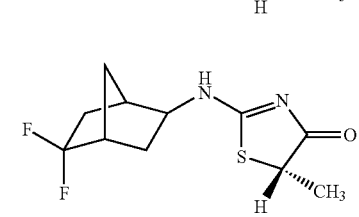 |
| 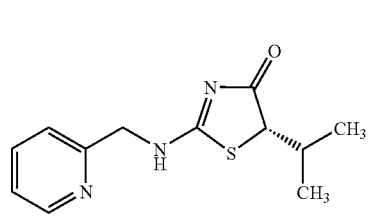 |
| 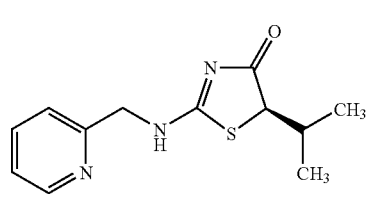 |
| 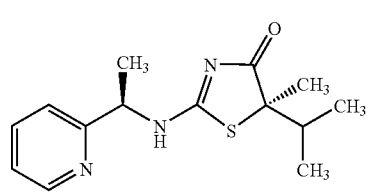 |
| 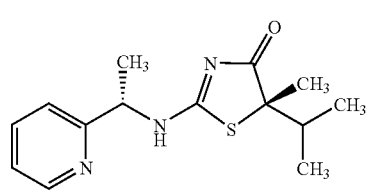 |

| MOLSTRUCTURE |
|---|
| 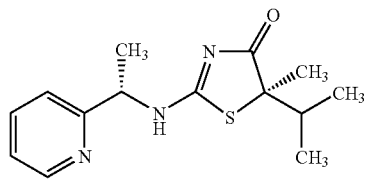 |
| 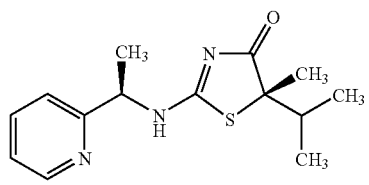 |
| 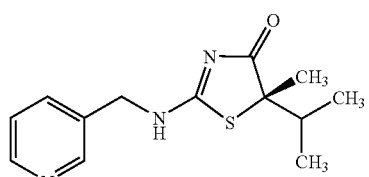 |
| 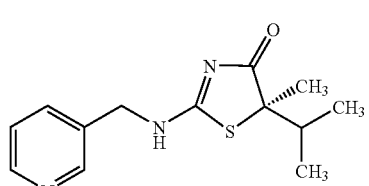 |
| 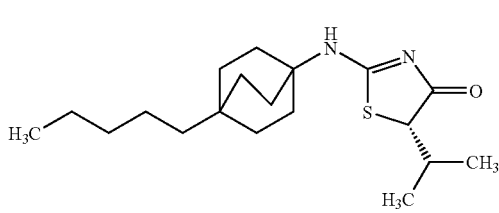 |
| 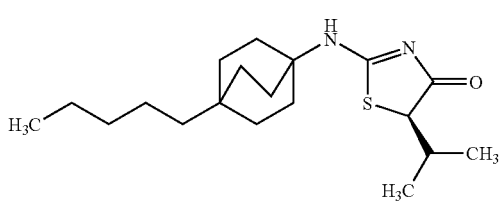 |
| 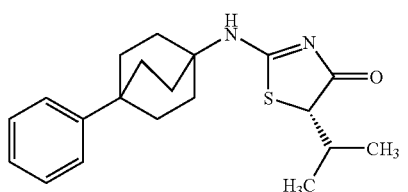 |
| 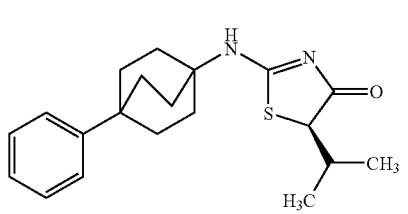 |

| MOLSTRUCTURE |
|---|
| 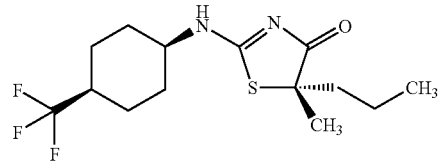 |
| 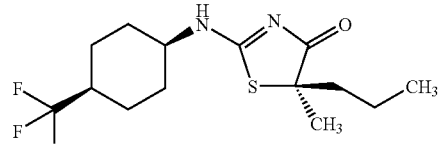 |

General Methodologies QQ-YY

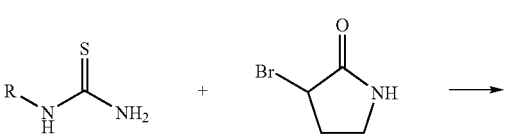

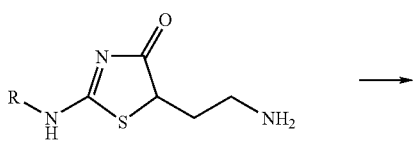

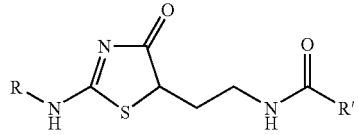

1 eq. of 3-bromopyrrolidin-2-one (*J. Med. Chem.* 1987, 30, 1995-1998. H. Ikuta, H. Shirota, S. Kobayashi, Y. Yamagashi, K. Yamada, I. Yamatsu, K. Katayama) and 1.0 eq. of the appropriate thiourea were dissolved in acetone and heated to reflux for 8 h. The reaction mixture was cooled to RT, NaHCO$_3$ (sat. solution) was added and the aqueous phase extracted with DCM. The organic phase was separated and concentrated in vacuo to give the crude product. The obtained crude product was dissolved in pyridine and a few drops of DMF were added followed by the appropriate benzoyl chloride (3.0 eq.) and the reaction mixture was shaken at RT. 10% HCl was added and the mixture extracted with DCM. The organic phase was concentrated in vaccum. Purification was performed using preparative HPLC.

Example 161

N-{2-[2-(bicyclo[2.2.1]hept-5-en-2-ylamino)-4-oxo-4,5-dihydro-1,3-thiazol-5-yl]ethyl}-6-chloronicotinamide

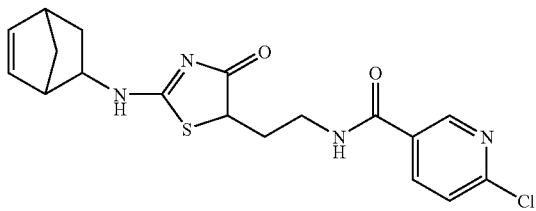

5-(2-aminoethyl)-2-(bicyclo[2.2.1]hept-5-en-2-ylamino)-1,3-thiazol-4(5H)-one (0.050 g, 0.199 mmol) was suspended in MeCN (1 ml). 6-chloronicotinoyl chloride (0.140 g, 0.796 mmol) dissolved in MeCN (1 ml) was added and the reaction mixture was shaken at room temperature for 18 h. Solvents were removed in vacuo. Purification was performed using preparative HPLC (System A, 20-40% MeCN over 5 min).

$^1$H NMR (500 MHz, Solvent) 1.44-1.79 (m, 5 H) 2.12-2.28 (m, 1 H) 2.40-2.49 (m, 1 H) 2.84-3.02 (m, 2 H) 3.56-3.65 (m, 2 H) 3.76 (d, J=7.54 Hz, 1 H) 4.37-4.47 (m, 1 H) 6.02-6.11 (m, 1 H) 6.19-6.24 (m, 1 H) 7.52-7.56 (m, 1 H) 8.15-8.20 (m, 1 H).

HPLC-MS: 93%, $R_T$=1.74 min (System A, 10-97% MeCN over 3 min), 92%, $R_T$=1.60 min (System B, 10-97% MeCN over 3 min)

MS (ESI+) for $C_{18}H_{19}N_4O_2S$ m/z 391 (M+H)$^+$

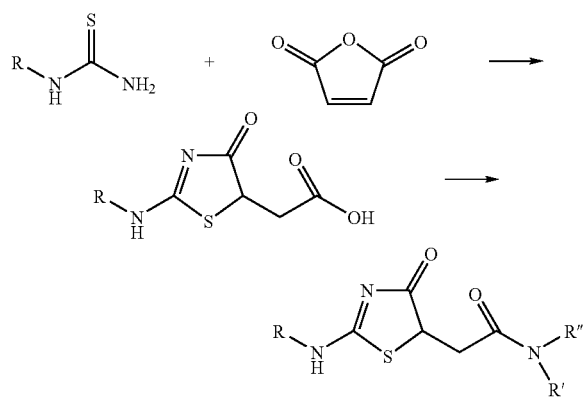

1.0 eq. of the appropriate thiourea and maleic anhydride (1.0 eq.) were heated to reflux in acetone for 5 h, yielding a white emulsion. Evaporation in vacuo afforded a white solid. The product was triturated with DCM, collected on a filter and air-dried giving the carboxylic acid product as a white powder.

The carboxylic acid (1.0 eq). and 2-chloro-1-methylpyridinium iodide (1.2 eq.), or similar coupling agent, were mixed in DCM for 10 minutes before the amine (1.0 eq.) was added followed by Et$_3$N (1.5 eq.). The reaction mixture was stirred at RT for 16 h. The reaction mixture was poured onto a Hydromatrix column (pretreated with 1 M HCl) and the crude product was eluted with DCM. The obtained crude product was purified by reverse phase.

Example 162

2-{2-[(cyclohexylmethyl)amino]-4-oxo-4,5-dihydro-1,3-thiazol-5-yl}-N-(cyclopropylmethyl)-N-propylacetamide

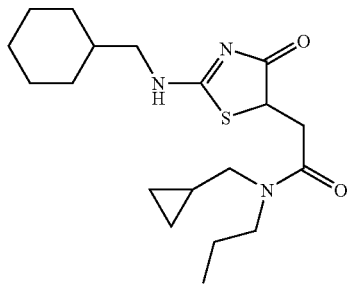

Cyclohexylmethyl thiourea (0.85 g, 4,94 mmol) and maleic anhydride (4.8 g, 4.94 mmol) were refluxed over night at 110° C. in acetic acid. The reaction was concentrated and triturated with EtOAc to give the product as a pure off-white solid. MS m/z 271 (M+H)$^+$. To a suspension of {2-[(cyclohexylmethyl)amino]-4-oxo-4,5-dihydro-1,3-thiazol-5-yl}acetic acid in DCM 5 ml was added thionyl chloride 1.5 eq and the reaction stirred for 30 minutes. The secondary amine (3 eq) was added and the reaction stirred overnight. Concentration and purification by reverse phase chromatography yielded the desired product.

$^1$H NMR (400 MHz, CHLOROFORM-D) δ ppm 0.26 (m, J=3.8, 1.10 Hz, 2 H) 0.54 (m, J=8.1, 1.22 Hz, 1 H) 0.65 (m, J=7.3 Hz, 1 H) 0.93 (m, 6 H) 1.25 (m, 3 H) 1.71 (m, 8 H) 2.82 (m, J=12.2 Hz, 1 H) 3.11 (m, 1 H) 3.23 (m, J=6.5 Hz, 2 H) 3.29 (m, 2 H) 3.42 (m, 1 H) 3.54 (m, 1 H) 4.44 (m, J=10.4, 1.7 Hz, 1 H) MS m/z 366 (M+H)$^+$ HPLC 100% $R_T$=3,15 min (System A. 10-97% MeCN over 3 min), 100% $R_T$=1,60 min (System B. 2-95% MeCN over 2 min).

Method SS

The synthesis of oxazolone analogues was carried out using the procedure detailed in the scheme below.

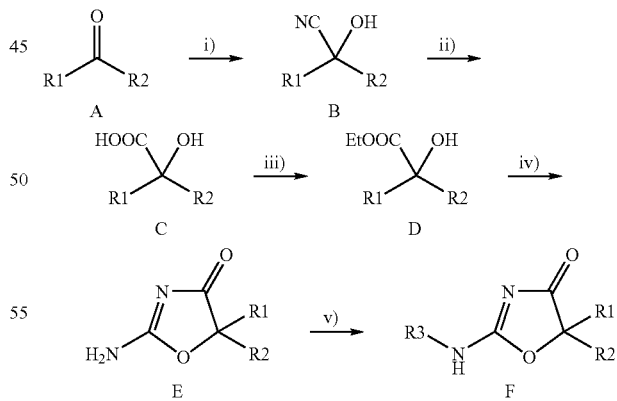

The oxazolones (F) were prepared according to the reaction scheme above from commercially available ketones (A), α-hydroxy acids (C), or α-hydroxy esters (D).

i) To a mixture of ketone (A) (1 eq) and KCN (1.1 eq) in H$_2$O at 0° C. was added 40% H$_2$SO$_4$ over 40 min. After stirring the reaction for an additional 1 h at ambient temperature, diethyl ether and H$_2$O were added. The phases were separated, and the aqueous layer was extracted with diethyl ether. The combined organic phases were washed with brine, dried over MgSO₄, and concentrated in vacuo to yield cyanohydrine (B).

ii) The cyanohydrine (B) was dissolved in concentrated HCl and the mixture was stirred under heating for 8-48 h. The solvent was evaporated, and the residue was dried in vacuo to give the crude acid (C).

iii) To a solution of the α-hydroxy acid (C) in ethanol was added acid catalyst, and the mixture was stirred under reflux for 1-3 days. The solvent was removed to give α-hydroxy ester (D).

iv) A mixture of α-hydroxy ester (D) (1 eq) and guanidine (1-3 eq) in ethanol was stirred under reflux overnight. The solvent was removed, and the residue was purified by recrystalization from water/ethyl acetate (alternatively silica gel flash chromatography) to give 2-aminooxazolone (E).

v) A mixture of 2-aminooxazolone (E) (1 eq) and amine (2.5-3 eq) in 99.5% ethanol was heated in microwave oven for 20-120 min at 160-180° C. The solvent was removed, and the residue was purified by reverse-phase preparative HPLC to give oxazolone (F).

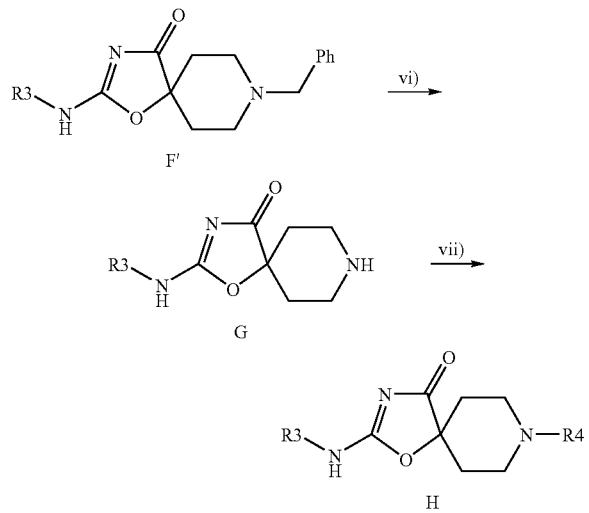

Spiropiperidines (H) were obtained from F' (synthesized from the corresponding ketone A) according to the scheme above.

vi) To a solution of the benzyl protected intermediate (F') in 2-methoxyethanol was added catalytic amounts of 5% Pd/C and the mixture was exposed to H₂ (50-60 psi) for 5-24 h. Celite was added to the reaction mixture, and after filtration and removal of the solvent crude spiropiperidine G was obtained.

vii) To a solution of spiropiperidine G (1 eq) and aldehyde (1 eq) in dichloroethane was added sodium triacetoxyborohydride (1.4 eq) and the reaction mixture was stirred at 25-50° C. overnight. The material was purified by reverse-phase preparative HPLC to give the product H.

Examples 163

2-Hydroxy-2,3-dimethylbutanenitrile

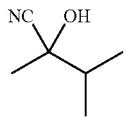

To mixture of 3-methylbutan-2-one (4.71 g, 54.7 mmol) and KCN (3.92 g, 60.2 mmol) in H₂O (10 mL) was dropwise added 40% H₂SO₄ (10 mL) over 40 min. The temperature was raised to ambient, and after stirring the reaction for 1 h, diethyl ether (25 mL) and H₂O (15 mL) were added. The aqueous layer was extracted with diethyl ether (25 mL), and the combined organic phases were washed with brine (10 mL) and dried over MgSO₄. Evaporation of the solvent yielded the product as a colorless liquid.

Example 164

2-Hydroxy-2,3-dimethylbutanoic acid

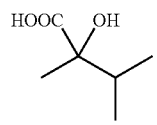

A solution of 2-hydroxy-2,3-dimethylbutanenitrile (4.71 g, 54.7 mmol) in concentrated HCl was stirred at 75° C. for 5 h and then under reflux for 8 h. The solvent was removed to give the crude title compound as an off-white solid.

Example 165

Ethyl 2-hydroxy-2,3-dimethylbutanoate

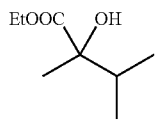

To a solution of 2-hydroxy-2,3-dimethylbutanoic acid (5.53 g, 41.8 mmol) in 99.5% ethanol (200 mL) was added 2 M HCl in diethyl ether (8 mL) and the mixture was stirred under reflux for 3 days. The solvent was carefully removed to give the crude α-hydroxy ester as a pale yellow liquid.

Example 166

2-Amino-5-isopropyl-5-methyl-1,3-oxazol-4(5H)-one

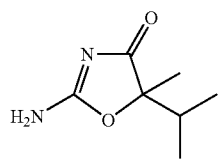

A mixture of ethyl 2-hydroxy-2,3-dimethylbutanoate (2.92 g, 18.2 mmol), guanidine hydrochloride (1.74 g, 18.2 mmol), and K₂CO₃ (2.52 g, 18.2 mmol) in 99.5% ethanol (40 mL) was stirred under reflux for 20 h. The solvent was removed, and the residue was purified by silica gel flash chromatography (ethyl acetate/methanol 9:1) to give the product as a white solid.

Example 167

2-(Cyclooctylamino)-5-isopropyl-5-methyl-1,3-oxazol-4(5H)-one

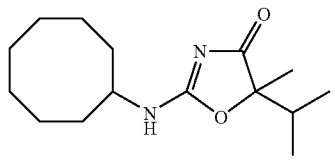

A solution of 2-amino-5-isopropyl-5-methyl-1,3-oxazol-4(5H)-one (55.7 mg, 0.357 mmol) and cyclooctylamine (147 µL, 1.07 mmol) in 99.5% ethanol (1 mL) was heated in microwave oven in a sealed tube for 40 min at 180° C. The solvent was removed, and the residue was purified by preparative reverse-phase HPLC chromatography to yield the product as a white solid.

HPLC 100%, $R_T$=2.56 (System A, 10-97% MeCN over 3 min), 100%, $R_T$=1.47 min (System B, 2-95% MeCN over 2 min).

$^1$H NMR (400 MHz, DMSO-$d_6$) δ 0.77-0.79 (m, 3 H), 0.90-0.93 (m, 3 H), 1.29 (s, 2.1 H, major rotamer), 1.31 (s, 0.9 H, minor rotamer), 1.40-1.80 (m, 14 H), 1.84-1.94 (m, 1 H), 3.67-3.77 (m, 1 H), 8.67 (d, J=7.9 Hz, 0.7 H, major isomer), 8.95 (d, J=7.9 Hz, 0.3 H, minor isomer).

MS (ESI+) for $C_{15}H_{26}N_2O_2$ m/z 267 (M+H)$^+$.

Method TT

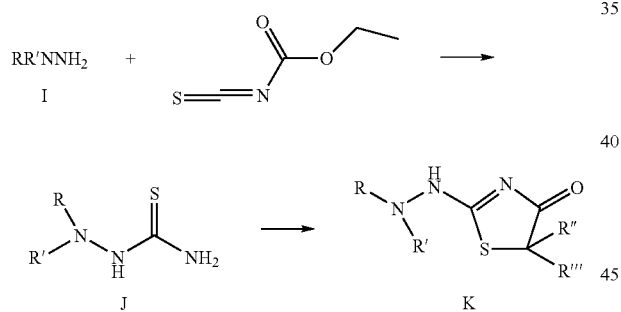

R and R' are bivalent alkylene and form a 3-8 membered ring with the nitrogen to which they are attached.

The thiazalones K were prepared according to the reaction scheme above from commercially available hydrazines. To a mixture of hydrazine I (1 eq) in DCM (5 mL/mmol amine) was added ethoxycarbonylisocyanate (1.1 eq) and the mixture stirred for 1 h at ambient temperature, followed by addition of 5M aq NaOH (5 mL/mmol amine) and heating for 1-2 h at 65° C. The cooled solution was extracted twice with DCM, then the combined organic layers washed consecutively with saturated aq NaHCO$_3$, water and brine, and finally concentrated to give the thiourea J. Thiourea J (1 eq) was reacted with the appropriate α-bromoester (1 eq) in the presence of diisopropylethylamine (1.1 eq) in EtOH (5 mL/mmol) in the microwave oven for 1-2 h 150-155° C., or by thermal heating at 95-140° C. for several days in dioxane (1 mL/mmol) in the absence of base. Concentration followed by chromatographic purification gave the thiazalone K.

Example 168

2-(Azepan-1-ylamino)-5-isopropyl-1,3-thiazol-4(5H)-one

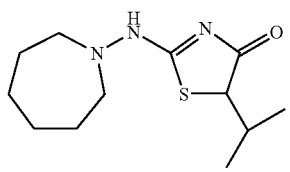

N-(Homopiperidine)thiourea was prepared by stirring a mixture of aminopiperidine (1.0 g, 8.8 mmol) and ethoxycarbonylisocyanate (1.1 mL, 9.7 mmol) in DCM (50 mL) for 1 h, followed by addition of 5M aq NaOH (50 mL) and heating for 2 h at 65° C., during which time DCM evaporates. The cooled solution was extracted twice with DCM, then the combined organic layers washed consecutively with saturated aq NaHCO$_3$, water and brine, and finally concentrated.

This thiourea (150 mg, 0.87 mmol) was then reacted with ethyl 2-bromoisovalerate (150 µL, 0.87 mmol) in the presence of Hunigs base (diisopropylethylamine, 160 µL, 0.96 mmol) in EtOH (4 mL) in the microwave for 1 h 15 min at 150° C. Concentration followed by purification by reversed-phase HPLC, then made basic with aq NaHCO$_3$, gave the product as a white solid. $^1$H NMR (400 MHz, DMSO-D$_6$) δ ppm 0.74 (d, J=6.59 Hz, 3 H) 0.91 (d, J=6.84 Hz, 3 H) 1.52 (d, J=2.20 Hz, 4 H) 1.60 (s, 4 H) 2.26 (td, J=6.53, 4.03 Hz, 1 H) 2.80-2.86 (m, 4 H) 3.95-4.00 (m, 1 H). MS(ESI) for $C_{12}H_{21}N_3OS$ m/z 256 (M+H).

METHOD UU

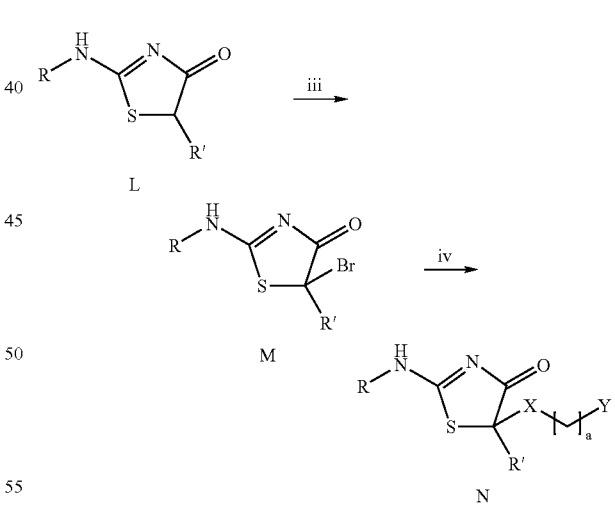

a = 1-4

R'2=alkyl or aryl, R=cycloalkyl, X=O or N, Y=C, O or N

The thiazalones were prepared according to the reaction scheme above from L (L was prepared according to Method A). (iii) To a solution of L (1 eq) in CCl$_4$ (12 mL/mmol L) was added N-bromosuccinimide (1.5 eq) and warmed to 60-70° C. for 1 h. The warm mixture was filtered and the filtrate concentrated to give the bromo intermediate M. (iv) Reaction of M with an alcohol (10-40 eq in THF or neat) at ambient temp –70° C. for 2-24 h gave, after concentration and purification, the ethers N (X=O Y=C,O). Reaction of M with a chloroalcohol (20 eq in THF) at 60° C. for 3-24 h gave, after concentration and purification, the chloroether intermediates. Amination was performed by warming a solution of the chloroether (1 eq) in THF (0.3 mL/mmol chloroether) with an amine (0.3 mL/mmol chloroether) and a crystal of NaI either thermally at 80° C. for 4-24 h or in the microwave oven 180° C. 1 h. Concentration and purification gave the aminoethers N (X=O Y=N). Reaction of M with an amine (10-40 eq in THF or neat) at ambient temp for 10-30 min gave, after concentration and purification, the amines N (X=N Y=C,N).

Example 169

2-(Bicyclo[2.2.1]hept-2-ylamino)-5-methyl-5-(3-morpholin-4-ylpropoxy)-1,3-thiazol-4(5H)-one

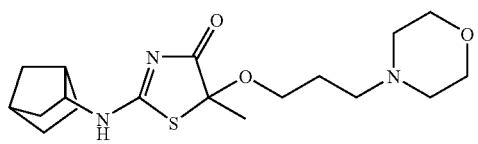

To a solution of the thiazolone (150 mg, 0.67 mmol) in CCl$_4$ (5 mL), was added N-bromosuccinimide (143 mg, 0.80 mmol) and warmed to 60° C. After 1 h, the mixture was filtered warm and concentrated to yield 244 mg of the product as a yellow solid. THF (3 mL) and 3-chloropropanol (2.2 mL, 26.8 mmol) were added and the solution warmed to 60° C. overnight. The resulting solution was concentrated and the product was purified by reversed-phase HPLC, then made basic with aq NaHCO$_3$, to yield the chloroether as a colourless oil.

Morpholine (3 mL) and THF (3 mL) were added and the solution was allowed to stir at 80° C. for 4 h. The resulting solution was concentrated and the product was purified by reversed-phase HPLC, then made basic with aq NaHCO$_3$, to yield the product as a white solid. $^1$H NMR (400 MHz, DMSO-D$_6$) δ ppm 1.06-1.18 (m, 3 H) 1.36-1.48 (m, 4 H) 1.58-1.64 (m, 2 H) 1.66-1.71 (m, 3 H) 2.19-2.30 (m, 8 H) 3.09-3.17 (m, 2 H) 3.37-3.45 (m, 1 H) 3.48-3.57 (m, 4 H), 3.80 (m, 0.5H) 4.05 (m, 0.5H). MS(ESI) for C$_{18}$H$_{29}$N$_3$O$_3$S m/Z 368 (M+H).

Example 170

2-(Bicyclo[2.2.1]hept-2-ylamino)-6-oxa-1-thia-3-azaspiro[4.4]non-2-en-4-one

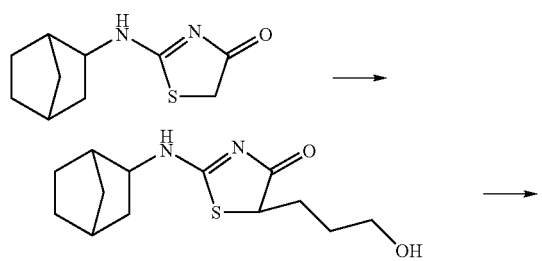

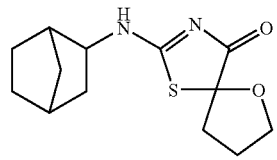

To a continuously N$_2$-flushed solution of the thiazolone (200 mg, 0.95 mmol) in dry THF (10 mL) was added lithium diisopropylamide (1.9 mL of a 2M solution in THF/heptane/ethyl benzene, 3.8 mmol) at −78° C. The resulting brown solution was allowed to stir 1 h at this temperature after which time (3-bromopropoxy)tert-butyldimethylsilane (0.6 mL, 2.6 mmol) was added and the solution allowed to warm to 5° C. (2.5 h). The reaction was quenched with 6 mL 2/1 MeOH/HOAc followed by addition of a saturated solution of aq NaHCO$_3$. The silyl-protected product (50% conversion according to HPLC) was extracted with EtOAc and the resulting solution was concentrated and the product was purified by reversed-phase HPLC. During purification, the alcohol function was deprotected to give the free alcohol.

To the free alcohol (0.17 mmol) in DCM (5 mL) was added Br$_2$ (10 μL, 0.17 mmol) and a drop HBr (48% aqueous) and warmed to 60° C. 1 h. The resulting solution was quenched with aq NaS$_2$O$_4$ and extracted with DCM. The product was purified by reversed-phase HPLC, then made basic with aq NaHCO$_3$, to yield the product as a white solid. $^1$H NMR (400 MHz, CHLOROFORM-D) δ ppm 1.09-1.19 (m, 2 H) 1.21-1.30 (m, 2 H) 1.49-1.59 (m, 2 H) 1.70-1.77 (m, 1 H) 1.93 (d, J=2.93 Hz, 1 H) 1.99-2.10 (m, 1 H) 2.22-2.32 (m, 1 H) 2.36-2.48 (m, 3 H) 2.66 (dt, J=9.22, 4.55 Hz, 1 H) 3.30-3.36 (m, 1 H) 4.04-4.14 (m, 1 H) 4.15-4.23 (m, 1 H). MS(ESI) for C$_{13}$H$_{18}$N$_2$O$_2$S m/z 267 (M+H).

Method VV

The following examples serve to illustrate the preparative procedure employed for the synthesis of thiazolone analogues containing a heterocyclic side-chain at the 5-position.

Example 171

N-(2-Aminophenyl)-2-(2-anilino-4-oxo-4,5-dihydro-1,3-thiazol-5-yl)acetamide

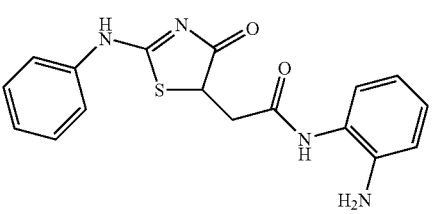

N-(2-Aminophenyl)-2-(2-anilino-4-oxo-4,5-dihydro-1,3-thiazol-5-yl)acetic acid, prepared using method 2 above, (30 mg, 1 eq) was dissolved in a mixture of DCM/DMF (2 mL/2 mL) and O-phenylendiamine (15 mg, 1.1 eq), and 1-[3-(dimethylamino)propyl]-3-ethylcarbodiimide hydrochloride (EDC, 30 mg, 1.3 eq) were then added sequentially. The reaction mixture was stirred 40° C. for 2 h. Separated between DCM and H$_2$O, the organic layer concentrated to give a crude orange brown oil used directly in the next step: HPLC 43%, $R_T$=0.93 min (System B, 2-95% MeCN over 2 min); MS [M+H]$^+$ m/z=341.

Example 172

2-Anilino-5-(1H-benzimidazol-2-ylmethyl)-1,3-thiazol-4(5H)-one

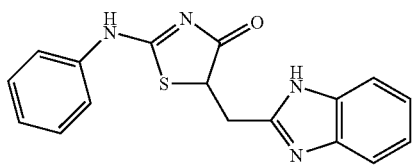

N-(2-Aminophenyl)-2-(2-anilino-4-oxo-4,5-dihydro-1,3-thiazol-5-yl)acetamide (40.8 mg, 1 eq) was taken up in HOAc (2 mL), transferred to a micro-tube and run at 100° C. for 600 s. The reaction mixture was evaporated to give 42 mg, as a crude brown oil. Purified by HP-LCMS, to the pooled fractions was added NaOH (1M) to pH=14, the MeCN was evaporated and the aqueous layer extracted with DCM/H$_2$O (9:1), dried and evaporated to give the title compound as an off-white powder: HPLC 99%, $R_T$=2.02 min (System A, 10-97% MeCN over 3 min), 99%, $R_T$=0.96 min (System B, 2-95% MeCN over 2 min); $^1$H NMR (400 MHz, METHANOL-D4) δ ppm 3.23 (m, 1 H) 3.80 (m, 1 H) 4.70 (m, 1 H) 7.02 (m, 1 H) 7.17 (m, 3 H) 7.32 (m, 2 H) 7.50 (m, 2 H) 7.62 (m, 1 H); MS [M+H]$^+$ m/z=323.

METHOD WW

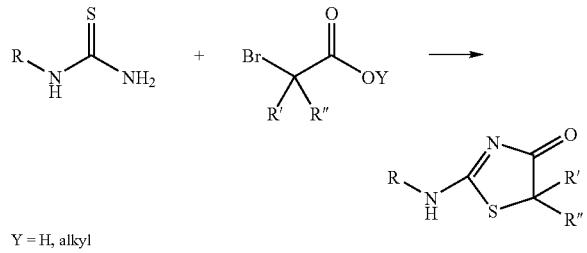

Y = H, alkyl

The thiourea (1.0 eq.) and the α-bromoester/α-bromoacid (1.0 eq.) were dissolved in acetone (alternatively water, 1,4-dioxane, THF, 2-propanol or MeCN) and heated at 60-140° C. in a sealed tube or by microwave irradiation for 15-72 hours. The solvent was removed. And the product purified by crystallization from MeOH or preparative reverse-phase HPLC.

Example 173

2-(Bicyclo[2.2.1]hept-2-ylamino)-1-thia-3-azaspiro[4.4]non-2-en-4-one

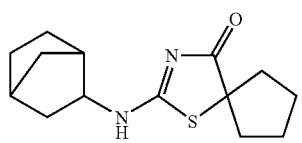

A solution of N-bicyclo[2.2.1]hept-2-ylthiourea (73.9 mg, 0.434 mmol) and methyl 1-bromocyclopentanecarboxylate (89.9 mg, 0.434 mmol) in 1,4-dioxane (600 µL) was stirred at 95° C. in a sealed tube for 20 h. The solvent was removed, and the residue was purified by silica gel flash chromatography (pentane/EtOAc, 6:4). The product-containing fractions were pooled, and the solvent was removed. Subsequent purification of the residue by preparative reverse-phase HPLC yielded the product as a white solid.

HPLC 100%, $R_T$=2.98 (System A, 10-97% MeCN over 3 min), 100%, $R_T$=1.45 min (System B, 2-95% MeCN over 2 min).

$^1$H NMR (400 MHz, DMSO-d$_6$) δ 1.04-1.19 (m, 3 H), 1.34-1.51 (m, 4 H), 1.59-1.73 (m, 3 H), 1.78-1.99 (m, 4 H), 2.08-2.25 (m, 4 H), 3.18 (m, 0.3 H, minor isomer), 3.77 (m, 0.7 H, major isomer), 9.01 (d, J=6.7 Hz, 0.7 H, major isomer), 9.68 (s br, 0.3 H, minor isomer).

MS (ESI+) for C$_{14}$H$_{20}$N$_2$OS m/z 265 (M+H)$^+$.

METHOD XX

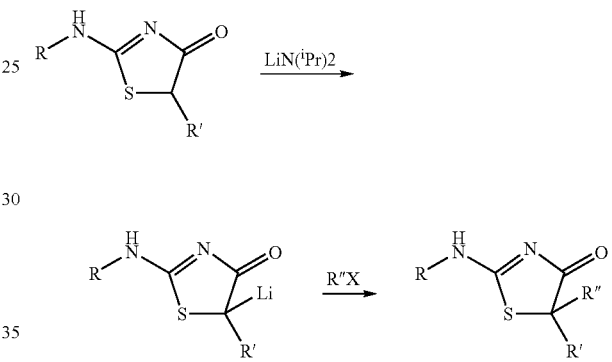

According to the above synthetic scheme, X of R"X is halogen.

5-monosubstituted thiazolones may also be further alkylated at the 5-position via the liathiated anion. The following examples illustrate how this methodology can be employed to introduce more complex side-chains.

Example 174

5-(4-Bromobutyl)-2-(cycloheptylamino)-5-methyl-1,3-thiazol-4(5H)-one

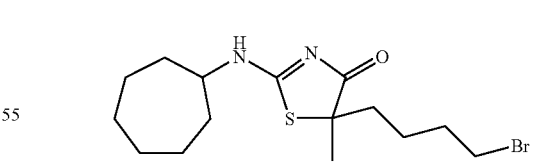

To a continuous N$_2$-flushed solution of 2-(cycloheptylamino)-5-methyl-1,3-thiazol-4(5H)-one hydrobromide (500 mg, 2.2 mmol) in dry THF (50 mL) was added lithium diisopropylamide (4.4 mL of a 2M solution in THF/heptane/ethyl benzene, 8.8 mmol) at −78° C. The resulting brown solution was allowed to stir 1 h at this temperature after which time 1,4-dibromobutane (2.1 mL, 17.7 mmol) was added and the solution allowed to warm to −30° C. After 1 h at this temperature, the reaction was quenched with 6 mL 2/1 MeOH/HOAc and allowed to stir overnight at rt. A saturated solution of aq. NaHCO$_3$ was added and the product was extracted with EtOAc and then purified on SiO$_2$ (gradient 4/1-1/1 hex/EtOAc) to give the bromide as a white solid. Yield 227 mg. HPLC 100% R$_T$=2.34 min (System B, 10-97% MeCN over 3 min), 100% R$_T$=2.41 min (System A, 10-97% MeCN over 3 min). $^1$H NMR (400 MHz, DMSO-D6) δ ppm 1.15 (td, J=7.20, 3.66 Hz, 1 H) 1.35-1.65 (m, 14 H) 1.68-1.79 (m, 4 H) 1.82-1.91 (m, 2 H) 3.49 (t, J=6.59 Hz, 2 H) 3.95 (dd, J=8.30, 3.91 Hz, 1 H) 9.10 (d, J=7.57 Hz, 1 H). MS(ESI) for C$_{15}$H$_{25}$BrN$_2$OS m/z 361 (M+H).

Example 175

2-(Cycloheptylamino)-5-methyl-5-(4-morpholin-4-ylbutyl)-1,3-thiazol-4(5H)-one

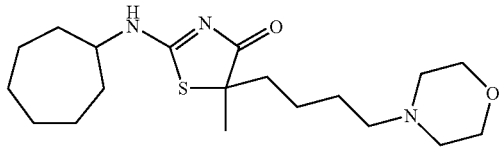

The bromide intermediate 5-(4-Bromobutyl)-2-(cycloheptylamino)-5-methyl-1,3-thiazol-4(5H)-one (52 mg, 0.14 mmol), described above, was dissolved in THF (3 mL), morpholine (0.84 mmol) added and warmed to 80° C. over the weekend. Purification by preprative HPLC and made basic with aq NaHCO$_3$, gave the product as a colourless oil. HPLC 100% R$_T$=1.45 min (System B, 10-97% MeCN over 3 min), 100% R$_T$=1.63 min (System A, 10-97% MeCN over 3 min). $^1$H NMR (400 MHz, DMSO-D6) δ ppm 0.96-1.08 (m, 1 H) 1.34-1.60 (m, 18 H) 1.82-1.90 (m, 2 H) 2.18 (t, J=6.96 Hz, 2 H) 2.24-2.32 (m, 4 H) 3.52 (m, 4 H) 3.95 (s, 1 H) 9.08 (br s, 1H). MS(ESI) for C$_{19}$H$_{33}$N$_3$O$_2$S m/z 368 (M+H).

Method YY

Example 176

5-[(dimethylamino)methyl]-5-methyl-2-[(2-methylphenyl)amino]-1,3-thiazol-4(5H)-one

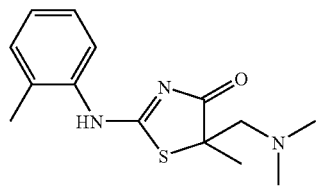

To a solution of {2-[(3-chloro-2-methylphenyl)amino]-4-oxo-4,5-dihydro-1,3-thiazol-5-yl}acetic acid (1 eq) in 1,4-dioxane was added N,N-dimethylmethyleneiminium chloride (2 eq) and the resulting mixture heated in a sealed tube in a microwave reactor at 150° C. for 5 minutes. The desired product was then isolated after removal of solvent in vacuo and purification by preperative HPLC.

$^1$H NMR (400 MHz, DMSO-D6) δ ppm 1.42 (s, 3 H) 2.12 (s, 2 H) 2.2.3 (s, 6H) 2.57 (d, J=14.0 Hz, 1H) 2.70 (d, J=14.0 Hz, 1 H) 3.30 (s, 3H) 6.83 (d, J=7.5 Hz, 1H) 7.03 (t, J=7.5 Hz, 1H) 7.15 (t, J=7.5 Hz, 1H) 7.21 (d, J=7.5 Hz, 1H); MS(ESI) for C$_{14}$H$_{19}$N$_3$OS m/z 278 (M+H).

The following table of compounds were prepared using the methodologies outlined above.

TABLE 2

| Structure | Calc mono mass | Exp mono mass | Name | Method of Prep. |
|---|---|---|---|---|
| 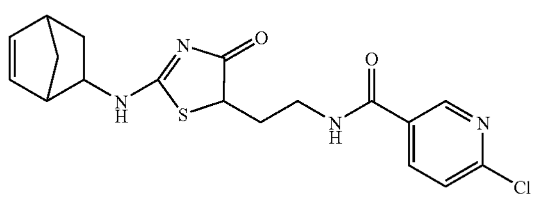 | — | 391 | N-{2-[2-(bicyclo[2.2.1]hept-5-en-2-ylamino)-4-oxo-4,5-dihydro-1,3-thiazol-5-yl]ethyl}-6-chloronicotinamide | QQ |
| 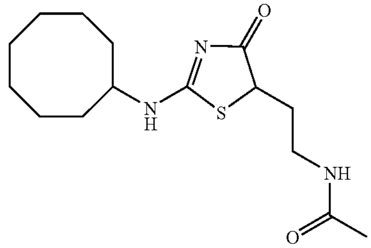 | 311.1667 | 311.1654 | N-{2-[2-(cyclooctylamino)-4-oxo-4,5-dihydro-1,3-thiazol-5-yl]ethyl}acetamide trifluoroacetate | QQ |

TABLE 2-continued

| Structure | Calc mono mass | Exp mono mass | Name | Method of Prep. |
|---|---|---|---|---|
| 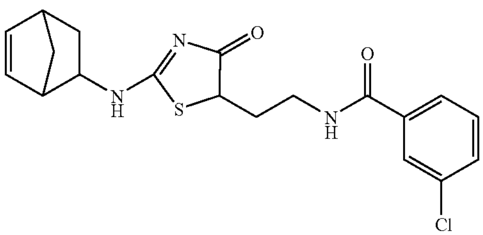 | 375.0808 | 375.0809 | 2-[2-(bicyclo[2.2.1]hept-5-en-2-ylamino)-4-oxo-4,5-dihydro-1,3-thiazol-5-yl]-N-(2-chlorophenyl)acetamide | RR |
| | | 366 | N-(2-chlorophenyl)-2-[2-(cyclohexylamino)-4-oxo-4,5-dihydro-1,3-thiazol-5-yl]acetamide trifluoroacetate | RR |
| | 359.1667 | 359.1662 | 2-[2-(cyclohexylamino)-4-oxo-4,5-dihydro-1,3-thiazol-5-yl]-N-(2,6-dimethylphenyl)acetamide | RR |
| | 359.1667 | 359.1664 | 2-[2-(cyclohexylamino)-4-oxo-4,5-dihydro-1,3-thiazol-5-yl]-N-(2,5-dimethylphenyl)acetamide | RR |
| | 359.1667 | 359.1664 | 2-[2-(cyclohexylamino)-4-oxo-4,5-dihydro-1,3-thiazol-5-yl]-N-(2,4-dimethylphenyl)acetamide | RR |
| 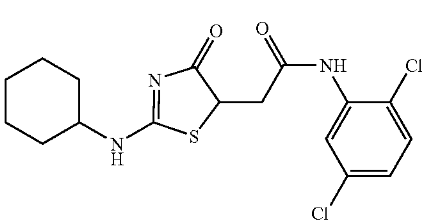 | 399.0575 | 399.582 | 2-[2-(cyclohexylamino)-4-oxo-4,5-dihydro-1,3-thiazol-5-yl]-N-(2,5-dichlorophenyl)acetamide | RR |

TABLE 2-continued

| Structure | Calc mono mass | Exp mono mass | Name | Method of Prep. |
|---|---|---|---|---|
| 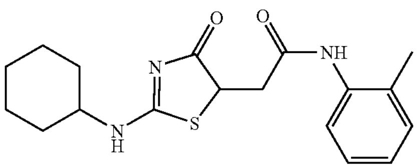 | 345.1511 | 345.1552 | 2-[2-(cyclohexylamino)-4-oxo-4,5-dihydro-1,3-thiazol-5-yl]-N-(2-methylphenyl)-acetamide | RR |
| 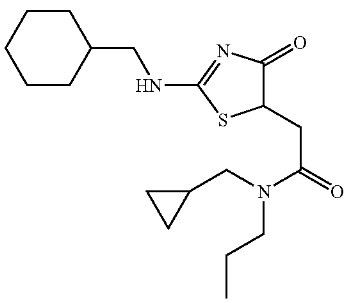 | 365.2137 | 365.2141 | 2-{2-[(cyclohexylmethyl)amino]-4-oxo-4,5-dihydro-1,3-thiazol-5-yl}-N-(cyclopropylmethyl)-N-propylacetamide | RR |
| | | 386 | 2-[(cyclohexylmethyl)amino]-5-[2-(3,4-dihydroquinolin-1(2H)-yl)-2-oxoethyl]-1,3-thiazol-4(5H)-one | RR |
| 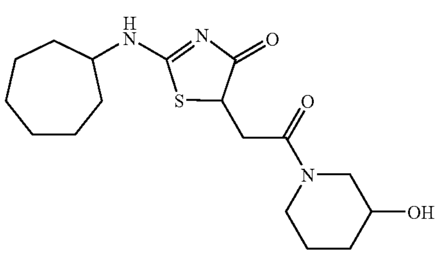 | 353.1773 | 353.1768 | 2-(cycloheptylamino)-5-[2-(3-hydroxypiperidin-1-yl)-2-oxoethyl]-1,3-thiazol-4(5H)-one | RR |
| 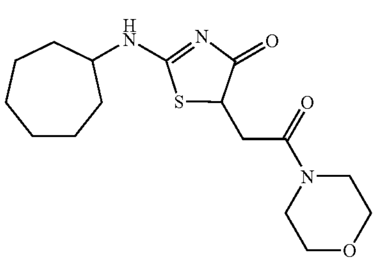 | 339.1617 | 339.1611 | 2-(cycloheptylamino)-5-(2-morpholin-4-yl-2-oxoethyl)-1,3-thiazol-4(5H)-one | RR |
| 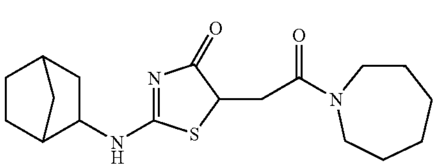 | 349.1824 | 349.1818 | 5-(2-azepan-1-yl-2-oxoethyl)-2-(bicyclo[2.2.1]hept-2-ylamino)-1,3-thiazol-4(5H)-one | RR |

TABLE 2-continued

| Structure | Calc mono mass | Exp mono mass | Name | Method of Prep. |
|---|---|---|---|---|
| 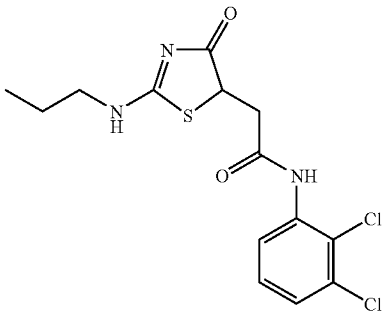 | 359.0262 | 359.0263 | N-(2,3-dichlorophenyl)-2-[4-oxo-2-(propylamino)-4,5-dihydro-1,3-thiazol-5-yl]acetamide | RR |
| 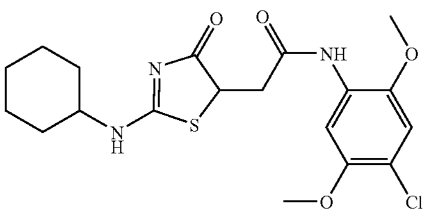 | 425.1176 | 425.1194 | N-(4-chloro-2,5-dimethoxyphenyl)-2-[2-(cyclohexylamino)-4-oxo-4,5-dihydro-1,3-thiazol-5-yl]acetamide | RR |
| 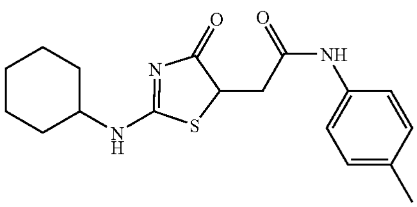 | 345.1511 | 345.1514 | 2-[2-(cyclohexylamino)-4-oxo-4,5-dihydro-1,3-thiazol-5-yl]-N-(4-methylphenyl)acetamide | RR |
| | 409.0419 | 409.0413 | 2-[2-(bicyclo[2.2.1]hept-5-en-2-ylamino)-4-oxo-4,5-dihydro-1,3-thiazol-5-yl]-N-(4-chlorophenyl)acetamide | RR |
| | 409.0419 | 409.0413 | 2-[2-(bicyclo[2.2.1]hept-5-en-2-ylamino)-4-oxo-4,5-dihydro-1,3-thiazol-5-yl]-N-(2,5-dichlorophenyl)acetamide | RR |
| 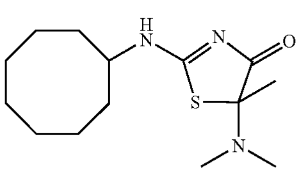 | 283.1718 | 283.1731 | 2-(cyclooctylamino)-5-(dimethylamino)-5-methyl-1,3-thiazol-4(5H)-one | UU |
| 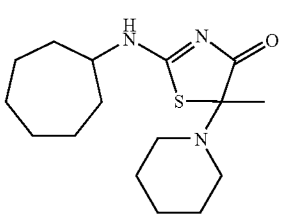 | 309.1875 | 309.1877 | 2-(cycloheptylamino)-5-methyl-5-piperidin-1-yl-1,3-thiazol-4(5H)-one | UU |

TABLE 2-continued

| Structure | Calc mono mass | Exp mono mass | Name | Method of Prep. |
|---|---|---|---|---|
| 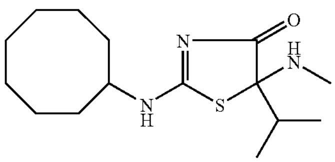 | 297.1875 | 297.1868 | 2-(cyclooctylamino)-5-isopropyl-5-(methylamino)-1,3-thiazol-4(5H)-one | UU |
| 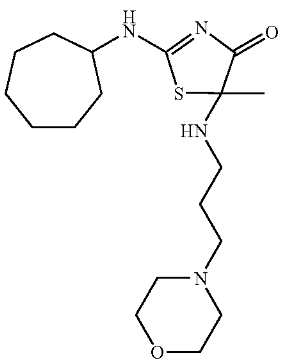 | 368.2246 | 368.2252 | 2-(cycloheptylamino)-5-methyl-5-[(3-morpholin-4-ylpropyl)amino]-1,3-thiazol-4(5H)-one | UU |
| 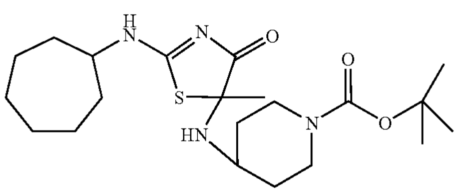 | 424.2508 | 424.2503 | tert-butyl 4-{[2-(cycloheptylamino)-5-methyl-4-oxo-4,5-dihydro-1,3-thiazol-5-yl]amino}piperidine-1-carboxylate | UU |
| 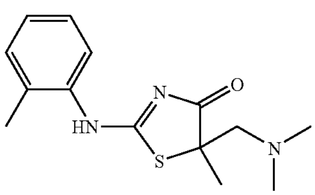 | 277.124882 | 277.126 | 5-[(dimethylamino)methyl]-5-methyl-2-[(2-methylphenyl)amino]-1,3-thiazol-4(5H)one | YY |
| 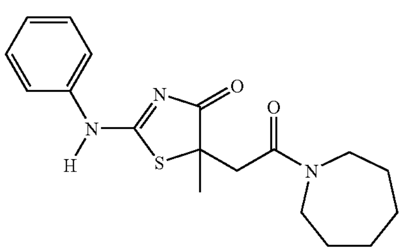 | 345.151097 | 345.15 | 2-anilino-5-(2-azepan-1-yl-2-oxoethyl)-5-methyl-1,3-thiazol-4(5H)-one | RR |
| 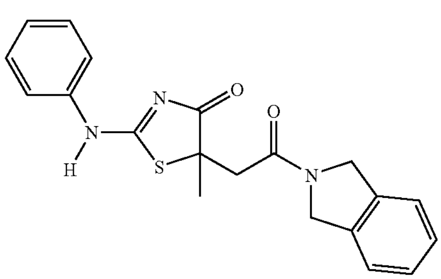 | 365.119797 | 365.119 | 2-anilino-5-[2-(1,3-dihydro-2H-isoindol-2-yl)-2-oxoethyl]-5-methyl-1,3-thiazol-4(5H)-one | RR |

TABLE 2-continued

| Structure | Calc mono mass | Exp mono mass | Name | Method of Prep. |
|---|---|---|---|---|
| 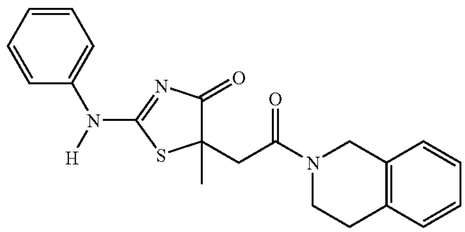 | 379.135447 | 379.136 | 2-anilino-5-[2-(3,4-dihydroisoquinolin-2(1H)-yl)-2-oxoethyl]-5-methyl-1,3-thiazol-4(5H)-one | RR |
| 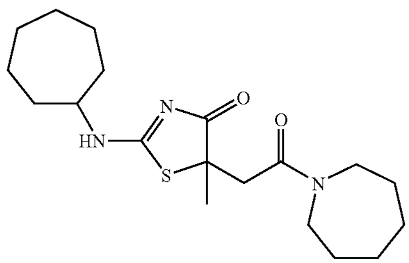 | 365.2129 | 365.213697 | 5-(2-azepan-1-yl-2-oxoethyl)-2-(cycloheptylamino)-5-methyl-1,3-thiazol-4(5H)-one | RR |
| 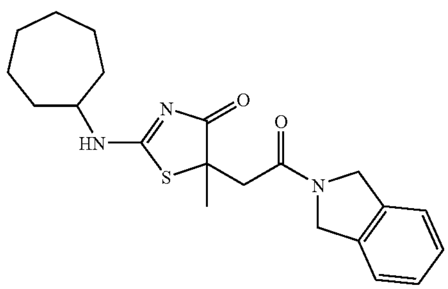 | 385.1835 | 385.182397 | 2-(cycloheptylamino)-5-[2-(1,3-dihydro-2H-issoindol-2-yl)-2-oxoethyl]-5-methyl-1,3-thiazol-4(5H)-one | RR |
| 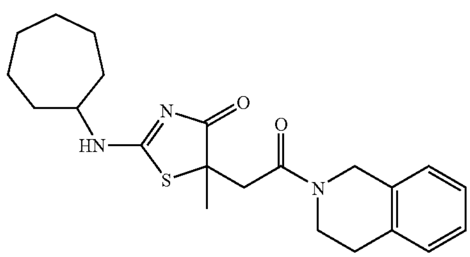 | 399.1995 | 399.198047 | 2-(cycloheptylamino)-5[2-(3,4-dihydroisoquinolin-2(1H)-yl)-2-oxoethyl]-5-methyl-1,3-thiazol-4(5H)-one | RR |
| 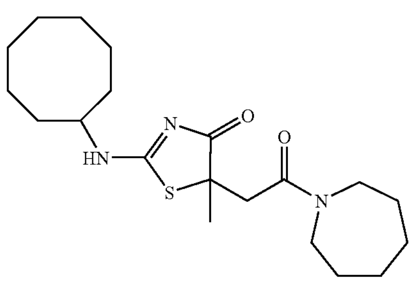 | 379.2275 | 379.229347 | 5-(2-azepan-1-yl-2-oxoethyl)-2-(cyclooctylamino)-5-methyl-1,3-thiazol-4(5H)-one | RR |

TABLE 2-continued

| Structure | Calc mono mass | Exp mono mass | Name | Method of Prep. |
|---|---|---|---|---|
| 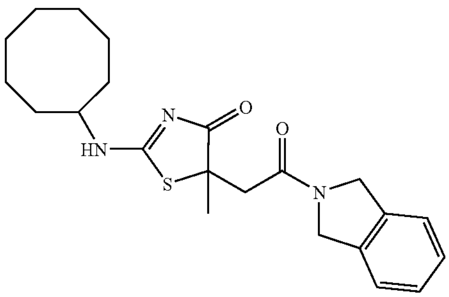 | 336.1049 | 336.10445 | 2-(cyclooctylamino)-5-[2-(1,3-dihydro-2H-isoindol-2-yl)-2-oxoethyl]-5-methyl-1,3-thiazol-4(5H)-one | RR |
| 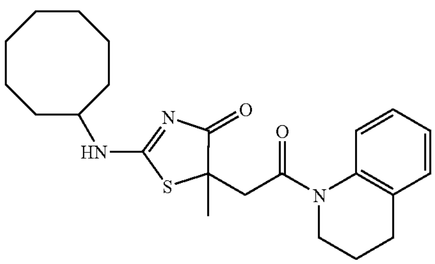 | 413.2138 | 413.213697 | 2-(cyclooctylamino)-5-[2-(3,4-dihydroquinolin-1(2H)-yl)-2-oxoethyl]-5-methyl-1,3-thiazol-4(5H)-one | RR |
| 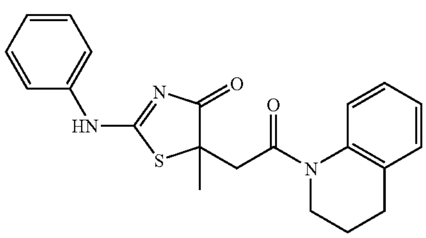 | 379.1352 | 379.135447 | 2-anilino-5-[2-(3,4-dihydroquinolin-1(2H)-yl)-2-oxoethyl]-5-methyl-1,3-thiazol-4(5H)-one | RR |
| 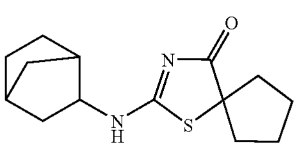 | 264.1296 | 264.1307 | 2-(bicyclo[2.2.1]hept-2-ylamino)-1-thia-3-azaspiro[4.4]non-2-en-4-one | WW |
| | 266.1453 | 266.1442 | 2-(cycloheptylamino)-1-thia-3-azaspiro[4.4]non-2-en-4-one | WW |
| 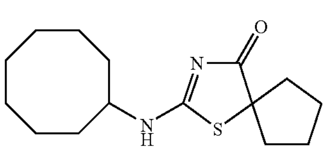 | 280.1609 | 280.1611 | 2-(cyclooctylamino)-1-thia-3-azaspiro[4.4]non-2-en-4-one | WW |
| | 266.1453 | 266.1445 | 2-[(2,2,3,3-tetramethylcyclopropyl)amino]-1-thia-3-azaspiro[4.4]non-2-en-4-one | WW |

TABLE 2-continued

| Structure | Calc mono mass | Exp mono mass | Name | Method of Prep. |
|---|---|---|---|---|
| 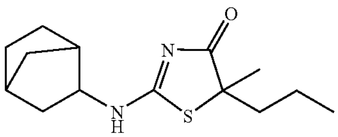 | 266.1453 | 266.146 | 2-(bicyclo[2.2.1]hept-2-ylamino)-5-methyl-5-propyl-1,3-thiazol-4(5H)-one | WW |
| | 268.1609 | 268.1618 | 2-(cycloheptylamino)-5-methyl-5-propyl-1,3-thiazol-4(5H)-one | WW |
| 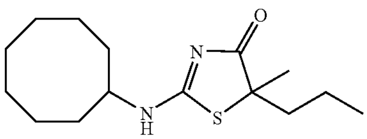 | 282.1766 | 282.1774 | 2-(cyclooctylamino)-5-methyl-5-propyl-1,3-thiazol-4(5H)-one | WW |
| | 268.1609 | 268.1609 | 5-methyl-5-propyl-2-[(2,2,3,3-tetramethylcyclopropyl)amino]-1,3-thiazol-4(5H)-one | WW |
| | 252.1296 | 252.1288 | 2-(bicyclo[2.2.1]hept-2-ylamino)-5-ethyl-5-methyl-1,3-thiazol-4(5H)-one | WW |
| | 254.1453 | 254.1448 | 2-(cycloheptylamino)-5-ethyl-5-methyl-1,3-thiazol-4(5H)-one | WW |
| | 254.1453 | 254.1443 | 5-ethyl-5-methyl-2-[(2,2,3,3-tetramethylcyclopropyl)amino]-1,3-thiazol-4(5H)-one | WW |
| 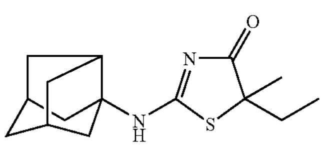 | 278.1453 | 278.1459 | 5-ethyl-5-methyl-2-(tricyclo[3.3.1.0~3,7~]non-3-ylamino)-1,3-thiazol-4(5H)-one | WW |
| 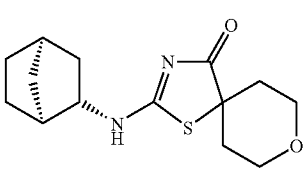 | 280.1245 | 278.0941 | 2-[(1S,2S,4R)-bicyclo[2.2.1]hept-2-ylamino]-8-oxa-1-thia-3-azaspiro[4.5]dec-2-en-4-one | WW |
| | 252.1296 | 252.1296 | 2-(bicyclo[2.2.1]hept-1-ylamino)-5-ethyl-5-methyl-1,3-thiazol-4(5H)-one | WW |

TABLE 2-continued

| Structure | Calc mono mass | Exp mono mass | Name | Method of Prep. |
|---|---|---|---|---|
| | 268.1609 | 268.1601 | 2-(cyclooctylamino)-5-ethyl-5-methyl-1,3-thiazol-4(5H)-one | WW |
| | 292.1609 | 292.1614 | 5-methyl-5-propyl-2-(tricyclo[3.3.1.0~3,7~]non-3-ylamino)-1,3-thiazol-4(5H)-one | WW |
| 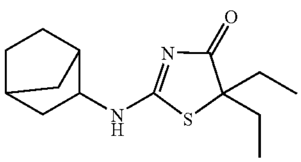 | 266.1453 | 266.1443 | 2-(bicyclo[2.2.1]hept-2-ylamino)-5,5-diethyl-1,3-thiazol-4(5H)-one | WW |
| | 282.1766 | 282.1758 | 2-(cyclooctylamino)-5,5-diethyl-1,3-thiazol-4(5H)-one | WW |
| | 292.1609 | 292.1622 | 5,5-diethyl-2-(tricyclo[3.3.1.0~3,7~]non-3-ylamino)-1,3-thiazol-4(5H)-one | WW |
| | 254.1453 | 254.1454 | 5-ethyl-5-methyl-2-[(1-methylcyclohexyl)amino]-1,3-thiazol-4(5H)-one trifluoroacetate | WW |
| | 268.1609 | 268.1609 | 5-methyl-2-[(1-methylcyclohexyl)amino]-5-propyl-1,3-thiazol-4(5H)-one trifluoroacetate | WW |
| | 254.1453 | 254.1442 | 5-ethyl-5-methyl-2-[(4-methylcyclohexyl)amino]-1,3-thiazol-4(5H)-one | WW |
| | 282.1766 | 282.1766 | 5-ethyl-5-methyl-2-[(3,3,5-trimethylcyclohexyl)amino]-1,3-thiazol-4(5H)-one | WW |

TABLE 2-continued

| Structure | Calc mono mass | Exp mono mass | Name | Method of Prep. |
|---|---|---|---|---|
| 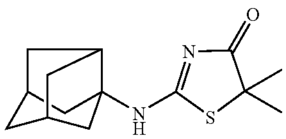 | 264.1296 | 264.1291 | 5,5-dimethyl-2-(tricyclo[3.3.1.1~3,7~]non-3-ylamino)-1,3-thiazol-4(5H)-one | WW |
| 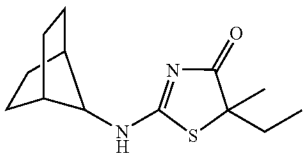 | 252.1296 | 252.1289 | 2-(bicyclo[2.2.1]hept-7-ylamino)-5-ethyl-5-methyl-1,3-thiazol-4(5H)-one | WW |
| | 266.1453 | 266.1459 | 2-(bicyclo[2.2.1]hept-7-ylamino)-5-methyl-5-propyl-1,3-thiazol-4(5H)-one | WW |
| | 254.1453 | 254.1444 | (5S)-2-(cycloheptylamino)-5-ethyl-5-methyl-1,3-thiazol-4(5H)-one | WW |
| | 254.1453 | 254.1445 | (5R)-2-(cycloheptylamino)-5-ethyl-5-methyl-1,3-thiazol-4(5H)-one | WW |
| | 266.1453 | 266.144 | 2-(bicyclo[2.2.1]hept-7-ylamino)-5,5-diethyl-1,3-thiazol-4(5H)-one | WW |
| | 266.1453 | 266.1445 | 2-(bicyclo[2.2.1]hept-1-ylamino)-5,5-diethyl-1,3-thiazol-4(5H)-one | WW |
| | 266.1453 | 266.1445 | 2-(bicyclo[2.2.1]hept-1-ylamino)-5-methyl-5-propyl-1,3-thiazol-4(5H)-one | WW |
| 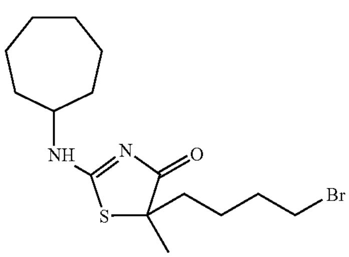 | 360.0871 | 360.0867 | 5-(4-bromobutyl)-2-(cycloheptylamino)-5-methyl-1,3-thiazol-4(5H)-one | XX |

TABLE 2-continued

| Structure | Calc mono mass | Exp mono mass | Name | Method of Prep. |
|---|---|---|---|---|
| 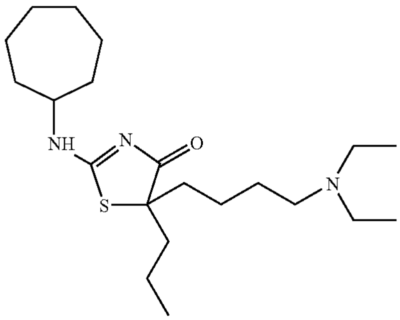 | 381.2814 | 381.281 | 2-(cycloheptylamino)-5-[4-(diethylamino)butyl]-5-propyl-1,3-thiazol-4(5H)-one | XX |
| 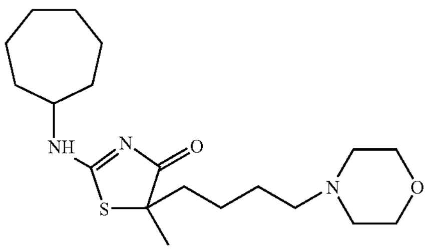 | 367.2293 | 367.2294 | 2-(cycloheptylamino)-5-methyl-5-(4-morpholin-4-ylbutyl)-1,3-thiazol-4(5H)-one | XX |
| 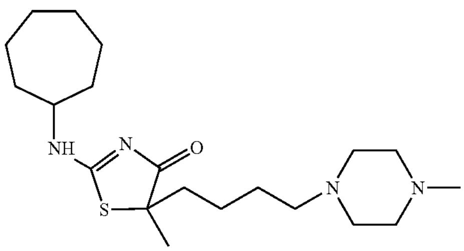 | 380.261 | 380.2612 | 2-(cycloheptylamino)-5-methyl-5-[4-(4-methylpiperazin-1-yl)butyl]-1,3-thiazol-4(5H)-one | XX |
| 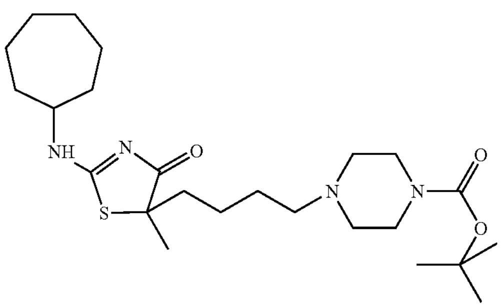 | 466.2978 | 466.2992 | tert-butyl 4-{4-[2-(cycloheptylamino)-5-methyl-4-oxo-4,5-dihydro-1,3-thiazol-5-yl]butyl}piperazine-1-carboxylate | XX |
| 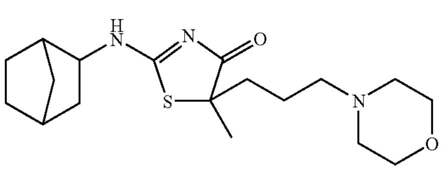 | 351.198 | 351.1977 | 2-(bicyclo[2.2.1]hept-2-ylamino)-5-methyl-5-(3-morpholin-4-ylpropyl)-1,3-thiazol-4(5H)one | XX |
| 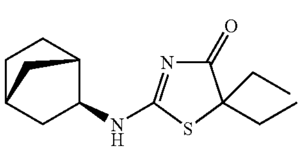 | 266.1453 | 266.1458 | 2-[(1S,2S,4R)-bicyclo[2.2.1]hept-2-ylamino]-5,5-diethyl-1,3-thiazol-4(5H)-one | WW |

TABLE 2-continued

| Structure | Calc mono mass | Exp mono mass | Name | Method of Prep. |
|---|---|---|---|---|
| | 270.1402 | 270.1401 | 2-(cyclooctylamino)-5-methoxy-5-methyl-1,3-thiazol-4(5H)-one | UU |
| | 270.1402 | 270.139 | 2-(cycloheptylamino)-5-ethoxy-5-methyl-1,3-thiazol-4(5H)-one | UU |
| 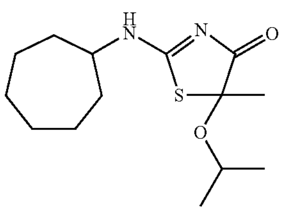 | 284.1558 | 284.156 | 2-(cycloheptylamino)-5-isopropoxy-5-methyl-1,3-thiazol-4(5H)-one | UU |
| | 298.1715 | 298.172 | 5-butoxy-2-(cycloheptylamino)-5-methyl-1,3-thiazol-4(5H)-one | UU |
| | 298.1715 | 298.1712 | 2-(cyclooctylamino)-5-isopropyl-5-methoxy-1,3-thiazol-4(5H)-one | UU |
| 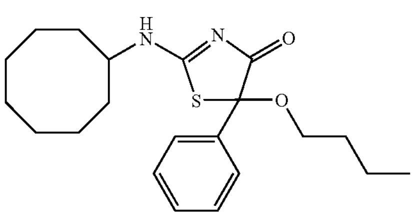 | 374.2028 | 374.2034 | 5-butoxy-2-(cyclooctylamino)-5-phenyl-1,3-thiazol-4(5H)-one | UU |
| 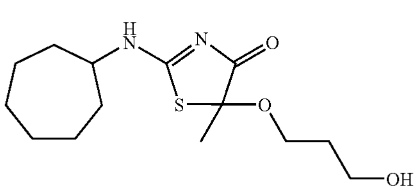 | 300.1508 | 300.1517 | 2-(cycloheptylamino)-5-(3-hydroxypropoxy)-5-methyl-1,3-thiazol-4(5H)-one | UU |

TABLE 2-continued

| Structure | Calc mono mass | Exp mono mass | Name | Method of Prep. |
|---|---|---|---|---|
| 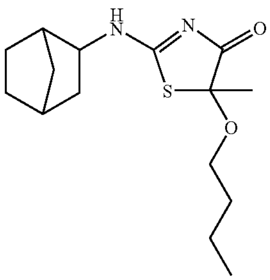 | 296.1558 | 296.1558 | 2-(bicyclo[2.2.1]hept-2-ylamino)-5-butoxy-5-methyl-1,3-thiazol-4(5H)-one | UU |
| 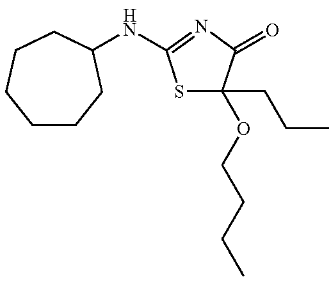 | 326.2028 | 326.2036 | 5-butoxy-2-(cycloheptylamino)-5-propyl-1,3-thiazol-4(5H)-one | UU |
| 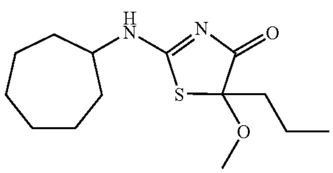 | 284.1558 | 284.1547 | 2-(cycloheptylamino)-5-methoxy-5-propyl-1,3-thiazol-4(5H)-one | UU |
| 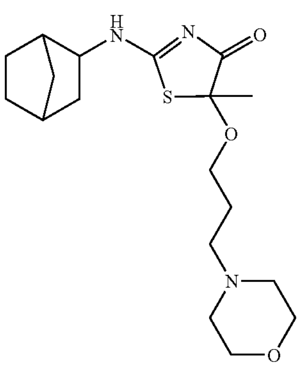 | 367.193 | 367.1934 | 2-(bicyclo[2.2.1]hept-2-ylamino)-5-methyl-5-(3-morpholin-4-ylpropoxy)-1,3-thiazol-4(5H)-one | UU |
| 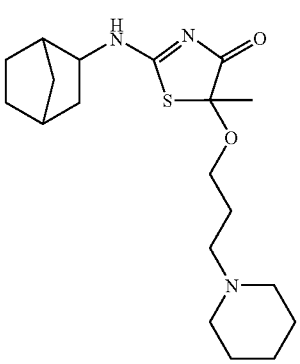 | 365.2137 | 365.2134 | 2-(bicyclo[2.2.1]hept-2-ylamino)-5-methyl-5-(3-piperidin-1-ylpropoxy)-1,3-thiazol-4(5H)-one | UU |

TABLE 2-continued

| Structure | Calc mono mass | Exp mono mass | Name | Method of Prep. |
|---|---|---|---|---|
| 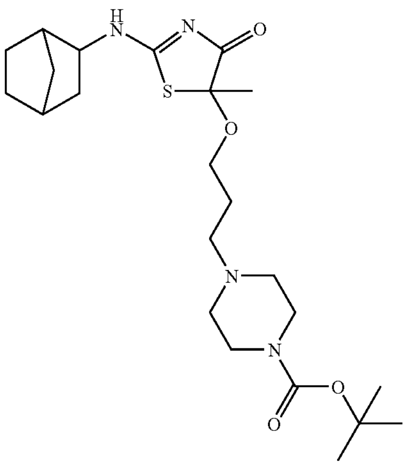 | 466.2614 | 466.2619 | tert-butyl 4-(3-{[2-(bicyclo[2.2.1]hept-2-ylamino)-5-methyl-4-oxo-4,5-dihydro-1,3-thiazol-5-yl]ocy}propyl)piperazine-1-carboxylate | UU |
| 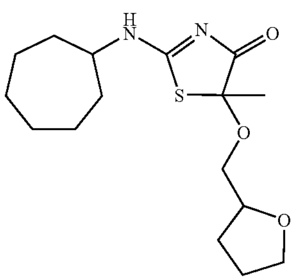 | 326.1664 | 326.1666 | 2-(cycloheptylamino)-5-methyl-5-(tetrahydrofuran-2-ylmethoxy)-1,3-thiazol-4(5H)-one | UU |
| 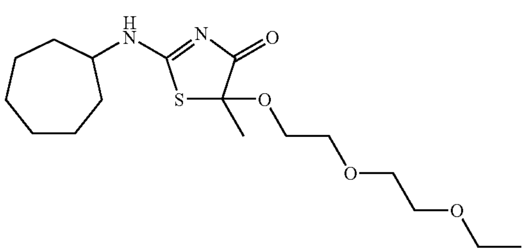 | 358.1926 | 358.1917 | 2-(cycloheptylamino)-5-[2-(2-ethoxyethoxy)ethoxy]-5-methyl-1,3-thiazol-4(5H)-one | UU |
| 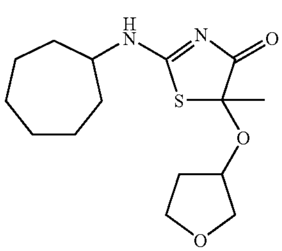 | 312.1508 | 312.1503 | 2-(cycloheptylamino)-5-methyl-5-(tetrahydrofuran-3-yloxy)-1,3-thiazol-4(5H)-one | UU |

TABLE 2-continued

| Structure | Calc mono mass | Exp mono mass | Name | Method of Prep. |
|---|---|---|---|---|
| 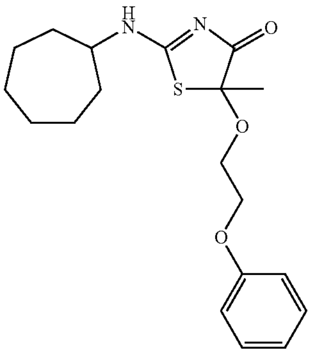 | 362.1664 | 362.1675 | 2-(cycloheptylamino)-5-methyl-5-(2-phenoxyethoxy)-1,3-thiazol-4(5H)-one | UU |
| 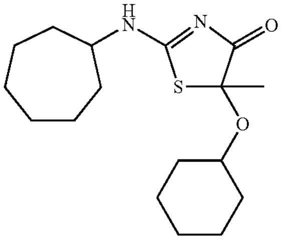 | 324.1871 | 324.1869 | 2-(cycloheptylamino)-5-(cyclohexyloxy)-5-methyl-1,3-thiazol-4(5H)-one | UU |
| 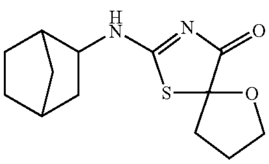 | 266.1089 | 266.1076 | 2-(bicyclo[2.2.1]hept-2-ylamino)-6-oxa-1-thia-3-azaspiro[4.4]non-2-en-4-one | UU |
| | | 323 | 2-anilino-5-(1H-benzimidazol-2-ylmethyl)-1,3-thiazol-4(5H)-one | VV |
| | | 343. | 5-(1H-benzimidazol-2-ylmethyl)-2-[(cyclohexylmethyl)amino]-1,3-thiazol-4(5H)-one | VV |
| 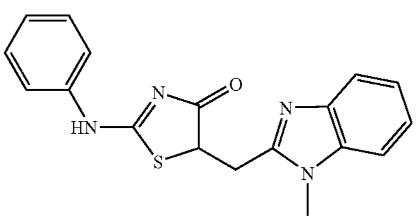 | 336.1049 | 336.1045 | 2-anilino-5-[(1-methyl-1H-benzimidazol-2-yl)methyl]-1,3-thiazol-4(5H)-one | VV |
| 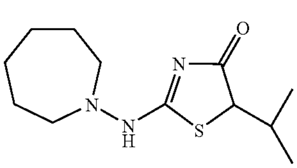 | 255.1405 | 255.1397 | 2-(azepan-1-ylamino)-5-isopropyl-1,3-thiazol-4(5H)-one | TT |

TABLE 2-continued

| Structure | Calc mono mass | Exp mono mass | Name | Method of Prep. |
|---|---|---|---|---|
| 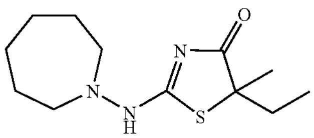 | 255.1405 | 255.1401 | 2-(azepan-1-ylamino)-5-ethyl-5-methyl-1,3-thiazol-4(5H)-one | TT |
| 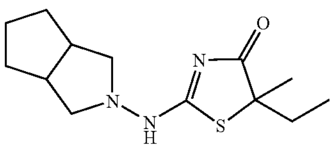 | 267.1405 | 267.1399 | 5-ethyl-2-(hexahydrocyclopenta[c]pyrrol-2(1H)-ylamino)-5-methyl-1,3-thiazol-4(5H)-one | TT |
| | 269.1562 | 269.157 | 2-(azepan-1-ylamino)-5,5-diethyl-1,3-thiazol-4(5H)-one | TT |
| 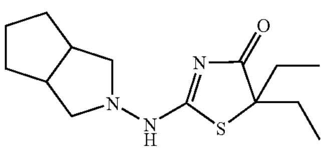 | 281.1562 | 281.1569 | 5,5-diethyl-2-(hexahydrocyclopenta[c]pyrrol-2(1H)-ylamino)-1,3-thiazol-4(5H)-one | TT |
| | 271.1354 | 271.1344 | 5-isopropyl-2-{[(2R)-2-(methoxymethyl)pyrrolidin-1-yl]amino}-1,3-thiazol-4(5H)-one | TT |
| | 271.1354 | 271.1342 | 5-isopropyl-2-{[2-(methoxymethyl)pyrrolidin-1-yl]amino}-1,3-thiazol-4(5H)-one | TT |
| 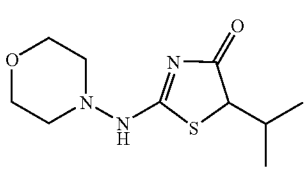 | 243.1041 | 243.1049 | 5-isopropyl-2-(morpholin-4-ylamino)-1,3-thiazol-4(5H)-one | TT |
| | 269.1562 | 269.1553 | 2-[(2,6-dimethylpiperidin-1-yl)amino]-5-isopropyl-1,3-thiazol-4(5H)-one | TT |
| 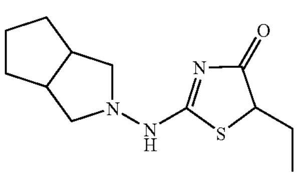 | 253.1249 | 253.1249 | 5-ethyl-2-(hexahydrocyclopenta[c]pyrrol-2(1H)-ylamino)-1,3-thiazol-4(5H)-one | TT |

TABLE 2-continued

| Structure | Calc mono mass | Exp mono mass | Name | Method of Prep. |
|---|---|---|---|---|
| 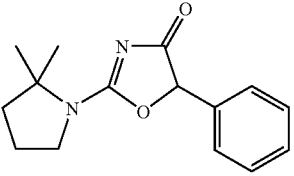 | 258.1368 | 258.136 | 2-(2,2-dimethylpyrrolidin-1-yl)-5-phenyl-1,3-oxazol-4(5H)-one | SS |
| 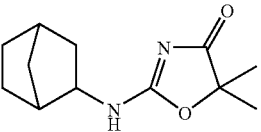 | 222.1368 | 222.1373 | 2-(bicyclo[2.2.1]hept-2-ylamino)-5,5-dimethyl-1,3-oxazol-4(5H)-one | SS |
| 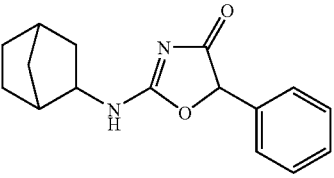 | 270.1368 | 270.1356 | 2-(bicyclo[2.2.1]hept-2-ylamino)-5-phenyl-1,3-oxazol-4(5H)-one | SS |
| 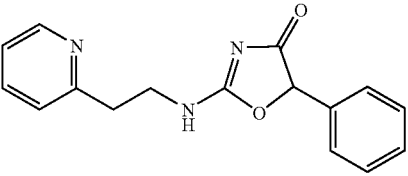 | 281.1164 | 281.1163 | 5-phenyl-2-[(2-pyridin-2-ylethyl)amino]-1,3-oxazol-4(5H)-one | SS |
| 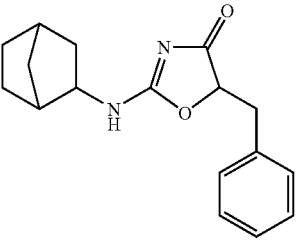 | 284.1525 | 284.1513 | 5-benzyl-2-(bicyclo[2.2.1]hept-2-ylamino)-1,3-oxazol-4(5H)-one | SS |
| 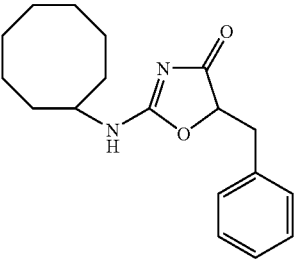 | 300.1838 | 300.1843 | 5-benzyl-2-(cyclooctylamino)-1,3-oxazol-4(5H)-one | SS |
| 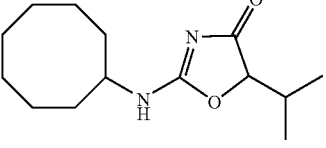 | 252.1838 | 252.183 | 2-(cyclooctylamino)-5-isopropyl-1,3-oxazol-4(5H)-one | SS |

TABLE 2-continued

| Structure | Calc mono mass | Exp mono mass | Name | Method of Prep. |
|---|---|---|---|---|
| 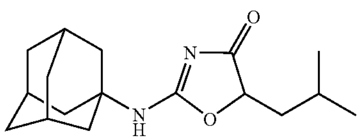 | 290.1994 | 290.1986 | 2-(1-adamantylamino)-5-issobutyl-1,3-oxazol-4(5H)-one | SS |
| | 266.1994 | 266 | 2-(cyclooctylamino)-5-isobutyl-1,3-oxazol-4(5H)-one | SS |
| 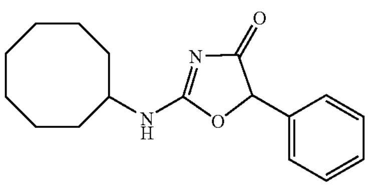 | 286.1681 | 286.1672 | 2-(cyclooctylamino)-5-phenyl-1,3-oxazol-4(5H)-one | SS |
| 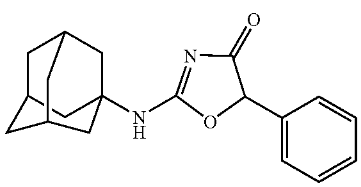 | 310.1681 | 310.169 | 2-(1-adamantylamino)-5-phenyl-1,3-oxazol-4(5H)-one | SS |
| 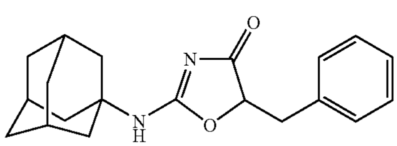 | 324.1838 | 324.1827 | 2-(1-adamantylamino)-5-benzyl-1,3-oxazol-4(5H)-one | SS |
| 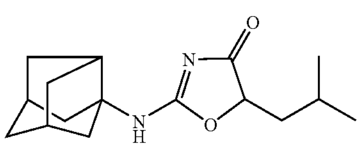 | 276.1838 | 276.1844 | 5-isobutyl-2-(tricyclo[3.3.1.0~3,7~]non-3-ylamino)-1,3-oxazol-4(5H)-one | SS |
| 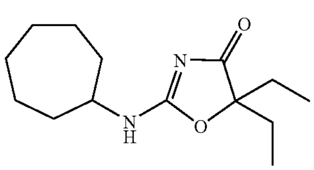 | 252.1838 | 252.1828 | 2-(cycloheptylamino)-5,5-diethyl-1,3-oxazol-4(5H)-one | SS |
| | 266.1994 | 266.1991 | 2-(cyclooctylamino)-5,5-diethyl-1,3-oxazol-4(5H)-one | SS |
| 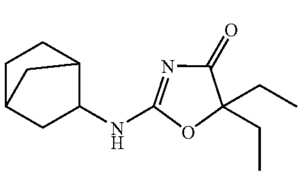 | 250.1681 | 250.1677 | 2-(bicyclo[2.2.1]hept-2-ylamino)-5,5-diethyl-1,3-oxazol-4(5H)-one | SS |

TABLE 2-continued

| Structure | Calc mono mass | Exp mono mass | Name | Method of Prep. |
|---|---|---|---|---|
| | 276.1838 | 276.183 | 5,5-diethyl-2-(tricyclo[3.3.1.0~3,7~]non-3-ylamino)-1,3-oxazol-4(5H)-one | SS |
| | 290.1994 | 290.1987 | 2-(1-adamantylamino)-5,5-diethyl-1,3-oxazol-4(5H)-one | SS |
| 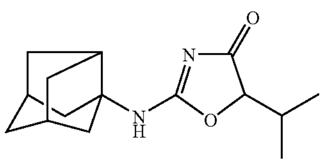 | 262.1681 | 262.1675 | 5-isopropyl-2-(tricyclo[3.3.1.0~3,7~]non-2-ylamino)-1,3-oxazol-4(5H)-one | SS |
| 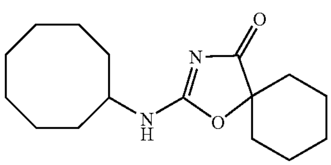 | 278.1994 | 278.1984 | 2-(cyclooctylamino)-1-oxa-3-azaspiro[4.5]dec-2-en-4-one trifluoroacetate | SS |
| | 276.1838 | 276.1839 | 2-(1-adamantylamino)-5-isopropyl-1,3-oxazol-4(5H)-one | SS |
| | 276.1838 | 276.1832 | 2-(2-adamantylamino)-5-isopropyl-1,3-oxazol-4(5H)-one | SS |
| 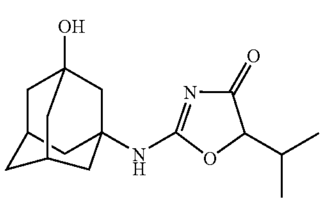 | 292.1787 | 292.1774 | 2-[(3-hydroxy-1-adamantyl)amino]-5-isopropyl-1,3-oxazol-4(5H)-one | SS |
| | 290.1994 | 290.1995 | 2-(2-adamantylamino)5,5-diethyl-1,3-oxazol-4(5H)-one | SS |

TABLE 2-continued

| Structure | Calc mono mass | Exp mono mass | Name | Method of Prep. |
|---|---|---|---|---|
| 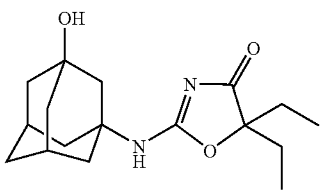 | 306.1943 | 306.1953 | 5,5-diethyl-2-[(3-hydroxy-1-adamantyl)amino]-1,3-oxazol-4(5H)-one | SS |
| 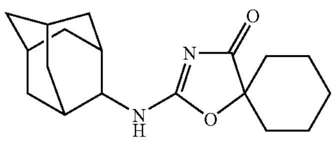 | 302.1994 | 302.1994 | 2-(2-adamantylamino)-1-oxa-3-azaspiro[4.5]dec-2-en-4-one | SS |
| | 288.1838 | 288.1833 | 2-(2-adamantylamino)-1-oxa-3-azaspiro[4.4]non-2-en-4-one | SS |
| 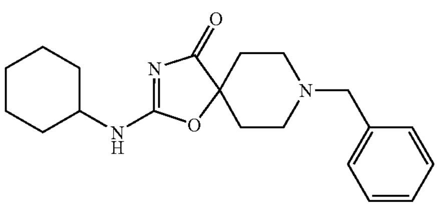 | 341.2103 | 341.2113 | 8-benzyl-2-(cyclohexylamino)-1-oxa-3,8-diazaspiro[4.5]dec-2-en-4-one | SS |
| 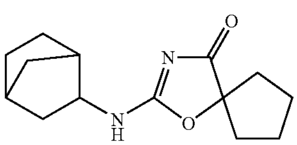 | 248.1525 | 248.1519 | 2-(bicyclo[2.2.1]hept-2-ylamino)-1-oxa-3-azaspiro[4.4]non-2-en-4-one | SS |
| 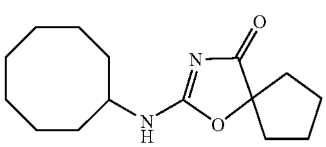 | 264.1838 | 264.1826 | 2-(cyclooctylamino)-1-oxa-3-azaspiro[4.4]non-2-en-4-one | SS |
| 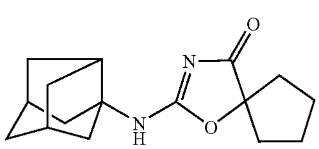 | 274.1681 | 274.1679 | 2-(tricyclo[3.3.1.0~3,7~]non-3-ylamino)-1-oxa-3-azaspiro[4.4]non-2-en-4-one | SS |
| | 288.1838 | 288.1825 | 2-(1-adamantylamino)-1-oxa-3-azaspiro[4.4]non-2-en-4-one | SS |
| 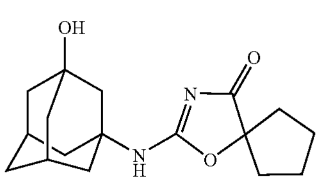 | 304.1787 | 304.1778 | 2-[(3-hydroxy-1-adamantyl)amino]-1-oxa-3-azaspiro[4.4]non-2-en-4-one | SS |

TABLE 2-continued

| Structure | Calc mono mass | Exp mono mass | Name | Method of Prep. |
|---|---|---|---|---|
| 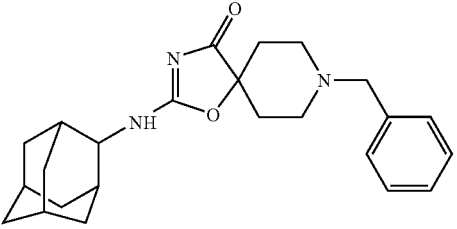 | 393.2416 | 393.2406 | 2-(2-adamantylamino)-8-benzyl-1-oxa-3,8-diazaspiro[4.5]dec-2-en-4-one | SS |
| 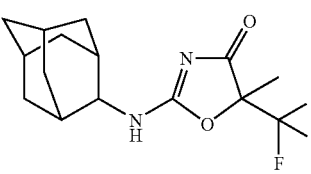 | 316.1399 | 316.139 | 2-(2-adamantylamino)-5-methyl-5-(trifluoromethyl)-1,3-oxazol-4(5H)-one | SS |
| 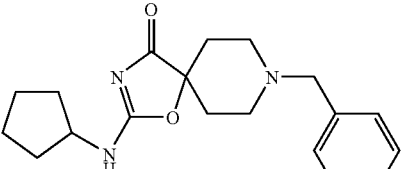 | 327.1947 | 327.1941 | 8-benzyl-2-(cyclopentylamino)-1-oxa-3,8-diazaspiro[4.5]dec-2-en-4-one | SS |
| 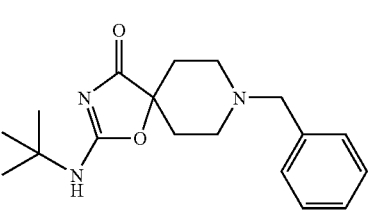 | 315.1947 | 315.1945 | 8-benzyl-2-(tert-butylamino)-1-oxa-3,8-diazaspiro[4.5]dec-2-en-4-one | SS |
| 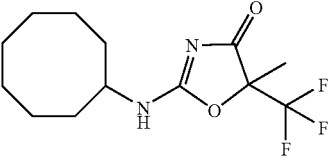 | 292.1399 | 292.1397 | 2-(cyclooctylamino)-5-methyl-5-(trifluoromethyl)-1,3-oxazol-4(5H)-one | SS |
| 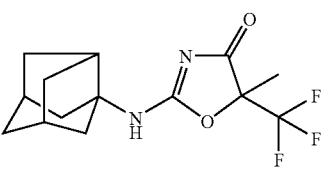 | 302.1242 | 302.1246 | 5-methyl-2-(tricyclo[3.3.1.0~3,7~]non-3-ylamino)-5-(trifluoromethyl)-1,3-oxazol-4(5H)-one | SS |
| 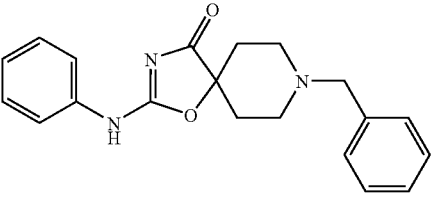 | 335.1634 | 335.1628 | 2-anilino-8-benzyl-1-oxa-3,8-diazaspiro[4,5]dec-2-en-4-one | SS |

TABLE 2-continued

| Structure | Calc mono mass | Exp mono mass | Name | Method of Prep. |
|---|---|---|---|---|
| 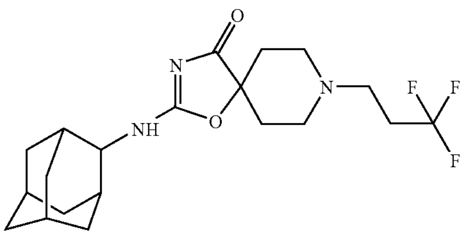 | 399.2134 | 399.2144 | 2-(2-adamantylamino)-8-(3,3,3-trifluoropropyl)-1-oxa-3,8-0 diazaspiro[4,.5]dec-2-en-4-one | SS |

The following tables of compounds are encompassed by the present invention and may be prepared by one of the above methodologies.

| Compound | Name |
|---|---|
| | (S)-2-((1R,2R,4R)-5-hydroxybicyclo[2.2.1]heptan-2-ylamino)-5-isopropyl-5-methylthiazol-4(5H)-one-M1 |
| | (S)-2-((1R,2S,4R)-5-hydroxybicyclo[2.2.1]heptan-2-ylamino)-5-isopropyl-5-methylthiazol-4(5H)-one-M2 |
| | (S)-2-((1S,2S,4R)-6-hydroxybicyclo[2.2.1]heptan-2-ylamino)-5-isopropyl-5-methylthiazol-4(5H)-one-M3 |
| | (S)-2-((1S,2S,4R)-bicyclo[2.2.1]heptan-2-ylamino)-5-((R)-1-hydroxypropan-2-yl)-5-methylthiazol-4(5H)-one-M4 |
| | (S)-2-((1S,2S,4R)-bicyclo[2.2.1]heptan-2-ylamino)-5-((S)-1-hydroxypropan-2-yl)-5-methylthiazol-4(5H)-one-M6 |

-continued

| Compound | Name |
|---|---|
|  | (S)-2-((1S,2S,4R)-bicyclo[2.2.1]heptan-2-ylamino)-5-(2-hydroxypropan-2-yl)-5-methylthiazol-4(5H)-one-M7 |
|  | (S)-2-((1S,2S,4R)-bicyclo[2.2.1]heptan-2-ylamino)-5-methyl-5-(prop-1-en-2-yl)thiazol-4(5H)-one-M8 |
|  | (S)-2-((1R,2S,4R)-5-hydroxybicyclo[2.2.1]heptaan-2-ylamino)-5-isopropyl-5-methylthiazol-4(5H)-one-M10 |

In the table which follows, the variable n is defined as 0-8, the variables R and $R_1$ and $R_2$ are independently defined as hydrogen, $C_1$-$C_8$ alkyl, $C_1$-$C_8$ alkoxy, —$NR^{10}R^{10}$, —S—($C_1$-$C_8$)alkyl, aryl and heterocyclyl; where $R^{10}$ independently selected from hydrogen, $C_1$-$C_8$ alkyl, aryl-$C_1$-$C_8$ alkyl, $C_1$-$C_8$ alkoxy, —S—($C_1$-$C_8$)alkyl, heterocyclyl and aryl; and any alkyl, alkoxy, heterocyclyl or aryl moiety may be substituted with one to three substituents selected from -halo, unsubstituted $C_1$-$C_8$ alkyl, unsubstituted $C_1$-$C_8$ alkoxy, unsubstituted $C_1$-$C_8$ thioalkoxy and unsubstituted aryl($C_1$-$C_4$)alkyl.

| Molecule | Name |
|---|---|
|  | 2-((S)-1-(2-chlorophenyl)ethylamino)-5-methyl-5-(trifluoromethyl)thiazol-4(5H)-one |
|  | 2-((S)-1-(2-bromophenyl)ethylamino)-5-methyl-5-(trifluoromethyl)thiazol-4(5H)-one |
|  | 2-((S)-1-(2-methoxyphenyl)ethylammino)-5-methyl-5-(trifluoromethyl)thiazol-4(5H)-one |

-continued

| Molecule | Name |
|---|---|
| 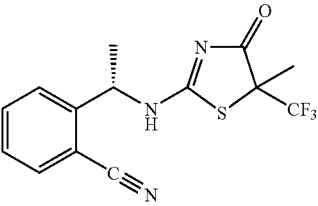 | 2-((S)-1-(5-methyl-4-oxo-5-(trifluoromethyl)-4,5-dihydrothiazol-2-ylamino)ethyl)benzonitrile |
| 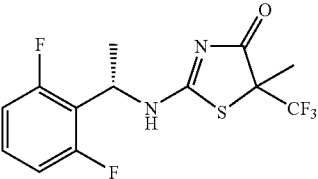 | 2-((S)-1-(2,6-difluorophenyl)ethylamino)-5-methyl-5-(trifluoromethyl)thiazol-4(5H)-one |
| 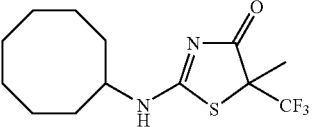 | 2-(cyclooctylamino)-5-methyl-5-(trifluoromethyl)thiazol-4(5H)-one |
| 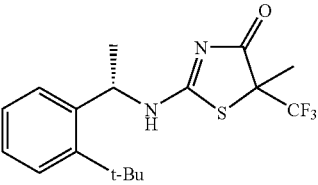 | 2-((S)-1-(2-tert-butylphhenyl)ethylamino)-5-methyyl-5-(trifluoromethyl)thiazol-4(5H)-one |
| 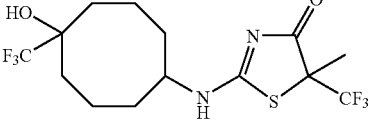 | 2-(5-hydroxy-5-(trifluoromethyl)cyclooctylamino)-5-methyl-5-(trifluoromethyl)thiazol-4(5H)-one |
| 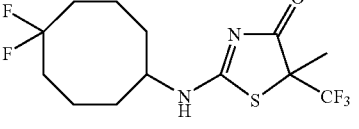 | 2-(5,5-difluorocyclooctylamino)-5-methyl-5-(trifluoromethyl)thiazol-4(5H)-one |
| 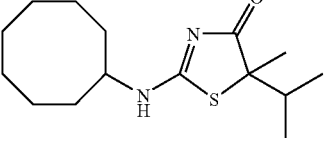 | 2-(cyclooctylamino)-5-isopropyl-5-methylthiazol-4(5H)-one |
| 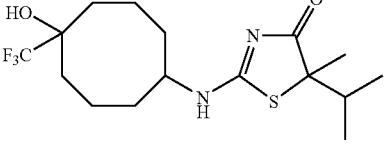 | 2-(5-hydroxy-5-(trifluoromethyl)cyclooctylamino)-5-isopropyl-5-methylthiazol-4(5H)-one |
| 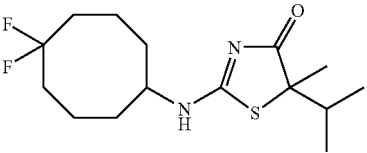 | 2-(5,5-difluorocyclooctylamino)-5-isopropyl-5-methylthiazol-4(5H)-one |

| Molecule | Name |
|---|---|
|  | 2-((S)-8-fluoro-1,2,3,4-tetrahydronaphthalen-1-ylamino)-5-methyl-5-(trifluoromethyl)thiazol-4(5H)-one |
|  | 2-((S)-8-chloro-1,2,3,4-tetrahydronaphthalen-1-ylamino)-5-methyl-5-(trifluoromethyl)thiazol-4(5H)-one |
|  | 2-((S)-7-chloro-2,3-dihydro-1H-inden-1-ylamino)-5-methyl-5-(trifluoromethyl)thiazol-4(5H)-one |
|  | 2-((S)-7-fluoro-2,3-dihydro-1H-inden-1-ylamino)-5-methyl-5-(trifluoromethyl)thiazol-4(5H)-one |
|  | 2-((S)-1-(2-fluoro-6-methylphenyl)ethylamino)-5-methyl-5-(trifluoromethyl)thiazol-4(5H)-one |
|  | 2-((S)-1-(2-chloro-6-methylphenyl)ethylamino)-5-methyl-5-(trifluoromethyl)thiazol-4(5H)-one |
|  | 2-((S)-1-(2-chlorophenyl)ethylamino)-5-isopropyl-5-methylthiazol-4(5H)-one |

| Molecule | Name |
|---|---|
| | 2-((S)-1-(2-ethynylphenyl)ethylamino)-5-isopropyl-5-methylthiazol-4(5H)-one |
| | 2-((S)-1-(2-ethynylphenyl)eethylamino)-5-methyl-5-(trifluoromethyl)thiazol-4(5H)-one |
| | 2-((S)-1-(2-chlorophenyl)ethylamino))-8-oxa-1-thia-3-azaspiro[4.5]non-2-ene-4-one |
| | 2-((S)-1-(2-bromophenyl)ethylamino))-8-oxa-1-thia-3-azaspiro[4.5]non-2-ene-4-one |
| | 2-((S)-1-(2-bromophenyl)ethylamino))-1-thia-3-azaspiro[4.4]non-2-ene-4-one |
| | 2-((S)-1-(2-chlorophenyl)ethylamino))-1-thia-3-azaspiro[4.4]non-2-ene-4-one |
| | 2-((1S,5R)-6,6-difluorobicyclo[3.1.0]hexan-3-ylamino)-5-isopropyl-5-methylthiazol-4(5H)-one |

-continued
| Molecule | Name |
|---|---|
| 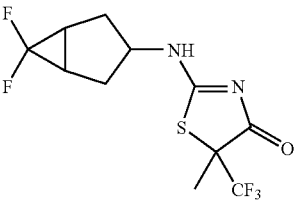 | 2-((1S,5R)-6,6-difluorobicyclo[3.1.0]hexan-3-ylamino)-5-methyl-5-(trifluoromethyl)thiazol-4(5H)-one |
| 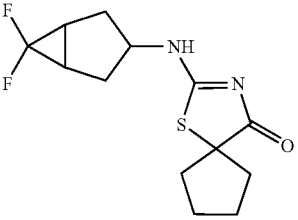 | 2-(6,6-difluorobicyclo[3.1.0]hexan-3-ylamino)-1-thia-3-azaspiro[4.4]none-2-ene-4-one |
| 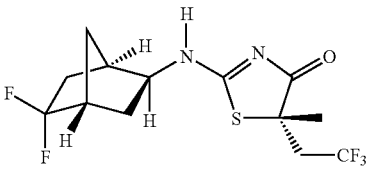 | |
| 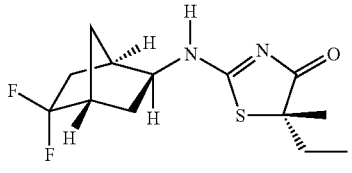 | |
| 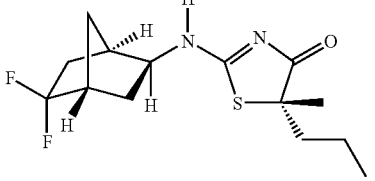 | |
| 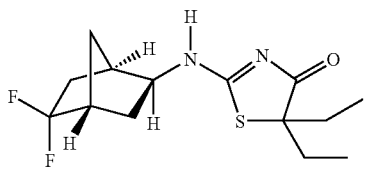 | |
| 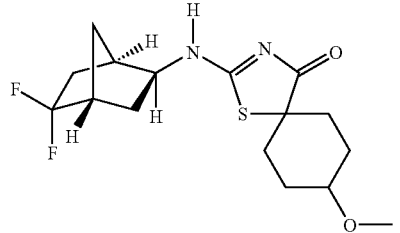 | |

-continued
| Molecule | Name |
|---|---|
| 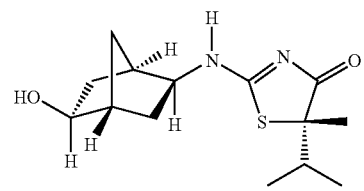 | |
| 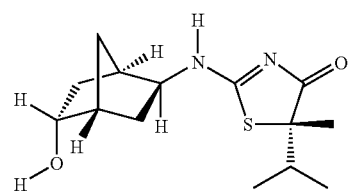 | |
| 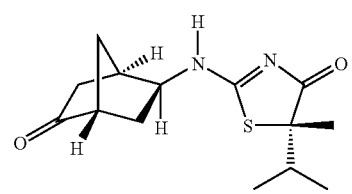 | |
| 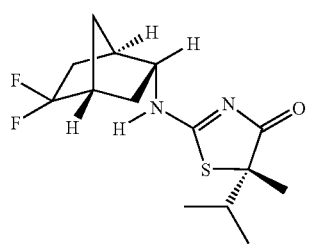 | |
| 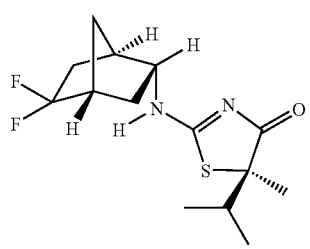 | |
| 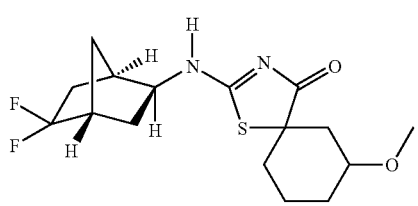 | |
| 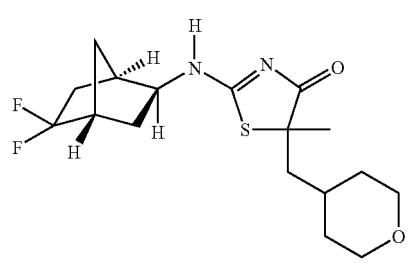 | |

-continued
| Molecule | Name |
|---|---|
| 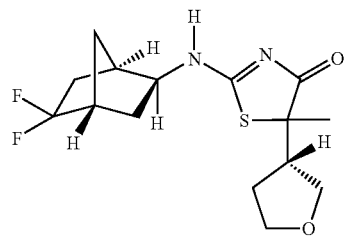 | |
| 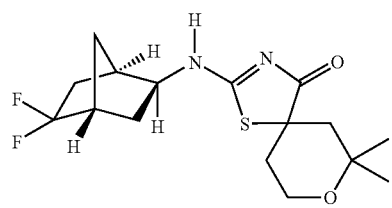 | |
| 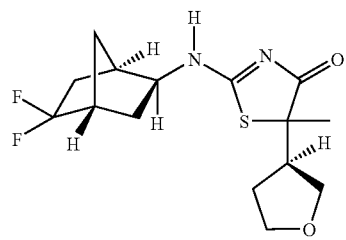 | |
| 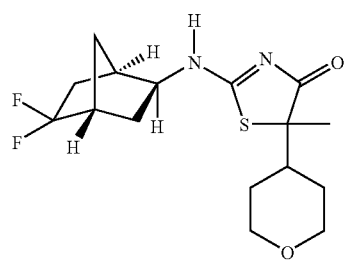 | |
| 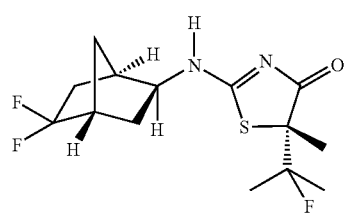 | |
| 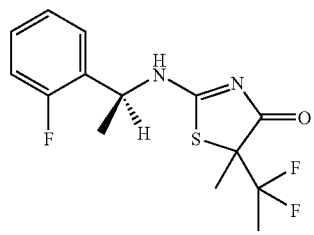 | |

| Molecule | Name |
|---|---|
| 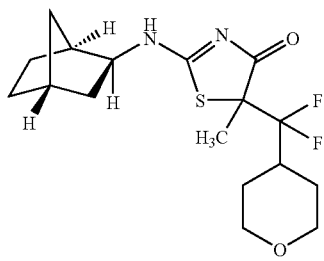 | |
| 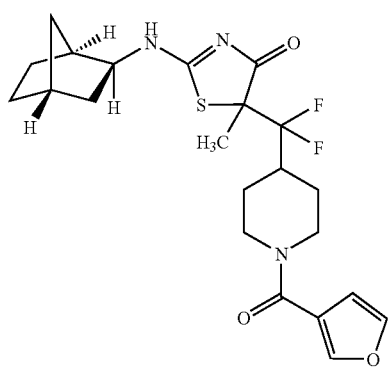 | |
| 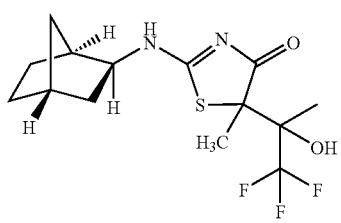 | |
| 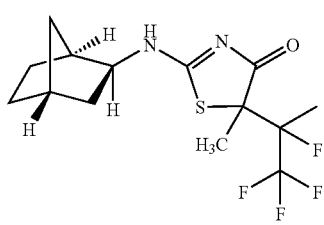 | |
| 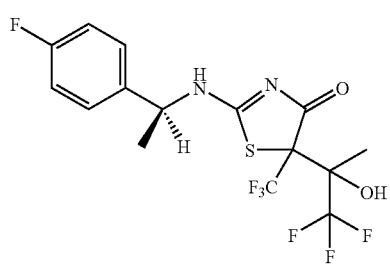 | |

| Molecule | Name |
|---|---|
| 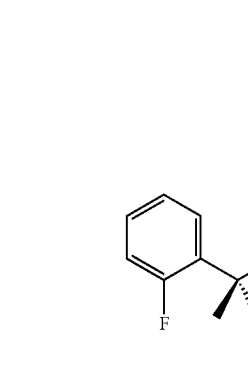 | |
| 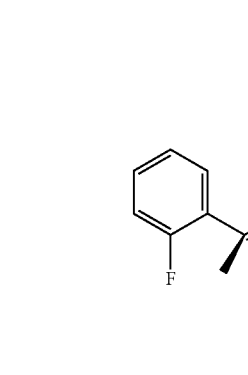 | |
| 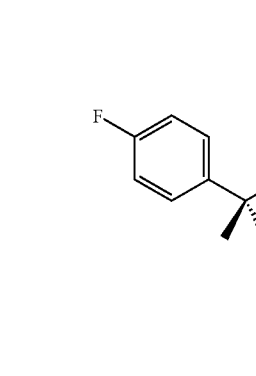 | |
| 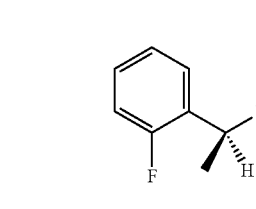 | |

| Molecule | Name |
|---|---|
| 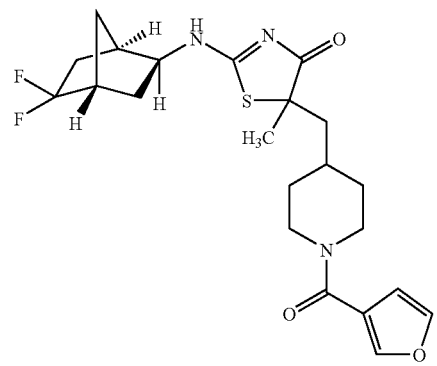 | |
| 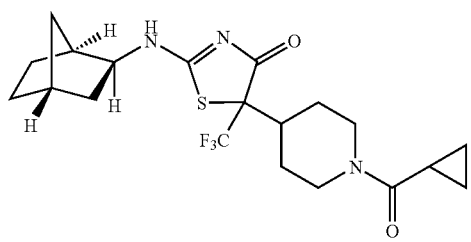 | |
| 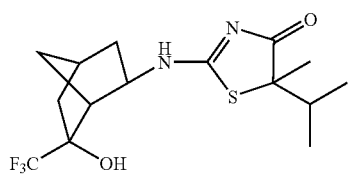 | |
| 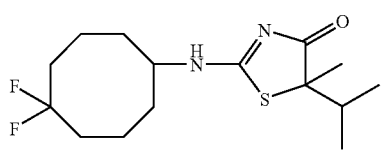 | |
| 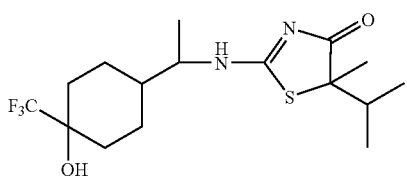 | |
| 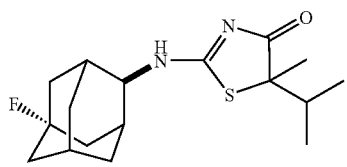 | |
| 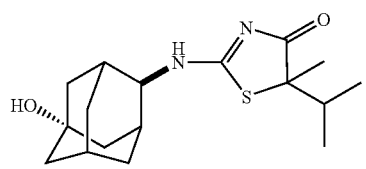 | |

-continued
| Molecule | Name |
|---|---|
| 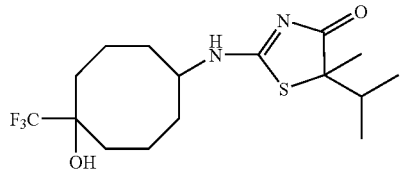 | |
| 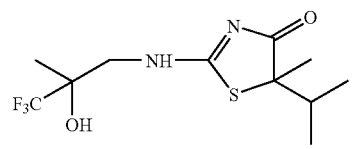 | |
| 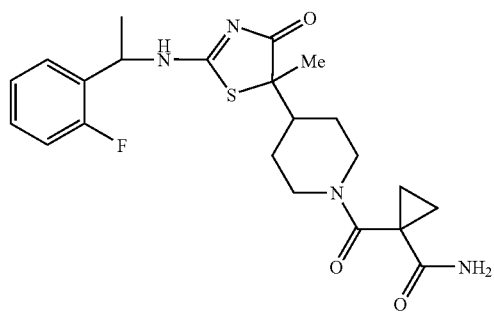 | |
| 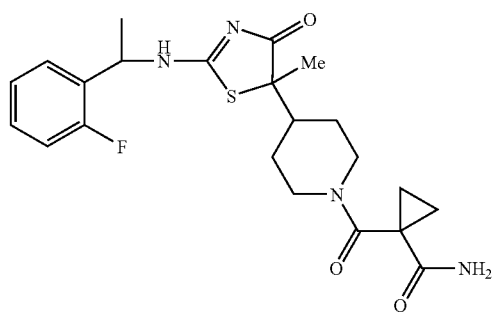 | |
| 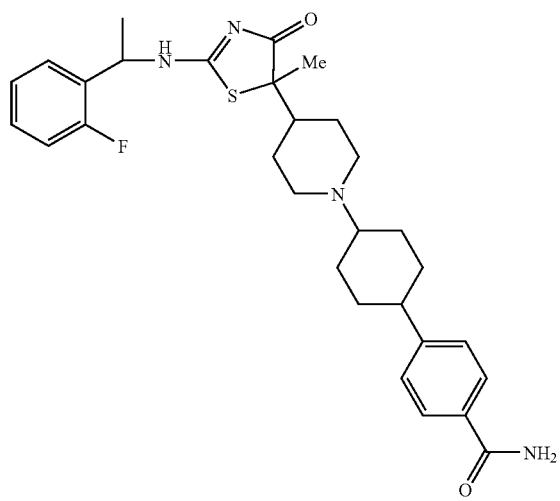 | |

-continued
| Molecule | Name |
|---|---|
| 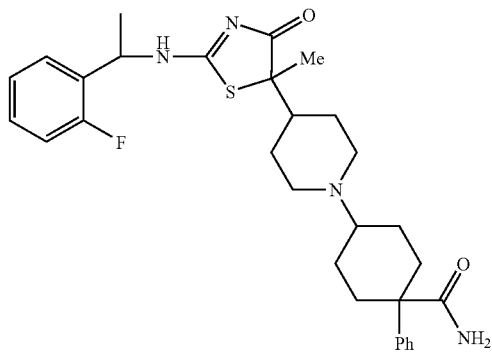 | |
| 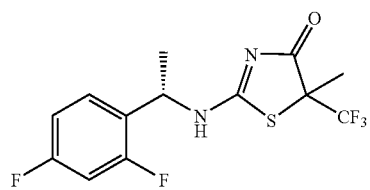 | |
| 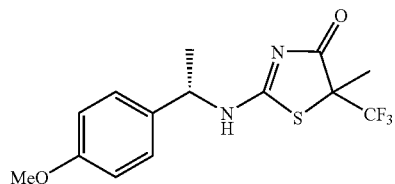 | |
| 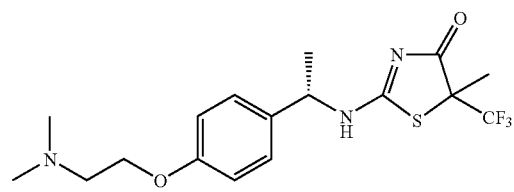 | |
| 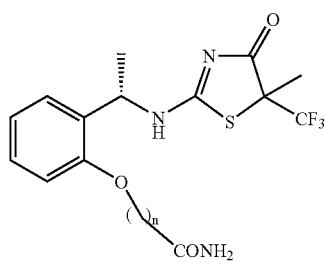 | |
| 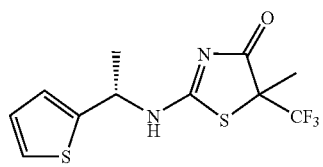 | |

-continued
| Molecule | Name |
|---|---|
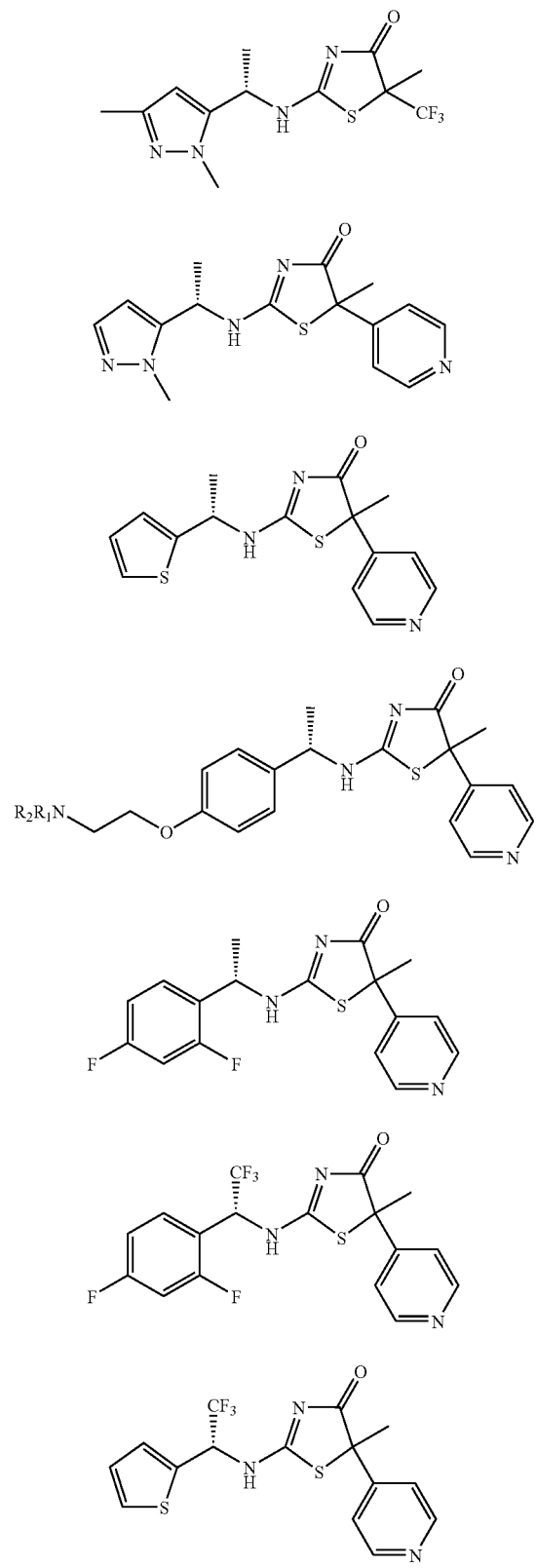

| Molecule | Name |
|---|---|
| 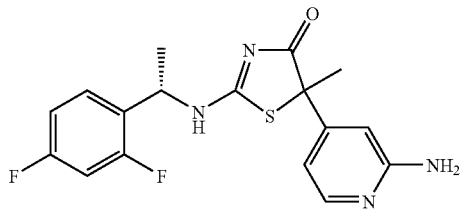 | |
| 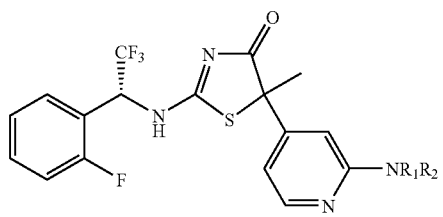 | |
| 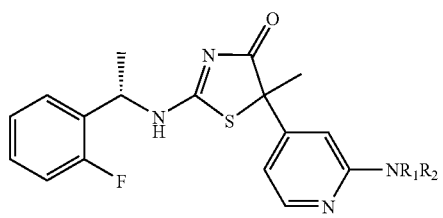 | |
| 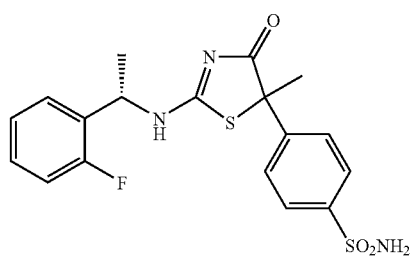 | |
| 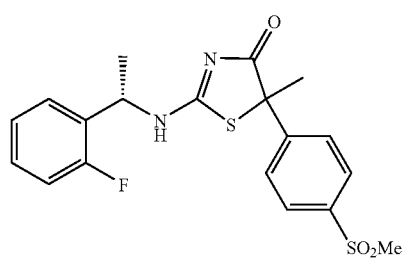 | |
| 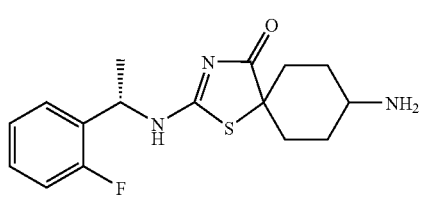 | |
| 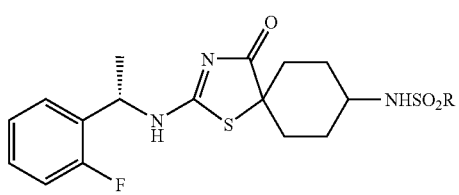 | |

-continued
| Molecule | Name |
|---|---|
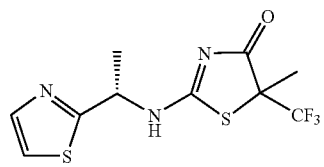
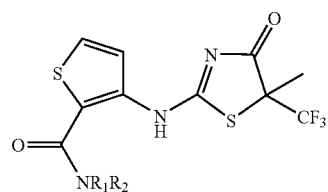
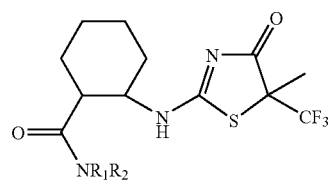
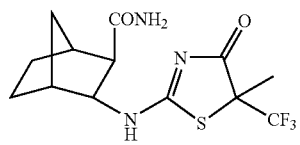
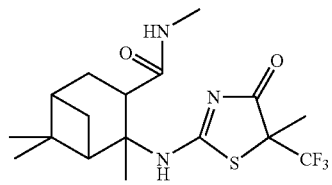
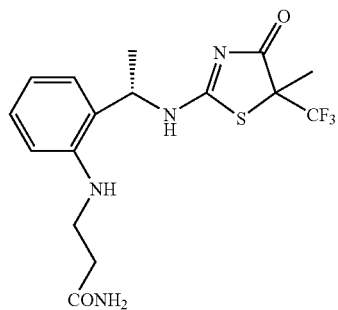
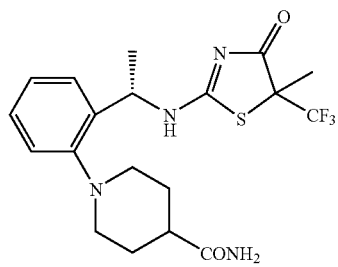

-continued
| Molecule | Name |
|---|---|
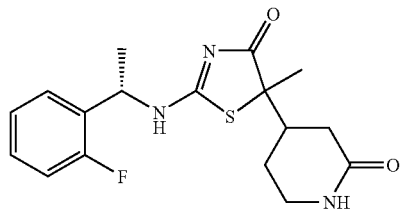
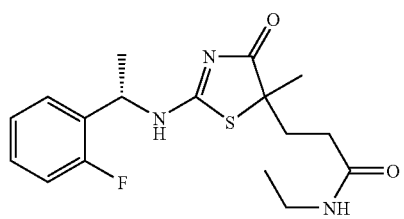
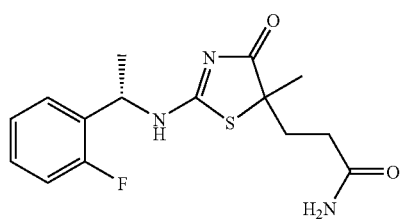
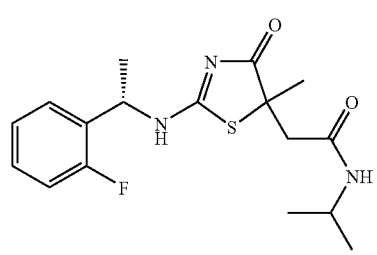
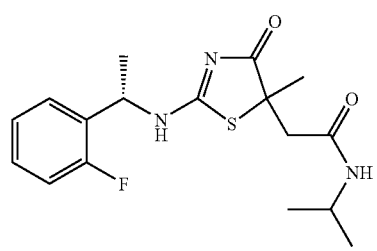
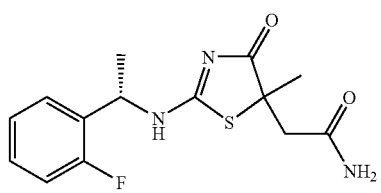

| Molecule | Name |
|---|---|
| 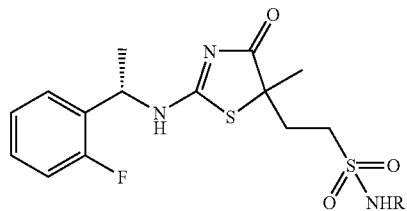 | |
| 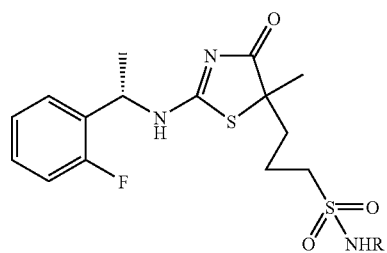 | |
| 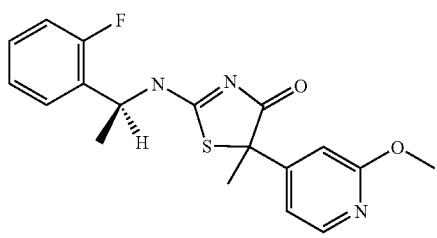 | |
| 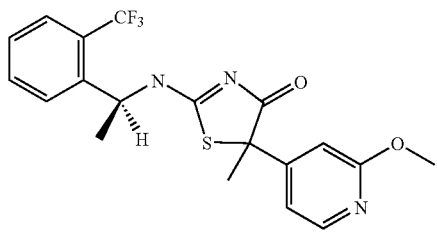 | |
| 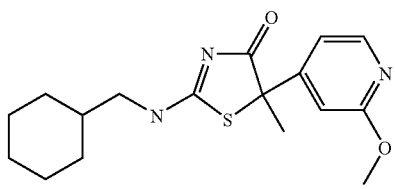 | |
| 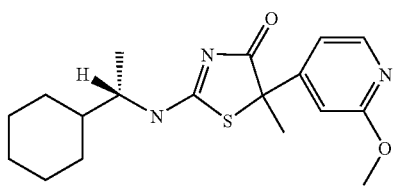 | |
| 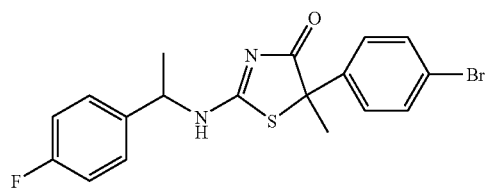 | |

-continued
| Molecule | Name |
|---|---|
| 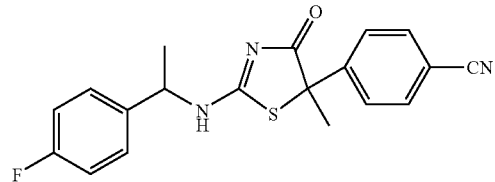 | |
| 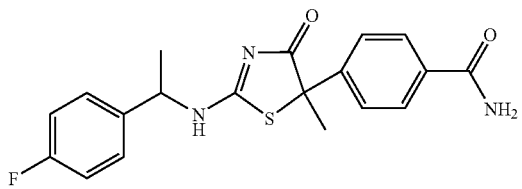 | |
| 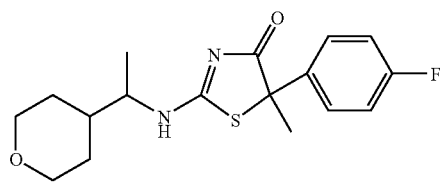 | |
| 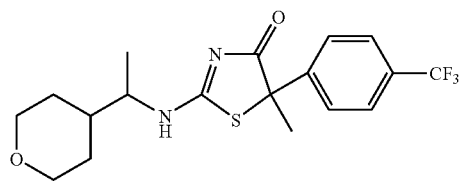 | |
| 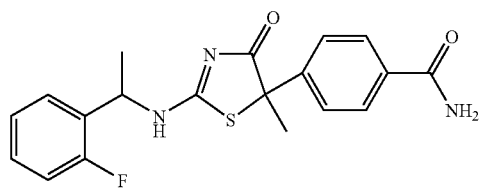 | |
| 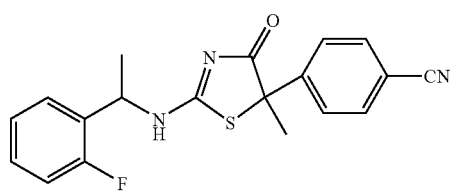 | |
| 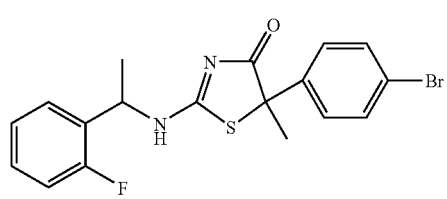 | |
| 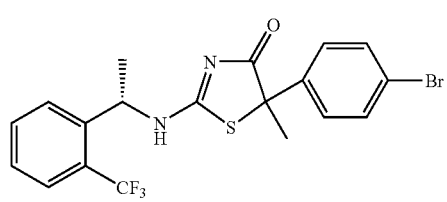 | |

-continued
| Molecule | Name |
|---|---|
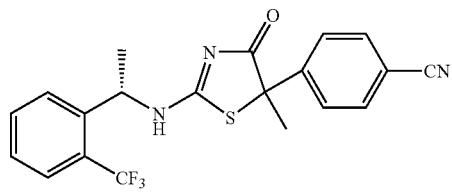
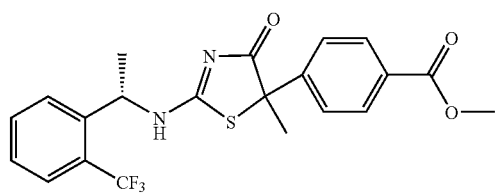
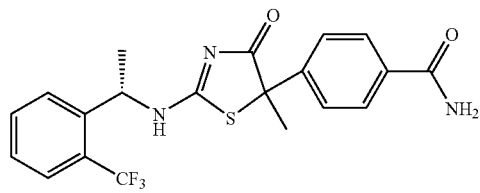
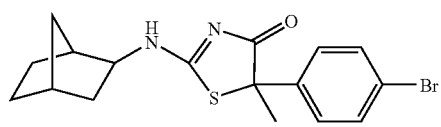
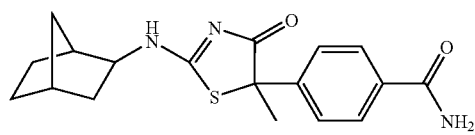
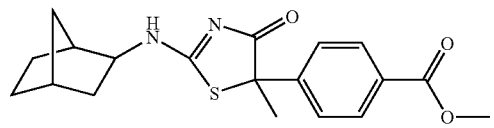
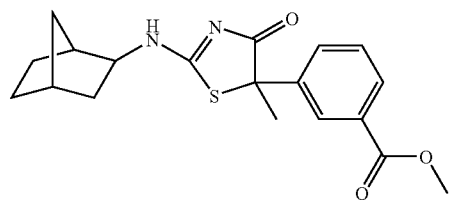
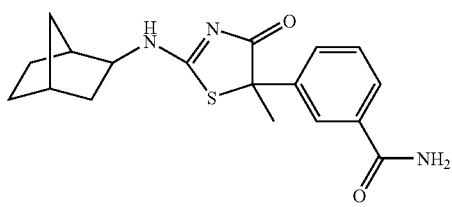

-continued
| Molecule | Name |
|---|---|
| 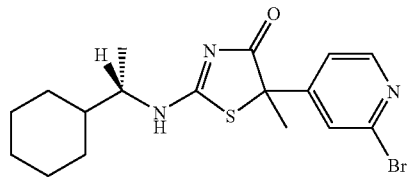 | |
| 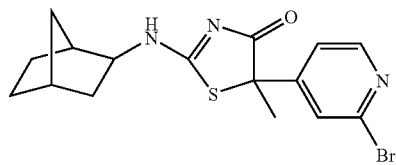 | |
| 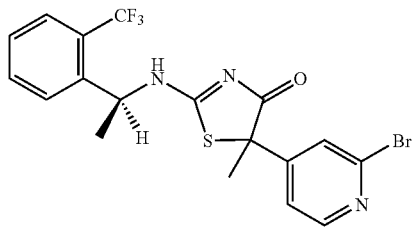 | |
| 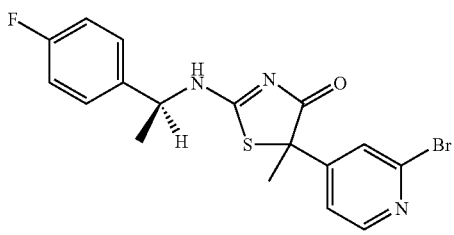 | |
| 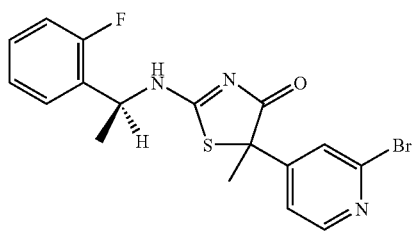 | |
| 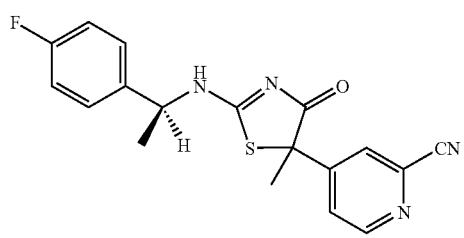 | |
| 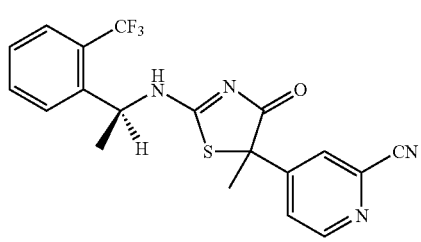 | |

| Molecule | Name |
|---|---|
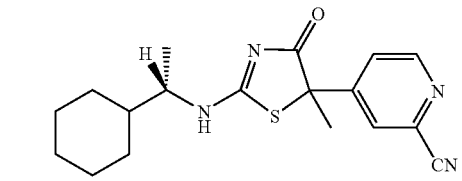
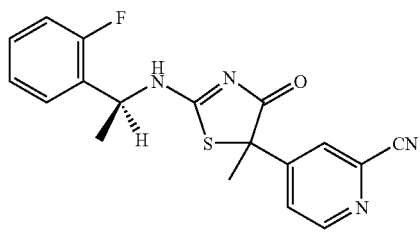
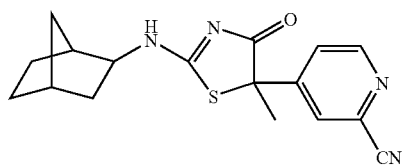
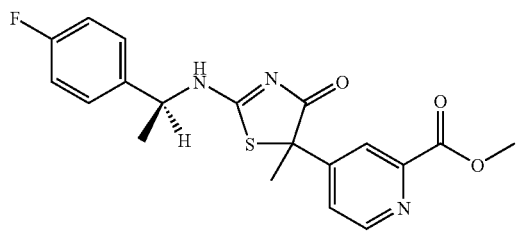
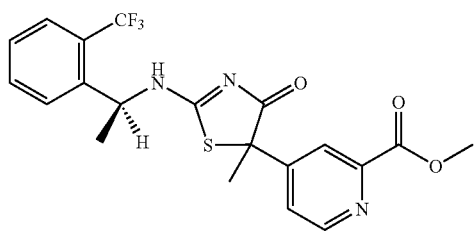
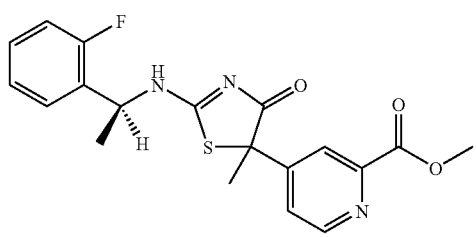
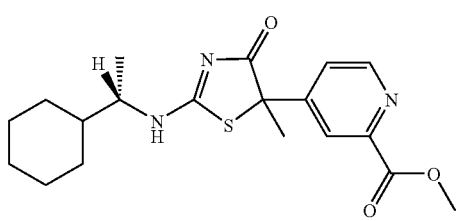

-continued
| Molecule | Name |
|---|---|
| 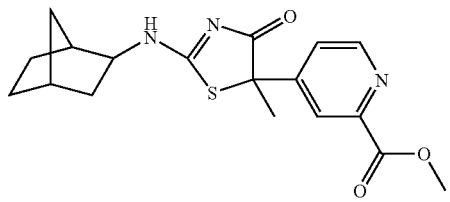 | |
| 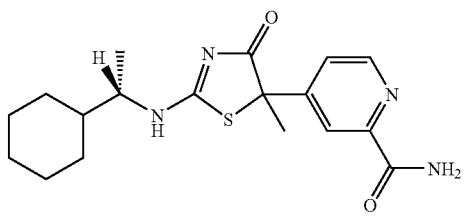 | |
| 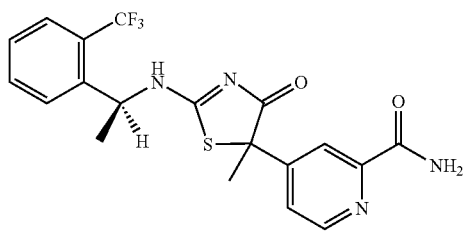 | |
| 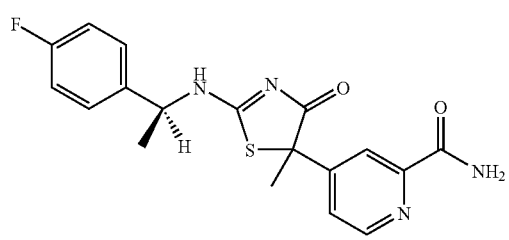 | |
| 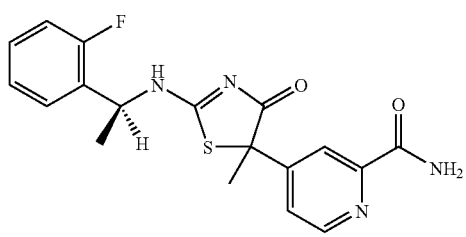 | |
| 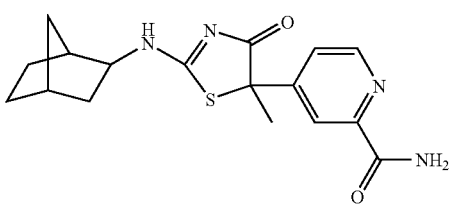 | |
| 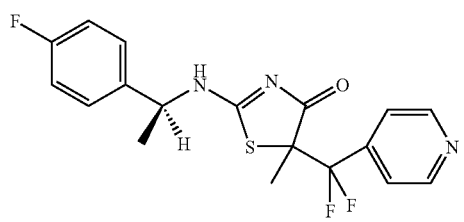 | |

-continued
| Molecule | Name |
|---|---|
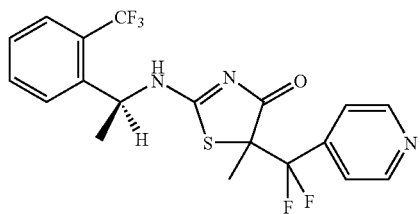
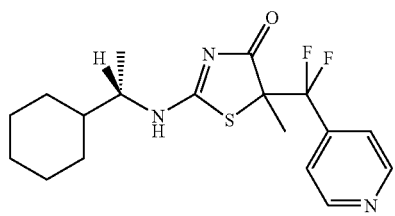
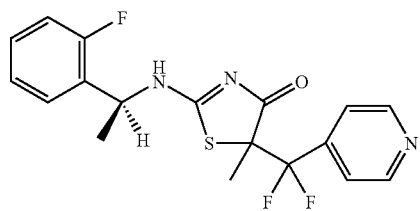
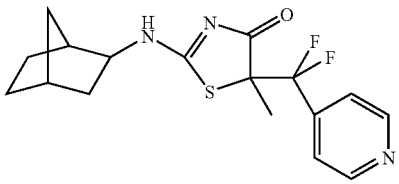
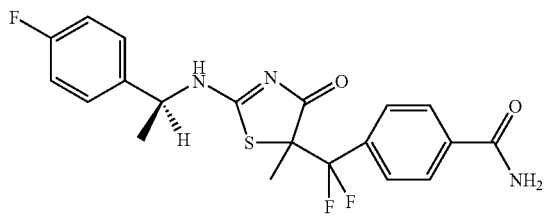
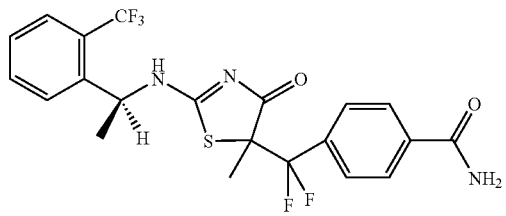
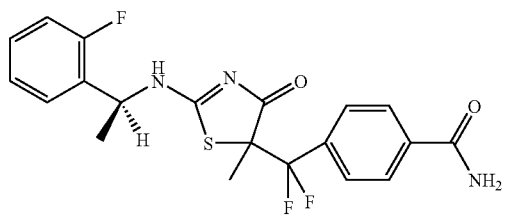

US 7,253,196 B2
-continued
| Molecule | Name |
|---|---|
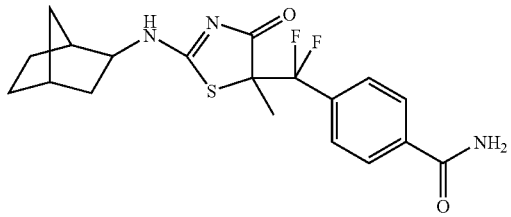
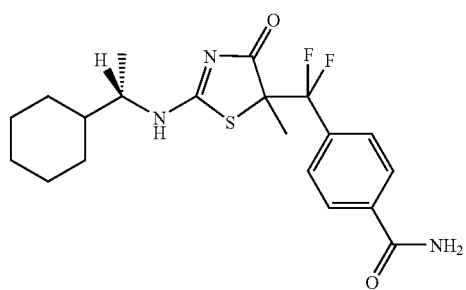
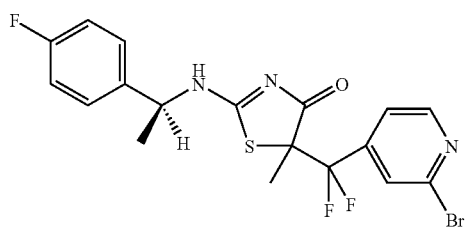
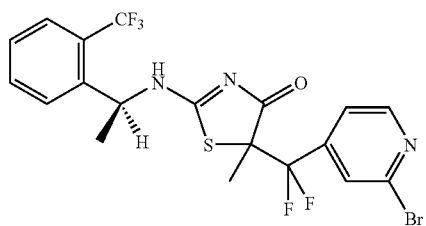
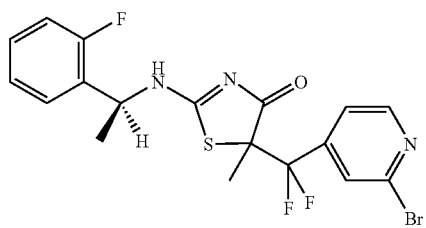
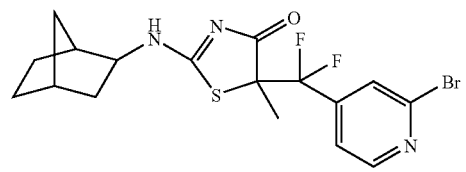

-continued
| Molecule | Name |
|---|---|
| 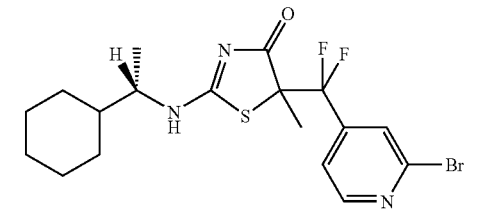 | |
| 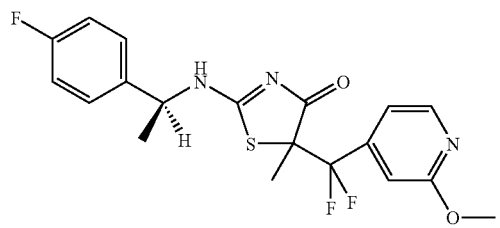 | |
| 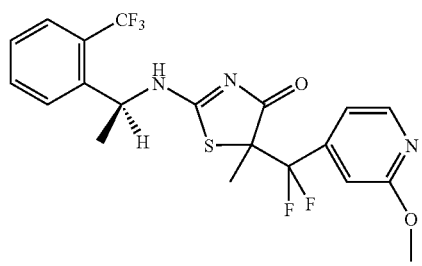 | |
| 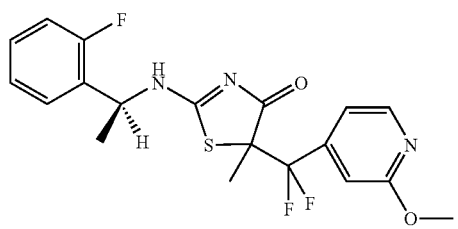 | |
| 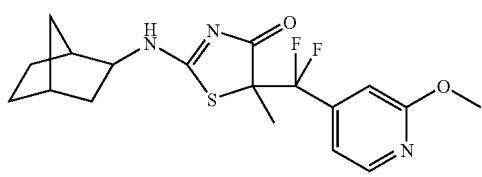 | |
| 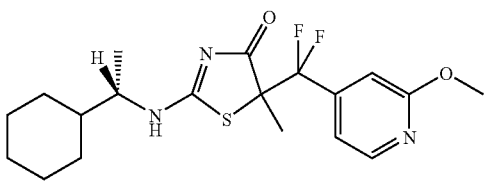 | |
| 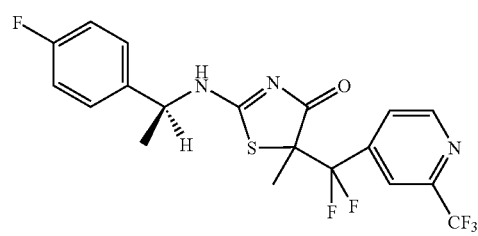 | |

-continued
| Molecule | Name |
|---|---|
| 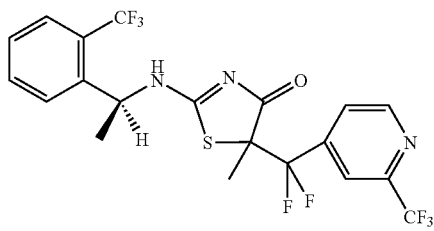 | |
| 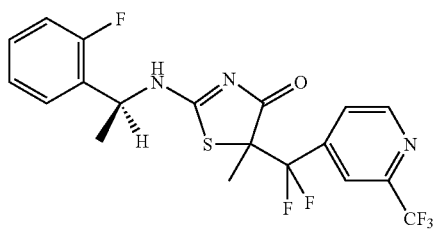 | |
| 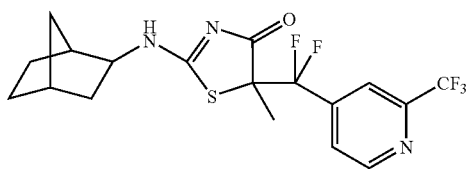 | |
| 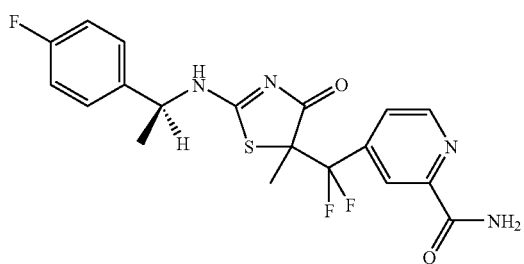 | |
| 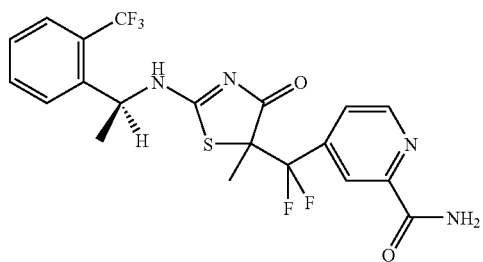 | |
| 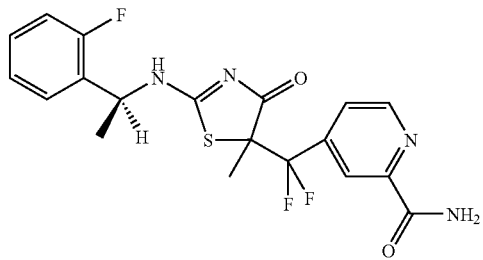 | |

-continued
| Molecule | Name |
|---|---|
| 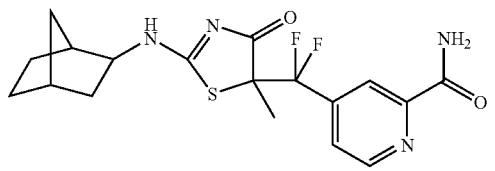 | |
| 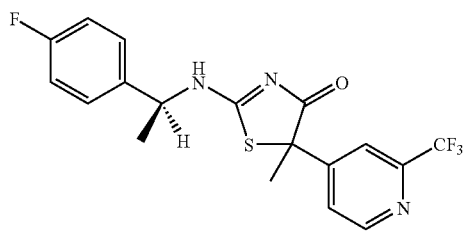 | |
| 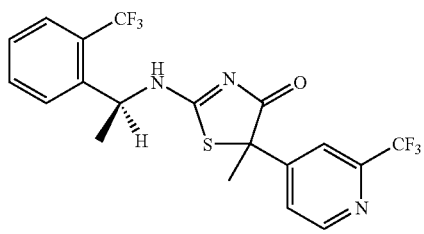 | |
| 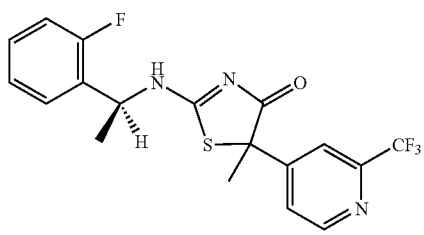 | |
| 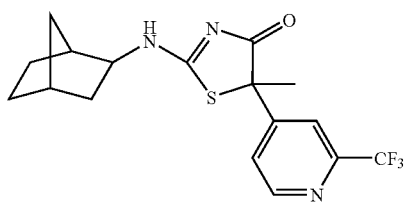 | |
| 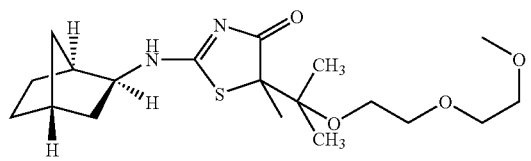 | |
| 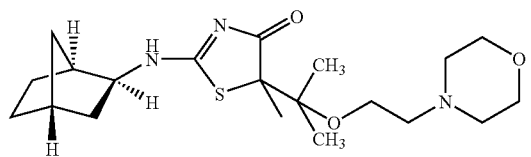 | |

-continued
| Molecule | Name |
|---|---|
| 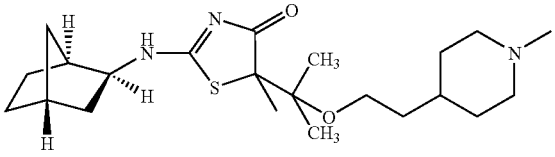 | |
| 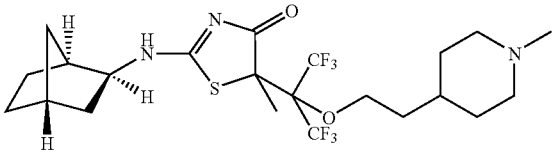 | |
| 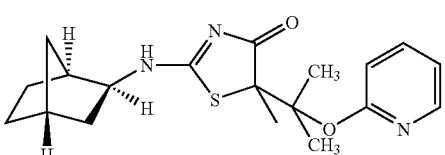 | |
| 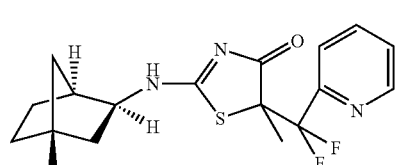 | |
| 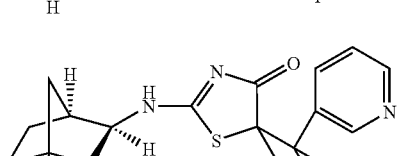 | |
| 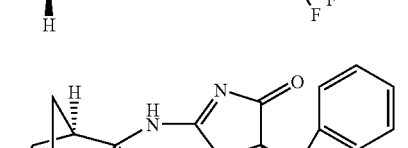 | |
| 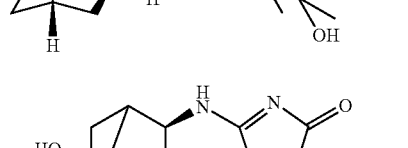 | |
| 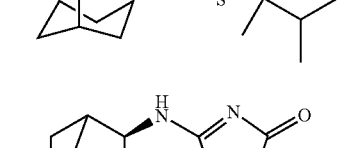 | |
| 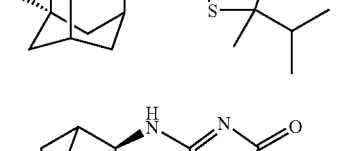 | |

-continued

| Molecule | Name |
|---|---|
| 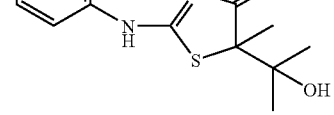 | |
| 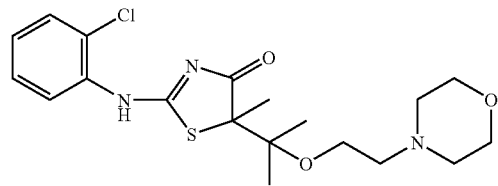 | |
| 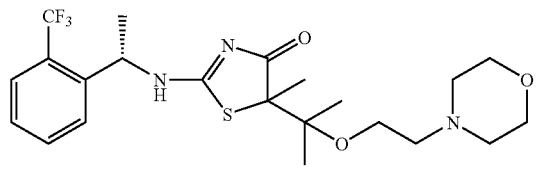 | |
| 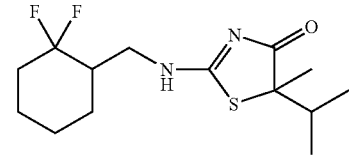 | |
| 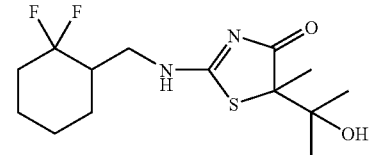 | |
| 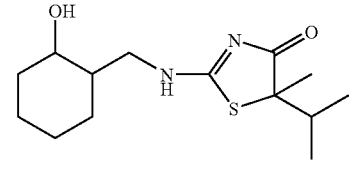 | |

Preparation of a Pharmaceutical Composition

Example 177

Preparation of Tablets

| | Ingredients | mg/tablet |
|---|---|---|
| 1. | Active compound of formula (I) | 10.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

The present invention is not to be limited in scope by the exemplified aspects which are intended as illustrations of single aspects of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

What is claimed is:

1. A compound of the general formula (III):

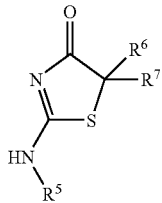

(III)

wherein:
R$^5$ is selected from C$_{3-10}$-cycloalkyl optionally independently substituted by one or more C$_{1-8}$-alkyl and aryl;
R$^6$ is C$_{1-8}$alkyl;
R$^7$ is C$_{1-8}$alkyl;
or a pharmaceutically acceptable salt, solvate, hydrate, geometrical isomer, tautomer, optical isomer, N-oxide, or prodrug form thereof.

2. The compound according to claim 1, wherein
R$^5$ is selected from cyclohexyl, cycloheptyl, cyclooctyl, 2,2,3,3-tetramethylcyclopropyl, 1-(4-chlorophenyl)cyclobutyl, bicyclo[2.2.1]hept-2-yl, tricyclo[3.3.1.0.~.3,7.~.]non-3-yl, and cyclohexylmethyl; and
R$^6$ and R$^7$ are each independently selected from methyl, ethyl, isopropyl, isobutyl, and tert-butyl.

3. The compound of claim 1, wherein R$^6$ is methyl and R$^7$ is isopropyl.

4. The compound of claim 1, wherein R$^5$ is selected from cyclohexyl, norbornyl and adamantyl.

5. The compound of claim 4, wherein R$^5$ is norbornyl.

6. The compound of claim 1, wherein R$^6$ is selected from methyl, ethyl, n-propyl or iso-propyl.

7. A compound selected from:
2-(bicyclo[2.2.1]hept-2-ylamino)-5,5-dimethyl-1,3-thiazol-4(5H)-one;
2-(Tricyclo[3.3.1.0~3,7]non-3-ylamino)-1,3-thiazol-4(5H)-one;
2[(cyclohexylmethyl)amino]-5,5-dimethyl-1,3-thiazol-4(5H)-one;
2-(Cyclooctylamino)-5,5-dimethyl-1,3-thiazol-4(5H)-one;
2-(cycloheptylamino)-5,5-diethyl-1,3-thiazol-4(5H)-one;
pharmaceutically acceptable salts, solvates, hydrates, geometrical isomers, tautomers, optical isomers, N-oxides and prodrug forms thereof.

8. A pharmaceutical formulation comprising a compound according to claim 1, as active ingredient, in combination with a pharmaceutically acceptable diluent or carrier.

9. The pharmaceutical formulation of claim 8, wherein the formulation is formulated for oral delivery.

10. The pharmaceutical formulation of claim 9, wherein the oral delivery is in the form of a tablet.

11. A compound selected from
2-(1-Cyclohexyl-ethylamino)-5-isopropyl-5-methyl-thiazol-4-one;
2-(bicyclo[2.2.1]hept-2-ylamino)-5-isopropyl-5-methyl-thiazol-4-one;
(5R)-2-((1S,2S,4R)-bicyclo[2.2.1]hept-2-ylamino)-5-methyl-5-(trifluoromethyl)-1,3-thiazol-4(5H)-one;
2-(Bicyclo[2.2.1]hept-2-ylamino)-5-(1-fluoro-1-methylethyl)-5-methyl-thiazol-4-one;
pharmaceutically acceptable salts, solvates, hydrates, geometrical isomers, tautomers, optical isomers, N-oxides and prodrug forms thereof.

12. A compound that is 2-(Cyclooctylamino)-5,5-dimethyl-1,3-thiazol-4(5H)-one or a pharmaceutically acceptable salt, solvate, geometrical isomer, tautomer, optical isomer, N-oxide or prodrug thereof.

13. A compound that is 5-ethyl-2-[(2-isopropylphenyl)amino]-1,3-thiazol-4(5H)-one one or a pharmaceutically acceptable salt, solvate, geometrical isomer, tautomer, optical isomer, N-oxide or prodrug thereof.

14. A compound that is 2-(bicyclo[2.2.1]hept-2-ylamino) 5-isopropyl-5-methyl-thiazol-4-one; or a pharmaceutically acceptable salt, solvate, geometrical isomer, tautomer, optical isomer, N-oxide or prodrug thereof.

15. A compound that is (S)-2-((1R,2R,4R)-5-hydroxybicyclo[2.2.1]heptan-2-ylamino)-5-isopropyl-5-methylthiazol-4(5H)-one or a pharmaceutically acceptable salt, solvate, hydrate, geometrical isomer, tautomer, optical isomer, N-oxide or prodrug thereof.

* * * * *